(12) United States Patent
Swayze et al.

(10) Patent No.: US 8,987,435 B2
(45) Date of Patent: Mar. 24, 2015

(54) OLIGOMERIC COMPOUNDS AND METHODS

(75) Inventors: Eric E. Swayze, Encinitas, CA (US); Balkrishen Bhat, Carlsbad, CA (US); Walter F. Lima, San Diego, CA (US); Thazha P. Prakash, Carlsbad, CA (US); Garth A. Kinberger, San Diego, CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 196 days.

(21) Appl. No.: 13/125,751

(22) PCT Filed: Oct. 23, 2009

(86) PCT No.: PCT/US2009/061959
§ 371 (c)(1),
(2), (4) Date: Sep. 7, 2011

(87) PCT Pub. No.: WO2010/048585
PCT Pub. Date: Apr. 29, 2010

(65) Prior Publication Data
US 2011/0313019 A1    Dec. 22, 2011

Related U.S. Application Data

(60) Provisional application No. 61/108,457, filed on Oct. 24, 2008, provisional application No. 61/108,464, filed on Oct. 24, 2008, provisional application No. 61/149,297, filed on Feb. 2, 2009, provisional application No. 61/150,492, filed on Feb. 6, 2009, provisional application No. 61/163,217, filed on Mar. 25, 2009, provisional application No. 61/174,137, filed on Apr. 30, 2009, provisional application No. 61/239,672, filed on Sep. 3, 2009.

(51) Int. Cl.
C07H 21/02    (2006.01)
C07H 21/04    (2006.01)
C07H 21/00    (2006.01)

(52) U.S. Cl.
CPC ..................................... C07H 21/00 (2013.01)
USPC .... 536/24.5; 536/23.1; 536/24.31; 536/24.33

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |

(Continued)

FOREIGN PATENT DOCUMENTS

| | | |
|---|---|---|
| AU | A-57590/94 | 9/1994 |
| AU | A-64522/94 | 12/1994 |

(Continued)

OTHER PUBLICATIONS

Of Elbashir et al. (The EBMO Journal, vol. 20, No. 23, pp. 6877-6888, 2001).*
Elbashir et al. (The EBMO Journal, vol. 20, No. 23, pp. 6877-6888, 2001).*
Bertrand et al. (Biochemical and Biophysical Research Communications, 296, 2002, 1000-1004).*
Chen et al., "Strand-specific 5'-O-methylation of siRNA duplexes controls guide strand selection and targeting specificity" RNA (2008) 14:263-274.
Haringsma et al., "mRNA knockdown by single strand RNA is improved by chemical modifications" Nucleic Acids Research (2012) 40(9):4125-4136.

(Continued)

*Primary Examiner* — Amy Bowman
(74) *Attorney, Agent, or Firm* — Casimir Jones, S.C.

(57) ABSTRACT

The present invention provides oligomeric compounds and uses thereof. In certain embodiments, such oligomeric compounds are useful as antisense compounds. Certain such antisense compounds are useful as RNase H antisense compounds or as RNAi compounds.

23 Claims, No Drawings

(56) References Cited

U.S. PATENT DOCUMENTS

| | | | |
|---|---|---|---|
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,712,378 A | 1/1998 | Wang |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Buhr et al. |
| 5,830,653 A | 11/1998 | Froehler et al. |
| 5,929,226 A | 7/1999 | Padmapriya et al. |
| 5,969,116 A | 10/1999 | Martin |
| 6,005,096 A | 12/1999 | Matteucci et al. |
| 6,426,220 B1 | 7/2002 | Bennett et al. |
| 6,600,032 B1 | 7/2003 | Manoharan et al. |
| 7,427,672 B2 | 9/2008 | Imanishi et al. |
| 7,452,987 B2 * | 11/2008 | Giese et al. ............... 536/24.5 |
| 2001/0044145 A1 * | 11/2001 | Monia et al. ............... 435/199 |
| 2004/0171570 A1 | 9/2004 | Allerson et al. |
| 2006/0074035 A1 | 4/2006 | Hong et al. |
| 2011/0076681 A1 * | 3/2011 | Waterhouse et al. ......... 435/6 |

FOREIGN PATENT DOCUMENTS

| | | |
|---|---|---|
| WO | WO 92/13869 | 8/1992 |
| WO | WO 94/02499 | 2/1994 |
| WO | WO 94/17093 | 8/1994 |
| WO | WO 94/22890 | 10/1994 |
| WO | WO 96/04295 | 2/1996 |
| WO | WO 98/00434 | 1/1998 |
| WO | WO 99/14226 | 3/1999 |
| WO | WO 01/14400 | 3/2001 |
| WO | WO 02/36743 | 5/2002 |
| WO | WO 03/073989 | 9/2003 |
| WO | WO 2005/012371 | 12/2005 |
| WO | WO 2005/012372 | 12/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |

OTHER PUBLICATIONS

Lima et al., "Binding and Cleavage Specificities of Human Argonatue2" Journal of Biological Chemistry (2009) 284(38):26017-26028.

Lima et al., "Single-Stranded siRNAs Activate RNAi in Animals" Cell (2012) 15:883-894.

Abbas et al., "Commercially Available 5'-DMT Phosphoramidites as Reagents for the Synthesis of Vinylphosphonate-Linked Oligonucleic Acids" Organic Letters (2001) 3(21):3365-3367.

Whittaker el al., "Stereoselective synthesis of highly funclionalised P-stereogenic nucleosides via palladium-catalysed P-C cross-coupling reactions" Tetrahedron Tetters (2008) 49:6984-6987.

Zhao, "Synthesis and preliminary biochemical studies with 5'-deoxy-5'-methylidyne phosphonate linked thymidine oligonucleotides" Tetrahedron Letters (1996) 37(35):6239-6242.

International Search Report for application PCT/US2011/033968 dated Mar. 11, 2013.

Swayze et al., "The Medicinal Chemistry of Oligonucleotides" Antisense Drug Technology: Principles, Strategies, and Applications, Chapter 6, pp. 143-182, Jul. 25, 2007, CRC Press.

European Search Report for application EP 12151431.9 dated Oct. 2, 2012.

Agrawal et al., *Protocols for Oligonucleotide Conjugates*, Humana Press; New Jersey, 1994, 26, Ch 3.

Altschul et al., "Basic Local Alignment Search Tool" J. Mol. Biol. (1990) 215:403-410.

Ausubel et al., Current Protocols in Molecular Biology, vol. 2, pp. 11.12.1-11.12.9, John Wiley & Sons, 1997.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

Bass, "Double-stranded RNA as a template for gene silencing" Cell (2000) 101:235-238.

Beaucage et al., "The Functionalization of Oligonucleotides via Phosphoramidite Derivatives" Tetrahedron (1993) 49:1925-1963.

(56) References Cited

OTHER PUBLICATIONS

Beaucage et al., "The Synthesis of Specific Ribonucleotides and Unrelated Phosphorylated Biomolecules by the Phosphoramidite Method" Tetrahedron (1993) 49:10441-10488.
Beaucage et al., "Advances in the Synthesis of Oligonucleotides by the Phosphoramidite Approach" Tetrahedron (1992) 48:2223-2311.
Belikova et al., "Synthesis of Ribonucleosides and Diribonucleoside Phosphates Containing 2-Chloro-Ethylamine and Nitrogen Mustard Residues" Tet. Lett. (1967) 37:3557-3562.
Brazma et al., "Gene expression data analysis" FEBS Letters (2000) 480:17-24.
Carulli et al., "High Throughput Analysis of Differential Gene Expression" J. Cell. Biochem. Suppl. (1998) 30:286-296.
Celis et al., "Gene expression profiling: monitoring transcription and translation products using DNA microarrays and proteomics" FEBS Lett (2000) 480:2-16.
De Mesmaeker et al., "Amide-Modified Oligonucleotides with Preorganized Backbone and Furanose Rings: Highly Increased Thermodynamic Stability of the Duplexes Formed with their RNA and DNA Complements" Synlett (1997) 1287-1290.
Elbashir, "Duplexes of 21-nucleotide RNAs mediate RNA interference in cultured mammalian cells" Nature (2001) 411:494-498.
Elbashir, "RNA interference is mediated by 21- and 22-nucleotide RNAs" Genes & Devel. (2001) 15:188-200.
Englisch et al., "Chemically Modified Oligonucleotides as Probes and Inhibitors" Agnew Chem. Int. Ed. Engl. (1991) 30:613-629.
Eppacher et al., "Synthesis and Incorporation of C(5')-Ethynylated Uracil-Derived Phosphoramidites into RNA" Helvetica Chimica Acta (2004) 87(12):3004-3020.
Fire et al., "Potent and Specific Genetic Interference by Double-Stranded RNA in Caenorhabditis elegans" Nature (1998) 391:806-811.
Fuchs et al., "Identification of Differentially Expressed Genes by Mutually Subtracted RNA Fingerprinting" Anal. Biochem. (2000) 286:91-98.
Gait et al., "Application of chemically synthesized RNA" RNA: Protein Interactions (1998) 1-36.
Gallo et al., "2'-C-Methyluridine Phosphoramidite: A New Building Block for the Preparation of RNA Analogues Carrying the 2'-Dydroxyl Group" Tetrahedron (2001) 57: 5707-5713.
Going et al., "Molecular Pathology and Future Developments" Eur. J. Cancer (1999) 35:1895-1904.
Jahn-Hofmann et al., "Efficient Solid Phase Synthesis of Cleavable Oligodeoxynucleotides Based on a Novel Strategy for the Synthesis of 5'-S-(4,4'-Dimethoxytrityl)-2'-deoxy-5'-thionucleoside Phosphoramidites" Helvetica Chimica Acta (2004) 87:2812-2828.
Jungblut et al., "Proteomics in human disease: Cancer, heart and infections diseases" Electrophoresis (1999) 20:2100-2110.
Jurecic et al., "Long-distance DD-PCR and cDNA microarrays" Curr. Opin. Microbiol. (2000) 3:316-321.
Kroschwitz, "Polynucleotides" Concise Encyclopedia of Polymer Science and Engineering (1990) John Wiley & Sons, NY pp. 858-859.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotech. (2000) 80:143-157.
Liu et al., "Uridylyl-(3'-5')-(5'-thiouridine). An Exceptionally Base-labile Di-ribonucleoside Phosphate Analogue" Tetrahedron Letters (1995) 36(19):3413-3416.
Madden et al., "Serial analysis of gene expression: from gene discovery to target identification" DDT (2000) 5:415-425.
Mag et al., "Synthesis and selective cleavage of oligodeoxyribonucleotldes containing non-chiral intemucieotlde phosphoramidate linkages" Nucleic Acids Res. (1989) 17(15):5973-5988.
Matulic-Ademic et al., "Synthesis and incorporation of 5'-amino- and 5'-mercapto-5'-deoxy-2'-O-methyl nucleosides into hammerhead ribozymes" Nucleosides & Nucleotides (1997) 16:1933-1950.
Mikhailov et al., "Substrate Properties of C'-Methylnucleoside and C'-Methyl-2'-Deoxynucleoside 5'Triphosphates in RNA and DNA Synthesis Reactions Catalysed by RNA and DNA Polymerases" Nucleosides &Nucleotides (1991) 10(1-3):339-343.
Miura et al., "Fluorometric determination of total mRNA with oligo(dT) immobilized on microtiter plates" Clin. Chem. (1996) 42:1758-1764.
Montgomery et al., "RNA as a target of double-stranded RNA-mediated genetic interference in Caenorhabditis elegans" Proc Natl. Acad. Sci. (1998) 95:15502-7.
Nishikura, "A Short Primer on RNAi: RNA-Directed RNA Polymerase Acts as a Key Catalyst" Cell (2001) 107:415-418.
Prashar et al., "Reads: A Method for Display of 3'-End Fragment of Restriction Enzyme-Digested cDNAs for Analysis of Differential Gene Expression" Methods Enzymol. (1999) 303:258-272.
Saha et al., "5'-Me-DNA—A New Oligonucleotide Analog: Synthesis and Biochemical Properties" J. Org. Chem. (1995) 60:788-789.
Sanghvi, Chapter 15, Antisense Research and Applications, pp. 289-302, Crooke and Lebleu ed., CRC Press (1993).
Sutcliffe et al., "TOGA: An automated parsing technology for analyzing expression of nearly all genes" PNAS (2000) 97:1976-1981.
Tabara et al., "RNAi in C. elegans: Soaking in the Genome Sequence" Science (1998) 282:430-431.
Tijsterman et al., "RNA hellcase MUT-14-dependent gene silencing triggered in C. elegans by short antisense RNAs" Science (2002) 295:694-7.
Timmons et al., "Ingestion of bacterially expressed dsRNAs can produce specific and potent genetic interference in Caenorhabditis elegans" Gene (2001) 263:103-112.
Timmons et al., "Specific Interference by Ingested dsRNA" Nature (1998) 395:854.
To, "Identification of Differential Gene Expression by High Throughput Analysis" Comb. Chem. High Throughput Screen (2000) 3:235-241.
Tuschl et al., "Targeted mRNA degradation by double-stranded RNA in vitro" Genes Dev. (1999) 13:3191-7.
Wang et al., "Biophysical and Biochemical Properties of Oligodeoxynucleotides Containing 4'-C- and 5'-C-Substituted Thymidines" Bioorg. Med. Chem. Lett. (1999) 9:885-890.
Wang et al., "Synthesis of Azole Nucleoside 5'-Monophosphate Mimics (P1Ms) and Their Inhibitory Properties of IMP Dehydrogenases" Nucleosides Nucleotides & Nucleic Acids (2004) 23(1&2):317-337.
Wu et al., "Functionalization of the Sugar Moiety of Oligoribonucleotides on Solid Support" Bioconjugate Chem. (1999) 10:921-924.
Wu et al., "Synthesis of 5'-C- and 2'-O-(Bromoalkyl)-Substituted Ribonucleoside Phosphoramidites for the Post-synthetic Functionalization of Oligonucleotides on Solid Support" Helvetica Chimica Acta (2000) 83:1127-1143.
Zamecnik et al., "Inhibition of Rous sarcoma virus replication and cell transformation by a specific oligodeoxynucleotide" PNAS (1978) 75:280-284.
Zhang et al., "PowerBLAST: A New Network BLAST Application for Interactive or Automated Sequence Analysis and Annotation" Genome Res. (1997) 7:649-656.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for application PCT/US2009/061913 dated Jul. 27, 2010.
International Search Report for application PCT/US2009/061959 dated Aug. 19, 2010.
Matulic-Ademic et al., "Synthesis of 5'-Deoxy-5'-difluoromethyl Phosphonate Nucleotide Analogs" J. Org. Chem. (1995) 60:2563-2569.
Bohringer et al., "Synthesis of 5'-deoxy-5'-methylphosphonate Linked Thymidine Oligonucleotides" Tetrahedron Lett. (1993) 34(17):2723-2726.

\* cited by examiner

US 8,987,435 B2

OLIGOMERIC COMPOUNDS AND METHODS

CROSS REFERENCED TO RELATED APPLICATIONS

This application is a U.S. National Phase filing under 35 U.S.C. 371 claiming priority to International Serial No. PCT/US2009/061959 filed Oct. 23, 2009, which claims priority to U.S. Provisional Applications: 61/108,457, filed Oct. 24, 2008; 61/149,297, filed Feb. 2, 2009; 61/163,217, filed Mar. 25, 2009; 61/174,137, filed Apr. 30, 2009; 61/239,672, filed Sep. 3, 2009; 61/150,492, filed Feb. 6, 2009; and 61/108,464, filed Oct. 24, 2008, each of which is incorporated herein by reference in its entirety.

STATEMENT OF GOVERNMENT SUPPORT

This invention was made with United States Government support under contract #5R44GM076793-03 awarded by the NIH. The United States Government has certain rights in the invention.

SEQUENCE LISTING

The present application is being filed along with a Sequence Listing in electronic format. The Sequence Listing is provided as a file entitled CHEM0055USASEQ.TXT, created on Apr. 13, 2011, which is 19 Kb in size. The information in the electronic format of the sequence listing is incorporated herein by reference in its entirety.

FIELD OF THE INVENTION

The present invention provides compounds and methods for modulating nucleic acids and proteins. Provided herein are modified nucleosides and oligomeric compounds prepared therefrom. In certain embodiments, modified nucleosides are provided having at least one 5'-substituent and a 2'-substituent, oligomeric compounds comprising at least one of these modified nucleosides and compositions comprising at least one of these oligomeric compounds. In some embodiments, the oligomeric compounds provided herein are expected to hybridize to a portion of a target RNA resulting in loss of normal function of the target RNA. The oligomeric compounds are also expected to be useful as primers and/or probes in diagnostic applications.

BACKGROUND OF THE INVENTION

Antisense compounds have been used to modulate target nucleic acids. Antisense compounds comprising a variety of modifications and motifs have been reported. In certain instances, such compounds are useful as research tools and as therapeutic agents. Certain double-stranded RNA-like compounds (siRNAs) are known to inhibit protein expression in cells. Such double-stranded RNA compounds function, at least in part, through the RNA-inducing silencing complex (RISC). Certain single-stranded RNA-like compounds (ssRNAs) have also been reported to function at least in part through RISC.

Targeting disease-causing gene sequences was first suggested more than thirty years ago (Belikova et al., Tet. Lett., 1967, 37, 3557-3562), and antisense activity was demonstrated in cell culture more than a decade later (Zamecnik et al., Proc. Natl. Acad. Sci. U.S.A., 1978, 75, 280-284). One advantage of antisense technology in the treatment of a disease or condition that stems from a disease-causing gene is that it is a direct genetic approach that has the ability to modulate (increase or decrease) the expression of specific disease-causing genes. Another advantage is that validation of a therapeutic target using antisense compounds results in direct and immediate discovery of the drug candidate; the antisense compound is the potential therapeutic agent.

Generally, the principle behind antisense technology is that an antisense compound hybridizes to a target nucleic acid and modulates gene expression activities or function, such as transcription or translation. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi generally refers to antisense-mediated gene silencing involving the introduction of dsRNA leading to the sequence-specific reduction of targeted endogenous mRNA levels. An additional example of modulation of RNA target function by an occupancy-based mechanism is modulation of microRNA function. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. Regardless of the specific mechanism, this sequence-specificity makes antisense compounds extremely attractive as tools for target validation and gene functionalization, as well as therapeutics to selectively modulate the expression of genes involved in the pathogenesis of malignancies and other diseases.

Antisense technology is an effective means for reducing the expression of one or more specific gene products and can therefore prove to be uniquely useful in a number of therapeutic, diagnostic, and research applications. Chemically modified nucleosides are routinely used for incorporation into antisense compounds to enhance one or more properties, such as nuclease resistance, pharmacokinetics or affinity for a target RNA. In 1998, the antisense compound, Vitravene® (fomivirsen; developed by Isis Pharmaceuticals Inc., Carlsbad, Calif.) was the first antisense drug to achieve marketing clearance from the U.S. Food and Drug Administration (FDA), and is currently a treatment of cytomegalovirus (CMV)-induced retinitis in AIDS patients.

New chemical modifications have improved the potency and efficacy of antisense compounds, uncovering the potential for oral delivery as well as enhancing subcutaneous administration, decreasing potential for side effects, and leading to improvements in patient convenience. Chemical modifications increasing potency of antisense compounds allow administration of lower doses, which reduces the potential for toxicity, as well as decreasing overall cost of therapy. Modifications increasing the resistance to degradation result in slower clearance from the body, allowing for less frequent dosing. Different types of chemical modifications can be combined in one compound to further optimize the compound's efficacy. The synthesis of 5'-substituted DNA and RNA derivatives and their incorporation into oligomeric compounds has been reported in the literature (Saha et al., *J. Org. Chem.*, 1995, 60, 788-789; Wang et al., *Bioorganic & Medicinal Chemistry Letters*, 1999, 9, 885-890; and Mikhailov et al., *Nucleosides & Nucleotides*, 1991, 10(1-3), 339-343; Leonid et al., 1995, 14(3-5), 901-905; and Eppacher et al., *Helvetica Chimica Acta*, 2004, 87, 3004-3020). The 5'-substituted monomers have also been made as the mono-phosphate with modified bases (Wang et al., *Nucleosides Nucleotides & Nucleic Acids*, 2004, 23 (1 & 2), 317-337).

A genus of modified nucleosides including optional modification at a plurality of positions including the 5'-position and the 2'-position of the sugar ring and oligomeric compounds incorporating these modified nucleosides therein has been reported (see International Application Number: PCT/US94/02993, Published on Oct. 13, 1994 as WO 94/22890).

The synthesis of 5'-CH$_2$ substituted 2'-O-protected nucleosides and their incorporation into oligomers has been previously reported (see Wu et al., *Helvetica Chimica Acta*, 2000, 83, 1127-1143 and Wu et al. *Bioconjugate Chem.* 1999, 10, 921-924).

Amide linked nucleoside dimers have been prepared for incorporation into oligonucleotides wherein the 3' linked nucleoside in the dimer (5' to 3') comprises a 2'-OCH$_3$ and a 5'-(S)—CH$_3$ (Mesmaeker et al., *Synlett*, 1997, 1287-1290).

A genus of 2'-substituted 5'-CH$_2$ (or O) modified nucleosides and a discussion of incorporating them into oligonucleotides has been previously reported (see International Application Number: PCT/US92/01020, published on Feb. 7, 1992 as WO 92/13869).

The synthesis of modified 5'-methylene phosphonate monomers having 2'-substitution and their use to make modified antiviral dimers has been previously reported (see U.S. patent application Ser. No. 10/418,662, published on Apr. 6, 2006 as US 2006/0074035).

There remains a long-felt need for agents that specifically regulate gene expression via antisense mechanisms. Disclosed herein are oligomeric compounds such as antisense compounds useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

SUMMARY OF THE INVENTION

In certain embodiments, provided herein are modified nucleosides having at least one 2' substituent group and either a 5' substituent group, a 5' phosphorus moiety or both a 5' substituent group and a 5' phosphorus moiety, oligomeric compounds that include such modified nucleosides and methods of using the oligomeric compounds. Also provided herein are intermediates and methods for preparing these modified nucleosides and oligomeric compounds. In certain embodiments, modified nucleosides are provided that are 5'-mono (R, S or mixed) or bis substituted and 2'-O-substituted, that can be incorporated into oligomeric compounds. The modified nucleosides provided herein are expected to be useful for enhancing one or more properties of the oligomeric compounds they are incorporated into such as for example nuclease resistance. In certain embodiments, the oligomeric compounds and compositions provided herein that incorporate one or more of these modified nucleosides are expected to hybridize to a portion of a target RNA resulting in loss of normal function of the target RNA. The oligomeric compounds are also expected to be useful as primers and probes in diagnostic applications.

The variables are defined individually in further detail herein. It is to be understood that the modified nucleosides and oligomeric compounds provided herein include all combinations of the embodiments disclosed and variables defined herein.

In certain embodiments, the invention provides oligomeric compounds comprising an oligonucleotide comprising a nucleoside having Formula VII:

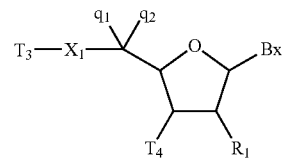

VII wherein:
Bx is a heterocyclic base moiety;
T$_3$ is a phosphorus moiety;
T$_4$ is an internucleoside linking group attaching the nucleoside of Formula I to the remainder of the oligonucleotide; and
each of q$_1$ and q$_2$ is, independently selected from H, C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl and substituted C$_2$-C$_6$ alkynyl;
X$_1$ is S, NR$_{16}$, or CR$_{10}$R$_{11}$ wherein each R$_{10}$ and R$_{11}$ is, independently, H, F, C$_1$-C$_6$ haloalkyl, or C$_1$-C$_6$ alkyl; and
R$_1$ is selected from a halogen, X$_2$—V, and O—X$_4$;
or
each of q$_1$ and q$_2$ is, independently, selected from H, C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl and substituted C$_2$-C$_6$ alkynyl;
X$_1$ is O, S, NR$_{16}$R$_{17}$, or CR$_{10}$R$_{11}$ wherein each R$_{10}$ and R$_{11}$ is, independently, H, F, C$_1$-C$_6$ haloalkyl, or C$_1$-C$_6$ alkyl; and
R$_1$ is X$_2$—V;
or
each of q$_1$ and q$_2$ is, independently, selected from C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl and substituted C$_2$-C$_6$ alkynyl;
X$_1$ is O, S, NR$_{16}$R$_{17}$, or CR$_{10}$R$_{11}$ wherein each R$_{10}$ and R$_{11}$ is, independently, H, F, C$_1$-C$_6$ haloalkyl, or C$_1$-C$_6$ alkyl; and
R$_1$ is selected from halogen, X$_2$—V, and O—X$_4$;
wherein:
X$_2$ is O, S or CR$_7$R$_8$ wherein each R$_7$ and R$_8$ is, independently, H or C$_1$-C$_6$ alkyl;
V is selected from cholesterol, (CH$_2$)$_2$[O(CH$_2$)$_2$]$_t$OCH$_3$, where t is from 1-3, (CH$_2$)$_2$F, CH$_2$COOH, CH$_2$CONH$_2$, CH$_2$CONR$_5$R$_6$, CH$_2$COOCH$_2$CH$_3$, CH$_2$CONH(CH$_2$)$_i$—S—R$_4$ where i is from 1 to 10, CH$_2$CONH(CH$_2$)$_j$NR$_5$R$_6$ where j is from 1 to 6, CH$_2$CONH[(CH$_2$)$_{k1}$—N(H)]$_{k2}$—(CH$_2$)$_{k1}$NH$_2$ where each k$_1$ is independently from 2 to 4 and k$_2$ is from 2 to 10, and aryl;
R$_4$ is selected from H, C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl, substituted C$_2$-C$_6$ alkynyl, C$_6$-C$_{14}$ aryl and a thio protecting group;
R$_5$ and R$_6$ are each, independently, selected from H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, and substituted C$_2$-C$_6$ alkynyl;
R$_{16}$ is selected from H, C$_1$-C$_6$ alkyl, or substituted C$_1$-C$_6$ alkyl;
X$_4$ is [C(R$_a$)(R$_b$)]$_n$[(C═O)$_m$X$_c$]$_k$—R$_d$ wherein each R$_a$ and R$_b$ is independently H or halogen;
X$_c$ is O, S, or N(E$_1$);

$R_d$ is H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl or $NE_2E_3$;

each $E_1$, $E_2$, and $E_3$ is independently H, $C_1$-$C_6$ alkyl, or substituted $C_1$-$C_6$ alkyl;

n is 1 to 6;

m is 0 or 1; and k is 0 or 1; and wherein each substituted group is, independently, mono or poly substituted with optionally protected substituent groups independently selected from halogen, oxo, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl; and $J_4$ is hydrogen, or a protecting group.

In certain embodiments, the invention provides oligomeric compounds comprising an oligonucleotide comprising a nucleoside having Formula VII:

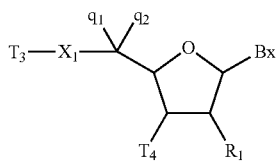

VII wherein:

Bx is a heterocyclic base moiety;

$X_1$ is O, S, $NR_{16}R_{17}$, or $CR_{10}R_{11}$ wherein each $R_{10}$ and $R_{11}$ is, independently, H, F, or $C_1$-$C_6$ alkyl, and each $R_{16}$ and $R_{17}$ is independently, H, $C_1$-$C_6$ alkyl, substituted $C_1$-$C_6$ alkyl, $T_3$ is a phosphorus moiety;

$T_4$ is an internucleoside linking group attaching the nucleoside of Formula I to the remainder of the oligonucleotide;

$R_1$ is selected from halogen, trifluoroalkoxy, azido, aminooxy, O-alkyl, S-alkyl, N($J_4$)-alkyl, O-alkenyl, S-alkenyl, N($J_4$)-alkenyl, O-alkynyl, S-alkynyl or N($J_4$)-alkynyl, O-alkoxy, and $X_2$—V, wherein:

$X_2$ is O, S or $CR_7R_8$ wherein each $R_7$ and $R_8$ is, independently, H or $C_1$-$C_6$ alkyl;

V is selected from $(CH_2)_2F$, $CH_2COOH$, $CH_2CONH_2$, $CH_2COOCH_2CH_3$, $CH_2CONH(CH_2)_i$—S—$R_4$ where i is from 1 to 10, $CH_2CONH(CH_2)_jNR_5R_6$ where j is from 1 to 6, and $CH_2CONH\{(CH_2)_{k1}$—N(H)$\}_{k2}$—$(CH_2)_{k1}NH_2$ where each $k_1$ is independently from 2 to 4 and $k_2$ is from 2 to 10;

$R_4$ is selected from H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl, substituted $C_2$-$C_6$ alkynyl, $C_6$-$C_{14}$ aryl and a thio protecting group;

$R_5$ and $R_6$ are each, independently, selected from H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, and substituted $C_2$-$C_6$ alkynyl; and each of $q_1$ and $q_2$ is, independently, selected from H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl;

provided that if each of $q_1$ and $q_2$ is H, then:

either:

$R_1$ is selected from, trifluoroalkoxy, azido, aminooxy, S-alkyl, N($J_4$)-alkyl, O-alkenyl, S-alkenyl, N($J_4$)-alkenyl, O-alkynyl, S-alkynyl and N($J_4$)-alkynyl, and $X_2$—V; and $X_1$ selected from O, S, N, and $CR_{10}R_{11}$;

or $R_1$ is selected from halogen, trifluoroalkoxy, azido, aminooxy, O-alkyl, S-alkyl, N($J_4$)-alkyl, O-alkenyl, S-alkenyl, N($J_4$)-alkenyl, O-alkynyl, S-alkynyl or N($J_4$)-alkynyl, O-alkoxy, and $X_2$—V; and $X_1$ is selected from S, N, or $CR_{10}R_{11}$; and wherein each substituted group is, independently, mono or poly substituted with optionally protected substituent groups independently selected from halogen, oxo, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl; and $J_4$ is hydrogen, or a protecting group.

In certain such embodiments, $R_1$ is selected from halogen, O-alkyl, O-haloalkyl, O-alkoxy. In certain embodiments, $R_1$ is F. In certain embodiments, $R_1$ is O—$C_2$-$C_4$ alkyl or haloalkyl. In certain embodiments, $R_1$ is $OCH_3$. In certain embodiments, $R_1$ is $O(CH_2)_2OCH_3$. In certain embodiments, $R_1$ is $FCH_2CH_3$. In certain embodiments, $R_1$ is $(CH_2)_2[O(CH_2)_2]_tOCH_3$, where t is from 1-3. In certain embodiments, $R_1$ is selected from, trifluoroalkoxy, azido, aminooxy, S-alkyl, N($J_4$)-alkyl, O-alkenyl, S-alkenyl, N($J_4$)-alkenyl, O-alkynyl, S-alkynyl, N($J_4$)-alkynyl, and $X_2$—V. In certain embodiments, $R_1$ is $X_2$—V. In certain embodiments, V is $(CH_2)_2F$. In certain embodiments, V is $CH_2CONH(CH_2)_i$—S—$R_4$. In certain embodiments, $CH_2CONH[(CH_2)_{k1}$—N(H)$]_{k2}$—$(CH_2)_{k1}NH_2$. In certain embodiments, V is $CH_2CONH$—$(CH_2)_3$—N(H)—$(CH_2)_4$—N(H)—$(CH_2)_3NH_2$. In certain embodiments, V is $CH_2CONH(CH_2)_jNR_5R_6$. In certain embodiments, at least one of $R_5$ and $R_6$ is other than H. In certain embodiments, at least one of $R_5$ and $R_6$ is methyl. In certain embodiments, $R_5$ is methyl and $R_6$ is methyl. In certain embodiments, $X_2$ is O. In certain embodiments, $X_2$ is S. In certain embodiments, $X_2$ is $CR_7R_8$. In certain embodiments, $R_7$ and $R_8$ are both H. In certain embodiments, at least one of $q_1$ and $q_2$ is $C_1$-$C_6$ alkyl or substituted $C_1$-$C_6$ alkyl. In certain embodiments, at least one of $q_1$ and $q_2$ is $C_1$-$C_6$ alkyl. In certain embodiments, at least one of $q_1$ and $q_2$ is methyl. In certain embodiments, at least one of $q_1$ and $q_2$ is H. In certain embodiments, one of $q_1$ and $q_2$ is methyl and the other of $q_1$ and $q_2$ is H. In certain embodiments, $q_1$ and $q_2$ are each $C_1$-$C_6$ alkyl or substituted $C_1$-$C_6$ alkyl. In certain embodiments, $X_1$ is O. In certain embodiments, $X_1$ is S. In certain embodiments, $X_1$ is $CR_{10}R_{11}$. In certain embodiments, $R_{10}$ and $R_{11}$ are both H. In certain embodiments, the phosphorus moiety is $P(Y_a)(Y_b)(Y_c)$ where $Y_a$ is O or S and each $Y_b$ and $Y_c$ is, independently, selected from OH, SH, alkyl, alkoxy, substituted $C_1$-$C_6$ alkyl and substituted $C_1$-$C_6$ alkoxy. In certain embodiments, $Y_a$ is 0 and $Y_b$ and $Y_c$ are each OH.

In certain embodiments, the invention provides such oligomeric compounds comprising a nucleoside of Formula VIII:

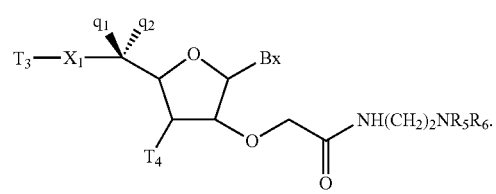

VIII

In certain embodiments, such oligomeric compounds have the configuration:

In certain such embodiments, $q_1$ is methyl and $q_2$ is H. In certain embodiments, $q_1$ is H and $q_2$ is methyl.

In certain embodiments, the invention provides oligomeric compounds comprising a di-nucleoside of Formula IX:

IX wherein:
each Bx is independently a heterocyclic base moiety;
$T_4$ is an internucleoside linking group attaching the nucleoside of Formula IV to the remainder of the oligonucleotide;
each of $q_1$ and $q_2$ is, independently selected from H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl;
$X_1$ is S, $NR_{16}$, or $CR_{10}R_{11}$ wherein each $R_{10}$ and $R_{11}$ is, independently, H, F, $C_1$-$C_6$ haloalkyl, or $C_1$-$C_6$ alkyl; and
$R_1$ is selected from a halogen, $X_2$—V, and O—$X_4$;
or
each of $q_1$ and $q_2$ is, independently, selected from H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl;
$X_1$ is O, S, $NR_{16}R_{17}$, or $CR_{10}R_{11}$ wherein each $R_{10}$ and $R_{11}$ is, independently, H, F, $C_1$-$C_6$ haloalkyl, or $C_1$-$C_6$ alkyl; and
$R_1$ is $X_2$—V;
or
each of $q_1$ and $q_2$ is, independently, selected from $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl;
$X_1$ is O, S, $NR_{16}R_{17}$, or $CR_{10}R_{11}$ wherein each $R_{10}$ and $R_{11}$ is, independently, H, F, $C_1$-$C_6$ haloalkyl, or $C_1$-$C_6$ alkyl; and
$R_1$ is selected from halogen, $X_2$—V, and O—$X_4$;
wherein:
$X_2$ is O, S or $CR_7R_8$ wherein each $R_7$ and $R_8$ is, independently, H or $C_1$-$C_6$ alkyl;
V is selected from cholesterol, $(CH_2)_2[O(CH_2)_2]_tOCH_3$, where t is from 1-3, $(CH_2)_2F$, $CH_2COOH$, $CH_2CONH_2$, $CH_2CONR_5R_6$, $CH_2COOCH_2CH_3$, $CH_2CONH(CH_2)_i$—S—$R_4$ where i is from 1 to 10, $CH_2CONH(CH_2)_jNR_5R_6$ where j is from 1 to 6, and $CH_2CONH[(CH_2)_{k1}N(H)]_{k2}$—$(CH_2)_{k1}NH_2$ where each $k_1$ is independently from 2 to 4 and $k_2$ is from 2 to 10;
$R_4$ is selected from H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl, substituted $C_2$-$C_6$ alkynyl, $C_6$-$C_{14}$ aryl and a thio protecting group;
$R_5$ and $R_6$ are each, independently, selected from H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, and substituted $C_2$-$C_6$ alkynyl;
$R_{16}$ is selected from H, $C_1$-$C_6$ alkyl, or substituted $C_1$-$C_6$ alkyl;
$X_4$ is $[C(R_a)(R_b)]_n$—$[(C=O)_mX_c]_k$—$R_d$ wherein
each $R_a$ and $R_b$ is independently H or halogen;
$X_c$ is O, S, or $N(E_1)$;
$R_d$ is H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl or $NE_2E_3$;
each $E_1$, $E_2$, and $E_3$ is independently H, $C_1$-$C_6$ alkyl, or substituted $C_1$-$C_6$ alkyl;
n is 1 to 6;
m is 0 or 1; and
k is 0 or 1; and wherein
$X_3$ is OH or SH;
$Y_a$ is O or S;
each $Y_b$ and $Y_c$ is, independently, selected from OH, SH, alkyl, alkoxy, substituted $C_1$-$C_6$ alkyl and substituted $C_1$-$C_6$ alkoxy;
$R_9$ is selected from is selected from a halogen, $X_2$—V, and O—$X_4$;
wherein each substituted group is, independently, mono or poly substituted with optionally protected substituent groups independently selected from halogen, oxo, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl; and $J_4$ is hydrogen, or a protecting group.

In certain embodiments, $R_1$ is F. In certain embodiments, $R_1$ is $OCH_3$. In certain embodiments, $R_1$ is O—$C_2$-$C_4$ alkyl or haloalkyl. In certain embodiments, $R_1$ is $O(CH_2)_2OCH_3$. In certain embodiments, $R_1$ is $FCH_2CH_3$. In certain embodiments, $R_1$ is $(CH_2)_2[O(CH_2)_2]_tOCH_3$, where t is from 1-3. In certain embodiments, $R_1$ is selected from, trifluoroalkoxy, azido, aminooxy, S-alkyl, $N(J_4)$-alkyl, O-alkenyl, S-alkenyl, $N(J_4)$-alkenyl, O-alkynyl, S-alkynyl, $N(J_4)$-alkynyl, and $X_2$—V. In certain embodiments, $R_1$ is $X_2$—V. In certain embodiments, V is $(CH_2)_2F$. In certain embodiments, V is $CH_2CONH(CH_2)$—S—$R_4$. In certain embodiments, V is $CH_2CONH[(CH_2)_{k1}$—$N(H)]_{k2}$—$(CH_2)_{k1}NH_2$. In certain embodiments, V is $CH_2CONH$—$(CH_2)_3$—$N(H)$—$(CH_2)_4$—$N(H)$—$(CH_2)_3NH_2$. In certain embodiments, V is $CH_2CONH(CH_2)_jNR_5R_6$. In certain such embodiments, j is 2. In certain embodiments, at least one of $R_5$ and $R_6$ is other than H. In certain embodiments, at least one of $R_5$ and $R_6$ is methyl. In certain embodiments, $R_5$ is methyl and $R_6$ is methyl. In certain embodiments, $X_2$ is O. In certain embodiments, $X_2$ is S. In certain embodiments, $X_2$ is $CR_7R_8$. In certain embodiments, $R_7$ and $R_8$ are both H. In certain embodiments, at least one of $q_1$ and $q_2$ is $C_1$-$C_6$ alkyl or substituted $C_1$-$C_6$ alkyl. In certain embodiments, at least one of $q_1$ and $q_2$ is $C_1$-$C_6$ alkyl. In certain embodiments, at least one of $q_1$ and $q_2$ is methyl. In certain embodiments, at least one of $q_1$ and $q_2$ is H. In certain embodiments, one of $q_1$ and $q_2$ is methyl and the other of $q_1$ and $q_2$ is H. In certain embodiments, $q_1$ and $q_2$ are each $C_1$-$C_6$ alkyl or substituted $C_1$-$C_6$ alkyl. In certain embodiments, $X_1$ is O. In certain embodiments, $X_1$ is S. In certain embodiments, $X_1$ is $CR_{10}R_{11}$. In certain embodiments, $R_{10}$ and $R_{11}$ are both H. In certain embodiments, $R_9$ is selected from F, $OCH_3$ and $O(CH_2)_2OCH_3$. In certain embodiments, $R_9$ is $OCH_3$. In certain embodiments, $R_9$ is F. In certain embodiments, $R_9$ is $O(CH_2)_2OCH_3$.

In certain embodiments, such di-nucleoside having Formula IX has Formula X:

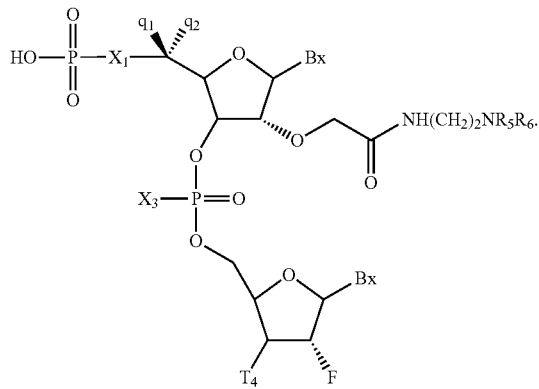

In certain such embodiments, $q_1$ is methyl and $q_2$ is H. In certain embodiments, $q_1$ is H and $q_2$ is methyl.

In certain embodiments, the invention provides oligomeric compounds comprising an oligonucleotide comprising a nucleoside having Formula II:

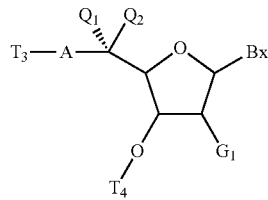

wherein independently for each monomer of Formula II:
Bx is a heterocyclic base moiety;
A is O, S or $N(R_1)$;
$R_1$ is H, $C_1$-$C_6$ alkyl or substituted $C_1$-$C_6$ alkyl;
one of $T_3$ and $T_4$ is an internucleoside linking group linking the monomer to the remainder of the oligomeric compound and the other of $T_3$ and $T_4$ is H, a protecting group, a phosphorus moiety, a 5' or 3'-terminal group or an internucleoside linking group linking the monomer to the oligomeric compound;
one of $Q_1$ and $Q^2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—$[C(R_2)(R_3)]_n$—$[(C=O)_m$—$X]_j$—Z or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;

n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and
when j is 1 then Z is other than halogen or $N(E_2)(E_3)$ and when A is O then $G_1$ is other than halogen.

In certain embodiments, each Bx is, independently, uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4]benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2'4,5]pyrrolo[2,3-d]pyrimidin-2-one. In certain embodiments, each Bx is, independently, uracil, thymine, cytosine, 5-methylcytosine, adenine or guanine.

In certain embodiments, each $Q_1$ is H. In certain embodiments, each $Q_2$ is H. In certain embodiments, each $Q_1$ and each $Q_2$ are other than H. In certain embodiments, at least one of $Q_1$ and $Q_2$ is substituted $C_1$-$C_6$ alkyl. In certain embodiments, such substituted $C_1$-$C_6$ alkyl comprises at least one substituent group independently selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, substituted $C_1$-$C_6$ alkyl comprises at least one substituent group independently selected from fluoro and $OCH_3$. In certain embodiments, at least one of $Q_1$ and $Q_2$ is $C_1$-$C_6$ alkyl. In certain embodiments, $Q_1$ is methyl. In certain embodiments, $Q_2$ is methyl.

In certain embodiments, $G_1$ is $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_4)(R_5)$, $O(CH_2)_2$—ON$(R_4)(R_5)$, $O(CH_2)_2$—$O(CH_2)_2$—$N(R_4)(R_5)$, $OCH_2C(=O)$—$N(R_4)(R_5)$, $OCH_2C(=O)$—$N(R_6)$—$(CH_2)_2$—$N(R_4)(R_5)$ or $O(CH_2)_2$—$N(R_6)$—$C(=NR_7)[N(R_4)(R_5)]$ wherein $R_4$, $R_5$, $R_6$ and $R_7$ are each, independently, H or $C_1$-$C_6$ alkyl. In certain embodiments, $G_1$ is $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—N$(H)CH_3$, $OCH_2C(=O)$—$N(H)$—$(CH_2)_2$—$N(CH_3)_2$ or $OCH_2$—$N(H)$—$C(=NH)NH_2$. In certain embodiments, $G_1$ is $OCH_3$, $O(CH_2)_2$—$OCH_3$, $OCH_2C(=O)$—$N(H)CH_3$ or $OCH_2C(=O)$—$N(H)$—$(CH_2)_2$—$N(CH_3)_2$. In certain embodiments, $G_1$ is F.

In certain embodiments, $T_3$ is a phosphorus moiety. In certain embodiments, said phosphorus moiety has the formula:

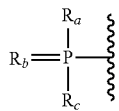

wherein:
$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
$R_b$ is O or S.

In certain embodiments, $R_a$ and $R_b$ are each OH. In certain embodiments, $R_a$ and $R_c$ are each $OCH_3$. In certain embodiments, $R_a$ and $R_c$ are each $OCH_2CH_3$. In certain embodiments, $R_b$ is O. In certain embodiments, $R_b$ is S. In certain embodiments, each monomer of Formula II has the configuration:

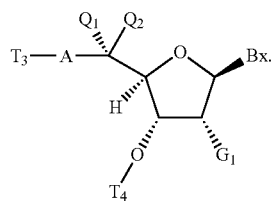

In certain embodiments, such monomer of Formula II is at the 5' end of an oligomeric compound.

In certain embodiments, the invention provides oligomeric compounds comprising an oligonucleotide comprising a nucleoside having Formula IV:

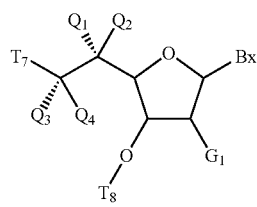

wherein independently for each monomer of Formula IV:
Bx is a heterocyclic base moiety;
one of $T_7$ and $T_8$ is an internucleoside linking group linking the monomer to the remainder of the oligomeric compound and the other of $T_7$ and $T_8$ is H, a hydroxyl protecting group, a phosphorus moiety, a 5' or 3'-terminal group or an internucleoside linking group linking the monomer to the oligomeric compound;
$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is $O$—$[C(R_2)(R_3)]_n$—$[(C{=}O)_m$—$X]_j$—$Z$ or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC({=}L)J_1$, $OC({=}L)N(J_1)(J_2)$ and $C({=}L)N(J_1)(J_2)$;
L is O, S or $NJ_3$;
each $J_1$, $J_2$ and $J_3$ is, independently, H or $C_1$-$C_6$ alkyl;
when j is 1 then Z is other than halogen or $N(E_2)(E_3)$; and
when $Q_1$, $Q_2$, $Q_3$ and $Q_4$ are each H or when $Q_1$ and $Q_2$ are H and $Q_3$ and $Q_4$ are each F or when $Q_1$ and $Q_2$ are each H and one of $Q_3$ and $Q_4$ is H and the other of $Q_3$ and $Q_4$ is $R_9$ then $G_1$ is other than H, hydroxyl, $OR_9$, halogen, $CF_3$, $CCl_3$, $CHCl_2$ and $CH_2OH$ wherein $R_9$ is alkyl, alkenyl, alkynyl, aryl or alkaryl.

In certain such embodiments, Bx is, independently, uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one), 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',:4,5]pyrrolo[2,3-d]pyrimidin-2-one. In certain embodiments, Bx is, independently, uracil, thymine, cytosine, 5-methylcytosine, adenine or guanine.

In certain embodiments, $G_1$ is $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—$CH{=}CH_2$, $O(CH_2)_2$—$OCH_3$, $O(CH_2)_2$—$SCH_3$, $O(CH_2)_2$—$OCF_3$, $O(CH_2)_3$—$N(R_4)(R_5)$, $O(CH_2)_2$—$ON(R_4)(R_5)$, $O(CH_2)_2$—$O(CH_2)N(R_4)(R_5)$, $OCH_2C({=}O)$—$N(R_4)(R_5)$, $OCH_2C({=}O)$—$N(R_6)$—$(CH_2)_2$—$N(R_4)(R_5)$ or $O(CH_2)_2$—$N(R_6)$—$C({=}NR_7)[N(R_4)(R_5)]$ wherein $R_4$, $R_5$, $R_6$ and $R_7$ are each, independently, H or $C_1$-$C_6$ alkyl. In certain embodiments, $G_1$ is $OCH_3$, $OCF_3$, $OCH_2CH_3$, $OCH_2CF_3$, $OCH$—$CH{=}CH_2$, $O(CH_2)_2$—$OCH_3$, $O(CH_2)_2$—$O(CH_2)_2$—$N(CH_3)_2$, $OCH_2C({=}O)$—$N(H)CH_3$, $OCH_2C({=}O)$—$N(H)$—$(CH_2)_2NCH_3)_2$ or $OCH_2$—$N(H)$—$C({=}NH)NH_2$. In certain embodiments, $G_1$ is $OCH_3$, $O(CH_2)_2$—$OCH_3$, $OCH_2C({=}O)$—$N(H)CH_3$ or $OCH_2C({=}O)$—$N(H)$—$(CH_2)_2$—$N(CH_3)_2$. In certain embodiments, $G_1$ is F.

In certain embodiments, $T_8$ is a 3'-terminal group. In certain embodiments, at least one of $T_7$ and $T_8$ is a conjugate group. In certain embodiments, one $T_7$ is a phosphorus moiety. In certain embodiments, said phosphorus moiety has the formula:

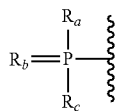

wherein:
$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
$R_b$ is O or S.

In certain embodiments, $R_a$ and $R_c$ are each OH. In certain embodiments, $R_a$ and $R_c$ are each $OCH_3$. In certain embodiments, $R_a$ and $R_c$ are each $OCH_2CH_3$. In certain embodiments, $R_b$ is O. In certain embodiments, $R_b$ is S.

In certain embodiments, each monomer of Formula IV one of $Q_1$, $Q_2$, $Q_3$ and $Q_4$ is substituted $C_1$-$C_6$ alkyl. In certain embodiments, each monomer of Formula IV one of $Q_1$, $Q_2$, $Q_3$ and $Q_4$ is substituted $C_1$-$C_6$ alkyl and the other three of $Q_1$, $Q_2$, $Q_3$ and $Q_4$ are H. In certain embodiments, said substituted $C_1$-$C_6$ alkyl comprises at least one substituent group selected from halogen, $C_2$-$C_6$ alkenyl, $OJ_1$, $NJ_1J_2$ and CN, wherein each hand $J_2$ is, independently, H or $C_1$-$C_6$ alkyl. In certain embodiments, said substituted $C_1$-$C_6$ alkyl comprises at least one substituent group selected from fluoro and $OCH_3$.

In certain embodiments, each monomer of Formula IV one of $Q_1$, $Q_2$, $Q_3$ and $Q_4$ is $C_1$-$C_6$ alkyl. In certain embodiments, for each monomer of Formula IV one of $Q_1$ and $Q_2$ is $C_1$-$C_6$ alkyl. In certain embodiments, one of $Q_3$ and $Q_4$ is $C_1$-$C_6$ alkyl. In certain embodiments, said $C_1$-$C_6$ alkyl group is methyl. In certain embodiments, for each monomer of Formula IV three of $Q_1$, $Q_2$, $Q_3$ and $Q_4$ are H. In certain embodiments, monomer of Formula IV one of $Q_1$, $Q_2$, $Q_3$ and $Q_4$ is F. In certain embodiments, two of $Q_1$, $Q_2$, $Q_3$ and $Q_4$ are F. In certain embodiments, monomer of Formula IV $Q_1$ and $Q_2$ are each F. In certain embodiments, for each monomer of Formula IV $Q_3$ and $Q_4$ are each F. In certain embodiments, for each monomer of Formula IV, $Q_1$, $Q_2$, $Q_3$ and $Q_4$ are each F or H.

In certain embodiments, each monomer of Formula IV has the configuration:

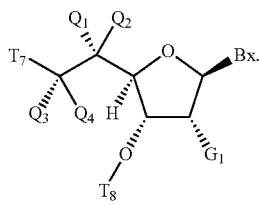

In certain embodiments, the invention provides an oligomeric compound comprising a monomer of Formula IV at the 5' end.

In certain embodiments, the invention provides oligomeric compounds comprising an oligonucleotide comprising a nucleoside at the 5'-end having Formula XIII:

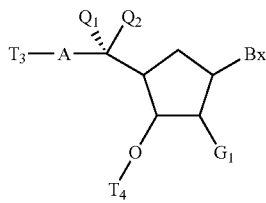

XIII wherein:
Bx is a heterocyclic base moiety;
A is O, S or $N(R_1)$;
$R_1$ is H, $C_1$-$C_6$ alkyl or substituted $C_1$-$C_6$ alkyl;
$T_3$ is a phosphorus moiety;
$T_4$ is an internucleoside linking group linking the monomer to the remainder of the oligomeric compound;
one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—$[C(R_2)(R_3)]_n$—$[(C=O)_m$—$X]_j$—Z, O—$C_1$-$C_6$ alkyl, O—$C_1$-$C_6$ substituted alkyl, O-aryl, or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, =$NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and
when j is 1 then Z is other than halogen or $N(E_2)(E_3)$ and when A is O then $G_1$ is other than halogen.

In certain such embodiments, Bx is uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one], 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, Bx is uracil, thymine, cytosine, 5-methylcytosine, adenine or guanine.

In certain embodiments, $Q_1$ is H. In certain embodiments, $Q_2$ is H. In certain embodiments, $Q_1$ and $Q_2$ are each other than H. In certain embodiments, at least one of $Q_1$ and $Q_2$ is substituted $C_1$-$C_6$ alkyl. In certain embodiments, each substituted $C_1$-$C_6$ alkyl comprises at least one substituent group independently selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain such embodiments, each substituted $C_1$-$C_6$ alkyl comprises at least one substituent group independently selected from fluoro and $OCH_3$. In certain embodiments, at least one of $Q_1$ and $Q_2$ is $C_1$-$C_6$ alkyl. In certain embodiments, $Q_1$ is methyl. In certain embodiments, $Q_2$ is methyl.

In certain embodiments, said phosphorus moiety has the formula:

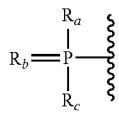

wherein:
$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
$R_b$ is O or S.

In certain embodiments, $R_a$ and $R_c$ are each OH. In certain embodiments, $R_a$ and $R_c$ are each $OCH_3$. In certain embodiments, $R_a$ and $R_c$ are each $OCH_2CH_3$. In certain embodiments, $R_b$ is O. In certain embodiments, $R_b$ is S.

In certain embodiments, $G_1$ is $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_4)(R_5)$, $O(CH_2)_2$—ON$(R_4)(R_5)$, $O(CH_2)_2$—$O(CH_2)_2$—$N(R_4)(R_5)$, $OCH_2C(=O)$—$N(R_4)(R_5)$, $OCH_2C(=O)$—$N(R_6)$—$(CH_2)_2$—$N(R_4)(R_5)$ or $O(CH_2)_2$—$N(R_6)$—$C(=NR_7)[N(R_4)(R_5)]$ wherein $R_4$, $R_5$, $R_6$ and $R_7$ are each, independently, H or $C_1$-$C_6$ alkyl. In certain embodiments, $G_1$ is $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—N$(H)CH_3$, $OCH_2C(=O)$—$N(H)$—$(CH_2)_2$—$N(CH_3)_2$ or $OCH_2$—$N(H)$—$C(=NH)NH_2$. In certain embodiments, $G_1$ is $OCH_3$, $O(CH_2)_2$—$OCH_3$, $OCH_2C(=O)$—$N(H)CH_3$ or $OCH_2C(=O)$—$N(H)$—$(CH_2)_2$—$N(CH_3)_2$. In certain embodiments, $G_1$ is F. In certain embodiments, $G_1$ is O—$C_1$-$C_6$ alkyl, O—$C_1$-$C_6$ substituted alkyl, O-aryl. In certain embodiments, $G_1$ is —O—$C_1$-$C_6$ substituted alkyl. In certain embodiments, $G_1$ is —OCH$_2$CH$_2$OCH$_3$. In certain embodiments, $G_1$ is —OCH$_2$CH$_2$F.

In certain embodiments, the monomer of Formula XIII has the configuration:

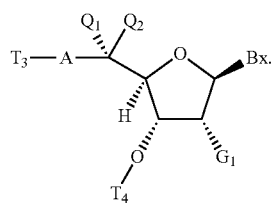

In certain embodiments, the invention provides oligomeric compounds comprising an oligonucleotide comprising a nucleoside at the 5'-end having Formula XIV:

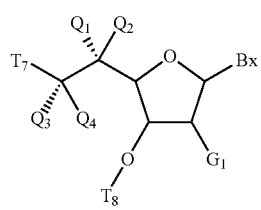

wherein:

Bx is a heterocyclic base moiety;

$T_7$ is a phosphorus moiety;

$T_8$ is an internucleoside linking group linking the monomer to the remainder of the oligomeric compound;

$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ is O—$[C(R_2)(R_3)]_n$—$[(C=O)_m$—$X]_j$—Z, O—$C_1$-$C_6$ alkyl, O—$C_1$-$C_6$ substituted alkyl, O-aryl, or halogen;

each $R_2$ and $R_3$ is, independently, H or halogen;

each $R_2$ and $R_3$ is, independently, H or halogen;

X is O, S or N($E_1$);

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or N($E_2$)($E_3$);

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl;

when j is 1 then Z is other than halogen or N($E_2$)($E_3$); and when $Q_1$, $Q_2$, $Q_3$ and $Q_4$ are each H or when $Q_1$ and $Q_2$ are H and $Q_3$ and $Q_4$ are each F or when $Q_1$ and $Q_2$ are each H and one of $Q_3$ and $Q_4$ is H and the other of $Q_3$ and $Q_4$ is $R_9$ then $G_1$ is other than H, hydroxyl, $OR_9$, halogen, $CF_3$, $CCl_3$, $CHCl_2$ and $CH_2OH$ wherein $R_9$ is alkyl, alkenyl, alkynyl, aryl or alkaryl.

In certain such embodiments, Bx is uracil, 5-thiazolo-uracil, 2-thio-uracil, 5-propynyl-uracil, thymine, 2'-thio-thymine, cytosine, 5-methylcytosine, 5-thiazolo-cytosine, 5-propynyl-cytosine, adenine, guanine, 2,6-diaminopurine, 1H-pyrimido[5,4-b][1,4benzoxazin-2(3H)-one], 1H-pyrimido[5,4-b][1,4]benzothiazin-2(3H)-one, 9-(2-aminoethoxy)-H-pyrimido[5,4-b][1,4]benzoxazin-2(3H)-one, 2H-pyrimido[4,5-b]indol-2-one or H-pyrido[3',2':4,5]pyrrolo[2,3-d]pyrimidin-2-one. In certain embodiments, Bx is uracil, thymine, cytosine, 5-methylcytosine, adenine or guanine.

In certain embodiments, one of $Q_1$, $Q_2$, $Q_3$ and $Q_4$ is substituted $C_1$-$C_6$ alkyl. In certain embodiments, one of $Q_1$, $Q_2$, $Q_3$ and $Q_4$ is substituted $C_1$-$C_6$ alkyl and the other three of $Q_1$, $Q_2$, $Q_3$ and $Q_4$ are H. In certain embodiments, said substituted $C_1$-$C_6$ alkyl comprises at least one substituent group selected from halogen, $C_2$-$C_6$ alkenyl, $OJ_1$, $NJ_1J_2$ and CN, wherein each $J_1$ and $J_2$ is, independently, H or $C_1$-$C_6$ alkyl. In certain embodiments, said substituted $C_1$-$C_6$ alkyl comprises at least one substituent group selected from fluoro and OCH$_3$. In certain embodiments, one of $Q_1$, $Q_2$, $Q_3$ and $Q_4$ is $C_1$-$C_6$ alkyl. In certain embodiments, one of $Q_1$ and $Q_2$ is $C_1$-$C_6$ alkyl. In certain embodiments, one of $Q_3$ and $Q_4$ is $C_1$-$C_6$ alkyl. In certain embodiments, said $C_1$-$C_6$ alkyl group is methyl. In certain embodiments, three of $Q_1$, $Q_2$, $Q_3$ and $Q_4$ are H. In certain embodiments, one of $Q_1$, $Q_2$, $Q_3$ and $Q_4$ is F. In certain embodiments, two of $Q_1$, $Q_2$, $Q_3$ and $Q_4$ are F. In certain embodiments, $Q_1$ and $Q_2$ are each F. In certain embodiments, $Q_3$ and $Q_4$ are each F. In certain embodiments, $Q_1$, $Q_2$, $Q_3$ and $Q_4$ are each F or H. In certain embodiments, $Q_1$ is H. In certain embodiments, $Q_2$ is H. In certain embodiments, $Q_1$ and $Q_2$ are each other than H. In certain embodiments, at least one of $Q_1$ and $Q_2$ is substituted $C_1$-$C_6$ alkyl. In certain embodiments, at least one of $Q_1$ and $Q_2$ is $C_1$-$C_6$ alkyl. In certain embodiments, $Q_1$ is methyl. In certain embodiments, $Q_2$ is methyl.

In certain embodiments, said phosphorus moiety has the formula:

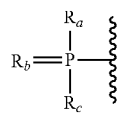

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S.

In certain embodiments, $R_a$ and $R_c$ are each OH. In certain embodiments, $R_a$ and $R_c$ are each OCH$_3$. In certain embodiments, $R_a$ and $R_c$ are each OCH$_2$CH$_3$. In certain embodiments, $R_b$ is O. In certain embodiments, $R_b$ is S.

In certain embodiments, $G_1$ is OCH$_3$, OCH$_2$F, OCHF$_2$, OCF$_3$, OCH$_2$CH$_3$, O(CH$_2$)$_2$F, OCH$_2$CHF$_2$, OCH$_2$CF$_3$, OCH$_2$—CH=CH$_2$, O(CH$_2$)$_2$—OCH$_3$, O(CH$_2$)$_2$—SCH$_3$, O(CH$_2$)$_2$—OCF$_3$, O(CH$_2$)$_3$—N(R$_4$)(R$_5$), O(CHO$_2$—ON(R$_4$)(R$_5$), O(CH$_2$)$_2$—O(CH$_2$)$_2$—N(R$_4$)(R$_5$), OCH$_2$C(=O)—N(R$_4$)(R$_5$), OCH$_2$C(=O)—N(R$_5$)—(CH$_2$)$_2$N(R$_4$)(R$_5$) or O(CH$_2$)$_2$—N(R$_6$)—C(=NR$_7$)[N(R$_4$)(R$_5$)] wherein R$_4$, R$_5$, R$_6$ and R$_7$ are each, independently, H or $C_1$-$C_6$ alkyl. In certain embodiments, $G_1$ is OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$ or OCH$_2$—N(H)—C(=NH)NH$_2$. In certain embodiments, $G_1$ is OCH$_3$, O(CH$_2$)$_2$—OCH$_3$, OCH$_2$(=O)—N(H)CH$_3$ or OCH$_2$C(=O)—N(H)—(CH$_2$)$_2$—N(CH$_3$)$_2$. In certain embodiments, G$_1$ is F. In certain embodiments, G$_1$ is O—C$_1$-C$_6$ alkyl, O—C$_1$-C$_6$ substituted alkyl, O-aryl. In certain embodiments, G$_1$ is —O—C$_1$-C$_6$ substituted alkyl. In certain embodiments, G$_1$ is —OCH$_2$CH$_2$OCH$_3$. In certain embodiments, G$_1$ is —OCH$_2$CH$_2$F.

In certain embodiments, a monomer of Formula XIV has the configuration:

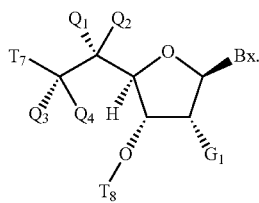

In certain embodiments, the invention provides an oligomeric compound comprising an oligonucleotide comprising a phosphate stabilizing nucleoside at the 5'-end, wherein the phosphate stabilizing nucleoside comprises:

a 5'-terminal modified or unmodified phosphate;
a modified sugar moiety comprising:
a 5'-modification; or a 2'-modification; or both a 5'-modification and a 2'-modification; and
a linking group linking the phosphate stabilizing nucleoside to the remainder of the oligonucleotide.

In certain such embodiments,
the 5'-terminal modified phosphate is selected from: phosphonate, alkylphosphonate, substituted alkylphosphonate, aminoalkyl phosphonate, substituted aminoalkyl phosphonate, phosphorothioate, phosphoramidate, alkylphosphonothioate, substituted alkylphosphonothioate, phosphorodithioate, thiophosphoramidate, and phosphotriester;
the 5'-modification of the sugar moiety of the phosphate stabilizing nucleoside is selected from 5'-alkyl and 5'-halogen;
the 2'-modification of the sugar moiety of the phosphate stabilizing nucleoside is selected from: halogen, allyl, amino, azido, thio, O-allyl, —O—C$_1$-C$_{10}$ alkyl, —O—C$_1$-C$_{10}$ substituted alkyl, —OCF$_3$, —O—(CH$_2$)$_2$—O—CH$_3$, —O(CH$_2$)$_2$SCH$_3$, —O—(CH$_2$)$_2$—O—N(R$_m$)(R$_n$), —O—CH2—C(=O)—N(R$_m$)(R$_n$), where each R$_m$ and R$_n$ is, independently, H or substituted or unsubstituted C$_1$-C$_{10}$ alkyl, —O[(CH$_2$)$_n$O]$_m$CH$_3$, —O(CH$_2$)$_n$NH$_2$, —O(CH$_2$)$_n$CH$_3$, —O(CH$_2$)$_n$ONH$_2$, —OCH$_2$C(=O)N(H)CH$_3$, —O(CH$_2$)$_n$ON[(CH$_2$)$_n$CH$_3$]$_2$, where n and m are from 1 to about 10; C$_1$ to C$_{10}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl.

In certain embodiments, the modified phosphate is selected from: phosphonate, alkylphosphonate, substituted alkylphosphonate, aminoalkyl phosphonate, substituted aminoalkyl phosphonate, phosphotriester, phosphorothioate, phosphorodithioate, thiophosphoramidate, and phosphoramidate.

In certain embodiments, the modified phosphate is selected from phosphonate, alkylphosphonate, and substituted alkylphosphonate. In certain embodiments, the 5'-phosphate is selected from 5'-deoxy-5'-thio phosphate, phosphoramidate, methylene phosphonate, mono-fluoro methylene phosphonate and di-fluoro methylene phosphonate.

In certain embodiments, the sugar moiety of the phosphate stabilizing nucleoside comprises a 5'-modification and a 2'-modification.

In certain of any of the above embodiments, the remainder of the oligonucleotide comprises at least one modified nucleoside. In certain embodiments, the oligomeric compound comprises a modified base. In certain embodiments, the oligomeric compound comprises a sugar surrogate. In certain embodiments, the sugar surrogate is a tetrahydropyran. In certain embodiments, the tetrahydropyran is F—HNA.

In certain embodiments, the remainder of the oligonucleotide comprises at least one nucleoside comprising a modified sugar. In certain embodiments, the at least one modified nucleoside comprising a modified sugar is selected from a bicyclic nucleoside and a 2'-modified nucleoside. In certain embodiments, the at least one modified nucleoside is a bicyclic nucleoside. In certain embodiments, the bicyclic nucleoside is a (4'-CH$_2$—O-2') BNA nucleoside. In certain embodiments, the bicyclic nucleoside is a (4'-(CH$_2$)$_2$—O-2') BNA nucleoside. In certain embodiments, the bicyclic nucleoside is a (4'-C(CH$_3$)H—O-2') BNA nucleoside. In certain embodiments, the at least one modified nucleoside is a 2'-modified nucleoside. In certain embodiments, the at least one 2'-modified nucleoside is selected from a 2'-F nucleoside, a 2'-OCH$_3$ nucleoside, and a 2'-O(CH$_2$)$_2$OCH$_3$ nucleoside. In certain embodiments, the at least one 2'-modified nucleoside is a 2'-F nucleoside. In certain embodiments, the at least one 2'-modified nucleoside is a 2% OCH$_3$ nucleoside. In certain embodiments, the at least one 2'-modified nucleoside is a 2'-O(CH$_2$)$_2$OCH$_3$ nucleoside.

In certain embodiments, the remainder of the oligonucleotide comprises at least one unmodified nucleoside. In certain embodiments, the unmodified nucleoside is a ribonucleoside. In certain embodiments, the unmodified nucleoside is a deoxyribonucleoside.

In certain embodiments, the remainder of the oligomeric oligonucleotide comprises at least two modified nucleosides. In certain embodiments, the at least two modified nucleosides comprise the same modification. In certain embodiments, the at least two modified nucleosides comprise different modifications. In certain embodiments, at least one of the at least two modified nucleosides comprises a sugar surrogate. In certain embodiments, at least one of the at least two modified nucleosides comprises a 2'-modification. In certain embodiments, each of the at least two modified nucleosides is independently selected from 2'-F nucleosides, 2'-OCH$_3$ nucleosides and 2'-O(CH$_2$)$_2$OCH$_3$ nucleosides. In certain embodiments, each of the at least two modified nucleosides is a 2'-F nucleoside. In certain embodiments, each of the at least two modified nucleosides is a 2'-OCH$_3$ nucleosides. In certain embodiments, each of the at least two modified nucleosides is a 2'-O(CH$_2$)$_2$OCH$_3$ nucleoside. In certain embodiments, essentially every nucleoside of the oligomeric compound is a modified nucleoside. In certain embodiments, every nucleoside of the oligomeric compound is a modified nucleoside.

In certain embodiments, the remainder of the oligonucleotide comprises:
1-20 first-type regions, each first-type region independently comprising 1-20 contiguous nucleosides wherein each nucleoside of each first-type region comprises a first-type modification;
0-20 second-type regions, each second-type region independently comprising 1-20 contiguous nucleosides wherein each nucleoside of each second-type region comprises a second-type modification; and
0-20 third-type regions, each third-type region independently comprising 1-20 contiguous nucleosides wherein each nucleoside of each third-type region comprises a third-type modification; wherein the first-type modification, the second-type modification, and the third-type modification are each independently selected from 2'-F, 2'-OCH$_3$, 2'-O(CH$_2$)$_2$OCH$_3$, BNA, 2'-H and 2'-OH;

provided that the first-type modification, the second-type modification, and the third-type modification are each different from one another.

In certain embodiments, the oligonucleotide comprises 2-20 first-type regions; 3-20 first-type regions; 4-20 first-type regions; 5-20 first-type regions; or 6-20 first-type regions. In certain embodiments, the oligonucleotide comprises 1-20 second-type regions; 2-20 second-type regions; 3-20 second-type regions; 4-20 second-type regions; or 5-20 second-type regions. In certain embodiments, the oligonucleotide comprises 1-20 third-type regions; 2-20 third-type regions; 3-20 third-type regions; 4-20 third-type regions; or 5-20 third-type regions.

In certain embodiments, the oligomeric compound comprises a third-type region at the 3'-end of the oligomeric compound. the oligomeric compound comprises a third-type region at the 3'-end of the oligomeric compound the third-type region contains from 1 to 3 modified nucleosides and the third-type modification is 2'-0(CH$_2$)$_2$OCH$_3$. In certain embodiments, the third same type region contains two modified nucleosides and the third-type modification is 2'-0(CH$_2$)$_2$OCH$_3$.

In certain embodiments, each first-type region contains from 1 to 5 modified nucleosides. In certain embodiments, each first-type region contains from 6 to 10 modified nucleosides. In certain embodiments, each first-type region contains from 11 to 15 modified nucleosides. In certain embodiments, each first-type region contains from 16 to 20 modified nucleosides.

In certain embodiments, the first-type modification is 2'-F. In certain embodiments, the first-type modification is 2'-OMe. In certain embodiments, the first-type modification is DNA. In certain embodiments, the first-type modification is 2'-0(CH$_2$)$_2$OCH$_3$. In certain embodiments, the first-type modification is 4'-CH$_2$—O-2'. In certain embodiments, the first-type modification is 4'-(CH$_2$)$_2$—O-2'. In certain embodiments, the first-type modification is 4'-C(CH$_3$)H—O-2'. In certain embodiments, each second-type region contains from 1 to 5 modified nucleosides. In certain embodiments, each second-type region contains from 6 to 10 modified nucleosides. In certain embodiments, each second-type region contains from 11 to 15 modified nucleosides. In certain embodiments, each second-type region contains from 16 to 20 modified nucleosides. In certain embodiments, the second-type modification is 2'-F. In certain embodiments, the second-type modification is 2'-OMe. In certain embodiments, the second-type modification is DNA. In certain embodiments, the second-type modification is 2'-0(CH$_2$)$_2$OCH$_3$. In certain embodiments, the second-type modification is 4'-CH$_2$—O-2'. In certain embodiments, the second-type modification is 4'-(CH$_2$)$_2$—O-2'. In certain embodiments, the second-type modification is 4'-C(CH$_3$)H—O-2'. In certain embodiments, the oligomeric compound has an alternating motif wherein the first-type regions alternate with the second-type regions.

In certain embodiments, the invention provides oligomeric compounds wherein the remainder of the oligonucleotide comprises at least one region of nucleosides having a nucleoside motif:

(A)$_n$-(B)$_n$-(A)$_n$-(B)$_n$, wherein:

A an B are differently modified nucleosides; and
each n is independently selected from 1, 2, 3, 4, and 5.

In certain embodiments, A and B are each independently selected from a bicyclic and a 2'-modified nucleoside. In certain embodiments, at least one of A and B is a bicyclic nucleoside. In certain embodiments, at least one of A and B is a (4'-CH$_2$—O-2') BNA nucleoside. In certain embodiments, at least one of A and B is a (4% (CH$_2$)$_2$—O-2') BNA nucleoside. In certain embodiments, at least one of A and B is a (4% C(CH$_3$)H—O-2') BNA nucleoside. In certain embodiments, at least one of A and B is a 2'-modified nucleoside. In certain embodiments, the 2'-modified nucleoside is selected from: a 2'-F nucleoside, a 2'-OCH$_3$ nucleoside, and a 2'-O(CH$_2$)$_2$OCH$_3$ nucleoside. In certain embodiments, A and B are each independently selected from: a 2'-F nucleoside, a 2'-OCH$_3$ nucleoside, a 2'-O(CH$_2$)$_2$OCH$_3$ nucleoside, a (4'-CH$_2$—O-2') BNA nucleoside, a (4% (CH$_2$)$_2$—O-2') BNA nucleoside, a (4'-C(CH$_3$)H—O-2') BNA nucleoside, a DNA nucleoside, an RNA nucleoside, and an F—HNA nucleoside. In certain embodiments, A and B are each independently selected from: a 2'-F nucleoside, a 2'-OCH$_3$ nucleoside, a (4'-CH$_2$—O-2') BNA nucleoside, a (4% (CH$_2$)$_2$—O-2') BNA nucleoside, a (4'-C(CH$_3$)H—O-2') BNA nucleoside, and a DNA nucleoside. In certain embodiments, one of A and B is a 2'-F nucleoside. In certain embodiments, one of A and B is a 2'-OCH$_3$ nucleoside. In certain embodiments, one of A and B is a 2'-O(CH$_2$)$_2$OCH$_3$ nucleoside. In certain embodiments, A is a 2'-F nucleoside and B is a 2'-OCH$_3$ nucleoside. In certain embodiments, A is a 2'-OCH$_3$ nucleoside and B is a 2'-F nucleoside. In certain embodiments, one of A and B is selected from a (4'-CH$_2$—O-2') BNA nucleoside, a (4% (CH$_2$)$_2$—O-2') BNA nucleoside, and a (4'-C(CH$_3$)H—O-2') BNA nucleoside and the other of A and B is a DNA nucleoside.

In certain embodiments, the invention provides oligomeric compounds wherein the remainder of the oligonucleotide comprises a nucleoside motif: (A)$_X$-(B)$_2$-(A)$_Y$-(B)$_2$-(A)$_Z$-(B)$_3$ wherein A is a nucleoside of a first type;
B is a nucleoside of a second type;
X is 0-10;
Y is 1-10; and
Z is 1-10.

In certain embodiments, X is selected from 0, 1, 2 and 3. In certain embodiments, X is selected from 4, 5, 6 and 7. In certain embodiments, Y is selected from 1, 2 and 3. In certain embodiments, Y is selected from 4, 5, 6 and 7. In certain embodiments, Z is selected from 1, 2 and 3. In certain embodiments, Z is selected from 4, 5, 6 and 7. In certain embodiments, A is a 2'-F nucleoside. In certain embodiments, B is a 2% OCH$_3$ nucleoside.

In certain embodiments, the invention provides oligomeric compounds of comprising a 3'-region consisting of from 1 to 5 nucleosides at the 3'-end of the oligomeric compound wherein:

the nucleosides of the 3'-region each comprises the same modification as one another; and the nucleosides of the 3'-region are modified differently than the last nucleoside adjacent to the 3% region.

In certain embodiments, the modification of the 3'-region is different from any of the modifications of any of the other nucleosides of the oligomeric compound. In certain embodiments, the nucleosides of the 3'-region are 2'-O(CH$_2$)$_2$OCH$_3$ nucleosides. In certain embodiments, the 3'-region consists of 2 nucleosides. In certain embodiments, the 3'-region consists of 3 nucleosides. In certain embodiments, each nucleoside of the 3'-region comprises a uracil base. In certain embodiments, each nucleoside of the 3'-region comprises an adenine base. In certain embodiments, each nucleoside of the 3'-region comprises a thymine base.

In certain embodiments, the remainder of the oligonucleotide comprises a region of uniformly modified nucleosides. In certain embodiments, the region of uniformly modified nucleosides comprises 2-20 contiguous uniformly modified nucleosides. In certain embodiments, the region of uniformly modified nucleosides comprises 3-20 contiguous uniformly modified nucleosides. In certain embodiments, the region of uniformly modified nucleosides comprises 4-20 contiguous uniformly modified nucleosides. In certain embodiments, the region of uniformly modified nucleosides comprises 5-20 contiguous uniformly modified nucleosides. In certain embodiments, the region of uniformly modified nucleosides comprises 6-20 contiguous uniformly modified nucleosides. In certain embodiments, the region of uniformly modified nucleosides comprises 5-15 contiguous uniformly modified nucleosides. In certain embodiments, the region of uniformly modified nucleosides comprises 6-15 contiguous uniformly modified nucleosides. In certain embodiments, the region of uniformly modified nucleosides comprises 5-10 contiguous uniformly modified nucleosides. In certain embodiments, the region of uniformly modified nucleosides comprises 6-10 contiguous uniformly modified nucleosides.

In certain embodiments, the remainder of the oligonucleotide comprises a region of alternating modified nucleosides and a region of uniformly modified nucleosides. In certain embodiments, the region of alternating nucleotides is 5' of the region of fully modified nucleosides. In certain embodiments, the region of alternating nucleotides is 3' of the region of fully modified nucleosides. In certain embodiments, the alternating region and the fully modified region are immediately adjacent to one another. In certain embodiments, the oligomeric compound has additional nucleosides between the alternating region and the fully modified region.

In certain embodiments, the remainder of the oligonucleotide comprises at least one region of nucleosides having a motif I:

$N_f(PS)N_m(PO)$, wherein:

$N_f$ is a 2'-F nucleoside,
$N_m$ is a 2'-OCH$_3$ nucleoside
PS is a phosphorothioate linking group; and
PO is a phosphodiester linking group.

In certain embodiments, the oligomeric compound comprises at least 2, or 3, or 4, or 6, or 7, or 8, or 9, or 10 separate regions of nucleosides having the motif I.

In certain embodiments, the invention provides oligomeric compounds comprising at least one region having a nucleoside motif selected from:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type.

In certain embodiments, oligomeric compounds of the invention comprise one or more conjugate groups. In certain embodiments, oligomeric compounds of the invention consist of the oligonucleotide.

In certain embodiments, the invention provides oligomeric compounds comprising an oligonucleotide comprising a contiguous sequence of linked nucleosides wherein the sequence has the formula:

$$5'-(Z)_w-(L-Q_1-L-Q_2)_t-(L-Q_1)_u-(L-Q_3)_v-G)_a-3'$$

wherein:
each L is an internucleoside linking group;
G is a conjugate or a linking group;
a is 0 or 1;
each of $Q_1$, $Q_2$ and $Q_3$ is, independently, a 2'-modified nucleoside having a 2'-substituent group selected from halogen, allyl, amino, azido, O-allyl, O—C$_1$-C$_6$ alkyl, OCF$_3$, O—(CH$_2$)$_2$—O—CH$_3$, O(CH$_2$)$_2$SCH$_3$, O—(CH$_2$)$_2$—O—N(J$_5$)(J$_6$) and O—CH$_2$—C(=O)—N(J$_5$)(J$_6$), where each J$_5$ and J$_6$ is, independently, H, an amino protecting group or substituted or unsubstituted C$_1$-C$_6$ alkyl; provided that $Q_1$, $Q_2$ and $Q_3$ are different from one another;
t is from 4 to 8;
u is 0 or 1;
v is from 1 to 3;
w is 0 or 1; and
Z is a 5' stabilizing nucleoside.

In certain embodiments, w is 1. In certain embodiments, w is 0. In certain embodiments, $Q_1$ and $Q_2$ is, independently, a 2'-modified nucleoside having a 2'-substituent group selected from halogen and O—C$_1$-C$_6$ alkyl. In certain embodiments, each $Q_1$ and $Q_2$ is, independently, a 2'-modified nucleoside having a 2'-substituent group selected from F and O-methyl. In certain embodiments, each $Q_3$ is a 2'-modified nucleoside having a 2'-substituent group of O—(CH$_2$)$_2$—OCH$_3$. In certain embodiments, a is 0. In certain embodiments, v is 2. In certain embodiments, u is 0. In certain embodiments, u is 1.

In certain of any of the above embodiments, the oligonucleotide consists of 8-80 linked nucleoside; 8-26 linked nucleosides; 10-24 linked nucleosides; 16-22 linked nucleosides; 16-18 linked nucleosides; 19-22 linked nucleosides.

In certain of any of the above embodiments, the second nucleoside from the 5'-end comprises a sugar moiety comprising a 2'-substituent selected from OH and a halogen. In certain embodiments, the second nucleoside from the 5'-end is a 2'-F modified nucleoside.

In certain of any of the above embodiments, the oligomeric compound comprises at least one modified linking group. In certain embodiments, each internucleoside linking group is, independently, phosphodiester or phosphorothioate. In certain embodiments, the 5'-most internucleoside linking group is a phosphorothioate linking group. In certain embodiments, at least one phosphorothioate region comprising at least two contiguous phosphorothioate linking groups. In certain embodiments, the at least one phosphorothioate region comprises from 3 to 12 contiguous phosphorothioate linking groups. In certain embodiments, the at least one phosphorothioate region comprises from 6 to 8 phosphorothioate linking groups. In certain embodiments, the at least one phosphorothioate region is located at the 3'-end of the oligomeric compound. In certain embodiments, the at least one phosphorothioate region is located within 3 nucleosides of the 3'-end of the oligomeric compound. In certain embodiments, the 7-9 internucleoside linkages at the 3' end of the oligonucleotide are phosphorothioate linkages and the internucleoside linkage at the 5'-end is a phosphorothioate linkage.

In certain embodiments, the invention provides oligomeric compounds comprising an oligonucleotide consisting of 10 to 30 linked nucleosides wherein:
(a) the nucleoside at the 5' end is a phosphate stabilizing nucleoside comprising:

a 5'-terminal modified or unmodified phosphate; and
a modified sugar moiety comprising:
  a 5'-modification; or a 2'-modification; or both a 5'-modification and a 2'-modification;
(b) the sugar moiety of the second nucleoside from the 5'-end is selected from an unmodified 2'-OH sugar, and a modified sugar comprising a modification selected from: 2'-halogen, 2'O-alkyl, and 2'-O-substituted alkyl; and
(c) the first internucleoside linkage at the 5'-end and the last seven internucleoside linkages at the 3'-end are phosphorothioate linkages; and
(d) at least one internucleoside linkage is other than a phosphorothioate linkage.

In certain embodiments,
the 5'-terminal modified phosphate is selected from: phosphonate, alkylphosphonate, substituted alkylphosphonate, aminoalkyl phosphonate, substituted aminoalkyl phosphonate, phosphorothioate, phosphoramidate, alkylphosphonothioate, substituted alkylphosphonothioate, phosphorodithioate, thiophosphoramidate, and phosphotriester;
  the 5'-modification of the sugar moiety of the phosphate stabilizing nucleoside is selected from 5'-alkyl and 5'-halogen; and
  the 2'-modification of the sugar moiety of the phosphate stabilizing nucleoside is selected from: halogen, allyl, amino, azido, thio, O-allyl, —O—$C_1$-$C_{10}$ alkyl, —O—$C_1$-$C_{10}$ substituted alkyl, —$OCF_3$, —O—$(CH_2)_2$—O—$CH_3$, —$O(CH_2)_2SCH_3$, —O—$(CH_2)_2$—O—$N(R_m)(R_n)$, —O—CH2-C(=O)—$N(R_m)(R_n)$, where each $R_m$ and $R_n$ is, independently, H or substituted or unsubstituted $C_1$-$C_{10}$ alkyl, —$O[(CH_2)_nO]_mCH_3$, —$O(CH_2)_nNH_2$, —$O(CH_2)_nCH_3$, —$O(CH_2)_nONH_2$, —$OCH_2C(=O)N(H)CH_3$, —$O(CH_2)_nON[(CH_2)_nCH_3]_2$, where n and m are from 1 to about 10; $C_1$ to $C_{10}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl.

In certain embodiments, the modified phosphate is selected from: phosphonate, alkylphosphonate, substituted alkylphosphonate, aminoalkyl phosphonate, substituted aminoalkyl phosphonate, phosphotriester, phosphorothioate, phosphorodithioate, thiophosphoramidate, and phosphoramidate.

In certain embodiments, the modified phosphate is selected from: phosphonate, alkylphosphonate, and substituted alkylphosphonate.

In certain embodiments, the modified phosphate is selected from 5'-deoxy-5'-thio phosphate, phosphoramidate, methylene phosphonate, mono-fluoro methylene phosphonate and di-fluoro methylene phosphonate. In certain embodiments, the sugar moiety of the phosphate stabilizing nucleoside comprises a 5'-modification and a 2'-modification.

In certain embodiments, the oligomeric compound is an antisense compound. In certain embodiments, the antisense compound is an RNAi compound. In certain embodiments, the antisense compound is an siRNAi compound. In certain embodiments, the antisense compound is a microRNA mimic. In certain embodiments, the antisense compound is an RNase H antisense compound. In certain embodiments, the antisense compound modulates splicing.

In certain embodiments, at least a portion of the nucleobase sequence of the oligonucleotide is complementary to a portion of a target nucleic acid, wherein the target nucleic acid is selected from: a target mRNA, a target pre-mRNA, a target microRNA, and a target non-coding RNA. In certain embodiments, the nucleobase sequence of the oligonucleotide a region of 100% complementarity to the target nucleic acid and wherein the region of 100% complementarity is at least 10 nucleobases. In certain embodiments, the region of 100% complementarity is at least 15 nucleobases. In certain embodiments, the region of 100% complementarity is at least 20 nucleobases. In certain embodiments, the oligonucleotide is at least 85% complementary to the target nucleic acid. In certain embodiments, the oligonucleotide is at least 90% complementary to the target nucleic acid. In certain embodiments, the oligonucleotide is at least 95% complementary to the target nucleic acid. In certain embodiments, the oligonucleotide is at least 98% complementary to the target nucleic acid. In certain embodiments, the oligonucleotide is 100% complementary to the target nucleic acid.

In certain embodiments, the antisense compound is a microRNA mimic having a nucleobase sequence comprising a portion that is at least 80% identical to the seed region of a microRNA and that has overall identity with the microRNA of at least 70%. In certain embodiments, the nucleobase sequence of the microRNA mimic has a portion that is at least 80% identical to the sequence of the seed region of a microRNA and has overall identity with the microRNA of at least 75%. In certain embodiments, the nucleobase sequence of the microRNA mimic has a portion that is at least 80% identical to the sequence of the seed region of a microRNA and has overall identity with the microRNA of at least 80%. In certain embodiments, the nucleobase sequence of the microRNA mimic has a portion that is at least 100% identical to the sequence of the seed region of a microRNA and has overall identity with the microRNA of at least 80%. In certain embodiments, the nucleobase sequence of the microRNA mimic has a portion that is at least 100% identical to the sequence of the seed region of a microRNA and has overall identity with the microRNA of at least 85%. In certain embodiments, the nucleobase sequence of the microRNA mimic has a portion that is 100% identical to the sequence of the microRNA. In certain embodiments, nucleobase sequence of the oligonucleotide comprises a region of 100% complementarity to a seed match segment of a target nucleic acid. In certain embodiments, the antisense compound is a microRNA mimic having a nucleobase sequence comprising a portion that is at least 80% identical to the seed region of a microRNA and that has overall identity with the microRNA of at least 50%. In certain embodiments, the antisense compound is a microRNA mimic having a nucleobase sequence comprising a portion that is at least 80% identical to the seed region of a microRNA and that has overall identity with the microRNA of at least 55%. In certain embodiments, the antisense compound is a microRNA mimic having a nucleobase sequence comprising a portion that is at least 80% identical to the seed region of a microRNA and that has overall identity with the microRNA of at least 60%. In certain embodiments, the antisense compound is a microRNA mimic having a nucleobase sequence comprising a portion that is at least 80% identical to the seed region of a microRNA and that has overall identity with the microRNA of at least 65%. In certain embodiments, the oligomeric compound comprises a nucleobase sequence selected from a microRNA sequence found in miRBase. In certain embodiments, the oligomeric compound consists of a nucleobase sequence selected from a microRNA sequence found in miRBase.

In certain embodiments, the target nucleic acid is a target mRNA. In certain embodiments, the target nucleic acid is a target pre-mRNA. In certain embodiments, the target nucleic acid is a non-coding RNA. In certain embodiments, the target nucleic acid is a microRNA. In certain embodiments, the target nucleic acid is a pre-mir. In certain embodiments, the target nucleic acid is a pri-mir.

In certain embodiments, the nucleobase sequence of the oligonucleotide comprises a region of 100% complementarity to the target nucleic acid and wherein the region of 100% complementarity is at least 10 nucleobases. In certain embodiments, the nucleobase sequence of the oligonucleotide comprises a region of 100% complementarity to the target nucleic acid and wherein the region of 100% complementarity is at least 6 nucleobases. In certain embodiments, the nucleobase sequence of the oligonucleotide comprises a region of 100% complementarity to the target nucleic acid and wherein the region of 100% complementarity is at least 7 nucleobases. In certain embodiments, the target nucleic acid is a mammalian target nucleic acid. In certain embodiments, the mammalian target nucleic acid is a human target nucleic acid.

In certain embodiments, oligomeric compounds comprise from 1 to 3 terminal group nucleosides on at least one end of the oligonucleotide. In certain embodiments, oligomeric compound comprise from 1 to 3 terminal group nucleosides at the 3'-end of the oligonucleotide. In certain embodiments, oligomeric compound comprise from 1 to 3 terminal group nucleosides at the 5'-end of the oligonucleotide.

In certain embodiments, oligomeric compounds of the invention are single stranded.

In certain embodiments, oligomeric compounds of the invention are double stranded.

In certain embodiments, the invention provides pharmaceutical compositions comprising an oligomeric compounds and a pharmaceutically acceptable diluent or carrier. In certain embodiments, the pharmaceutically acceptable diluent or carrier is pharmaceutical grade sterile saline.

In certain embodiments, the invention provides methods comprising contacting a cell with an oligomeric compound described herein. In certain embodiments, such methods comprise detecting antisense activity. In certain embodiments, the detecting antisense activity comprises detecting a phenotypic change in the cell. In certain embodiments, the detecting antisense activity comprises detecting a change in the amount of target nucleic acid in the cell. In certain embodiments, the detecting antisense activity comprises detecting a change in the amount of a target protein. In certain embodiments, the cell is in vitro. In certain embodiments, the cell is in an animal. In certain embodiments, animal is a mammal. In certain embodiments, the mammal is a human.

In certain embodiments, the invention provides methods of modulating a target mRNA in a cell comprising contacting the cell with an oligomeric compound of the invention and thereby modulating the mRNA in a cell. In certain embodiments, such methods comprise detecting a phenotypic change in the cell. In certain embodiments, methods comprise detecting a decrease in mRNA levels in the cell. In certain embodiments, methods comprise detecting a change in the amount of a target protein. In certain embodiments, the cell is in vitro. In certain embodiments, the cell is in an animal. In certain embodiments, the animal is a mammal. In certain embodiments, the mammal is a human.

In certain embodiments, the invention provides methods of administering to an animal a pharmaceutical composition of the invention. In certain embodiments, the animal is a mammal. In certain embodiments, the mammal is a human. In certain embodiments, the methods comprise detecting antisense activity in the animal. In certain embodiments, the methods comprise detecting a change in the amount of target nucleic acid in the animal. In certain embodiments, the methods comprise detecting a change in the amount of a target protein in the animal. In certain embodiments, the methods comprise detecting a phenotypic change in the animal. In certain embodiments, the phenotypic change is a change in the amount or quality of a biological marker of activity.

In certain embodiments, the invention provides use of an oligomeric compound of the invention for the manufacture of a medicament for the treatment of a disease characterized by undesired gene expression.

In certain embodiments, the invention provides use of an oligomeric compound of the invention for the manufacture of a medicament for treating a disease by inhibiting gene expression.

In certain embodiments, the invention provides methods of comprising detecting antisense activity wherein the antisense activity is microRNA mimic activity. In certain embodiments, the detecting microRNA mimic activity comprises detecting a change in the amount of a target nucleic acid in a cell. In certain embodiments, the detecting microRNA mimic activity comprises detecting a change in the amount of a target protein in cell.

In certain embodiments, the invention provides a nucleoside having the Formula I:

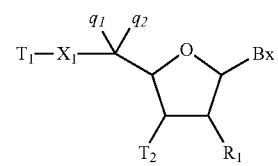

wherein:

Bx is a heterocyclic base moiety;

$T_1$ is H, a hydroxyl protecting group, or a phosphorous moiety;

$T_2$ is H, a hydroxyl protecting group, or a reactive phosphorous group; and each of $q_1$ and $q_2$ is, independently selected from $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl;

$X_1$ is S, $NR_{16}$, or $C_{10}R_{11}$ wherein each $R_{10}$ and $R_{11}$ is, independently, H, F, $C_1$-$C_6$ haloalkyl, or $C_1$-$C_6$ alkyl; and $R_1$ is selected from a halogen, $X_2$—V, and O—$X_4$;

or each of $q_1$ and $q_2$ is, independently, selected from H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl;

$X_1$ is S, $NR_{16}R_{17}$, or $CR_{10}R_{11}$ wherein each $R_{10}$ and $R_{11}$ is, independently, H, F, $C_1$-$C_6$ haloalkyl, or $C_1$-$C_6$ alkyl; and $R_1$ is $X_2$—V;

or each of $q_1$ and $q_2$ is, independently, selected from $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl;

$X_1$ is O, S, $NR_{16}R_{17}$, or $CR_{10}R_{11}$ wherein each $R_{10}$ and $R_{11}$ is, independently, H, F, $C_1$-$C_6$ haloalkyl, or $C_1$-$C_6$ alkyl; and $R_1$ is $X_2$—V;

wherein:

$X_2$ is O, S or $CR_7R_8$ wherein each $R_7$ and $R_8$ is, independently, H or $C_1$-$C_6$ alkyl;

V is selected from cholesterol, $(CH_2)_2[O(CH_2)_2]_tOCH_3$, where t is from 1-3, $(CH_2)_2F$, $CH_2COOH$, $CH_2CONH_2$, $CH_2CONR_5R_6$, $CH_2COOCH_2CH_3$, $CH_2CONH(CH_2)_i$—S—$R_4$ where i is from 1 to 10, $CH_2CONH(CH_2)_jNR_5R_6$ where j is from 1 to 6, and $CH_2CONH[(CH_2)_{k1}$—N(H)$]_{k2}$—$(CH_2)_{k1}NH_2$ where each $k_1$ is independently from 2 to 4 and $k_2$ is from 2 to 10;

$R_4$ is selected from H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl, substituted $C_2$-$C_6$ alkynyl, $C_6$-$C_{14}$ aryl and a thio protecting group;

$R_5$ and $R_6$ are each, independently, selected from H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, and substituted $C_2$-$C_6$ alkynyl;

$R_{16}$ is selected from H, $C_1$-$C_6$ alkyl, or substituted $C_1$-$C_6$ alkyl;

$X_4$ is $[C(R_a)(R_b)]_n$—$[(C=O)_mX_c]_k$—$R_d$ wherein
each $R_a$ and $R_b$ is independently H or halogen;
$X_c$ is O, S, or $N(E_1)$;
$R_d$ is H, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl and substituted $C_2$-$C_6$ alkynyl or $NE_2E_3$;
each $E_1$, $E_2$, and $E_3$ is independently H, $C_1$-$C_6$ alkyl, or substituted $C_1$-$C_6$ alkyl;
n is 1 to 6;
m is 0 or 1; and
k is 0 or 1; and wherein each substituted group is, independently, mono or poly substituted with optionally protected substituent groups independently selected from halogen, oxo, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl; and $J_4$ is hydrogen, or a protecting group.

In certain embodiments, at least one of $q_1$ and $q_2$ is $C_1$-$C_6$ alkyl or substituted $C_1$-$C_6$ alkyl. In certain embodiments, at least one of $q_1$ and $q_2$ is $C_1$-$C_6$ alkyl. In certain embodiments, at least one of $q_1$ and $q_2$ is methyl. In certain embodiments, one of $q_1$ and $q_2$ is H. In certain embodiments, one of $q_1$ and $q_2$ is methyl and the other of $q_1$ and $q_2$ is H. In certain embodiments, Z is O. In certain embodiments, Y is $CH_2CONH(CH_2)_jNR_5R_6$. In certain embodiments, j is 2. In certain embodiments, one of $R_5$ and $R_6$ is other than H. In certain embodiments, at least one of $R_5$ and $R_6$ is selected from $C_1$-$C_6$ alkyl, substituted $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl, and substituted $C_2$-$C_6$ alkynyl. In certain embodiments, at least one of $R_5$ and $R_6$ is $C_1$-$C_6$ alkyl or substituted $C_1$-$C_6$ alkyl. In certain embodiments, at least one of $R_5$ and $R_6$ is methyl. In certain embodiments, both $R_5$ and $R_6$ are other than H. In certain embodiments, $X_1$ is O. In certain embodiments, $X_1$ is S. In certain embodiments, $X_1$ is $CR_{10}R_{11}$. In certain embodiments, $R_{10}$ and $R_{11}$ are both H.

In certain embodiments, $T_1$ is a phosphorus moiety. In certain embodiments, the phosphorus moiety is selected from $P(Y_a)Y_bY_c$, where $Y_a$ is O or S and each $Y_b$ and $Y_c$ is, independently, OH, SH, alkyl, substituted $C_1$-$C_6$ alkyl, alkoxyl and substituted $C_1$-$C_6$ alkoxyl. In certain embodiments, $Y_a$ is 0 and $Y_b$ and $Y_c$ are each OH.

In certain embodiments:
i. $Y_a$ is O;
ii. $Y_b$ and $Y_c$ are each OH; and
iii. $T_2$ is diisopropylcyanoethoxy phosphoramidite.

In certain embodiments, In certain embodiments, $T_2$ is a reactive phosphorus group. In certain embodiments, the reactive phosphorous group is diisopropylcyanoethoxy phosphoramidite or H-phosphonate.

In certain embodiments, a nucleoside has Formula XII:

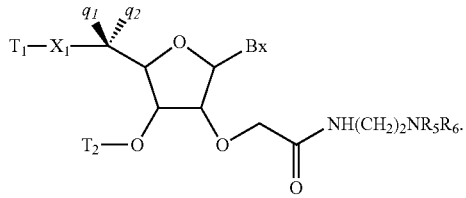

XII

In certain embodiments, both $R_5$ and $R_6$ are other than H. In certain embodiments, both $R_5$ and $R_6$ are methyl. In certain embodiments, $q_1$ is methyl and $q_2$ is H. In certain embodiments, $q_1$ is H and $q_2$ is methyl.

In certain embodiments, such nucleosides have the configuration:

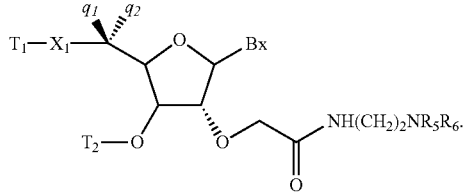

In certain embodiments, the oligomeric compound has a microRNA sequence associated with an accession number from miRBase version 10.1 released December 2007 selected from:

MIMAT0000062, MIMAT0004481, MIMAT0000063,
MIMAT0004482, MIMAT0000064, MIMAT0004483,
MIMAT0000065, MIMAT0004484, MIMAT0000066,
MIMAT0004485, MIMAT0000067, MIMAT0004486,
MIMAT0004487, MIMAT0000414, MIMAT0004584,
MIMAT0000415, MIMAT0004585, MIMAT0000416,
MIMAT0000098, MIMAT0004512, MIMAT0000099,
MIMAT0004513, MIMAT0000101, MIMAT0000102,
MIMAT0004516, MIMAT0000103, MIMAT0004517,
MIMAT0000680, MIMAT0004672, MIMAT0000104,
MIMAT0000253, MIMAT0004555, MIMAT0000254,
MIMAT0004556, MIMAT0000421, MIMAT0004590,
MIMAT0005459, MIMAT0005458, MIMAT0005573,
MIMAT0005572, MIMAT0005577, MIMAT0005576,
MIMAT0005580, MIMAT0005583, MIMAT0005582,
MIMAT0005584, MIMAT0005586, MIMAT0005588,
MIMAT0005589, MIMAT0005591, MIMAT0005592,
MIMAT0005593, MIMAT0000422, MIMAT0004591,
MIMAT0004602, MIMAT0000443, MIMAT0000423,
MIMAT0000423, MIMAT0004592, MIMAT0004603,
MIMAT0000445, MIMAT0000444, MIMAT0000446,
MIMAT0004604, MIMAT0000424, MIMAT0004548,
MIMAT0004605, MIMAT0000242, MIMAT0000425,
MIMAT0004593, MIMAT0000691, MIMAT0004680,
MIMAT0000426, MIMAT0004594, MIMAT0000427,
MIMAT0000770, MIMAT0000447, MIMAT0000428,
MIMAT0004595, MIMAT0000758, MIMAT0004698,
MIMAT0000448, MIMAT0004606, MIMAT0000429,
MIMAT0000430, MIMAT0004607, MIMAT0004596,
MIMAT0004552, MIMAT0000250, MIMAT0004597,
MIMAT0000431, MIMAT0000432, MIMAT0004598,
MIMAT0000434, MIMAT0000433, MIMAT0000435,
MIMAT0004599, MIMAT0000436, MIMAT0004600,
MIMAT0000437, MIMAT0004601, MIMAT0000449,
MIMAT0004608, MIMAT0004766, MIMAT0002809,

MIMAT0000251, MIMAT0004928, MIMAT0000243, MIMAT0004695, MIMAT0000763, MIMAT0004701,
MIMAT0004549, MIMAT0000759, MIMAT0004699, MIMAT0004702, MIMAT0000764, MIMAT0000091,
MIMAT0000450, MIMAT0004609, MIMAT0000451, MIMAT0004506, MIMAT0003301, MIMAT0004811,
MIMAT0004610, MIMAT0000757, MIMAT0004697, MIMAT0004692, MIMAT0000750, MIMAT0000753,
MIMAT0000438, MIMAT0000439, MIMAT0000439, MIMAT0004694, MIMAT0000772, MIMAT0000773,
MIMAT0000452, MIMAT0000453, MIMAT0000646, MIMAT0000255, MIMAT0004557, MIMAT0004676,
MIMAT0004658, MIMAT0000068, MIMAT0004488, MIMAT0000685, MIMAT0004677, MIMAT0000686,
MIMAT0000417, MIMAT0004586, MIMAT0000069, MIMAT0004682, MIMAT0000703, MIMAT0004683,
MIMAT0004489, MIMAT0004518, MIMAT0000070, MIMAT0000705, MIMAT0000707, MIMAT0003385,
MIMAT0000071, MIMAT0000256, MIMAT0000270, MIMAT0000710, MIMAT0000719, MIMAT0004686,
MIMAT0004558, MIMAT0000257, MIMAT0000258, MIMAT0000721, MIMAT0001621, MIMAT0000722,
MIMAT0004559, MIMAT0002821, MIMAT0000259, MIMAT0000723, MIMAT0004687, MIMAT0000724,
MIMAT0000260, MIMAT0000261, MIMAT0004560, MIMAT0000726, MIMAT0000725, MIMAT0000727,
MIMAT0000454, MIMAT0004611, MIMAT0000456, MIMAT0004688, MIMAT0004955, MIMAT0004956,
MIMAT0004612, MIMAT0000262, MIMAT0004561, MIMAT0000728, MIMAT0000729, MIMAT0003386,
MIMAT0004613, MIMAT0000457, MIMAT0000072, MIMAT0002172, MIMAT0000720, MIMAT0000730,
MIMAT0002891, MIMAT0001412, MIMAT0004751, MIMAT0004689, MIMAT0000732, MIMAT0000731,
MIMAT0000458, MIMAT0004929, MIMAT0000440, MIMAT0000733, MIMAT0004690, MIMAT0000735,
MIMAT0001618, MIMAT0000222, MIMAT0004543, MIMAT0000734, MIMAT0000736, MIMAT0000737,
MIMAT0000459, MIMAT0004614, MIMAT0002819, MIMAT0000738, MIMAT0001075, MIMAT0001639,
MIMAT0004767, MIMAT0000460, MIMAT0004671, MIMAT0001638, MIMAT0002171, MIMAT0003329,
MIMAT0000461, MIMAT0004615, MIMAT0000226, MIMAT0004813, MIMAT0002170, MIMAT0003339,
MIMAT0004562, MIMAT0001080, MIMAT0000227, MIMAT0001339, MIMAT0001340, MIMAT0004748,
MIMAT0000228, MIMAT0000232, MIMAT0000231, MIMAT0001341, MIMAT0004749, MIMAT0003393,
MIMAT0004563, MIMAT0000263, MIMAT0000073, MIMAT0001343, MIMAT0001536, MIMAT0001625,
MIMAT0004490, MIMAT0000074, MIMAT0004491, MIMAT0004757, MIMAT0002814, MIMAT0002815,
MIMAT0004492, MIMAT0000682, MIMAT0001620, MIMAT0001627, MIMAT0001532, MIMAT0001541,
MIMAT0000318, MIMAT0004571, MIMAT0000617, MIMAT0003327, MIMAT0001545, MIMAT0004910,
MIMAT0004657, MIMAT0002811, MIMAT0002810, MIMAT0004909, MIMAT0001631, MIMAT0001635,
MIMAT0000264, MIMAT0000265, MIMAT0000266, MIMAT0001636, MIMAT0001630, MIMAT0003885,
MIMAT0000462, MIMAT0000241, MIMAT0004960, MIMAT0003884, MIMAT0004784, MIMAT0003150,
MIMAT0000075, MIMAT0004493, MIMAT0001413, MIMAT0002173, MIMAT0004761, MIMAT0002174,
MIMAT0004752, MIMAT0000076, MIMAT0004494, MIMAT0002176, MIMAT0002175, MIMAT0004762,
MIMAT0000267, MIMAT0000268, MIMAT0000269, MIMAT0002177, MIMAT0002178, MIMAT0003180,
MIMAT0000271, MIMAT0004564, MIMAT0000272, MIMAT0004763, MIMAT0002804, MIMAT0002805,
MIMAT0000273, MIMAT0004959, MIMAT0000274, MIMAT0002806, MIMAT0004764, MIMAT0004765,
MIMAT0000275, MIMAT0004565, MIMAT0004566, MIMAT0002807, MIMAT0002812, MIMAT0003161,
MIMAT0004567, MIMAT0004675, MIMAT0000276, MIMAT0002813, MIMAT0002816, MIMAT0002817,
MIMAT0000077, MIMAT0004495, MIMAT0000277, MIMAT0002818, MIMAT0002820, MIMAT0004768,
MIMAT0004908, MIMAT0004915, MIMAT0000278, MIMAT0002824, MIMAT0004772, MIMAT0002870,
MIMAT0004568, MIMAT0000279, MIMAT0004569, MIMAT0004773, MIMAT0002871, MIMAT0004774,
MIMAT0000280, MIMAT0004570, MIMAT0000281, MIMAT0002872, MIMAT0004775, MIMAT0002873,
MIMAT0000078, MIMAT0004496, MIMAT0000418, MIMAT0002874, MIMAT0002875, MIMAT0002876,
MIMAT0004587, MIMAT0000080, MIMAT0000079, MIMAT0004776, MIMAT0002878, MIMAT0002879,
MIMAT0004497, MIMAT0000081, MIMAT0004498, MIMAT0002880, MIMAT0004778, MIMAT0004975,
MIMAT0000082, MIMAT0004499, MIMAT0004681, MIMAT0002881, MIMAT0004779, MIMAT0002882,
MIMAT0000083, MIMAT0004500, MIMAT0000084, MIMAT0002808, MIMAT0002823, MIMAT0002822,
MIMAT0004501, MIMAT0000419, MIMAT0004588, MIMAT0004777, MIMAT0002877, MIMAT0005788,
MIMAT0004502, MIMAT0000085, MIMAT0004679, MIMAT0005789, MIMAT0002883, MIMAT0002827,
MIMAT0000690, MIMAT0004450, MIMAT0004901, MIMAT0002826, MIMAT0002860, MIMAT0004770,
MIMAT0000687, MIMAT0002890, MIMAT0000086, MIMAT0002859, MIMAT0002851, MIMAT0002852,
MIMAT0004503, MIMAT0000100, MIMAT0004514, MIMAT0002857, MIMAT0002866, MIMAT0002863,
MIMAT0004515, MIMAT0000681, MIMAT0004673, MIMAT0005457, MIMAT0002844, MIMAT0002848,
MIMAT0004903, MIMAT0000688, MIMAT0004958, MIMAT0002847, MIMAT0002864, MIMAT0005456,
MIMAT0000684, MIMAT0000683, MIMAT0000715, MIMAT0002861, MIMAT0005450, MIMAT0002842,
MIMAT0000714, MIMAT0000717, MIMAT0000716, MIMAT0002841, MIMAT0002869, MIMAT0005452,
MIMAT0000718, MIMAT0004685, MIMAT0000087, MIMAT0002837, MIMAT0005454, MIMAT0002832,
MIMAT0000088, MIMAT0000420, MIMAT0004589, MIMAT0002831, MIMAT0002853, MIMAT0002829,
MIMAT0000244, MIMAT0004674, MIMAT0004550, MIMAT0002828, MIMAT0002834, MIMAT0002833,
MIMAT0000245, MIMAT0004551, MIMAT0000692, MIMAT0002843, MIMAT0002846, MIMAT0005455,
MIMAT0000693, MIMAT0000089, MIMAT0004504, MIMAT0002856, MIMAT0002855, MIMAT0002825,
MIMAT0000090, MIMAT0004505, MIMAT0000510, MIMAT0002830, MIMAT0002858, MIMAT0002867,
MIMAT0000755, MIMAT0004696, MIMAT0000762, MIMAT0002854, MIMAT0002868, MIMAT0005451,
MIMAT0000761, MIMAT0000771, MIMAT0000756, MIMAT0002840, MIMAT0005449, MIMAT0005450,
MIMAT0000752, MIMAT0001629, MIMAT0000751, MIMAT0002849, MIMAT0002839, MIMAT0002838,
MIMAT0004693, MIMAT0000760, MIMAT0004700, MIMAT0002845, MIMAT0002835, MIMAT0002836,
MIMAT0000765, MIMAT0004703, MIMAT0000754, MIMAT0002862, MIMAT0004780, MIMAT0002888,

MIMAT0003163, MIMAT0004920, MIMAT0004919, MIMAT0003389, MIMAT0003340, MIMAT0004954, MIMAT0003164, MIMAT0003165, MIMAT0004785, MIMAT0003251, MIMAT0003254, MIMAT0003254, MIMAT0004798, MIMAT0003285, MIMAT0004806, MIMAT0003323, MIMAT0003323, MIMAT0004812, MIMAT0003333, MIMAT0004800, MIMAT0003257, MIMAT0003214, MIMAT0003233, MIMAT0004794, MIMAT0003215, MIMAT0003216, MIMAT0003217, MIMAT0003219, MIMAT0004793, MIMAT0003220, MIMAT0003221, MIMAT0003222, MIMAT0003223, MIMAT0003225, MIMAT0003226, MIMAT0003227, MIMAT0003228, MIMAT0003230, MIMAT0003231, MIMAT0003232, MIMAT0003234, MIMAT0003235, MIMAT0003236, MIMAT0003237, MIMAT0003238, MIMAT0003239, MIMAT0004795, MIMAT0003240, MIMAT0004796, MIMAT0003241, MIMAT0003242, MIMAT0003243, MIMAT0003244, MIMAT0003245, MIMAT0003246, MIMAT0004797, MIMAT0003247, MIMAT0003248, MIMAT0003249, MIMAT0003250, MIMAT0003252, MIMAT0003253, MIMAT0003255, MIMAT0004799, MIMAT0003256, MIMAT0004801, MIMAT0003258, MIMAT0003259, MIMAT0003260, MIMAT0004802, MIMAT0003261, MIMAT0003263, MIMAT0003264, MIMAT0003265, MIMAT0003266, MIMAT0003267, MIMAT0003268, MIMAT0003269, MIMAT0003270, MIMAT0003271, MIMAT0003272, MIMAT0003273, MIMAT0003274, MIMAT0003275, MIMAT0003276, MIMAT0003277, MIMAT0003278, MIMAT0003279, MIMAT0003280, MIMAT0003281, MIMAT0003282, MIMAT0003283, MIMAT0004804, MIMAT0004805, MIMAT0003284, MIMAT0003286, MIMAT0003287, MIMAT0003288, MIMAT0003289, MIMAT0003290, MIMAT0003291, MIMAT0003292, MIMAT0004807, MIMAT0003293, MIMAT0003294, MIMAT0004808, MIMAT0003295, MIMAT0003296, MIMAT0003297, MIMAT0004809, MIMAT0004810, MIMAT0003298, MIMAT0003299, MIMAT0003300, MIMAT0003302, MIMAT0003303, MIMAT0003304, MIMAT0003305, MIMAT0003306, MIMAT0003307, MIMAT0003308, MIMAT0003309, MIMAT0003310, MIMAT0003311, MIMAT0003312, MIMAT0003313, MIMAT0003314, MIMAT0003315, MIMAT0003316, MIMAT0003317, MIMAT0003318, MIMAT0003319, MIMAT0003320, MIMAT0003321, MIMAT0003322, MIMAT0003328, MIMAT0004814, MIMAT0003330, MIMAT0003331, MIMAT0003332, MIMAT0003335, MIMAT0003336, MIMAT0003337, MIMAT0003338, MIMAT0003324, MIMAT0003325, MIMAT0003326, MIMAT0004952, MIMAT0003881, MIMAT0004819, MIMAT0003880, MIMAT0004284, MIMAT0000252, MIMAT0004926, MIMAT0004927, MIMAT0004553, MIMAT0004554, MIMAT0004945, MIMAT0004946, MIMAT0003879, MIMAT0004957, MIMAT0003945, MIMAT0003888, MIMAT0003883, MIMAT0003882, MIMAT0003947, MIMAT0003946, MIMAT0003887, MIMAT0003886, MIMAT0003948, MIMAT0004209, MIMAT0004185, MIMAT0004953, MIMAT0004911, MIMAT0004923, MIMAT0004922, MIMAT0004925, MIMAT0004924, MIMAT0004949, MIMAT0004950, MIMAT0004948, MIMAT0004947, MIMAT0004906, MIMAT0004905, MIMAT0004951, MIMAT0004916, MIMAT0004917, MIMAT0004921, MIMAT0004912, MIMAT0004902, MIMAT0004913, MIMAT0004907, MIMAT0004918, MIMAT0000441, MIMAT0000442, MIMAT0004970, MIMAT0004971, MIMAT0004972, MIMAT0004973, MIMAT0004974, MIMAT0000092, MIMAT0004507, MIMAT0004508, MIMAT0003218, MIMAT0004792, MIMAT0000093, MIMAT0004509, MIMAT0004976, MIMAT0004977, MIMAT0004978, MIMAT0004979, MIMAT0004980, MIMAT0004981, MIMAT0004982, MIMAT0004983, MIMAT0004984, MIMAT0004985, MIMAT0004986, MIMAT0004987, MIMAT0000094, MIMAT0000095, MIMAT0004510, MIMAT0000096, MIMAT0000097, MIMAT0004511, MIMAT0000689, and MIMAT0004678.

In certain embodiments the invention provides oligomeric compounds having a nucleobase sequence selected from among SEQ ID NOs 20, 21, 23, 24, 25, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, and 91.

In certain embodiments, the present invention provides oligomeric compounds having a nucleobase sequence selected from the table below.

| miR ID | SEQUENCE | SEQ ID NO |
|---|---|---|
| hsa-let-7a-1 | UGAGGUAGUAGGUUGUAUAGUU | 38 |
| hsa-let-7b | UGAGGUAGUAGGUUGUGUGGUU | 39 |
| hsa-let-7c | UGAGGUAGUAGGUUGUAUGGUU | 40 |
| hsa-let-7i | UGAGGUAGUAGUUUGUGCUGUU | 41 |
| hsa-miR-1-1 | UGGAAUGUAAAGAAGUAUGUAU | 42 |
| hsa-miR-10a | UACCCUGUAGAUCCGAAUUUGUG | 43 |
| hsa-miR-15a | UAGCAGCACAUAAUGGUUUGUG | 44 |
| hsa-miR-16-1 | UAGCAGCACGUAAAUAUUGGCG | 45 |
| hsa-miR-29a | UAGCACCAUCUGAAAUCGGUUA | 46 |
| hsa-miR-29b-1 | UAGCACCAUUUGAAAUCAGUGUU | 47 |
| hsa-miR-29c | UAGCACCAUUUGAAAUCGGUUA | 48 |
| hsa-miR-34a | UGGCAGUGUCUUAGCUGGUUGU | 49 |
| hsa-miR-34b | CAAUCACUAACUCCACUGCCAU | 50 |
| hsa-miR-34c-5p | AGGCAGUGUAGUUAGCUGAUUGC | 51 |
| hsa-miR-93 | CAAAGUGCUGUUCGUGCAGGUAG | 52 |
| hsa-miR-101-1 | UACAGUACUGUGAUAACUGAA | 53 |
| hsa-miR-122 | UGGAGUGUGACAAUGGUGUUUG | 54 |
| hsa-miR-124-1 | UAAGGCACGCGGUGAAUGCC | 55 |
| hsa-miR-125a-5p | UCCCUGAGACCCUUUAACCUGUGA | 56 |
| hsa-miR-125b-1 | UCCCUGAGACCCUAACUUGUGA | 57 |
| hsa-miR-126 | UCGUACCGUGAGUAAUAAUGCG | 58 |
| hsa-miR-132 | UAACAGUCUACAGCCAUGGUCG | 59 |
| hsa-miR-133a-1 | UUUGGUCCCCUUCAACCAGCUG | 60 |
| hsa-miR-133b | UUUGGUCCCCUUCAACCAGCUA | 61 |
| hsa-miR-146a | UGAGAACUGAAUUCCAUGGGUU | 62 |
| hsa-miR-150 | UCUCCCAACCCUUGUACCAGUG | 63 |
| hsa-miR-155 | UUAAUGCUAAUCGUGAUAGGGGU | 64 |

-continued

| miR ID | SEQUENCE | SEQ ID NO |
|---|---|---|
| hsa-miR-181a-1 | AACAUUCAACGCUGUCGGUGAGU | 65 |
| hsa-miR-181b-1 | AACAUUCAUUGCUGUCGGUGGGU | 66 |
| hsa-miR-193a-5p | UGGGUCUUUGCGGGCGAGAUGA | 67 |
| hsa-miR-196a-1 | UAGGUAGUUUCAUGUUGUUGGG | 68 |
| hsa-miR-203 | GUGAAAUGUUUAGGACCACUAG | 69 |
| hsa-miR-206 | UGGAAUGUAAGGAAGUGUGUGG | 70 |
| hsa-miR-210 | CUGUGCGUGUGACAGCGGCUGA | 71 |
| hsa-miR-296-5p | AGGGCCCCCCCUCAAUCCUGU | 72 |
| hsa-miR-335 | UCAAGAGCAAUAACGAAAAAUGU | 73 |
| hsa-miR-7 | UGGAAGACUAGUGAUUUUGUUGU | 74 |
| hsa-miR-21 | UAGCUUAUCAGACUGAUGUUGA | 75 |
| hsa-miR-22 | AAGCUGCCAGUUGAAGAACUGU | 76 |
| hsa-miR-26a | UUCAAGUAAUCCAGGAUAGGCU | 77 |
| hsa-miR-26b | UUCAAGUAAUUCAGGAUAGGU | 78 |
| hsa-miR-141 | UAACACUGUCUGGUAAAGAUGG | 79 |
| hsa-miR-143 | UGAGAUGAAGCACUGUAGCUC | 80 |
| hsa-miR-145 | GUCCAGUUUUCCCAGGAAUCCCU | 81 |
| hsa-miR-195 | UAGCAGCACAGAAAUAUUGGC | 82 |
| hsa-miR-200a | UAACACUGUCUGGUAACGAUGU | 83 |
| hsa-miR-200b | UAAUACUGCCUGGUAAUGAUGA | 84 |
| hsa-miR-200c | UAAUACUGCCGGGUAAUGAUGGA | 85 |
| hsa-miR-205 | UCCUUCAUUCCACCGGAGUCUG | 86 |
| hsa-miR-208a | AUAAGACGAGCAAAAAGCUUGU | 87 |
| hsa-miR-208b | AUAAGACGAACAAAAGGUUUGU | 88 |
| hsa-miR-221 | AGCUACAUUGUCUGCUGGGUUUC | 89 |
| hsa-miR-222 | AGCUACAUCUGGCUACUGGGU | 90 |
| hsa-miR-223 | UGUCAGUUUGUCAAAUACCCCA | 91 |

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose. Each of the following patent applications is hereby incorporated by reference in its entirety: U.S. Provisional Applications 61/108,457, filed 2008 Oct. 24; 61/108,464, filed 2008 Oct. 24; 61/149,297, filed 2009 Feb. 6; 61/150,492, filed 2009 Feb. 6; 61/163,217, filed 2009 Mar. 25; 61/174,137, filed 2009 Apr. 30; 61/239,672, filed 2009 Sep. 3; and PCT/US2009/061913 and PCT/US2009/061916 each filed 2009 Oct. 23 (the same day as the present application).

I. Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, "nucleoside" refers to a compound comprising a heterocyclic base moiety and a sugar moiety. Nucleosides include, but are not limited to, naturally occurring nucleosides (as found in DNA and RNA), abasic nucleosides, modified nucleosides, and nucleosides having mimetic bases and/or sugar groups. Nucleosides may be modified with any of a variety of substituents. Nucleosides may include a phosphate moiety.

As used herein, "sugar moiety" means a natural or modified sugar ring or sugar surrogate.

As used herein the term "sugar surrogate" refers to a structure that is capable of replacing the furanose ring of a naturally occurring nucleoside. In certain embodiments, sugar surrogates are non-furanose (or 4'-substituted furanose) rings or ring systems or open systems. Such structures include simple changes relative to the natural furanose ring, such as a six membered ring or may be more complicated as is the case with the non-ring system used in peptide nucleic acid. Sugar surrogates includes without limitation morpholinos, cyclohexenyls and cyclohexitols. In most nucleosides having a sugar surrogate group the heterocyclic base moiety is generally maintained to permit hybridization.

As used herein, "nucleotide" refers to a nucleoside further comprising a phosphate linking group. As used herein, "linked nucleosides" may or may not be linked by phosphate linkages and thus includes "linked nucleotides."

As used herein, "nucleobase" refers to the heterocyclic base portion of a nucleoside. Nucleobases may be naturally occurring or may be modified. In certain embodiments, a nucleobase may comprise any atom or group of atoms capable of hydrogen bonding to a base of another nucleic acid.

As used herein, "modified nucleoside" refers to a nucleoside comprising at least one modification compared to naturally occurring RNA or DNA nucleosides. Such modification may be at the sugar moiety and/or at the nucleobases.

As used herein, "bicyclic nucleoside" or "BNA" refers to a nucleoside wherein the sugar moiety of the nucleoside comprises a bridge connecting two carbon atoms of the sugar ring, thereby forming a bicyclic sugar moiety.

As used herein, "4'-2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "phosphorous moiety" refers to a to monovalent $P^V$ phosphorus radical group. In certain embodiments, a phosphorus moiety is selected from: a phosphate, phosphonate, alkylphosphonate, aminoalkyl phosphonate, phosphorothioate, phosphoramidite, alkylphosphonothioate, phosphorodithioate, thiophosphoramidate, phosphotriester and the like. In certain embodiments, modified phosphorous moieties have the following structural formula:

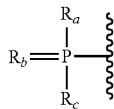

wherein:

$R_a$ and $R_b$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S.

The term "phosphate moiety" as used herein, refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified or modified.

As used herein, "phosphate stabilizing modification" refers to a nucleoside modification that results in stabilization of a 5'-phosphate group of nucleoside, relative to the stability of a 5'-phosphate of an unmodified nucleoside under biologic conditions. Such stabilization of a 5'-phosphate group includes but is not limit to resistance to removal by phosphatases.

As used herein, "phosphate stabilizing nucleoside" refers to a nucleoside comprising at least one phosphate stabilizing modification. In certain embodiments the phosphate stabilizing modification is a 2'-modification. In certain embodiments, the phosphate stabilizing modification is at the 5' position of the nucleoside. In certain embodiments, a phosphate stabilizing modification is at the 5' position of the nucleoside and at the 2' position of the nucleoside.

As used herein, "5'-stabilizing nucleoside" refers to a nucleoside that, when placed at the 5'-end of an oligonucleotide, results in an oligonucleotide that is more resistant to exonuclease digestion, and/or has a stabilized phosphate group.

As used herein, "oligonucleotide" refers to a compound comprising a plurality of linked nucleosides.

In certain embodiments, one or more of the plurality of nucleosides is modified. In certain embodiments, an oligonucleotide comprises one or more ribonucleosides (RNA) and/or deoxyribonucleosides (DNA).

As used herein "oligonucleoside" refers to an oligonucleotide in which none of the internucleoside linkages contains a phosphorus atom. As used herein, oligonucleotides include oligonucleosides.

As used herein, "modified oligonucleotide" refers to an oligonucleotide comprising at least one modified nucleoside and/or at least one modified internucleoside linkage.

As used herein "internucleoside linkage" refers to a covalent linkage between adjacent nucleosides.

As used herein "naturally occurring internucleoside linkage" refers to a 3' to 5' phosphodiester linkage.

As used herein, "modified internucleoside linkage" refers to any internucleoside linkage other than a naturally occurring internucleoside linkage.

As used herein, "oligomeric compound" refers to a polymeric structure comprising two or more sub-structures. In certain embodiments, an oligomeric compound is an oligonucleotide. In certain embodiments, an oligomeric compound is a single-stranded oligonucleotide. In certain embodiments, an oligomeric compound is a double-stranded duplex comprising two oligonucleotides. In certain embodiments, an oligomeric compound is a single-stranded or double-stranded oligonucleotide comprising one or more conjugate groups and/or terminal groups.

As used herein, "duplex" refers to two separate oligomeric compounds that are hybridized together.

As used herein, "terminal group" refers to one or more atom attached to either, or both, the 3' end or the 5' end of an oligonucleotide. In certain embodiments a terminal group is a conjugate group. In certain embodiments, a terminal group comprises one or more additional nucleosides.

As used herein, "conjugate" refers to an atom or group of atoms bound to an oligonucleotide or oligomeric compound. In general, conjugate groups modify one or more properties of the compound to which they are attached, including, but not limited to pharmakodynamic, pharmakokinetic, binding, absorption, cellular distribution, cellular uptake, charge and clearance. Conjugate groups are routinely used in the chemical arts and are linked directly or via an optional linking moiety or linking group to the parent compound such as an oligomeric compound. In certain embodiments, conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. In certain embodiments, conjugates are terminal groups. In certain embodiments, conjugates are attached to a 3' or 5' terminal nucleoside or to an internal nucleosides of an oligonucleotide.

As used herein, "conjugate linking group" refers to any atom or group of atoms used to attach a conjugate to an oligonucleotide or oligomeric compound. Linking groups or bifunctional linking moieties such as those known in the art are amenable to the present invention.

As used herein, "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound. This allows for selective chemistry to arrive at a desired compound or oligomeric compound.

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins. Antisense mechanisms contemplated herein include, but are not limited to an RNase H mechanism, RNAi mechanisms, splicing modulation, translational arrest, altering RNA processing, inhibiting microRNA function, or mimicking microRNA function.

As used herein, "expression" refers to the process by which a gene ultimately results in a protein. Expression includes, but is not limited to, transcription, splicing, post-transcriptional modification, and translation.

As used herein, "RNAi" refers to a mechanism by which certain antisense compounds effect expression or amount of a target nucleic acid. RNAi mechanisms involve the RISC pathway.

As used herein, "RNAi compound" refers to an oligomeric compound that acts, at least in part, through an RNAi mechanism to modulate a target nucleic acid and/or protein encoded by a target nucleic acid. RNAi compounds include, but are not limited to double-stranded short interfering RNA (siRNA), single-stranded RNA (ssRNA), and microRNA, including microRNA mimics.

As used herein, "antisense oligonucleotide" refers to an antisense compound that is an oligonucleotide.

As used herein, "antisense activity" refers to any detectable and/or measurable activity attributable to the hybridization of an antisense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. For example, in certain embodiments, antisense activity is assessed by detecting and/or measuring the amount of target protein or the relative amounts of splice variants of a target protein. In certain embodiments, antisense activity is assessed by detecting and/or measuring the amount of target nucleic acids and/or cleaved target nucleic acids and/or alternatively spliced target nucleic acids. In certain embodiments, antisense activity is assessed by observing a phenotypic change in a cell or animal.

As used herein "detecting" or "measuring" in connection with an activity, response, or effect indicate that a test for detecting or measuring such activity, response, or effect is performed. Such detection and/or measuring may include values of zero. Thus, if a test for detection or measuring results in a finding of no activity (activity of zero), the step of detecting or measuring the activity has nevertheless been performed. For example, in certain embodiments, the present invention provides methods that comprise steps of detecting antisense activity, detecting toxicity, and/or measuring a marker of toxicity. Any such step may include values of zero.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

As used herein, "target mRNA" refers to a pre-selected RNA molecule that encodes a protein.

As used herein, "target pre-mRNA" refers to a pre-selected RNA transcript that has not been fully processed into mRNA. Notably, pre-RNA includes one or more intron.

As used herein, "target microRNA" refers to a pre-selected non-coding RNA molecule about 18-30 nucleobases in length that modulates expression of one or more proteins or to a precursor of such a non-coding molecule.

As used herein, "target pdRNA" refers to refers to a pre-selected RNA molecule that interacts with one or more promoter to modulate transcription.

As used herein, "microRNA" refers to a naturally occurring, small, non-coding RNA that represses gene expression at the level of translation. In certain embodiments, a microRNA represses gene expression by binding to a target site within a 3' untranslated region of a target nucleic acid. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 10.1 released December 2007, which is herein incorporated by reference in its entirety. In certain embodiments, a microRNA has a nucleobase sequence as set forth in miRBase version 12.0 released September 2008, which is herein incorporated by reference in its entirety.

As used herein, "microRNA mimic" refers to an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids.

As used herein, "seed region" refers to a region at or near the 5' end of an antisense compound having a nucleobase sequence that is import for target nucleic acid recognition by the antisense compound. In certain embodiments, a seed region comprises nucleobases 2-8 of an antisense compound. In certain embodiments, a seed region comprises nucleobases 2-7 of an antisense compound. In certain embodiments, a seed region comprises nucleobases 1-7 of an antisense compound. In certain embodiments, a seed region comprises nucleobases 1-6 of an antisense compound. In certain embodiments, a seed region comprises nucleobases 1-8 of an antisense compound.

As used herein, "microRNA seed region" refers to a seed region of a microRNA or microRNA mimic. In certain embodiments, a microRNA seed region comprises nucleobases 2-8 of a microRNA or microRNA mimic. In certain embodiments, a microRNA seed region comprises nucleobases 2-7 of a microRNA or microRNA mimic. In certain embodiments, a microRNA seed region comprises nucleobases 1-7 of a microRNA or microRNA mimic. In certain embodiments, a microRNA seed region comprises nucleobases 1-6 of a microRNA or microRNA mimic. In certain embodiments, a microRNA seed region comprises nucleobases 1-8 of a microRNA or microRNA mimic.

As used herein, "seed match segment" refers to a portion of a target nucleic acid having nucleobase complementarity to a seed region. In certain embodiments, a seed match segment has nucleobase complementarity to nucleobases 2-8 of an siRNA, ssRNA, natural microRNA or microRNA mimic. In certain embodiments, a seed match segment has nucleobase complementarity to nucleobases 2-7 of an siRNA, ssRNA, microRNA or microRNA mimic. In certain embodiments, a seed match segment has nucleobase complementarity to nucleobases 1-6 of an siRNA, ssRNA, microRNA or microRNA mimic. In certain embodiments, a seed match segment has nucleobase complementarity to nucleobases 1-7 of an siRNA, ssRNA, microRNA or microRNA mimic. In certain embodiments, a seed match segment has nucleobase complementarity to nucleobases 1-8 of an siRNA, ssRNA, microRNA or microRNA mimic.

As used herein, "seed match target nucleic acid" refers to a target nucleic acid comprising a seed match segment.

As used herein, "microRNA family" refers to a group of microRNAs that share a microRNA seed sequence. In certain embodiments, microRNA family members regulate a common set of target nucleic acids. In certain embodiments, the shared microRNA seed sequence is found at the same nucleobase positions in each member of a microRNA family. In certain embodiments, the shared microRNA seed sequence is not found at the same nucleobase positions in each member of a microRNA family. For example, a microRNA seed sequence found at nucleobases 1-7 of one member of a microRNA family may be found at nucleobases 2-8 of another member of a microRNA family.

As used herein, "target non-coding RNA" refers to a pre-selected RNA molecule that is not translated to generate a protein. Certain non-coding RNA are involved in regulation of expression.

As used herein, "target viral nucleic acid" refers to a pre-selected nucleic acid (RNA or DNA) associated with a virus. Such viral nucleic acid includes nucleic acids that constitute the viral genome, as well as transcripts (including reverse-transcripts and RNA transcribed from RNA) of those nucleic acids, whether or not produced by the host cellular machinery. In certain instances, viral nucleic acids also include host nucleic acids that are recruited by a virus upon viral infection.

As used herein, "targeting" or "targeted to" refers to the association of an antisense compound to a particular target nucleic acid molecule or a particular region of nucleotides within a target nucleic acid molecule. An antisense compound targets a target nucleic acid if it is sufficiently complementary to the target nucleic acid to allow hybridization under physiological conditions.

As used herein, "target site" refers to a region of a target nucleic acid that is bound by an antisense compound. In certain embodiments, a target site is at least partially within the 3' untranslated region of an RNA molecule. In certain embodiments, a target site is at least partially within the 5' untranslated region of an RNA molecule. In certain embodiments, a target site is at least partially within the coding region of an RNA molecule. In certain embodiments, a target site is at least partially within an exon of an RNA molecule. In certain embodiments, a target site is at least partially within an intron of an RNA molecule. In certain embodiments, a target site is at least partially within a microRNA target site of an RNA molecule. In certain embodiments, a target site is at least partially within a repeat region of an RNA molecule.

As used herein, "target protein" refers to a protein, the expression of which is modulated by an antisense compound. In certain embodiments, a target protein is encoded by a target nucleic acid. In certain embodiments, expression of a target protein is otherwise influenced by a target nucleic acid.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases refers to a pair of nucleobases that do not form hydrogen bonds with one another or otherwise support hybridization.

As used herein, "complementary" in reference to linked nucleosides, oligonucleotides, or nucleic acids, refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid.

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "specifically hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "overall identity" refers to the nucleobase identity of an oligomeric compound relative to a particular nucleic acid or portion thereof, over the length of the oligomeric compound.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, "motif" refers to a pattern of modifications in an oligomeric compound or a region thereof. Motifs may be defined by modifications at certain nucleosides and/or at certain linking groups of an oligomeric compound.

As used herein, "nucleoside motif" refers to a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "linkage motif" refers to a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "different modifications" or "differently modified" refer to modifications relative to naturally occurring molecules that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified, unless otherwise indicated. For example, a nucleoside comprising a 2'-OMe modified sugar and an adenine nucleobase and a nucleoside comprising a 2'-OMe modified sugar and a thymine nucleobase are not differently modified.

As used herein, "the same modifications" refer to modifications relative to naturally occurring molecules that are the same as one another, including absence of modifications. Thus, for example, two unmodified DNA nucleoside have "the same modification," even though the DNA nucleoside is unmodified.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "separate regions" refers to a portion of an oligomeric compound wherein the nucleosides and internucleoside linkages within the region all comprise the same modifications; and the nucleosides and/or the internucleoside linkages of any neighboring portions include at least one different modification.

As used herein, "alternating motif" refers to an oligomeric compound or a portion thereof, having at least four separate regions of modified nucleosides in a pattern $(AB)_nA_m$, where A represents a region of nucleosides having a first type of modification; B represent a region of nucleosides having a different type of modification; n is 2-15; and m is 0 or 1. Thus, in certain embodiments, alternating motifs include 4, 5, 6, 7, 8, 9, 10, 11, 12, 13, 14, 15, 16, 17, 18, 19, or 20 or more alternating regions. In certain embodiments, each A region and each B region independently comprises 1-4 nucleosides.

As used herein, "fully modified" refers to an oligomeric compound or portion thereon wherein each nucleoside is a modified nucleoside. The modifications of the nucleosides of a fully modified oligomeric compound may all be the same or one or more may be different from one another.

As used herein, "uniform modified" or "uniformly modified" refer to oligomeric compounds or portions thereof that comprise the same modifications. The nucleosides of a region of uniformly modified nucleosides all comprise the same modification.

As used herein, "pharmaceutically acceptable salts" refers to salts of active compounds that retain the desired biological activity of the active compound and do not impart undesired toxicological effects thereto.

As used herein, "cap structure" or "terminal cap moiety" refers to chemical modifications incorporated at either terminus of an antisense compound.

As used herein, "mitigation" refers to a lessening of at least one activity or one indicator of the severity of a condition or disease. The severity of indicators may be determined by subjective or objective measures which are known to those skilled in the art. In certain embodiments, the condition may be a toxic effect of a therapeutic agent.

As used herein, "pharmaceutical agent" refers to a substance that provides a therapeutic effect when administered to a subject. In certain embodiments, a pharmaceutical agent provides a therapeutic benefit. In certain embodiments, a pharmaceutical agent provides a toxic effect.

As used herein, "therapeutic index" refers to the toxic dose of a drug for 50% of the population ($TD_{50}$) divided by the minimum effective dose for 50% of the population ($ED_{50}$). A high therapeutic index is preferable to a low one: this corresponds to a situation in which one would have to take a much higher amount of a drug to cause a toxic effect than the amount taken to cause a therapeutic benefit.

As used herein, "therapeutically effective amount" refers to an amount of a pharmaceutical agent that provides a therapeutic benefit to an animal.

As used herein, "administering" refers to providing a pharmaceutical agent to an animal, and includes, but is not limited to administering by a medical professional and self-administering.

As used herein, "co-administer" refers to administering more than one pharmaceutical agent to an animal. The more than one agent may be administered together or separately; at the same time or different times; through the same route of administration or through different routes of administration.

As used herein, "co-formulation" refers to a formulation comprising two or more pharmaceutically active agents. In certain embodiments, a co-formulation comprises two or more oligomeric compounds. In certain such embodiments, two or more oligomeric compound are oligomeric compounds of the present invention. In certain embodiments, one or more oligomeric compound present in a co-formulation is not a compound of the present invention. In certain embodiments, a co-formulation includes one or more non-oligomeric pharmaceutical agents.

As used herein, "route of administration" refers to the means by which a pharmaceutical agent is administered to an animal.

As used herein, "pharmaceutical composition" refers to a mixture of substances suitable for administering to an animal. For example, a pharmaceutical composition may comprise an antisense oligonucleotide and a sterile aqueous solution.

As used herein, "pharmaceutically acceptable carrier or diluent" refers to any substance suitable for use in administering to an animal. In certain embodiments, a pharmaceutically acceptable carrier or diluent is sterile saline. In certain embodiments, such sterile saline is pharmaceutical grade saline.

As used herein, "animal" refers to a human or a non-human animal, including, but not limited to, mice, rats, rabbits, dogs, cats, pigs, and non-human primates, including, but not limited to, monkeys and chimpanzees.

As used herein, "parenteral administration," refers to administration through injection or infusion. Parenteral administration includes, but is not limited to, subcutaneous administration, intravenous administration, or intramuscular administration.

As used herein, "subcutaneous administration" refers to administration just below the skin. "Intravenous administration" refers to administration into a vein.

As used herein, "active pharmaceutical ingredient" refers to the substance in a pharmaceutical composition that provides a desired effect.

As used herein, "prodrug" refers to a therapeutic agent that is prepared in an inactive form that is converted to an active form (i.e., drug) within the body or cells thereof by the action of endogenous enzymes or other chemicals and/or conditions.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

As used herein, "alkyl," refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms ($C_1$-$C_6$ alkyl) being more preferred. The term "lower alkyl" as used herein includes from 1 to about 6 carbon atoms ($C_1$-$C_6$ alkyl). Alkyl groups as used herein may optionally include one or more further substituent groups. Herein, the term "alkyl" without indication of number of carbon atoms means an alkyl having 1 to about 12 carbon atoms ($C_1$-$C_{12}$ alkyl).

As used herein, "alkenyl," refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "aminoalkyl" refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

As used herein, "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substituent groups.

As used herein, "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "alkoxy," refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "halo" and "halogen," refer to an atom selected from fluorine, chlorine, bromine and iodine.

As used herein, "aryl" and "aromatic," refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "aralkyl" and "arylalkyl," refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

As used herein, "heterocyclic radical" refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

As used herein, "heteroaryl," and "heteroaromatic," refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

As used herein, "heteroarylalkyl," refers to a heteroaryl group as previously defined having an alky radical that can attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

As used herein, "mono or poly cyclic structure" refers to any ring systems that are single or polycyclic having rings that are fused or linked and is meant to be inclusive of single and mixed ring systems individually selected from aliphatic, alicyclic, aryl, heteroaryl, aralkyl, arylalkyl, heterocyclic, heteroaryl, heteroaromatic, heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In another aspect, mono or poly cyclic structures can be attached to a parent molecule directly through a ring atom, through a substituent group or a bifunctional linking moiety.

As used herein, "acyl," refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "hydrocarbyl" refers to any group comprising C, O and H. Included are straight, branched and cyclic groups having any degree of saturation. Such hydrocarbyl groups can include one or more heteroatoms selected from N, O and S and can be further mono or poly substituted with one or more substituent groups.

As used herein, "substituent" and "substituent group," include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Unless otherwise indicated, the term substituted or "optionally substituted" refers to the following substituents: halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxo (—O—R$_{aa}$), aryl, aralkyl, heterocyclic, heteroaryl, hetero-arylalkyl, amino (—NR$_{bb}$R$_{cc}$), imino(=NR$_{bb}$), amido (—C(O)NR$_{bb}$R$_{cc}$ or —N(R$_{bb}$)C(O)R$_{aa}$), azido (—N$_3$), nitro (—NO$_2$), cyano (—CN), carbamido (—OC(O)NR$_{bb}$R$_{cc}$ or —N(R$_{bb}$)C(O)OR$_{aa}$), ureido (—N(R$_{bb}$)C(O)NR$_{bb}$R$_{cc}$), thioureido (—N(R$_{bb}$)C(S)NR$_{bb}$R$_{cc}$), guanidinyl (—N(R$_{bb}$)C(=NR$_{bb}$)NR$_{bb}$R$_{cc}$), amidinyl (—C(=NR$_{bb}$)NR$_{bb}$R$_{cc}$ or —N(R$_{bb}$)C(NR$_{bb}$)R$_{aa}$), thiol (—SR$_{bb}$), sulfinyl (—S(O)R$_{bb}$), sulfonyl (—S(O)$_2$R$_{bb}$), sulfonamidyl (—S(O)$_2$NR$_{bb}$R$_{cc}$ or —N(R$_{bb}$)S(O)$_2$R$_{bb}$) and conjugate groups. Wherein each R$_{aa}$, R$_{bb}$ and R$_{cc}$ is, independently, H, an optionally linked chemical functional group or a further substituent group with a preferred list including without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

As used herein, a zero (0) in a range indicating number of a particular unit means that the unit may be absent. For example, an oligomeric compound comprising 0-2 regions of a particular motif means that the oligomeric compound may comprise one or two such regions having the particular motif, or the oligomeric compound may not have any regions having the particular motif. In instances where an internal portion of a molecule is absent, the portions flanking the absent portion are bound directly to one another. Likewise, the term "none" as used herein, indicates that a certain feature is not present.

II. Certain Modified Nucleosides

In certain embodiments, the invention provides modified nucleosides. Certain modified nucleosides comprise modified sugar moieties, modified heterocyclic bases, modified phosphorus moieties, or combinations of those modifications. In certain embodiments, modified oligonucleotides of the present invention comprise modified nucleosides comprising a modified sugar moiety. In certain embodiments, modified oligonucleotides of the present invention comprise modified nucleosides comprising a modified nucleobase. In certain embodiments, modified oligonucleotides of the present invention comprise modified nucleosides comprising a modified sugar moiety and a modified nucleobase.

A. Modified Sugar and Phosphorous Moieties

In certain embodiments in which a nucleoside is not linked to another nucleoside at its 5'-end (e.g., it is a monomer or it is the 5'-terminal nucleoside of an oligonucleotide), the nucleoside may comprise a modified phosphate or phosphorus moiety at the 5'-end (note that in certain embodiments, nucleoside that are linked to another nucleoside at the 5'-end may also comprise modified phosphates or phosphorus moieties, though such circumstance is typically referred to herein as a modified internucleoside linkage). In certain embodiments, the invention provides nucleosides comprising a modification at the 5'-position of the sugar. Herein, modifications at the 5'-position of the sugar or its substituents are typically referred to as modified sugars and modifications distal to that position are referred to as modified phosphates.

One of skill in the art will appreciate that the boundary between these terms, particularly once modifications are introduced, becomes arbitrary. The example below shows a modified nucleoside comprising an a sulfur atom in place of the oxygen that links the phosphorus moiety and the sugar of a natural nucleoside. Herein, such modifications are typically referred to as modified phosphates, however, one of skill in the art will recognize that such a modification could also be referred to as a modified sugar comprising a sulfer linked to the 5'-position of the sugar.

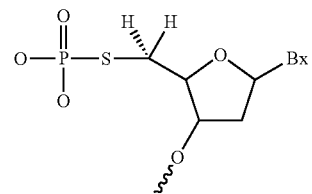

In certain embodiments, nucleosides of the present invention comprise modified phosphates. In certain embodiments, nucleosides of the present invention comprise 5'-sugar modifications. In certain embodiments, nucleosides of the present invention comprise both modified phosphates and 5'-sugar modifications. Examples of nucleosides having such modified phosphorus moieties and/or 5'-modifications include, but are not limited to:

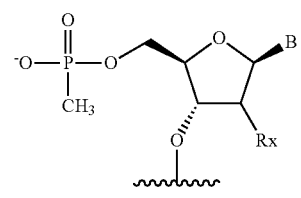

Methylphosphate

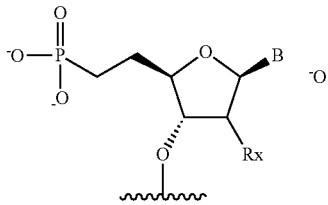 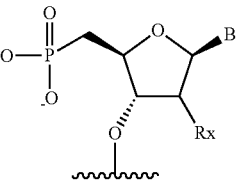

Methylenephosphonate      Phosphonate

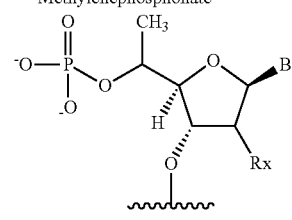

5'-Methyl-Phosphate

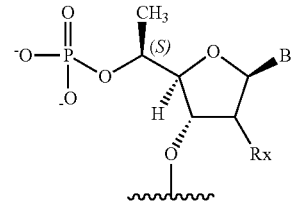

(S)-5'-Methyl-Phosphate

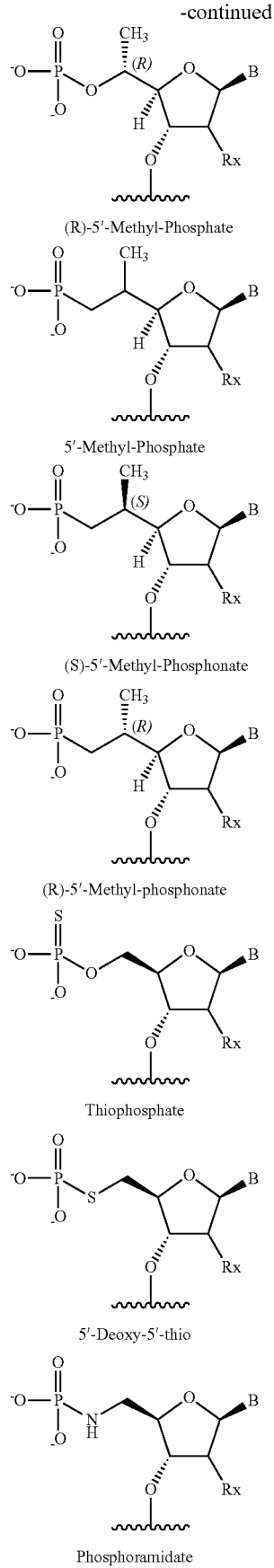

(R)-5'-Methyl-Phosphate

5'-Methyl-Phosphate (S)-5'-Methyl-Phosphonate (R)-5'-Methyl-phosphonate

Thiophosphate

5'-Deoxy-5'-thio

Phosphoramidate

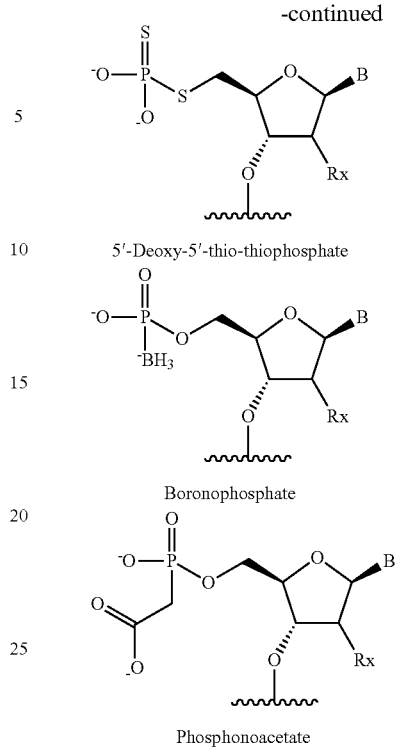

5'-Deoxy-5'-thio-thiophosphate

Boronophosphate

Phosphonoacetate

The above examples are intended to illustrate and not to limit the invention as regards modifications at the 5'-phosphate and the 5'-position of the sugar. In the above illustrative examples, the 2'-position of the sugar is labeled Rx. However, in certain embodiments of the present invention, nucleosides comprising modified phosphate and/or 5'-modified sugar groups may further comprise a modification at the 2'-position of the sugar. Many such 2'-modifications are known in the art. In certain embodiments, Rx in any of the above examples may be selected from: a halogen (including, but not limited to F), allyl, amino, azido, thio, O-allyl, —O—$C_1$-$C_{10}$ alkyl, —O—$C_1$-$C_{10}$ substituted alkyl, —$OCF_3$, —O—$(CH_2)_2$—O—$CH_3$, —$O(CH_2)_2SCH_3$, —O—$(CH_2)_2$—O—$N(R_m)(R_n)$, —O—CH2—C(=O)—$N(R_m)(R_n)$, where each $R_m$ and $R_n$ is, independently, H or substituted or unsubstituted $C_1$-$C_{10}$ alkyl, —$O[(CH_2)_nO]_mCH_3$, —$O(CH_2)_nNH_2$, —$O(CH_2)_nCH_3$, —$O(CH_2)_nONH_2$, —$OCH_2C(=O)N(H)CH_3$, —$O(CH_2)_nON[(CH_2)_nCH_3]_2$, where n and m are from 1 to about 10; $C_1$ to $C_{10}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, poly-alkylamino, substituted silyl. In certain embodiments, Rx is selected from: —O-Methyl, —O-Ethyl, —O-Propyl, —O-Phenyl, O-methoxyethyl, S-Methyl, NMA, DMAEAc, DMAEOE, —O—$CH_2CH_2F$. In certain embodiments, Rx is any substituents described herein or known in the art. In certain embodiments, the nucleoside is not modified at the 2'-position (i.e., Rx is H (DNA) or Rx is OH(RNA)). In certain embodiments, such nucleosides are at the 5' end of an oligonucleotide.

In certain embodiments, nucleosides have Formula I:

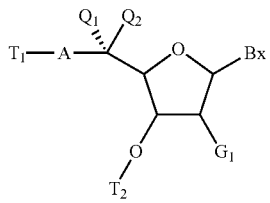

I wherein:
Bx is a heterocyclic base moiety;
A is O, S or $N(R_1)$;
$R_1$ is H, $C_1$-$C_6$ alkyl or substituted $C_1$-$C_6$ alkyl;
one of $T_1$ and $T_2$ is H, a protecting group or a phosphorus moiety and the other of $T_1$ and $T_2$ is H, a protecting group or a reactive phosphorus group;
one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—$[C(R_2)(R_3)]_n$—$[(C=O)_m$—$X]_j$—Z or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and
when j is 1 then Z is other than halogen or $N(E_2)(E_3)$ and when A is O then $G_1$ is other than halogen.

In certain embodiments, the compounds of Formula I are provided having the configuration:

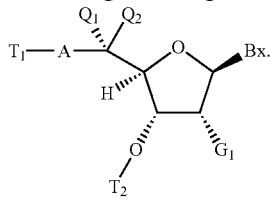

In certain embodiments, nucleosides have Formula II:

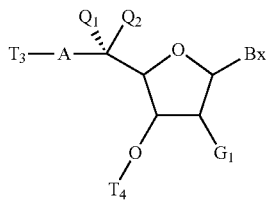

II wherein independently for each monomer of Formula II:
Bx is a heterocyclic base moiety;
A is O, S or $N(R_1)$;
$R_1$ is H, $C_1$-$C_6$ alkyl or substituted $C_1$-$C_6$ alkyl;
one of $T_3$ and $T_4$ is an internucleoside linking group linking the monomer to the oligomeric compound and the other of $T_3$ and $T_4$ is H, a protecting group, a phosphorus moiety, a 5' or 3'-terminal group or an internucleoside linking group linking the monomer to the oligomeric compound;
one of $Q_1$ and $Q_2$ is H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl and the other of $Q_1$ and $Q_2$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—$[C(R_2)(R_3)]_n$—$[(C=O)_m$—$X]_j$—Z or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;
$E_1$, $E_2$ and $E_3$ are each, independently, H, $C_1$-$C_6$ alkyl or substituted $C_1$-$C_6$ alkyl;
n is from 1 to about 6;
m is 0 or 1;
j is 0 or 1;
each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;
L is O, S or $NJ_3$;
each $J_1$, $J_2$ and $J_3$ is, independently, H or $C_1$-$C_6$ alkyl; and
when j is 1 then Z is other than halogen or $N(E_2)(E_3)$ and when A is O then $G_1$ is other than halogen.

In certain embodiments, nucleosides of Formula II have the configuration:

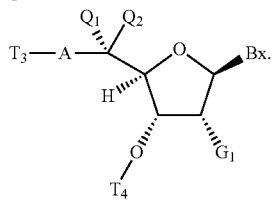

In certain embodiments, nucleosides have Formula III:

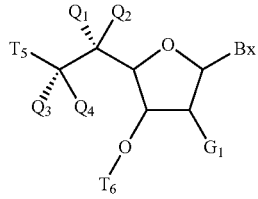

III wherein:
Bx is a heterocyclic base moiety;
$T_5$ is a phosphorus moiety or a reactive phosphorus group;
$T_6$ is H, a protecting group or a reactive phosphorus group;
$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
$G_1$ is O—$[C(R_2)(R_3)]_n$—$[(C=O)_m$—$X]_j$—Z or halogen;
each $R_2$ and $R_3$ is, independently, H or halogen;
X is O, S or $N(E_1)$;
Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and when $Q_1$, $Q_2$, $Q_3$ and $Q_4$ are each H or when $Q_1$ and $Q_2$ are H and $Q_3$ and $Q_4$ are each F or when $Q_1$ and $Q_2$ are each H and one of $Q_3$ and $Q_4$ is H and the other of $Q_3$ and $Q_4$ is $R_9$ then $G_1$ is other than H, hydroxyl, $OR_9$, halogen, $CF_3$, $CCl_3$, $CHCl_2$ and $CH_2OH$ wherein $R_9$ is alkyl, alkenyl, alkynyl, aryl or alkaryl.

In certain embodiments, the compounds of Formula III have the configuration:

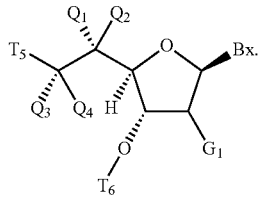

In certain embodiments, nucleosides have Formula IV:

IV

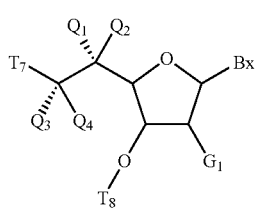

wherein independently for each monomer of Formula IV:

Bx is a heterocyclic base moiety;

one of $T_7$ and $T_8$ is an internucleoside linking group linking the monomer to the oligomeric compound and the other of $T_7$ and $T_8$ is H, a hydroxyl protecting group, a phosphorus moiety, a 5' or 3'-terminal group or an internucleoside linking group linking the monomer to the oligomeric compound;

$Q_1$, $Q_2$, $Q_3$ and $Q_4$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

$G_1$ is O—$[C(R_2)(R_3)]_n$—$[(C=O)—X]_j$—Z or halogen;

each $R_2$ and $R_3$ is, independently, H or halogen;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and when $Q_1$, $Q_2$, $Q_3$ and $Q_4$ are each H or when $Q_1$ and $Q_2$ are H and $Q_3$ and $Q_4$ are each F or when $Q_1$ and $Q_2$ are each H and one of $Q_3$ and $Q_4$ is H and the other of $Q_3$ and $Q_4$ is $R_9$ then $G_1$ is other than H, hydroxyl, $OR_9$, halogen, $CF_3$, $CCl_3$, $CHCl_2$ and $CH_2OH$ wherein $R_9$ is alkyl, alkenyl, alkynyl, aryl or alkaryl.

In certain embodiments, oligomeric compounds are provided comprising at least one monomer having Formula IV, wherein each monomer of Formula IV has the configuration:

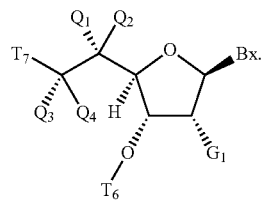

In certain embodiments, the present invention provides nucleosides comprising a modification at the 2'-position of the sugar. In certain embodiments, the invention provides nucleosides comprising a modification at the 5'-position of the sugar. In certain embodiments, the invention provides nucleosides comprising modifications at the 2'-position and the 5'-position of the sugar. In certain embodiments, modified nucleosides may be useful for incorporation into oligonucleotides. In certain embodiment, modified nucleosides are incorporated into oligonucleosides at the 5'-end of the oligonucleotide. In certain embodiments, modified nucleosides of the present invention have Formula VII:

VII

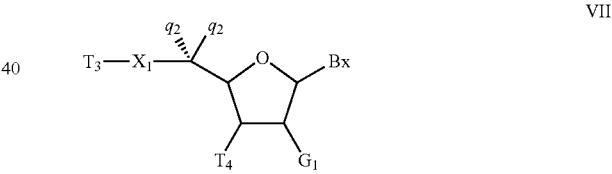

wherein:

Bx is a heterocyclic base moiety;

$X_1$ is O, S, N, or $CR_{10}R_{11}$ wherein each $R_{10}$ and $R_{11}$ is, independently, H or $C_1$-$C_6$ alkyl;

$T_3$ is a phosphorus moiety;

$T_4$ is an internucleoside linking group attaching the nucleoside to the remainder of the oligonucleotide;

$R_1$ is selected from halogen, amino, trifluoroalkyl, trifluoroalkoxy, azido, aminooxy, $C_1$-$C_6$ alkyl, $C_2$-$C_6$ alkenyl, $C_2$-$C_6$ alkynyl, substituted $C_1$-$C_6$ alkyl, substituted $C_1$-$C_6$ alkenyl, substituted $C_2$-$C_6$ alkynyl, O-alkyl, S-alkyl, $N(J_4)$-alkyl, O-alkenyl, S-alkenyl, $N(J_4)$-alkenyl, O-alkynyl, S-alkynyl or $N(J_4)$-alkynyl, O-aryl, S-aryl, N-aryl, O-aralkyl, S-aralkyl, $N(J_4)$-aralkyl and —$X_2$—V, wherein:

$X_2$ is O, S or $CR_7R_8$ wherein each $R_7$ and $R_8$ is, independently, H or $C_1$-$C_6$ alkyl;

V is selected from —$CH_2COOH$, —$CH_2CONH_2$, —$CH_2COOCH_2CH_3$, —$CH_2CONH(CH_2)_i$—S—$R_4$ where i is from 1 to 10, —$CH_2CONH(CH_2)_jNR_5R_6$ where j is from 1 to 6, and —$CH_2CONH\{(CH_2)_{k1}$—$N(H)\}_{k2}$—$(CH_2)_{k1}NH_2$ where each k1 is independently from 2 to 4 and k2 is from 2 to 10;

R$_4$ is selected from H, C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl, substituted C$_2$-C$_6$ alkynyl, C$_6$-C$_{14}$ aryl and a thio protecting group;

R$_5$ and R$_6$ are each, independently, selected from H, C$_1$-C$_6$ alkyl, substituted C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl and substituted C$_2$-C$_6$ alkynyl; and each q$_1$ and q$_2$ is, independently, selected from H, C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl and substituted C$_2$-C$_6$ alkynyl; provided that if q$_1$ and q$_2$ are both H, then:

R$_1$ is selected from, trifluoroalkoxy, azido, aminooxy, S-alkyl, N(J$_4$)-alkyl, O-alkenyl, S-alkenyl, N(J$_4$)-alkenyl, O-alkynyl, S-alkynyl or N(J$_4$)-alkynyl, and X$_2$—V; or X$_1$ is S, N, or CR$_7$R$_8$;

wherein each substituted group is, independently, mono or poly substituted with optionally protected substituent groups independently selected from halogen, oxo, OJ$_1$, NJ$_1$J$_2$, SJ$_1$, N$_3$, OC(=O)J$_1$ and CN, wherein each J$_1$ and J$_2$ is, independently, H or C$_1$-C$_6$ alkyl; and J$_4$ is hydrogen, or a protecting group.

In certain embodiments, the present invention provides modified nucleosides. In certain embodiments, modified nucleosides of the present invention have Formula XI.

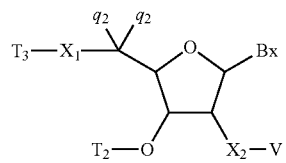

XI wherein:

Bx is a heterocyclic base moiety;

X$_1$ is O, S, N, or CR$_{10}$R$_{11}$ wherein each R$_{10}$ and R$_{11}$ is, independently, H or C$_1$-C$_6$ alkyl;

T$_1$ is H, a hydroxyl protecting group, or a phosphorus moiety;

T$_2$ is H, a hydroxyl protecting group, or a reactive phosphorus group;

each q$_1$ and q$_2$ is, independently, selected from H, C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl, and substituted C$_2$-C$_6$ alkynyl, provided that at least one of q$_1$ and q$_2$ is other than H;

X$_2$ is O, S or CR$_7$R$_8$ wherein each R$_7$ and R$_8$ is, independently, H, C$_1$-C$_6$ alkyl, or substituted C$_1$-C$_6$;

V is selected from C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl, substituted C$_2$-C$_6$ alkynyl, CH$_2$COOH, CH$_2$COONH$_2$, CH$_2$COOEt, —CH$_2$CONH(CH$_2$)$_i$—S—R$_4$ where i is from 1 to 10, CH$_2$CONH(CH$_2$)$_j$NR$_5$R$_6$ where j is from 1 to 6, and —CH$_2$CONH{(CH$_2$)$_{k1}$—N(H)}$_{k2}$—(CH$_2$)$_{k1}$NH$_2$ where each k1 is independently from 2 to 4 and k2 is from 2 to 10;

R$_4$ is selected from H, C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl, substituted C$_2$-C$_6$ alkynyl, C$_6$-C$_{14}$ aryl and a thio protecting group;

R$_5$ and R$_6$ are each, independently selected from H, C$_1$-C$_6$ alkyl, substituted C$_1$-C$_6$ alkyl, C$_2$-C$_6$ alkenyl, C$_2$-C$_6$ alkynyl, substituted C$_1$-C$_6$ alkyl, substituted C$_1$-C$_6$ alkenyl and substituted C$_2$-C$_6$ alkynyl; and wherein each substituted group is, independently selected from mono or poly substituted with optionally protected substituent groups independently selected from halogen, oxo, OJ$_1$, NJ$_1$J$_2$, SJ$_1$, N$_3$, OC(=O)J$_1$ and CN, wherein each J$_1$ and J$_2$ is independently H or C$_1$-C$_6$ alkyl.

In certain embodiments, nucleosides of the present invention include, but are not limited to any of the following:

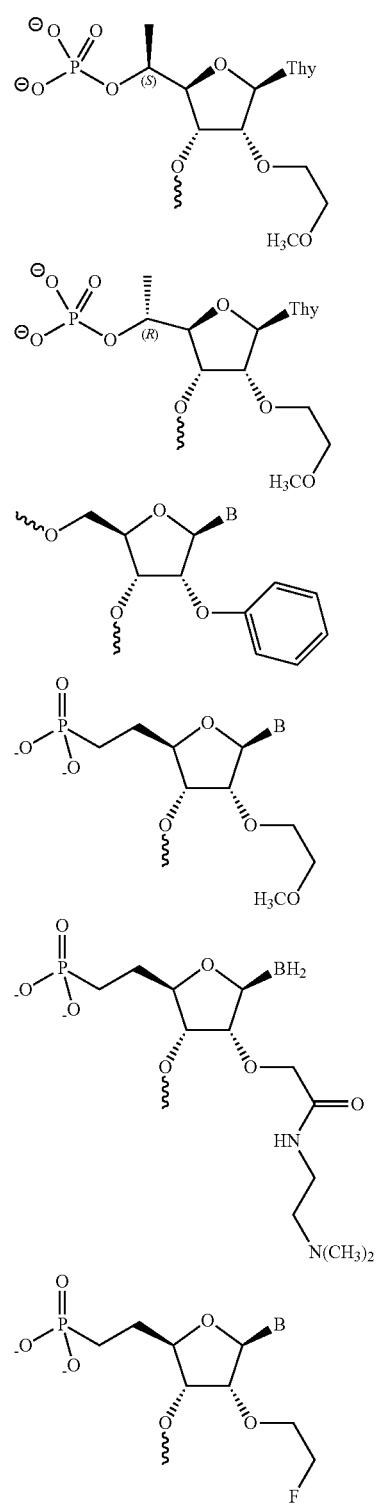

57
-continued
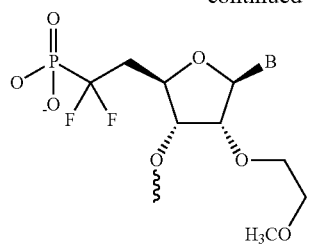
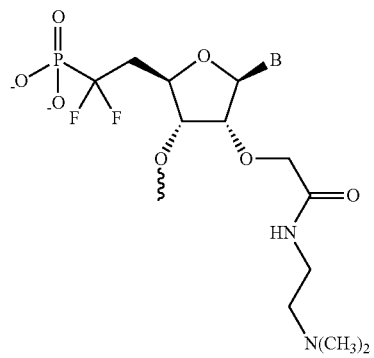
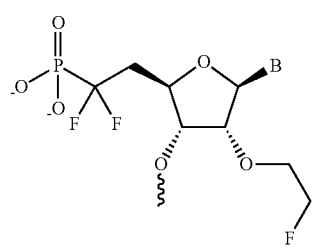
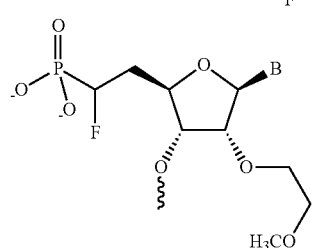
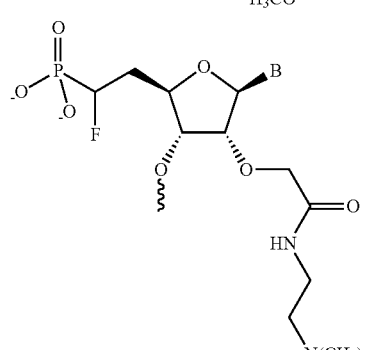
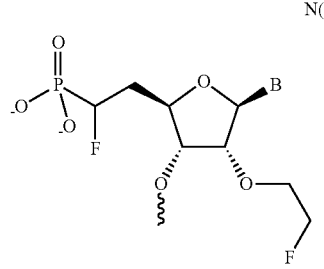
58
-continued
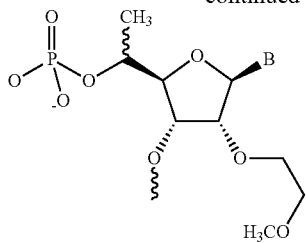
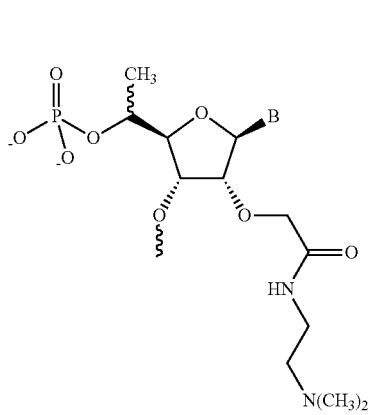
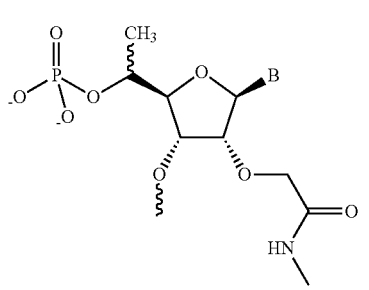
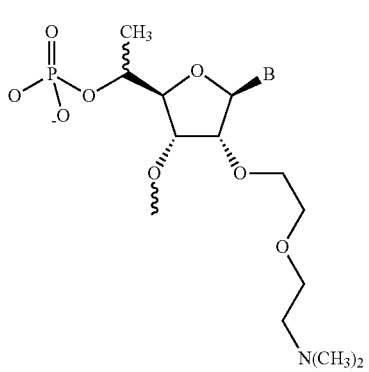
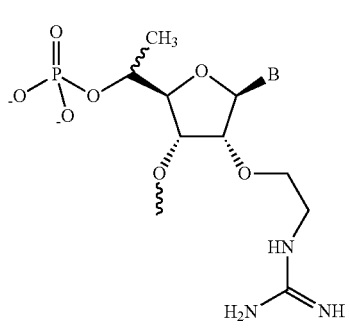

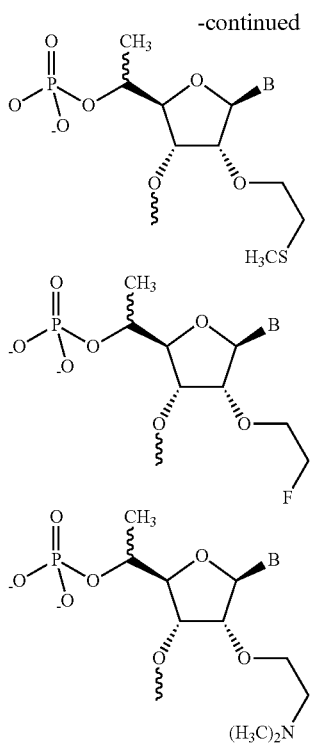

In certain embodiments, such nucleosides are incorporated into oligomeric compounds. In certain embodiments, such nucleosides are incorporated at the 5'-terminal end of an oligonucleotide or oligomeric compound.

In certain embodiments, the present invention provides modified oligonucleotides comprising one or more nucleosides comprising one or more previously described modification. In certain embodiments, such previously described modification is a modified sugar moiety. In certain embodiments, a modified sugar moiety is a bicyclic sugar moiety. In certain embodiments a modified sugar moiety is a non-bicyclic modified sugar moiety.

Certain modified sugar moiety moieties are known and can be used to alter, typically increase, the affinity of the antisense compound for its target and/or increase nuclease resistance. A representative list of preferred modified sugar moieties includes but is not limited to bicyclic modified sugar moieties (BNA's), including methyleneoxy BNA, ethyleneoxy (4'4-CH$_2$)$_2$—O-2') BNA and methyl(methyleneoxy) (4'-C(CH$_3$) H—O-2') BNA; substituted sugar moieties, especially 2'-substituted sugar moieties having a 2'-F, 2'-OCH$_3$ or a 2'-O(CH$_2$)$_2$—OCH$_3$ substituent group; and 4'-thio modified sugar moieties. Sugar moieties can also be replaced with sugar moiety mimetic groups among others. Methods for the preparations of modified sugar moieties are well known to those skilled in the art. Some representative patents and publications that teach the preparation of such modified sugar moieties include, but are not limited to, U.S. Pat. Nos. 4,981, 957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,531,584; 6,172,209; 6,271,358; and 6,600,032; and WO 2005/121371.

Certain Bicyclic Sugar Moieties

In certain embodiments, the present invention provides modified nucleosides comprising a bicyclic sugar moiety. Examples of bicyclic nucleosides include without limitation nucleosides comprising a bridge between the 4' and the 2' ribosyl ring atoms. In certain embodiments, oligomeric compounds provided herein include one or more bicyclic nucleosides wherein the bridge comprises one of the formulae: 4'40-(CH$_2$)—O-2' (LNA); 4'4-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., J. Org. Chem., 2009, 74, 118-134); and 4'-CH$_2$—C(=CH$_2$)-2' (and analogs thereof see published International Application WO 2008/154401, published on Dec. 8, 2008). Certain such sugar moieties have been described. See, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-79 (Jul. 4, 2007); U.S. Pat. Nos. 7,053,207; 6,268,490; 6,770,748; 6,794,499; 7,034,133; and 6,525,191; Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; and U.S. Pat. No. 6,670,461; International applications WO 2004/106356; WO 94/14226; WO 2005/021570; U.S. Patent Publication Nos. US2004-0171570; US2007-0287831; US2008-0039618; U.S. Pat. No. 7,399,845; U.S. patent Ser. Nos. 12/129,154; 60/989,574; 61/026,995; 61/026,998; 61/056,564; 61/086, 231; 61/097,787; 61/099,844; PCT International Applications Nos. PCT/US2008/064591; PCT/US2008/066154; PCT/US2008/068922; and Published PCT International Applications WO 2007/134181. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, nucleosides comprising a bicyclic sugar moiety have increased affinity for a complementary nucleic acid. In certain embodiments, nucleosides comprising a bicyclic sugar moiety provide resistance to nuclease degradation of an oligonucleotide in which they are incorporated. For example, methyleneoxy (4'-CH$_2$—O-2') BNA and other bicyclic sugar moiety analogs display duplex thermal stabilities with complementary DNA and RNA (Tm=+3 to +10° C.), stability towards 3'-exonucleolytic degradation and good solubility properties. Antisense oligonucleotides comprising BNAs have been described (Wahlestedt et al., Proc. Natl. Acad. Sci. U.S.A., 2000, 97, 5633-5638).

Certain bicyclic-sugar moiety containing nucleosides (or BNA nucleosides) comprise a bridge linking the 4' carbon and the 2' carbon of the sugar moiety. In certain embodiments, the bridging group is a methyleneoxy (4'-CH$_2$—O-2'). In certain embodiments, the bridging group is an ethyleneoxy (4'-CH$_2$CH$_2$—O-2') (Singh et al., Chem. Commun., 1998, 4, 455-456: Morita et al., Bioorganic Medicinal Chemistry, 2003, 11, 2211-2226).

In certain embodiments, bicyclic sugar moieties of BNA nucleosides include, but are not limited to, compounds having at least one bridge between the 4' and the 2' position of the sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_1$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOL acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R$_1$)—O— or —C(R$_a$R$_b$)—O—N(R$_a$)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'CH$_2$—O—N(R$_a$)-2' and 4'-CH$_2$—N(R$_a$)—O-2'- wherein each R$_a$ is, independently, H, a protecting group or C$_1$-C$_{12}$ alkyl.

In certain embodiments, bicyclic nucleosides are further defined by isomeric configuration. For example, a nucleoside comprising a 4'-2' methylenoxy bridge, may be in the α-L configuration or in the β-D configuration. Previously, alpha-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, and (F) Methyl(methyleneoxy) (4'-C(CH$_3$)H—O-2') BNA, as depicted below.

(A)

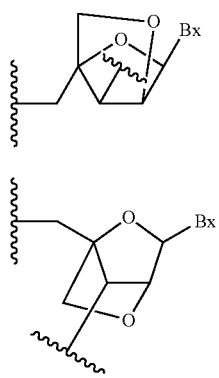

(B)

(C)

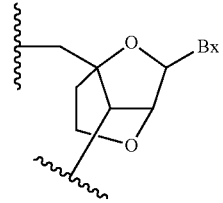

(D)

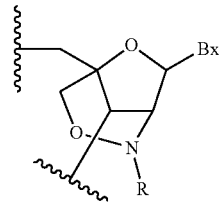

(E)

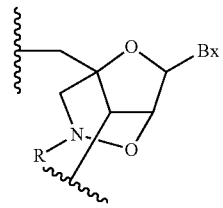

(F)

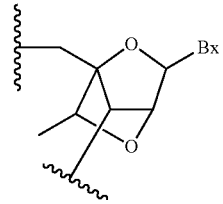

wherein Bx is the base moiety. In certain embodiments, bicyclic nucleosides include, but are not limited to, the structures below:

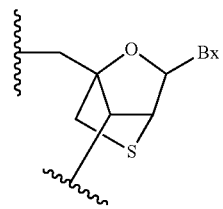 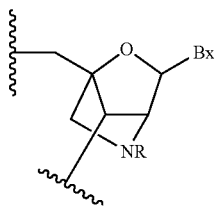

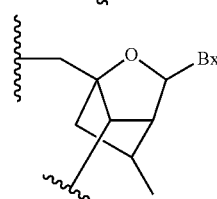

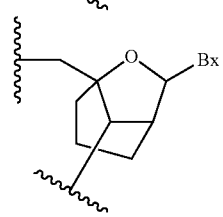

wherein Bx is the base moiety.

In certain embodiments, bicyclic nucleoside having the formula:

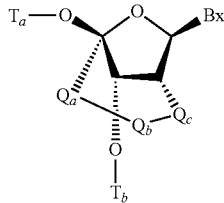

wherein
Bx is a heterocyclic base moiety;
$-Q_a-Q_b-Q_c-$ is $-CH_2-N(R_c)-CH_2-$, $-C(=O)-N(R_c)-CH_2-$, $-CH_2-O-N(R_c)-$ or $N(R_c)-O-CH_2-$;
$R_c$ is $C_1-C_{12}$ alkyl or an amino protecting group; and
$T_a$ and $T_b$ are each, independently, hydroxyl, a protected hydroxyl, a conjugate group, an activated phosphorus moiety or a covalent attachment to a support medium.

In certain embodiments, bicyclic nucleoside having the formula:

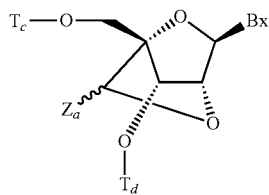

wherein:
Bx is a heterocyclic base moiety;
$T_c$ is H or a hydroxyl protecting group;
$T_d$ is H, a hydroxyl protecting group or a reactive phosphorus group;
$Z_a$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl, acyl, substituted acyl, or substituted amide.

In one embodiment, each of the substituted groups, is, independently, mono or poly substituted with optionally protected substituent groups independently selected from halogen, oxo, hydroxyl, $OJ_c$, $NJ_cJ_d$, $SJ_c$, $N_3$, $OC(=X)J_c$, $OC(=X)NJ_cJ_d$, $NJ_eC(=X)NJ_cJ_d$ and CN, wherein each $J_c$, $J_d$ and $J_e$ is, independently, H or $C_1-C_6$ alkyl, and X is O, S or $NJ_c$.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1-C_6$ alkyl, or substituted $C_1-C_6$ alkyl and X is O or $NJ_c$.

In one embodiment, the $Z_a$ group is $C_1-C_6$ alkyl substituted with one or more $X^x$, wherein each $X^x$ is independently $OJ_c$, $NJ_cJ_d$, $SJ_c$, $N_3$, $OC(=X)J_c$, $OC(=X)NJ_cJ_d$, $NJ_eC(=X)NJ_cJ_d$ or CN; wherein each $J_c$, $J_d$ and $J_e$ is, independently, H or $C_1-C_6$ alkyl, and X is O, S or $NJ_c$. In another embodiment, the $Z_a$ group is $C_1-C_6$ alkyl substituted with one or more $X^x$, wherein each $X^x$ is independently halo (e.g., fluoro), hydroxyl, alkoxy (e.g., $CH_3O-$), substituted alkoxy or azido.

In certain embodiments, bicyclic nucleoside having the formula:

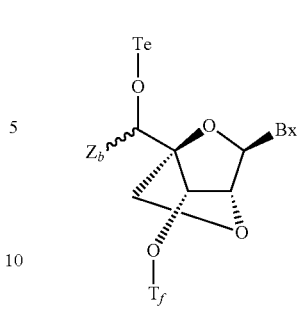

wherein:
Bx is a heterocyclic base moiety;
one of $T_e$ and $T_f$ is H or a hydroxyl protecting group and the other of $T_e$ and $T_f$ is H, a hydroxyl protecting group or a reactive phosphorus group;
$Z_b$ is $C_1-C_6$ alkyl, $C_2-C_6$ alkenyl, $C_2-C_6$ alkynyl, substituted $C_1-C_6$ alkyl, substituted $C_2-C_6$ alkenyl, substituted $C_2-C_6$ alkynyl or substituted acyl ($C(=O)-$);
wherein each substituted group is mono or poly substituted with substituent groups independently selected from halogen, $C_1-C_6$ alkyl, substituted $C_1-C_6$ alkyl, $C_2-C_6$ alkenyl, substituted $C_2-C_6$ alkenyl, $C_2-C_6$ alkynyl, substituted $C_2-C_6$ alkynyl, $OJ_1$, $SJ_1$, $NJ_fJ_g$, $N_3$, $COOJ_f$, CN, $O-C(=O)NJ_fJ_g$, $N(H)C(=NH)NR_dR_e$ or $N(H)C(=X)N(H)J_g$ wherein X is O or S; and
each $J_f$ and $J_g$ is, independently, H, $C_1-C_6$ alkyl, substituted $C_1-C_6$ alkyl, $C_2-C_6$ alkenyl, substituted $C_2-C_6$ alkenyl, $C_2-C_6$ alkynyl, substituted $C_2-C_6$ alkynyl, $C_1-C_6$ aminoalkyl, substituted $C_1-C_6$ aminoalkyl or a protecting group.

In certain embodiments, bicyclic nucleoside having the formula:

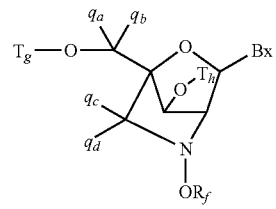

wherein:
Bx is a heterocyclic base moiety;
one of $T_g$ and $T_h$ is H or a hydroxyl protecting group and the other of $T_g$ and $T_b$ is H, a hydroxyl protecting group or a reactive phosphorus group;
$R_f$ is $C_1-C_6$ alkyl, substituted $C_1-C_6$ alkyl, $C_2-C_6$ alkenyl, substituted $C_2-C_6$ alkenyl, $C_2-C_6$ alkynyl or substituted $C_2-C_6$ alkynyl;
$q_a$ and $q_b$ are each independently, H, halogen, $C_1-C_6$ alkyl, substituted $C_1-C_6$ alkyl, $C_2-C_6$ alkenyl, substituted $C_2-C_6$ alkenyl, $C_2-C_6$ alkynyl or substituted $C_2-C_6$ alkynyl, $C_1-C_6$ alkoxyl, substituted $C_1-C_6$ alkoxyl, acyl, substituted acyl, $C_1-C_6$ aminoalkyl or substituted $C_1-C_6$ aminoalkyl;
$q_c$ and $q_d$ are each independently, H, halogen, $C_1-C_6$ alkyl, substituted $C_1-C_6$ alkyl, $C_2-C_6$ alkenyl, substituted $C_2-C_6$ alkenyl, $C_2-C_6$ alkynyl or substituted $C_2-C_6$ alkynyl, $C_1-C_6$ alkoxyl, substituted $C_1-C_6$ alkoxyl, acyl, substituted acyl, $C_1-C_6$ aminoalkyl or substituted $C_1-C_6$ aminoalkyl;
wherein each substituted group is, independently, mono or poly substituted with substituent groups independently selected from halogen, $OJ_h$, $SJ_h$, $NJ_hJ_i$, $N_3$, $COOJ_h$, CN, O—C(=O)$NJ_hJ_i$, N(H)C(=NH)$NJ_hJ_i$ or N(H)C(=X)N(H) $J_i$ wherein X is O or S; and each $J_h$ and $J_i$ is, independently, H, $C_1$-$C_6$ alkyl, $C_2$-$C_6$ alkenyl, $C_2$-$C_6$ alkynyl, $C_1$-$C_6$ aminoalkyl or a protecting group.

In certain embodiments, bicyclic nucleoside having the formula:

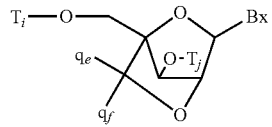

wherein:

Bx is a heterocyclic base moiety;

one of $T_i$ and $T_j$ is H or a hydroxyl protecting group and the other of $T_i$ and $T_j$ is H, a hydroxyl protecting group or a reactive phosphorus group;

$q_e$ and $q_f$ are each, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl;

each substituted group is, independently, mono or poly substituted with substituent groups independently selected from halogen, $C_1$-$C_6$ alkyl, $C_2$-$C_6$ alkenyl, $C_2$-$C_6$ alkynyl, $OJ_j$, $SJ_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=O)$NJ_jJ_k$ or N(H)C(=S)$NJ_jJ_k$; and each $J_j$ and $J_k$ is, independently, H, $C_1$-$C_6$ alkyl, $C_2$-$C_6$ alkenyl, $C_2$-$C_6$ alkynyl, $C_1$-$C_6$ aminoalkyl or a protecting group.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA and 2'-thio-BNAs, have also been prepared (Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., J. Org. Chem., 1998, 63, 10035-10039). In addition, 2'-Amino- and 2'-methylamino-BNA's have been prepared and the thermal stability of their duplexes with complementary RNA and DNA strands has been previously reported.

Certain Non-Bicyclic Modified Sugar Moieties

In certain embodiments, the present invention provides modified nucleosides comprising modified sugar moieties that are not bicyclic sugar moieties. Certain such modified nucleosides are known. In certain embodiments, the sugar ring of a nucleoside may be modified at any position. Examples of sugar modifications useful in this invention include, but are not limited to compounds comprising a sugar substituent group selected from: OH, F, O-alkyl, S-alkyl, N-alkyl, or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. In certain such embodiments, such substituents are at the 2' position of the sugar.

In certain embodiments, modified nucleosides comprise a substituent at the 2' position of the sugar. In certain embodiments, such substituents are selected from: a halide, including, but not limited to F, allyl, amino, azido, thio, O-allyl, O—$C_1$-$C_{10}$ alkyl, —$OCF_3$, O—$(CH_2)_2$—O—$CH_3$, 2'-O($CH_2$)$_2SCH_3$, O—$(CH_2)_2$—O—N($R_m$)($R_n$), or O—CH2—C(=O)—N($R_m$)($R_n$), where each $R_m$ and $R_n$ is, independently, H or substituted or unsubstituted $C_1$-$C_{10}$ alkyl.

In certain embodiments, modified nucleosides suitable for use in the present invention are: 2-methoxyethoxy, 2'-O-methyl (2'-O—$CH_3$), 2'-fluoro (2'-F).

In certain embodiments, modified nucleosides having a substituent group at the 2'-position selected from: O[($CH_2$)$_n$O]$_mCH_3$, O($CH_2$)$_nNH_2$, O($CH_2$)$_nCH_3$, O($CH_2$)$_nONH_2$, $OCH_2$C(=O)N(H)$CH_3$, and O($CH_2$)$_n$ON[($CH_2$)$_nCH_3$]$_2$, where n and m are from 1 to about 10. Other 2'-sugar substituent groups include: $C_1$ to $C_{10}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an oligomeric compound, and other substituents having similar properties.

In certain embodiments, modified nucleosides comprise a 2'-MOE side chain (Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

In certain embodiments, 2'-Sugar substituent groups are in either the arabino (up) position or ribo (down) position. In certain such embodiments, a 2'-arabino modification is 2'-F arabino (FANA). Similar modifications can also be made at other positions on the sugar, particularly the 3' position of the sugar on a 3'-terminal nucleoside or in 2'-5' linked oligonucleotides and the 5' position of 5' terminal nucleotide.

In certain embodiments, nucleosides suitable for use in the present invention have sugar surrogates such as cyclobutyl in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

In certain embodiments, nucleosides suitable for use in the present invention comprise sugar surrogates, which replace the pentafuranose ring of an unmodified nucleoside. In certain embodiments, such sugar surrogates include but are not limited to substituted or unsubstituted tetrahydropyran rings, such as F—HNA.

In certain embodiments, modified tetrahydropyran nucleoside (F-HNA) having the formula:

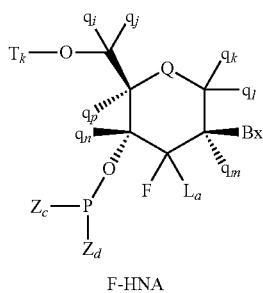

F-HNA wherein:

Bx is a heterocyclic base moiety;

$T_k$ is a hydroxyl protecting group;

$L_a$ is H, halogen, $C_1$-$C_6$ alkyl or substituted $C_1$-$C_6$ alkyl;

$Z_c$ is O⁻ or $OE_a$;

$Z_d$ is OH, $OE_a$ or $N(E_a)(E_b)$;

each $E_a$ and $E_b$ is, independently, alkyl or substituted alkyl;

$q_i$, $q_j$, $q_k$, $q_l$, $q_m$, $q_n$ and $q_p$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

wherein each substituted group comprises one or more optionally protected substituent groups independently selected from halogen, $OJ_m$, $NJ_mJ_n$, $SJ_m$, $N_3$, $OC(=X)J_m$, $OC(=X)NJ_mJ_m$, $NJ_pC(=X)NJ_mJ_n$ and CN, wherein each $J_m$, $J_n$ and $J_p$ is, independently, H or $C_1$-$C_6$ alkyl, and X is O, S or $NJ_m$.

In certain embodiments, tetrahydropyran nucleoside analogs having Formula F are provided wherein $q_i$, $q_j$, $q_k$, $q_l$, $q_m$, $q_n$ and $q_p$ are each H. In certain embodiments, at least one of $q_i$, $q_j$, $q_k$, $q_l$, $q_m$, $q_n$ and $q_p$ is other than H. In certain embodiments, at least one of $q_i$, $q_j$, $q_k$, $q_l$, $q_m$, $q_n$ and $q_p$ is methyl.

In certain embodiments, tetrahydropyran nucleoside analogs having Formula F are provided wherein $L_a$ is F. In certain embodiments, $L_a$ is H.

In certain embodiments, tetrahydropyran nucleoside analogs having Formula F are provided wherein $Z_c$ is O⁻ and $Z_d$ is OH. In certain embodiments, $Z_c$ is $O(CH_2)_2CN$, $Z_d$ is $N[CH_2(CH_3)_2]_2$ and $T_k$ is 4,4'-dimethoxytrityl. In certain embodiments, $Z_c$ is O⁻ and $Z_d$ is OH which provides an H phosphonate group at the 4' position of the tetrahydropyran nucleoside analog which can also be written as 3'-O—P(=O)(H)(OH or O⁻amine⁺). In certain embodiments, $Z_c$ is $O(CH_2)_2CN$, $Z_d$ is $N[CH_2(CH_3)_2]_2$ and $T_k$ is 4,4'-dimethoxytrityl which provides a phosphoramidite at the 3'-position.

B. Certain Nucleobases

In certain embodiments, nucleosides of the present invention comprise unmodified nucleobases. In certain embodiments, nucleosides of the present invention comprise modified nucleobases.

In certain embodiments, nucleobase modifications can impart nuclease stability, binding affinity or some other beneficial biological property to the oligomeric compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases, many examples of which such as 5-methylcytosine (5-me-C), 5-hydroxymethyl cytosine, 7-deazaguanine and 7-deazaadenine among others.

Heterocyclic base moieties can also include those in which the purine or pyrimidine base is replaced with other heterocycles, for example 7-deaza-adenine, 7-deazaguanosine, 2-aminopyridine and 2-pyridone. Certain modified nucleobases are disclosed in, for example, Swayze, E. E. and Bhat, B., *The medicinal Chemistry of Oligonucleotides* in ANTISENSE DRUG TECHNOLOGY, Chapter 6, pages 143-182 (Crooke, S. T., ed., 2008); U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2 aminopropyladenine, 5-propynyluracil and 5-propynylcytosine.

In certain embodiments, nucleobases comprise polycyclic heterocyclic compounds in place of one or more heterocyclic base moieties of a nucleobase. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs.

Representative cytosine analogs that make 3 hydrogen bonds with a guanosine in a second strand include 1,3-diazaphenoxazine-2-one (Kurchavov, et al., *Nucleosides and Nucleotides*, 1997, 16, 1837-1846), 1,3-diazaphenothiazine-2-one (Lin, K.-Y.; Jones, R. J.; Matteucci, M. J. Am. Chem. Soc. 1995, 117, 3873-3874) and 6,7,8,9-tetrafluoro-1,3-diazaphenoxazine-2-one (Wang, J.; Lin, K.-Y., Matteucci, M. Tetrahedron Lett. 1998, 39, 8385-8388). When incorporated into oligonucleotides, these base modifications have been shown to hybridize with complementary guanine and the latter was also shown to hybridize with adenine and to enhance helical thermal stability by extended stacking interactions (also see U.S. Patent Application Publication 20030207804 and U.S. Patent Application Publication 20030175906, both of which are incorporated herein by reference in their entirety).

Helix-stabilizing properties have been observed when a cytosine analog/substitute has an aminoethoxy moiety attached to the rigid 1,3-diazaphenoxazine-2-one scaffold (Lin, K.-Y.; Matteucci, M. J. Am. Chem. Soc. 1998, 120, 8531-8532). Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification. On the other hand, the gain in helical stability does not compromise the specificity of the oligonucleotides.

The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Tricyclic heterocyclic compounds and methods of using them that are amenable to the present invention are disclosed in U.S. Pat. Nos. 6,028,183, and 6,007,992, the contents of both are incorporated herein in their entirety.

The enhanced binding affinity of the phenoxazine derivatives together with their sequence specificity makes them valuable nucleobase analogs for the development of more potent antisense-based drugs. The activity enhancement was even more pronounced in case of G-clamp, as a single substitution was shown to significantly improve the in vitro potency of a 20mer 2'-deoxyphosphorothioate oligonucleotides (Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518).

Modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. Patent Application Publication 20030158403, each of which is incorporated herein by reference in its entirety.

III. Certain Oligonucleotides

In certain embodiments, the present invention provides modified oligonucleotides. In certain embodiments, modified oligonucleotides of the present invention comprise modified nucleosides. In certain embodiments, modified oligonucleotides of the present invention comprise modified internucleoside linkages. In certain embodiments, modified oligonucleotides of the present invention comprise modified nucleosides and modified internucleoside linkages.

A. Certain Internucleoside Linkages

In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)2—O—); and N,N'-dimethylhydrazine (—CH$_2$—N(CH$_3$)—N(CH$_3$)—). Oligonucleotides having non-phosphorus internucleoside linking groups may be referred to as oligonucleosides. Modified linkages, compared to natural phosphodiester linkages, can be used to alter, typically increase, nuclease resistance of the oligomeric compound. In certain embodiments, internucleoside linkages having a chiral atom can be prepared a racemic mixture, as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids et al. Included in the antisense compounds provided herein are all such possible isomers, as well as their racemic and optically pure forms.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-CH$_2$—C(=O)—N(H)-5'), amide-4 (3'-CH$_2$—N(H)—C(=O)-5') and methylphosphonate wherein a phosphorus atom is not always present.

As used herein the phrase "neutral internucleoside linkage" is intended to include internucleoside linkages that are non-ionic. Neutral internucleoside linkages include without limitation, phosphotriesters, methylphosphonates, MMMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

B. Certain Lengths

In certain embodiments, the invention provides oligomeric compounds comprising oligonucleotides. In certain embodiments, the present invention provides oligomeric compounds including oligonucleotides of any of a variety of ranges of lengths. In certain embodiments, the invention provides oligomeric compounds comprising oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide consisting of 8-30 nucleosides excludes oligonucleotides having 31 nucleosides, but, unless otherwise indicated, such an oligonucleotide may further comprise, for example one or more conjugates, terminal groups, or other substituents. In certain embodiments, terminal groups include, but are not limited to, terminal group nucleosides. In such embodiments, the terminal group nucleosides are differently modified than the terminal nucleoside of the oligonucleotide, thus distinguishing such terminal group nucleosides from the nucleosides of the oligonucleotide.

C. Certain Motifs

In certain embodiments, the present invention provides oligonucleotides comprising one or more regions having a particular nucleoside motif.

1. Certain 5'-Terminal Nucleosides

In certain embodiments, the 5'-terminal nucleoside of a modified oligonucleotide of the present invention comprises a phosphorous moiety at the 5'-end. In certain embodiments the 5'-terminal nucleoside comprises a 2'-modification. In certain such embodiments, the 2'-modification of the 5'-terminal nucleoside is a cationic modification. In certain embodiments, the 5'-terminal nucleoside comprises a 5'-modification. In certain embodiments, the 5'-terminal nucleoside comprises a 2'-modification and a 5'-modification.

In certain embodiments, the 5'-terminal nucleoside of an oligonucleotide is a nucleoside of Formula II. In certain embodiments, the 5'-terminal nucleoside is a nucleoside of Formula IV. In certain embodiments, the 5'-terminal nucleoside is a nucleoside of Formula VI. In certain embodiments, the 5'-terminal nucleoside is a nucleoside of Formula VII. In certain embodiments, the 5'-terminal nucleoside is a nucleoside of Formula VII. In certain embodiments, the 5'-terminal nucleoside is a nucleoside of Formula XIII. In certain embodiments, the 5'-terminal nucleoside is a nucleoside of Formula XIV. In certain embodiments, the two 5'-terminal nucleosides have Formula IX. In certain embodiments, the two 5'-terminal nucleosides have Formula X.

In certain embodiments, the 5'-terminal nucleoside is a 5'-stabilizing nucleoside. In certain embodiments, the modifications of the 5'-terminal nucleoside stabilize the 5'-phosphate. In certain embodiments, oligonucleotides comprising modifications of the 5'-terminal nucleoside are resistant to exonucleases. In certain embodiments, oligonucleotides comprising modifications of the 5'-terminal nucleoside have improved antisense properties. In certain such embodiments, oligonucleotides comprising modifications of the 5'-terminal nucleoside have improved association with members of the RISC pathway. In certain embodiments, oligonucleotides comprising modifications of the 5'-terminal nucleoside have improved affinity for Ago2.

In certain embodiments, the 5' terminal nucleoside is attached to a plurality of nucleosides by a modified linkage. In certain such embodiments, the 5' terminal nucleoside is a plurality of nucleosides by a phosphorothioate linkage.

2. Certain Alternating Regions

In certain embodiments, oligonucleotides of the present invention comprise one or more regions of alternating modifications. In certain embodiments, oligonucleotides comprise one or more regions of alternating nucleoside modifications. In certain embodiments, oligonucleotides comprise one or more regions of alternating linkage modifications. In certain embodiments, oligonucleotides comprise one or more regions of alternating nucleoside and linkage modifications.

In certain embodiments, oligonucleotides of the present invention comprise one or more regions of alternating 2'-F modified nucleosides and 2'-OMe modified nucleosides. In certain such embodiments, such regions of alternating 2'F modified and 2'OMe modified nucleosides also comprise alternating linkages. In certain such embodiments, the linkages at the 3' end of the 2'-F modified nucleosides are phosphorothioate linkages. In certain embodiments, the linkages at the 3' end of the 2'OMe nucleosides are phosphodiester linkages. In certain embodiments, such alternating regions are:

(2'-F)—(PS)-(2'-OMe)-(PO)

In certain embodiments, oligomeric compounds comprise 2, 3, 4, 5, 6, 7, 8, 9, 10, or 11 such alternating regions. Such regions may be contiguous or may be interrupted by differently modified nucleosides or linkages.

In certain embodiments, one or more alternating regions in an alternating motif include more than a single nucleoside of a type. For example, oligomeric compounds of the present invention may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA; or
ABABBAABBABABAA;

wherein A is a nucleoside of a first type and B is a nucleoside of a second type. In certain embodiments, A and B are each selected from 2'-F, 2'-OMe, BNA, DNA, and MOE.

In certain embodiments, A is DNA. In certain embodiments, B is 4'-CH$_2$O-2'-BNA. In certain embodiments, A is DNA and B is 4'-CH$_2$O-2'-BNA. In certain embodiments A is 4'-CH$_2$O-2'-BNA. In certain embodiments, B is DNA. In certain embodiments A is 4'-CH$_2$O-2'-BNA and B is DNA. In certain embodiments, A is 2'-F. In certain embodiments, B is 2'-OMe. In certain embodiments, A is 2'-F and B is 2'-OMe. In certain embodimentns, A is 2'-OMe. In certain embodiments, B is 2'-F. In certain embodiments, A is 2'-OMe and B is 2'-F. In certain embodiments, A is DNA and B is 2'-OMe. In certain embodiments, A is 2'-OMe and B is DNA.

In certain embodiments, oligomeric compounds having such an alternating motif also comprise a 5' terminal nucleoside comprising a phosphate stabilizing modification. In certain embodiments, oligomeric compounds having such an alternating motif also comprise a 5' terminal nucleoside comprising a 2'-cationic modification. In certain embodiments, oligomeric compounds having such an alternating motif also comprise a 5' terminal nucleoside of formula II, IV, VI, VII, VIII, XIII, or XIV. In certain embodiments, oligomeric compounds having such an alternating motif comprise a 5' terminal di-nucleoside of formula IX or X.

3. Two-Two-Three Motifs

In certain embodiments, oligonucleotides of the present invention comprise a region having a 2-2-3 motif. Such regions comprises the following motif:

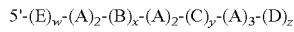

wherein: A is a first type of modified nucleosde;
B, C, D, and E are nucleosides that are differently modified than A, however, B, C, D, and E may have the same or different modifications as one another;
w and z are from 0 to 15;
x and y are from 1 to 15.

In certain embodiments, A is a 2'-OMe modified nucleoside. In certain embodiments, B, C, D, and E are all 2'-F modified nucleosides. In certain embodiments, A is a 2'-OMe modified nucleoside and B, C, D, and E are all 2'-F modified nucleosides.

In certain embodiments, the linkages of a 2-2-3 motif are all modified linkages. In certain embodiments, the linkages are all phosphorothioate linkages. In certain embodimentns, the linkages at the 3'-end of each modification of the first type are phosphodiester.

In certain embodiments, Z is 0. In such embodiments, the region of three nucleosides of the first type are at the 3'-end of the oligonucleotide. In certain embodiments, such region is at the 3'-end of the oligomeric compound, with no additional groups attached to the 3' end of the region of three nucleosides of the first type. In certain embodiments, an oligomeric compound comprising an oligonucleotide where Z is 0, may comprise a terminal group attached to the 3'-terminal nucleoside. Such terminal groups may include additional nucleosides. Such additional nucleosides are typically non-hybridizing nucleosides.

In certain embodiments, Z is 1-3. In certain embodiments, Z is 2. In certain embodiments, the nucleosides of Z are 2'-MOE nucleosides. In certain embodiments, Z represents non-hybridizing nucleosides. To avoid confussion, it is noted that such non-hybridizing nucleosides might also be described as a 3'-terminal group with Z=0.

D. Combinations of Motifs

It is to be understood, that certain of the above described motifs and modifications may be combined. Since a motif may comprises only a few nucleosides, a particular oligonucleotide may comprise two or more motifs. By way of non-limiting example, in certain embodiments, oligomeric compounds may have nucleoside motifs as described in the table below. In the table below, the term "None" indicates that a particular feature is not present in the oligonucleotide. For example, "None" in the column labeled "5' motif/modification" indicates that the 5' end of the oligonucleotide comprises the first nucleoside of the central motif.

| 5' motif/modification | Central Motif | 3'-motif |
|---|---|---|
| Formula II, IV, VI, VII, VIII, IX, X, XIII, or XIV | Alternating | 2 MOE nucleosides |
| Formula II, IV, VI, VII, VIII, IX, X, XIII, or XIV | 2-2-3 motif | 2 MOE nucleosides |
| Formula II, IV, VI, VII, VIII, IX, X, XIII, or XIV | Uniform | 2 MOE nucleosides |
| Formula II, IV, VI, VII, VIII, IX, X, XIII, or XIV | Alternating | 2 MOE nucleosides |
| Formula II, IV, VI, VII, VIII, IX, X, XIII, or XIV | Alternating | 2 MOE A's |
| Formula II, IV, VI, VII, VIII, IX, X, XIII, or XIV | 2-2-3 motif | 2 MOE A's |
| Formula II, IV, VI, VII, VIII, IX, X, XIII, or XIV | Uniform | 2 MOE A's |
| Formula II, IV, VI, VII, VIII, IX, X, XIII, or XIV | Alternating | 2 MOE U's |
| Formula II, IV, VI, VII, VIII, IX, X, XIII, or XIV | 2-2-3 motif | 2 MOE U's |
| Formula II, IV, VI, VII, VIII, IX, X, XIII, or XIV | Uniform | 2 MOE U's |
| None | Alternating | 2 MOE nucleosides |
| None | 2-2-3 motif | 2 MOE nucleosides |
| None | Uniform | 2 MOE nucleosides |

Oligomeric compounds having any of the various nucleoside motifs described herein, may have any linkage motif. For example, the oligomeric compounds, including but not limited to those described in the above table, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS |

As is apparent from the above, non-limiting tables, the lengths of the regions defined by a nucleoside motif and that of a linkage motif need not be the same. For example, the 3' region in the nucleoside motif table above is 2 nucleosides, while the 3'-region of the linkage motif table above is 6-8 nucleosides. Combining the tables results in an oligonucleotide having two 3'-terminal MOE nucleosides and six to eight 3'-terminal phosphorothioate linkages (so some of the linkages in the central region of the nucleoside motif are phosphorothioate as well). To further illustrate, and not to limit in any way, nucleoside motifs and sequence motifs are combined to show five non-limiting examples in the table below. The first column of the table lists nucleosides and linkages by position from N1 (the first nucleoside at the 5'-end) to N20 (the $20^{th}$ position from the 5'-end). In certain embodiments, oligonucleotides of the present invention are longer than 20 nucleosides (the table is merely exemplary). Certain positions in the table recite the nucleoside or linkage "none" indicating that the oligonucleotide has no nucleoside at that position.

| Pos | A | B | C | D | E | F |
|-----|---|---|---|---|---|---|
| N1 | Formula II, IV, VI, VII, VIII, IX, X, XIII, or XIV | Formula II, IV, VI, VII, VIII, IX, X, XIII, or XIV | Formula II, IV, VI, VII, VIII, IX, X, XIII, or XIV | Formula II, IV, VI, VII, VIII, IX, X, XIII, or XIV | Formula II, IV, VI, VII, VIII, IX, X, XIII, or XIV | 2'-F |
| L1 | PS | PS | PS | PS | PO | PO |
| N2 | 2'-F | 2'-F | 2'-F | 2'-OMe | MOE | 2'-OMe |
| L2 | PS | PS | PS | PO | PS | PO |
| N3 | 2'-OMe | 2'-F | 2'-F | 2'-F | 2'-F | 2'-F |
| L3 | PO | PS | PS | PS | PS | PS |
| N4 | 2'-F | 2'-F | 2'-F | 2'-OMe | 2'-F | 2'-OMe |
| L4 | PS | PS | PS | PO | PS | PO |
| N5 | 2'-OMe | 2'-F | 2'-F | 2'-F | 2'-OMe | 2'-F |
| L5 | PO | PS | PS | PS | PO | PS |
| N6 | 2'-F | 2'-OMe | 2'-F | 2'-OMe | 2'-OMe | 2'-OMe |
| L6 | PS | PO | PS | PO | PO | PO |
| N7 | 2'-OMe | 2'-OMe | 2'-F | 2'-F | 2'-OMe | 2'-F |
| L7 | PO | PO | PS | PS | PO | PS |
| N8 | 2'-F | 2'-F | 2'-F | 2'-OMe | 2'-F | 2'-OMe |
| L8 | PS | PS | PS | PO | PS | PO |
| N9 | 2'-OMe | 2'-F | 2'-F | 2'-F | 2'-F | 2'-F |
| L9 | PO | PS | PS | PS | PS | PS |
| N10 | 2'-F | 2'-OMe | 2'-F | 2'-OMe | 2'-OMe | 2'-OMe |
| L10 | PS | PO | PS | PO | PO | PO |
| N11 | 2'-OMe | 2'-OMe | 2'-F | 2'-F | 2'OMe | 2'-F |
| L11 | PO | PO | PS | PS | PO | PS |
| N12 | 2'-F | 2'-F | 2'-F | 2'-F | 2'-F | 2'-OMe |
| L12 | PS | PS | PS | PO | PS | PO |
| N13 | 2'-OMe | 2'-F | 2'-F | 2'-F | 2'-F | 2'-F |
| L13 | PO | PS | PS | PS | PS | PS |
| N14 | 2'-F | 2'-OMe | 2'-F | 2'-F | 2'-F | 2'-F |
| L14 | PS | PS | PS | PS | PS | PS |
| N15 | 2'-OMe | 2'OMe | 2'-F | 2'-F | 2'-MOE | 2'-F |
| L15 | PS | PS | PS | PS | PS | PS |
| N16 | 2'-F | 2'OMe | 2'-F | 2'-F | 2'-MOE | 2'-F |
| L16 | PS | PS | PS | PS | PS | PS |
| N17 | 2'-OMe | 2'-MOE U | 2'-F | 2'-F | 2'-MOE | 2'-F |
| L17 | PS | PS | PS | PS | None | PS |
| N18 | 2'-F | 2'-MOE U | 2'-F | 2'-OMe | None | MOE A |
| L18 | PS | None | PS | PS | None | PS |
| N19 | 2'-MOE U | None | 2'-MOE U | 2'-MOE A | None | MOE U |
| L19 | PS | None | PS | PS | None | None |
| N20 | 2'-MOE U | None | 2'-MOE U | 2'-MOE A | None | None |

In the above, non-limiting examples:

Column A represent an oligomeric compound consisting of 20 linked nucleosides, wherein the oligomeric compound comprises: a modified 5'-terminal nucleoside of Formula II, IV, VI, VII, VIII, IX, X, XIII, or XIV; a region of alternating nucleosides; a region of alternating linkages; two 3'-terminal MOE nucleosides, each of which comprises a uracil base; and a region of six phosphorothioate linkages at the 3'-end.

Column B represents an oligomeric compound consisting of 18 linked nucleosides, wherein the oligomeric compound comprises: a modified 5'-terminal nucleoside of Formula II, IV, VI, VII, VIII, IX, X, XIII, or XIV; a 2-2-3 motif wherein the modified nucleoside of the 2-2-3 motif are 2'O-Me and the remaining nucleosides are all 2'-F; two 3'-terminal MOE nucleosides, each of which comprises a uracil base; and a region of six phosphorothioate linkages at the 3'-end.

Column C represents an oligomeric compound consisting of 20 linked nucleosides, wherein the oligomeric compound comprises: a modified 5'-terminal nucleoside of Formula II, N, VI, VII, VIII, IX, X, XIII, or XIV; a region of uniformly modified 2'-F nucleosides; two 3'-terminal MOE nucleosides, each of which comprises a uracil base; and wherein each internucleoside linkage is a phosphorothioate linkage.

Column D represents an oligomeric compound consisting of 20 linked nucleosides, wherein the oligomeric compound comprises: a modified 5'-terminal nucleoside of Formula II, IV, VI, VII, VIII, IX, X, XIII, or XIV; a region of alternating 2'-OMe/2'-F nucleosides; a region of uniform 2'F nucleosides; a region of alternating phosphorothioate/phosphodiester linkages; two 3'-terminal MOE nucleosides, each of which comprises an adenine base; and a region of six phosphorothioate linkages at the 3'-end.

Column E represents an oligomeric compound consisting of 17 linked nucleosides, wherein the oligomeric compound comprises: a modified 5'-terminal nucleoside of Formula II, IV, VI, VII, VIII, IX, X, XIII, or XIV; a 2-2-3 motif wherein the modified nucleoside of the 2-2-3 motif are 2'F and the remaining nucleosides are all 2'-OMe; three 3'-terminal MOE nucleosides.

Column F represents an oligomeric compound consisting of 18 linked nucleosides, wherein the oligomeric compound comprises: a region of alternating 2'-OMe/2'-F nucleosides; a region of uniform 2'F nucleosides; a region of alternating phosphorothioate/phosphodiester linkages; two 3'-terminal MOE nucleosides, one of which comprises a uracil base and the other of which comprises an adenine base; and a region of six phosphorothioate linkages at the 3'-end.

The above examples are provided solely to illustrate how the described motifs may be used in combination and are not intended to limit the invention to the particular combinations or the particular modifications used in illustrating the combinations. Further, specific examples herein, including, but not limited to those in the above table are intended to encompass more generic embodiments. For example, column A in the above table exemplifies a region of alternating 2'-OMe and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of oligomeric compounds, such as those exemplified in the above tables, can be easily manipulated by lengthening or shortening one or more of the described regions, without disrupting the motif.

IV. Oligomeric Compounds

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

A. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted C1-C10 alkyl, substituted or unsubstituted C2-C10 alkenyl or substituted or unsubstituted C2-C10 alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group. Solely to illustrate such groups at a 3'-end, and not to limit such groups, the following examples are provided.

| Exemplified oligomeric compounds | SEQ ID NO: |
|---|---|
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ | 6 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_{es}$py-acetyl | 6 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_{es}$py-ibuprofin | 6 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_{es}$py-$C_{16}$ | 26 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}$py-acetyl | 27 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}$py-ibuprofin | 27 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}$py-$C_{16}$ | 26 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}$py-acetyl-$A_{es}$ | 6 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}$py-ibuprofin-$A_{es}$ | 6 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}$py-$C_{16}$-$A_{es}$ | 28 |

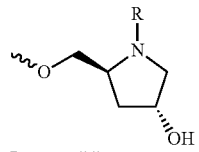

Py = pyrrolidine

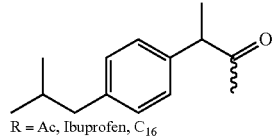

R = Ac, Ibuprofen, $C_{16}$

In certain embodiments, conjugate groups are attached to a nucleoside. Such a nucleoside may be incorporated into an oligomeric compound or oligonucleotide. In certain embodiments conjugated nucleotides may be incorporated into an oligonucleotide at the 5' terminal end. In certain embodiments conjugated nucleotides may be incorporated into an oligonucleotide at the 3' terminal end. In certain embodiments conjugated nucleotides may be incorporated into an oligonucleotide internally. Solely for illustration, and not to limit the conjugate or its placement, the following example shows oligonucleotides where each uracil nucleoside is, separately replaced with a conjugated thymidine nucleoside:

|  | SEQ ID NO: |
|---|---|
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ | 6 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}T_{Xs}A_{es}A_e$ | 29 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}T_{Xs}U_{fs}A_{es}A_e$ | 30 |
| Po-$U_{fo}U_{fo}G_{fo}U_{fo}C_{fo}U_{fo}C_{fo}U_{fo}G_{fo}G_{fo}U_{fo}C_{fo}C_{fo}U_{fs}T_{Xs}A_{fs}C_{fs}U_{fs}U_{fs}A_{es}A_e$ | 31 |
| Po-$U_{fo}U_{fo}G_{fo}U_{fo}C_{fo}U_{fo}C_{fo}U_{fo}G_{fo}G_{fo}U_{fo}C_{fo}C_{fo}T_{Xs}U_{fs}A_{fs}C_{fs}U_{fs}U_{fs}A_{es}A_e$ | 32 |
| Po-$U_{fo}U_{fo}G_{fo}U_{fo}C_{fo}U_{fo}C_{fo}U_{fo}G_{fo}G_{fo}T_{Xo}C_{fo}C_{fo}U_{fs}U_{fs}A_{fs}C_{fs}U_{fs}U_{fs}A_{es}A_e$ | 33 |
| Po-$U_{fo}U_{fo}G_{fo}U_{fo}C_{fo}U_{fo}C_{fo}T_{Xo}G_{fo}G_{fo}U_{fo}C_{fo}C_{fo}U_{fs}U_{fs}A_{fs}C_{fs}U_{fs}U_{fs}A_{es}A_e$ | 34 |
| Po-$U_{fo}U_{fo}G_{fo}U_{fo}C_{fo}T_{Xo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ | 35 |
| Po-$U_{fo}U_{fo}G_{fo}T_{Xo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ | 36 |
| Po-$U_{fo}T_{Xo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ | 37 |
| Po-$T_{Xo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ | 5 |

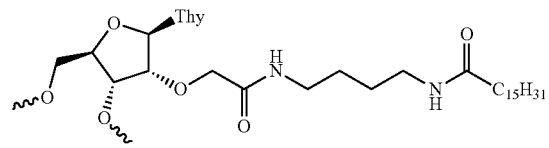

x = aba-$C_{16}$

B. Terminal Groups

In certain embodiments, oligomeric compounds comprise terminal groups at one or both ends. In certain embodiments, a terminal group may comprise any of the conjugate groups discussed above. In certain embodiments, terminal groups may comprise additional nucleosides and/or inverted abasic nucleosides. In certain embodiments, a terminal group is a stabilizing group.

In certain embodiments, oligomeric compounds comprise one or more terminal stabilizing group that enhances properties such as for example nuclease stability. Included in stabilizing groups are cap structures. The terms "cap structure" or "terminal cap moiety," as used herein, refer to chemical modifications, which can be attached to one or both of the termini of an oligomeric compound. These terminal modifications protect the oligomeric compounds having terminal nucleic acid moieties from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl riboucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270).

Particularly suitable 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxy-pentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925 and Published U.S. Patent Application Publication No. US 2005/0020525 published on Jan. 27, 2005). Further 3' and 5'-stabilizing groups that can be used to cap one or both ends of an oligomeric compound to impart nuclease stability include those disclosed in WO 03/004602.

1. Terminal-group Nucleosides

In certain embodiments, one or more additional nucleosides is added to one or both terminal ends of an oligonucleotide of an oligomeric compound. Such additional terminal nucleosides are referred to herein as terminal-group nucleosides. In a double-stranded compound, such terminal-group nucleosides are terminal (3' and/or 5') overhangs. In the setting of double-stranded antisense compounds, such terminal-group nucleosides may or may not be complementary to a target nucleic acid.

In a single-stranded antisense oligomeric compound, terminal-group nucleosides are typically non-hybridizing. The terminal-group nucleosides are typically added to provide a desired property other than hybridization with target nucleic acid. Nonetheless, the target may have complementary bases at the positions corresponding with the terminal-group nucleosides. Whether by design or accident, such complementarity of one or more terminal-group nucleosides does not alter their designation as terminal-group nucleosides. In certain embodiments, the bases of terminal-group nucleosides are each selected from adenine (A), uracil (U), guanine (G), cytosine (C), thymine (T), and analogs thereof. In certain embodiments, the bases of terminal-group nucleosides are each selected from adenine (A), uracil (U), guanine (G), cytosine (C), and thymine (T). In certain embodiments, the bases of terminal-group nucleosides are each selected from adenine (A), uracil (U), and thymine (T). In certain embodiments, the bases of terminal-group nucleosides are each selected from adenine (A) and thymine (T). In certain embodiments, the bases of terminal-group nucleosides are each adenine (A). In certain embodiments, the bases of terminal-group nucleosides are each thymine (T). In certain embodiments, the bases of terminal-group nucleosides are each uracil (U). In certain embodiments, the bases of terminal-group nucleosides are each cytosine (C). In certain embodiments, the bases of terminal-group nucleosides are each guanine (G).

In certain embodiments, terminal-group nucleosides are sugar modified. In certain such embodiments, such additional nucleosides are 2'-modified. In certain embodiments, the 2'-modification of terminal-group nucleosides are selected from 2'-F, 2'-OMe, and 2'-MOE. In certain embodiments, terminal-group nucleosides are 2'-MOE modified. In certain embodiments, terminal-group nucleosides comprise 2'-MOE sugar moieties and adenine nucleobases (2'-MOE A nucleosides). In certain embodiments, terminal-group nucleosides comprise 2'-MOE sugar moieties and uracil nucleobases (2'-MOE U nucleosides). In certain embodiments, terminal-group nucleosides comprises 2'-MOE sugar moieties and guanine nucleobases (2'-MOE G nucleosides). In certain embodiments, terminal-group nucleosides comprises 2'-MOE sugar moieties and thymine nucleobases (2'-MOE T nucleosides). In certain embodiments, terminal-group nucleosides comprises 2'-MOE sugar moieties and cytosine nucleobases (2'-MOE C nucleosides).

In certain embodiments, terminal-group nucleosides comprise bicyclic sugar moieties. In certain such embodiments, terminal-group nucleosides comprise LNA sugar moieties. In certain embodiments, terminal-group nucleosides comprise LNA sugar moieties and adenine nucleobases (LNA A nucleosides). In certain embodiments, terminal-group nucleosides comprise LNA sugar moieties and uracil nucleobases (LNA nucleosides). In certain embodiments, terminal-group nucleosides comprise LNA sugar moieties and guanine nucleobases (LNA G nucleosides). In certain embodiments, terminal-group nucleosides comprise LNA sugar moieties and thymine nucleobases (LNA T nucleosides). In certain embodiments, terminal-group nucleosides comprise LNA sugar moieties and cytosine nucleobases (LNA C nucleosides). In certain embodiments, oligomeric compounds comprise 1-4 terminal-group nucleosides at the 3' end of the oligomeric compound. In certain embodiments, oligomeric compounds comprise 1-3 terminal-group nucleosides at the 3' end of the oligomeric compound. In certain embodiments, oligomeric compounds comprise 1-2 terminal-group nucleosides at the 3' end of the oligomeric compound. In certain embodiments, oligomeric compounds comprise 2 terminal-group nucleosides at the 3' end of the oligomeric compound. In certain embodiments, oligomeric compounds comprise 1 terminal-group nucleoside at the 3' end of the oligomeric compound. In certain embodiments having two or more terminal-group nucleosides, the two or more terminal-group nucleosides all have the same modification type and the same base. In certain embodiments having two or more terminal-group nucleosides, the terminal-group nucleosides differ from one another by modification and/or base.

In certain embodiments, oligomeric compounds comprise a 3'-terminal group comprising 2 terminal-group nucleosides, wherein each terminal group nucleoside is a 2'-MOE T. In certain embodiments, oligomeric compounds comprise a 3'-terminal group comprising 2 terminal-group nucleosides, wherein each terminal group nucleoside is a 2'-MOE A. In certain embodiments, oligomeric compounds comprise a 3'-terminal group comprising 2 terminal-group nucleosides, wherein each terminal group nucleoside is a 2'-MOE U. In certain embodiments, oligomeric compounds comprise a 3'-terminal group comprising 2 terminal-group nucleosides, wherein each terminal group nucleoside is a 2'-MOE C. In certain embodiments, oligomeric compounds comprise a 3'-terminal group comprising 2 terminal-group nucleosides, wherein each terminal group nucleoside is a 2'-MOE G.

In certain embodiments, oligomeric compounds comprise a 3'-terminal group comprising 2 terminal-group nucleosides, wherein each terminal group nucleoside is a LNA T. In certain embodiments, oligomeric compounds comprise a 3'-terminal group comprising 2 terminal-group nucleosides, wherein each terminal group nucleoside is a LNA A. In certain embodiments, oligomeric compounds comprise a 3'-terminal group comprising 2 terminal-group nucleosides, wherein each terminal group nucleoside is a LNA U. In certain embodiments, oligomeric compounds comprise a 3'-terminal group comprising 2 terminal-group nucleosides, wherein each terminal group nucleoside is a LNA C. In certain embodiments, oligomeric compounds comprise a 3'-terminal group comprising 2 terminal-group nucleosides, wherein each terminal group nucleoside is a LNA G.

V. Antisense Compounds

In certain embodiments, oligomeric compounds of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

Antisense mechanisms include any mechanism involving the hybridization of an oligomeric compound with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is RNase H mediated antisense. RNase H is a cellular endonuclease which cleaves the RNA strand of an RNA:DNA duplex. It is known in the art that single-stranded antisense compounds which are "DNA-like" elicit RNase H activity in mammalian cells. Activation of RNase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms. Such mechanism include creation of a microRNA mimic and/or an anti-microRNA.

Antisense mechanisms also include, without limitation, mechanisms that hybridize or mimic non-coding RNA other than microRNA or mRNA. Such non-coding RNA includes, but is not limited to promoter-directed RNA and short and long RNA that effects transcription or translation of one or more nucleic acids.

In certain embodiments, antisense compounds specifically hybridize when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated.

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of ordinary skill in the art is capable of determining an appropriate number of mismatches between oligonucleotides, or between an oligonucleotide and a target nucleic acid, such as by determining melting temperature ($T_m$). $T_m$ or $\Delta T_m$ can be calculated by techniques that are familiar to one of ordinary skill in the art. For example, techniques described in Freier et al. (*Nucleic Acids Research*, 1997, 25, 22: 4429-4443) allow one of ordinary skill in the art to evaluate nucleotide modifications for their ability to increase the melting temperature of an RNA:DNA duplex.

In certain embodiments, oligomeric compounds of the present invention are RNAi compounds. In certain embodiments, oligomeric compounds of the present invention are ssRNA compounds. In certain embodiments, oligomeric compounds of the present invention are paired with a second oligomeric compound to form an siRNA. In certain such embodiments, the second oligomeric compound is also an oligomeric compound of the present invention. In certain embodiments, the second oligomeric compound is any modified or unmodified nucleic acid. In certain embodiments, the oligomeric compound of the present invention is the antisense strand in an siRNA compound. In certain embodiments, the oligomeric compound of the present invention is the sense strand in an siRNA compound.

1. Single-stranded Antisense Compounds

In certain embodiments, oligomeric compounds of the present invention are particularly suited for use as single-stranded antisense compounds. In certain such embodiments, such oligomeric compounds are single-stranded RNAi compounds. In certain embodiments, such oligomeric compounds are ssRNA compounds or microRNA mimics. Certain 5'-terminal nucleosides described herein are suited for use in such single-stranded oligomeric compounds. In certain embodiments, such 5'-terminal nucleosides stabilize the 5'-phosphorous moiety. In certain embodiments, 5'-terminal nucleosides of the present invention are resistant to nucleases. In certain embodiments, the motifs of the present invention are particularly suited for use in single-stranded oligomeric compounds.

Use of single-stranded RNAi compounds has been limited. In certain instances, single stranded RNAi compounds are quickly degraded and/or do not load efficiently into RISC. Certain compounds of the present invention possess properties superior to previously described ssRNAi compounds. In certain embodiments, oligomeric compounds of the present invention are superior ssRNAi compounds in vitro. In certain such embodiments, the 5'-terminal phosphorous moiety is stabilized. In certain such embodiments, the 5'-nucleoside is resistant to nuclease cleavage. In certain embodiments, the 5'-terminal end loads efficiently into RISC. In certain embodiments, the motif stabilizes the oligomeric compound. In certain embodiments the 3'-terminal end of the oligomeric compound is stabilized.

Design of single-stranded RNAi compounds for use in cells and/or for use in vivo presents several challenges. For example, the compound must be chemically stable, resistant to nuclease degradation, capable of entering cells, capable of loading into RISC (e.g., binding Ago1 or Ago2), capable of hybridizing with a target nucleic acid, and not toxic to cells or animals. In certain instances, a modification or motif that improves one such feature may worsen another feature, rendering a compound having such modification or motif unsuitable for use as an RNAi compound. For example, certain modifications, particularly if placed at or near the 5'-end of an oligomeric compound, may make the compound more stable and more resistant to nuclease degradation, but may also inhibit or prevent loading into RISC by blocking the interaction with RISC components, such as Ago1 or Ago2. Despite its improved stability properties, such a compound would be unsuitable for use in RNAi. Thus, the challenge is to identify modifications and combinations and placement of modifications that satisfy each parameter at least sufficient to provide a functional single-stranded RNAi compound. In certain embodiments, oligomeric compounds of the present invention combine modifications to provide single-stranded RNAi compounds that are active as single-stranded RNAi compounds.

In certain instances, a single-stranded oligomeric compound comprising a 5'-phosphorous moiety is desired. For example, in certain embodiments, such 5'-phosphorous moiety is necessary or useful for RNAi compounds, particularly, single-stranded RNAi compounds. In such instances, it is further desirable to stabilize the phosphorous moiety against degradation or de-phosphorolation, which may inactivate the compound. Further, it is desirable to stabilize the entire 5'-nucleoside from degradation, which could also inactivate the compound. Thus, in certain embodiments, oligonucleotides in which the 5'-phosphorous moiety and the 5'-nucleoside have been stabilized are desired. In certain embodiments, the present invention provides modified nucleosides that may be placed at the 5'-end of an oligomeric compound, resulting in stabilized phosphorous and stabilized nucleoside. In certain such embodiments, the phosphorous moiety is resistant to removal in biological systems, relative to unmodified nucleosides and/or the 5'-nucleoside is resistant to cleavage by nucleases. In certain embodiments, such nucleosides are modified at one, at two or at all three of: the 2'-position, the 5'-position, and at the phosphorous moiety. Such modified nucleosides may be incorporated at the 5'-end of an oligomeric compound.

Although certain oligomeric compounds of the present invention have particular use as single-stranded compounds, such compounds may also be paired with a second strand to create a double-stranded oligomeric compound. In such embodiments, the second strand of the double-stranded duplex may or may not also be an oligomeric compound of the present invention.

In certain embodiments, oligomeric compounds of the present invention bind and/or activate one or more nucleases. In certain embodiments, such binding and/or activation ultimately results in antisense activity. In certain embodiments, an oligomeric compound of the invention interacts with a target nucleic acid and with a nuclease, resulting in activation of the nuclease and cleavage of the target nucleic acid. In certain embodiments, an oligomeric compound of the invention interacts with a target nucleic acid and with a nuclease, resulting in activation of the nuclease and inactivation of the target nucleic acid. In certain embodiments, an oligomeric compound of the invention forms a duplex with a target nucleic acid and that duplex activates a nuclease, resulting in cleavage and/or inactivation of one or both of the oligomeric compound and the target nucleic acid. In certain embodiments, an oligomeric compound of the invention binds and/or activates a nuclease and the bound and/or activated nuclease cleaves or inactivates a target nucleic acid. Nucleases include, but are not limited to, ribonucleases (nucleases that specifically cleave ribonucleotides), double-strand nucleases (nucleases that specifically cleave one or both strands of a double-stranded duplex), and double-strand ribonucleases. For example, nucleases include, but are not limited to RNase H, an argonaute protein (including, but not limitied to Ago2), and dicer.

In certain embodiments, oligomeric compounds of the present invention activate RNase H. RNase H is a cellular nuclease that cleaves the RNA strand of a duplex comprising an RNA strand and a DNA or DNA-like strand. In certain embodiments, an oligomeric compound of the present invention is sufficiently DNA-like to activate RNase H, resulting in cleavage of an RNA nucleic acid target. In certain such embodiments, the oligomeric compound comprises at least one region comprised of DNA or DNA-like nucleosides and one or more regions comprised of nucleosides that are otherwise modified. In certain embodiments, such otherwise modified nucleosides increase stability of the oligomeric compound and/or its affinity for the target nucleic acid. Certain such oligomeric compounds posses a desirable combination of properties. For example, certain such compounds, by virtue of the DNA or DNA-like region, are able to support RNase H activity to cleave a target nucleic acid; and by virtue of the otherwise modified nucleosides, have enhanced affinity for the target nucleic acid and/or enhanced stability (including resistance to single-strand-specific nucleases). In certain embodiments, such otherwise modified nucleosides result in oligomeric compounds having desired properties, such as metabolic profile and/or pharmacologic profile.

In certain embodiments, oligomeric compounds of the present invention interact with an argonaute protein (Ago). In certain embodiments, such oligomeric compounds first enter the RISC pathway by interacting with another member of the pathway (e.g., dicer). In certain embodiments, oligomeric compounds first enter the RISC pathway by interacting with Ago. In certain embodiments, such interaction ultimately results in antisense activity. In certain embodiments, the invention provides methods of activating Ago comprising contacting Ago with an oligomeric compound. In certain embodiments, such oligomeric compounds comprise a modified 5'-phosphate group. In certain embodiments, the invention provides methods of modulating the expression or amount of a target nucleic acid in a cell comprising contacting the cell with an oligomeric compound capable of activating Ago, ultimately resulting in cleavage of the target nucleic acid. In certain embodiments, the cell is in an animal. In certain embodiments, the cell is in vitro. In certain embodiments, the methods are performed in the presence of manganese. In certain embodiments, the manganese is endogenous. In certain embodiment the methods are performed in the absence of magnesium. In certain embodiments, the Ago is endogenous to the cell. In certain such embodiments, the cell is in an animal. In certain embodiments, the Ago is human Ago. In certain embodiments, the Ago is Ago2. In certain embodiments, the Ago is human Ago2.

In certain embodiments, oligomeric compounds of the present invention interact with the enzyme dicer. In certain such embodiments, oligomeric compounds bind to dicer and/or are cleaved by dicer. In certain such embodiments, such interaction with dicer ultimately results in antisense activity. In certain embodiments, the dicer is human dicer. In certain embodiments, oligomeric compounds that interact with dicer are double-stranded oligomeric compounds. In certain embodiments, oligomeric compounds that interact with dicer are single-stranded oligomeric compounds.

In embodiments in which a double-stranded oligomeric compound interacts with dicer, such double-stranded oligomeric compound forms a dicer duplex. In certain embodiments, any oligomeric compound described herein may be suitable as one or both strands of a dicer duplex. In certain embodiments, each strand of the dicer duplex is an oligomeric compound of the present invention. In certain embodiments, one strand of the dicer duplex is an oligomeric compound of the present invention and the other strand is any modified or unmodified oligomeric compound. In certain embodiments, one or both strands of a dicer duplex comprises a nucleoside of Formula II, IV, VI, VII, VIII, IX, X, XIII, or XIV at the 5' end. In certain embodiments, one strand of a dicer duplex is an antisense oligomeric compound and the other strand is its sense complement.

In certain embodiments, the dicer duplex comprises a 3'-overhang at one or both ends. In certain embodiments, such overhangs are additional nucleosides. In certain embodiments, the dicer duplex comprises a 3' overhang on the sense oligonucleotide and not on the antisense oligonucleotide. In certain embodiments, the dicer duplex comprises a 3' overhang on the antisense oligonucleotide and not on the sense oligonucleotide. In certain embodiments, 3' overhangs of a dicer duplex comprise 1-4 nucleosides. In certain embodiments, such overhangs comprise two nucleosides. In certain embodiments, the nucleosides in the 3'-overhangs comprise purine nucleobases. In certain embodiments, the nucleosides in the 3' overhangs comprise adenine nucleobases. In certain embodiments, the nucleosides in the 3' overhangs comprise pyrimidines. In certain embodiments, dicer duplexes comprising 3'-purine overhangs are more active as antisense compounds than dicer duplexes comprising 3' pyrimidine overhangs. In certain embodiments, oligomeric compounds of a dicer duplex comprise one or more 3' deoxy nucleosides. In certain such embodiments, the 3' deoxy nucleosides are dT nucleosides.

In certain embodiments, the 5' end of each strand of a dicer duplex comprises a phosphate moiety. In certain embodiments the antisense strand of a dicer duplex comprises a phosphate moiety and the sense strand of the dicer duplex does not comprise a phosphate moiety. In certain embodiments the sense strand of a dicer duplex comprises a phosphate moiety and the antisense strand of the dicer duplex does not comprise a phosphate moiety. In certain embodiments, a dicer duplex does not comprise a phosphate moiety at the 3' end. In certain embodiments, a dicer duplex is cleaved by dicer. In such embodiments, dicer duplexes do not comprise 2'-OMe modifications on the nucleosides at the cleavage site. In certain embodiments, such cleavage site nucleosides are RNA.

In certain embodiments, interaction of an oligomeric compound with dicer ultimately results in antisense activity. In certain embodiments, dicer cleaves one or both strands of a double-stranded oligomeric compound and the resulting product enters the RISC pathway, ultimately resulting in antisense activity. In certain embodiments, dicer does not cleave either strand of a double-stranded oligomeric compound, but nevertheless facilitates entry into the RISC pathway and ultimately results in antisense activity. In certain embodiments, dicer cleaves a single-stranded oligomeric compound and the resulting product enters the RISC pathway, ultimately resulting in antisense activity. In certain embodiments, dicer does not cleave the single-stranded oligomeric compound, but nevertheless facilitates entry into the RISC pathway and ultimately results in antisense activity.

In certain embodiments, the invention provides methods of activating dicer comprising contacting dicer with an oligomeric compound. In certain such embodiments, the dicer is in a cell. In certain such embodiments, the cell is in an animal.

Dicer

In certain embodiments, oligomeric compounds of the present invention interact with the enzyme dicer. In certain such embodiments, oligomeric compounds bind to dicer and/or are cleaved by dicer. In certain such embodiments, such interaction with dicer ultimately results in antisense activity. In certain embodiments, the dicer is human dicer. In certain embodiments, oligomeric compounds that interact with dicer are double-stranded oligomeric compounds. In certain embodiments, oligomeric compounds that interact with dicer are single-stranded oligomeric compounds.

In embodiments in which a double-stranded oligomeric compound interacts with dicer, such double-stranded oligomeric compound forms a dicer duplex. In certain embodiments, any oligomeric compound described herein may be suitable as one or both strands of a dicer duplex. In certain embodiments, each strand of the dicer duplex is an oligomeric compound of the present invention. In certain embodiments, one strand of the dicer duplex is an oligomeric compound of the present invention and the other strand is any modified or unmodified oligomeric compound. In certain embodiments, one or both strands of a dicer duplex comprises a nucleoside of Formula II, W, VI, VII, VIII, IX, X, XIII, or XIV at the 5'. In certain embodiments, one strand of a dicer duplex is an antisense oligomeric compound and the other strand is its sense complement.

In certain embodiments, a dicer duplex comprises a first and second oligomeric compound wherein each oligomeric compound comprises an oligonucleotide consisting of 25 to 30 linked nucleosides. In certain such embodiments, each oligonucleotide of the dicer duplex consists of 27 linked nucleosides.

In certain embodiments, the dicer duplex comprises a 3'-overhang at one or both ends. In certain embodiments, such overhangs are additional nucleosides. In certain embodiments, the dicer duplex comprises a 3' overhang on the sense oligonucleotide and not on the antisense oligonucleotide. In certain embodiments, the dicer duplex comprises a 3' overhang on the antisense oligonucleotide and not on the sense oligonucleotide. In certain embodiments, 3' overhangs of a dicer duplex comprise 1-4 nucleosides. In certain embodiments, such overhangs comprise two nucleosides. In certain embodiments, 3'-overhangs comprise purine nucleobases. In certain embodiments, 3'-overhangs comprise adenine overhangs. In certain embodiments, 3'-overhangs are pyrimidines. In certain embodiments, dicer duplexes comprising 3'-purine overhangs are more active as antisense compounds than dicer duplexes comprising 3'-pyrimidine overhangs. In certain embodiments, oligomeric compounds of a dicer duplex comprise 3'-deoxy nucleosides. In certain such embodiments, the 3'-deoxy nucleosides are dT nucleosides.

In certain embodiments, the 5' end of each strand of a dicer duplex comprises phosphate moiety. In certain embodiments the antisense strand of a dicer duplex comprises a phosphate moiety and the sense strand of the dicer duplex does not comprises a phosphate moiety. In certain embodiments the sense strand of a dicer duplex comprises a phosphate moiety and the antisense strand of the dicer duplex does not comprises a phosphate moiety. In certain embodiments, a dicer duplex does not comprise a phosphate moiety at the 3'-end. In certain embodiments, a dicer duplex is cleaved by dicer. In such embodiments, dicer duplexes do not comprise 2'-OMe modifications at the nucleosides at the cleavage site. In certain embodiments, such cleavage site nucleosides are RNA.

One of skill will appreciate that the above described features of dicer duplexes may be combined. For example, in certain embodiments, a dicer duplex comprises a first oligomeric compound comprising an antisense oligonucleotide and a second oligomeric compound comprising a sense oligonucleotide; wherein the sense oligonucleotide comprises a 3' overhang consisting of two purine nucleosides and the antisense oligonucleotide comprises a 3' overhang consisting of two adenosine or modified adenosine nucleosides; each of the sense and antisense oligonucleotides consists of 25 to 30 linked nucleosides, the 5' end of the antisense oligonucleotide comprises a phosphorous moiety, and wherein the dicer cleavage sites of the dicer duplex are not O-Me modified nucleosides.

In certain embodiments, the invention provides single-stranded oligomeric compounds that interact with dicer. In certain embodiments, such single-stranded dicer compounds comprise a nucleoside of Formula II, IV, VI, VII, VIII, IX, X, XIII, or XIV. In certain embodiments, single-stranded dicer compounds do not comprise a phosphorous moiety at the 3'-end. In certain embodiments, such single-stranded dicer compounds may comprise a 3'-overhangs. In certain embodiments, such 3'-overhangs are additional nucleosides. In certain embodiments, such 3'-overhangs comprise 1-4 additional nucleosides that are not complementary to a target nucleic acid and/or are differently modified from the adjacent 3' nucleoside of the oligomeric compound. In certain embodiments, a single-stranded oligomeric compound comprises an antisense oligonucleotide having two 3'-end overhang nucleosides wherein the overhang nucleosides are adenine or modified adenine nucleosides. In certain embodiments, single stranded oligomeric compounds that interact with dicer comprise a nucleoside of Formula II, IV, VI, VII, VIII, IX, X, XIII, or XIV.

In certain embodiments, interaction of an oligomeric compound with dicer ultimately results in antisense activity. In certain embodiments, dicer cleaves one or both strands of a double-stranded oligomeric compound and the resulting product enters the RISC pathway, ultimately resulting in antisense activity. In certain embodiments, dicer does not cleave either strand of a double-stranded oligomeric compound, but nevertheless facilitates entry into the RISC pathway and ultimately results in antisense activity. In certain embodiments, dicer cleaves a single-stranded oligomeric compound and the resulting product enters the RISC pathway, ultimately resulting in antisense activity. In certain embodiments, dicer does not cleave the single-stranded oligomeric compound, but nevertheless facilitates entry into the RISC pathway and ultimately results in antisense activity.

In certain embodiments, the invention provides methods of activating dicer comprising contacting dicer with an oligomeric compound. In certain such embodiments, the dicer is in a cell. In certain such embodiments, the cell is in an animal.

Ago

In certain embodiments, oligomeric compounds of the present invention interact with Ago. In certain embodiments, such oligomeric compounds first enter the RISC pathway by interacting with another member of the pathway (e.g., dicer). In certain embodiments, oligomeric compounds first enter the RISC pathway by interacting with Ago. In certain embodiments, such interaction ultimately results in antisense activity. In certain embodiments, the invention provides methods of activating Ago comprising contacting Ago with an oligomeric compound. In certain such embodiments, the Ago is in a cell. In certain such embodiments, the cell is in an animal.

2. Oligomeric Compound Identity

In certain embodiments, a portion of an oligomeric compound is 100% identical to the nucleobase sequence of a microRNA, but the entire oligomeric compound is not fully identical to the microRNA. In certain such embodiments, the length of an oligomeric compound having a 100% identical portion is greater than the length of the microRNA. For example, a microRNA mimic consisting of 24 linked nucleosides, where the nucleobases at positions 1 through 23 are each identical to corresponding positions of a microRNA that is 23 nucleobases in length, has a 23 nucleoside portion that is 100% identical to the nucleobase sequence of the microRNA and has approximately 96% overall identity to the nucleobase sequence of the microRNA.

In certain embodiments, the nucleobase sequence of oligomeric compound is fully identical to the nucleobase sequence of a portion of a microRNA. For example, a single-stranded microRNA mimic consisting of 22 linked nucleosides, where the nucleobases of positions 1 through 22 are each identical to a corresponding position of a microRNA that is 23 nucleobases in length, is fully identical to a 22 nucleobase portion of the nucleobase sequence of the microRNA. Such a single-stranded microRNA mimic has approximately 96% overall identity to the nucleobase sequence of the entire microRNA, and has 100% identity to a 22 nucleobase portion of the microRNA.

E. Synthesis, Purification and Analysis

Oligomerization of modified and unmodified nucleosides and nucleotides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds provided herein can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Methods of purification and analysis of oligomeric compounds are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

F. Compositions and Methods for Formulating Pharmaceutical Compositions

Oligomeric compounds may be admixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Oligomeric compounds, including antisense compounds, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in certain embodiments, employed in the methods described herein is a pharmaceutical composition comprising an antisense compound and a pharmaceutically acceptable diluent. In certain embodiments, the pharmaceutically acceptable diluent is PBS.

Pharmaceutical compositions comprising oligomeric compounds encompass any pharmaceutically acceptable salts, esters, or salts of such esters. In certain embodiments, pharmaceutical compositions comprising oligomeric compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active oligomeric compound.

Lipid-based vectors have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid.

In certain methods, preparations are made that include a polyamine compound or a lipid moiety complexed with a nucleic acid. In certain embodiments, such preparations comprise one or more compounds each individually having a structure defined by formula (I) or a pharmaceutically acceptable salt thereof,

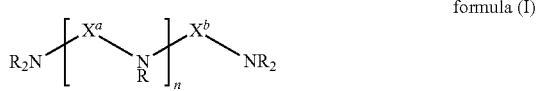

formula (I)

wherein each $X^a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (I) in the preparation are not H; m is 1, 2, 3 or 4; Y is O, $NR^2$, or S; $R^1$ is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO/2008/042973, which is herein incorporated by reference in its entirety.

Certain preparations, some of which are shown below, are described in Akinc et al., *Nature Biotechnology* 26, 561-569 (1 May 2008), which is herein incorporated by reference in its entirety.

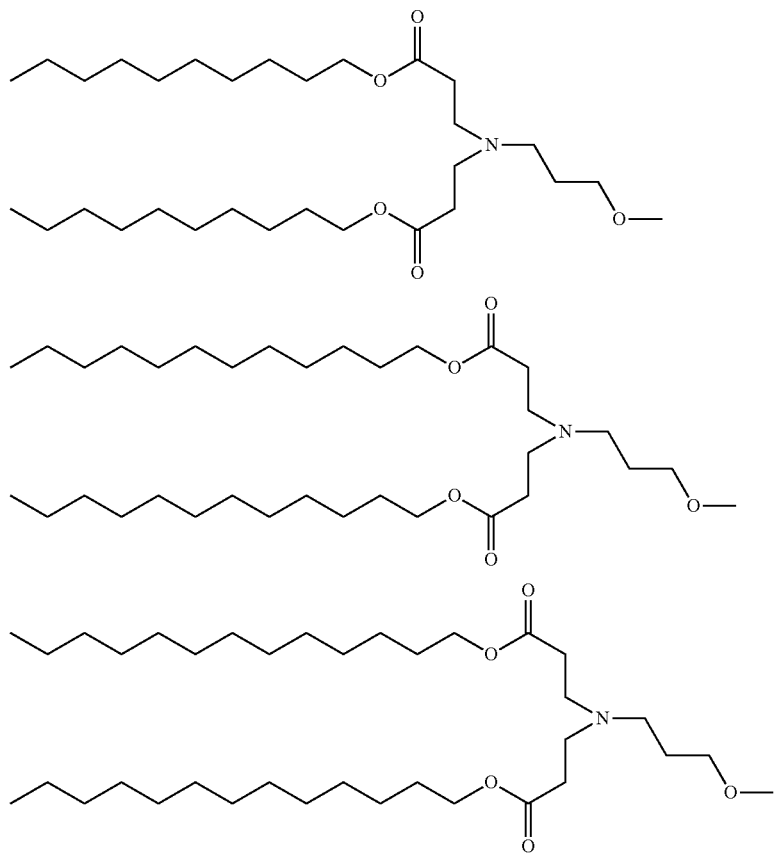

-continued
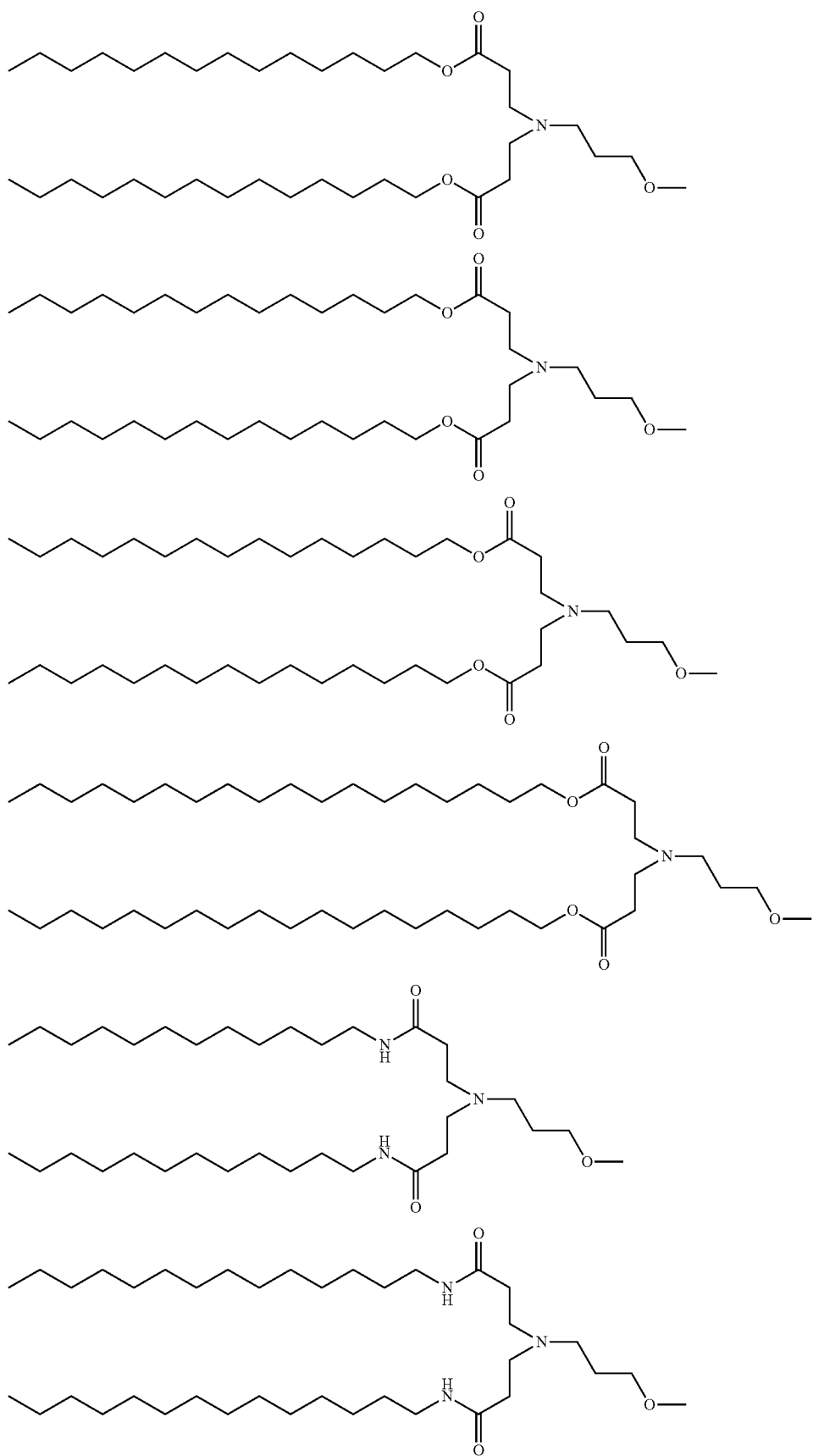

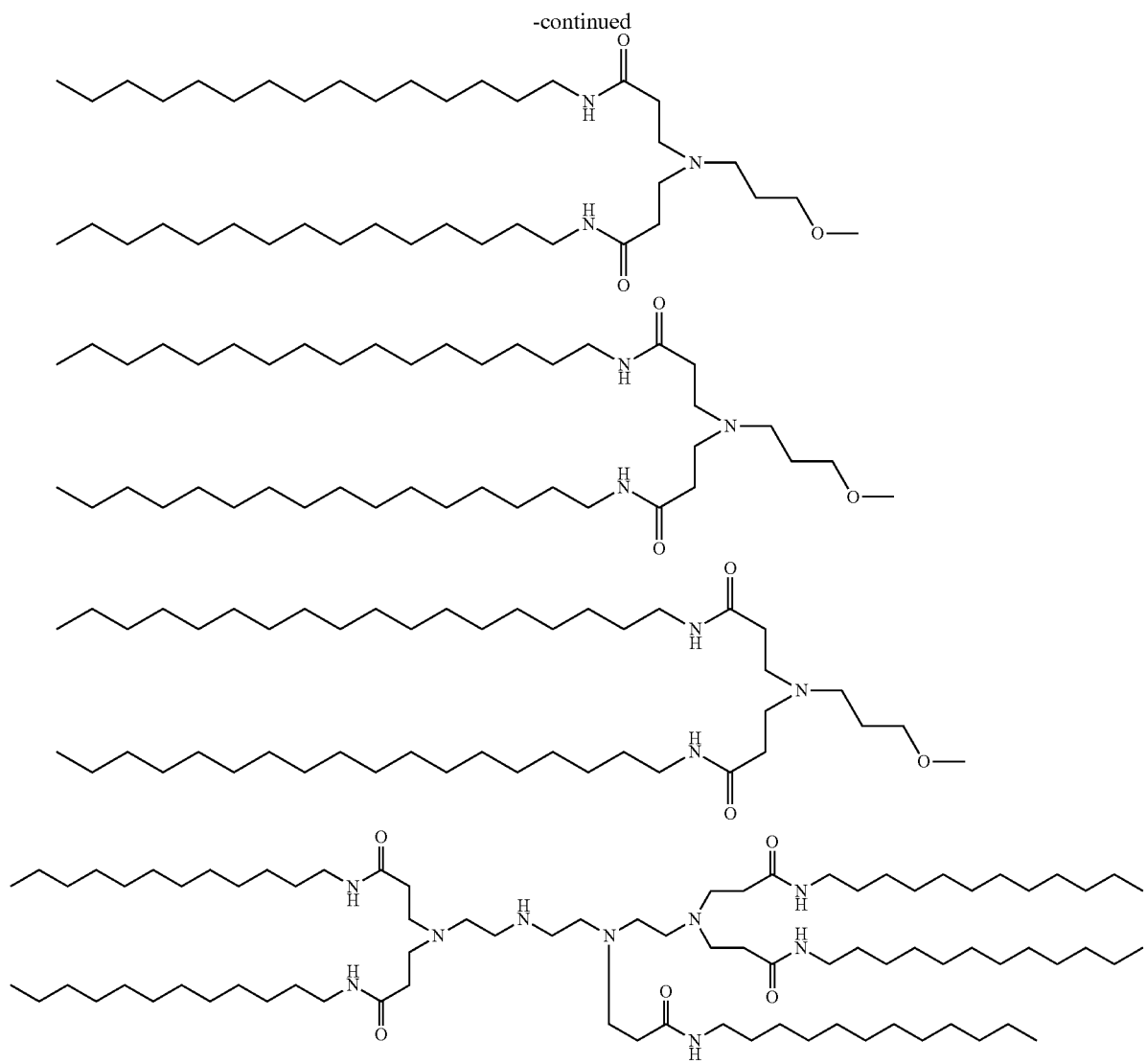

Certain Antisense Oligomeric Compounds

In certain embodiments, the invention provides oligomeric compounds comprising or consisting of antisense oligonucleotides. In certain embodiments, an antisense oligonucleotide comprises a phosphate stabilizing nucleoside. In certain embodiments, an antisense oligonucleotide comprises a phosphate stabilizing nucleoside at the 5'-end. In certain embodiments, a phosphate stabilizing nucleoside comprises a modified phosphate group and/or a modified sugar moiety.

In certain embodiments, an antisense oligonucleotide comprises a 5'-stabilizing nucleotide. In certain embodiments, the 5'-stabilizing nucleoside comprises a modified sugar moiety.

In certain embodiments, the 5'-end of an antisense compound comprises a phosphate stabilizing modification and a 5'-stabilizing nucleoside. In certain embodiments, a single modification results in both phosphate stabilization and nucleoside stabilization. In certain embodiments, the phosphate stabilizing modification and the nucleoside stabilizing modification are different modifications. In certain embodiments, tow or more modifications at the 5'-end of an oligomeric compound together provide phosphate stabilization and nucleoside stabilization.

In certain embodiments, an antisense oligomeric compound comprises the following features selected from: a 5'-phosphate or 5'-modified phosphate; a 5'-most nucleoside (position 1 nucleoside); a nucleoside second from the 5'-end (position 2 nucleoside); a nucleoside third from the 5'-end (position 3 nucleoside); a region having a nucleoside motif; a region having a linkage motif; a terminal group.

In certain embodiments, the 5'-phosphate is selected from: unmodified phosphate, modified phosphate, phosphonate, alkylphosphonate, substituted alkylphosphonate, aminoalkyl phosphonate, substituted aminoalkyl phosphonate, phosphorothioate, phosphoramidate, alkylphosphonothioate, substituted alkylphosphonothioate, phosphorodithioate, thiophosphoramidate, and phosphotriester.

In certain embodiments, the 5'-phosphate is selected from: modified phosphate, phosphonate, alkylphosphonate, substituted alkylphosphonate, aminoalkyl phosphonate, substituted aminoalkyl phosphonate, phosphotriester, phosphorothioate, phosphorodithioate, thiophosphoramidate, and phosphoramidate.

In certain embodiments, the 5'-phosphate is selected from: modified phosphate, phosphonate, alkylphosphonate, and substituted alkylphosphonate. In certain embodiments, the 5'-phosphate is selected from 5'-deoxy-5'-thio phosphate, phosphoramidate, methylene phosphonate, mono-fluoro methylene phosphonate and di-fluoro methylene phosphonate.

In certain embodiments, the position 1 nucleoside comprises a modified sugar. In certain such embodiments, the sugar comprises a 5'-modification. In certain embodiments, the sugar of the position 1 nucleoside comprises a 2'-modification. In certain embodiments, the sugar of the position 1 nucleoside comprises a 5'-modification and a 2'-modification. In certain embodiments, the 5'-modification of the sugar of the position 1 nucleoside is selected from 5'-alkyl,5'-substituted alkyl, 5'-olkoxy, 5'-substitued alkoxy, and 5'-halogen. In certain embodiments, the 5' modification of the sugar at position 1 is selected from 5'-alkyl and 5'-substituted alkyl. In certain such embodiments, the modification is selected from methyl and ethyl. In certain embodiments, the 2' modification is selected from: halogen (including, but not limited to F), allyl, amino, azido, thio, O-allyl, —O—$C_1$-$C_{10}$ alkyl, —O—$C_1$-$C_{10}$ substituted alkyl, —$OCF_3$, —O—$(CH_2)_2$—O—$CH_3$, —$O(CH_2)_2SCH_3$, —O—$(CH_2)_2$—O—$N(R_m)$($R_n$), —O—CH2—C(=O)—$N(R_m)(R_n)$, where each $R_m$ and $R_n$ is, independently, H or substituted or unsubstituted $C_1$-$C_{10}$ alkyl, —$O[(CH_2)_nO]_mCH_3$, —$O(CH_2)_nNH_2$, —$O(CH_2)_n$$CH_3$, —$O(CH_2)_nONH_2$, —$OCH_2C$(=O)N(H)$CH_3$, —$O(CH_2)_nON[(CH_2)_nCH_3]_2$, where n and m are from 1 to about 10; $C_1$ to $C_{10}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl. In certain embodiments, the 2'-modification of the sugar of the position 1 nucleoside is selected from: F, —O—$C_1$-$C_{10}$ alkyl, —O—$C_1$-$C_{10}$ substituted alkyl, —$OCF_3$, —O—$(CH_2)_2$—O—$CH_3$, —$O(CH_2)_2$$SCH_3$, —O—$(CH_2)_2$—O—$N(R_m)(R_n)$, —O—CH2—C(=O)—$N(R_m)(R_n)$, where each $R_m$ and $R_n$ is, independently, H or substituted or unsubstituted $C_1$-$C_{10}$ alkyl, —$O[(CH_2)_nO]_mCH_3$, —$O(CH_2)_nNH_2$, —$O(CH_2)_nCH_3$, —$O(CH_2)_nONH_2$, —$OCH_2C$(=O)N(H)$CH_3$, —$O(CH_2)_nON[(CH_2)_nCH_3]_2$, where n and m are from 1 to about 10; —O-aryl, S-alkyl, NMA, DMAEAc, DMAEOE, and —O-alkyl-F. In certain embodiments, the 2'-modification of the sugar of the position 1 nucleoside is selected from: F, —O—$C_1$-$C_{10}$ alkyl, —O—$C_1$-$C_{10}$ substituted alkyl, —O—$(CH_2)_2$—O—$CH_3$, —$O(CH_2)_2SCH_3$, —O—$(CH_2)_2$—O—$N(R_m)(R_n)$, —O—CH2—C(=O)—$N(R_m)(R_n)$, where each $R_m$ and $R_n$ is, independently, H or substituted or unsubstituted $C_1$-$C_{10}$ alkyl, —$O[(CH_2)_nO]_mCH_3$, —$O(CH_2)_nNH_2$, —$O(CH_2)_n$$CH_3$, —$O(CH_2)_nONH_2$, —$OCH_2C$(=O)N(H)$CH_3$, —$O(CH_2)_nON[(CH_2)_nCH_3]_2$, where n and m are from 1 to about 10; —O-aryl, S-alkyl, NMA, DMAEAc, DMAEOE, and —O-alkyl-F.

In certain embodiments, the position 2 nucleoside comprises a 2'-modification. In certain such embodiments, the 2'-modification of the position 2 nucleoside is selected from halogen, alkyl, and substituted alkyl. In certain embodiments, the 2'-modification of the position 2 nucleoside is selected from 2'-F and 2'-alkyl. In certain embodiments, the 2'-modification of the position 2 nucleoside is 2'-F. In certain embodiments, the 2'-substituted of the position 2 nucleoside is an unmodified OH (as in naturally occurring RNA).

In certain embodiments, the position 3 nucleoside is a modified nucleoside. In certain embodiments, the position 3 nucleoside is a bicyclic nucleoside. In certain embodiments, the position 3 nucleoside comprises a sugar surrogate. In certain such embodiments, the sugar surrogate is a tetrahydropyran. In certain embodiments, the sugar of the position 3 nucleoside is a F—HNA.

In certain embodiments, an antisense oligomeric compound comprises an oligonucleotide comprising 10 to 30 linked nucleosides wherein the oligonucleotide comprises:

a 5'-terminal phosphate or modified phosphate:

a position 1 modified nucleoside comprising a modified sugar moiety comprising:

a 5'-modification; or a 2'-modification; or both a 5'-modification and a 2'-modification;

a position 2 nucleoside comprising a sugar moiety which is differently modified compared to the sugar moiety of the position 1 modified nucleoside; and from 1 to 4 3'-terminal group nucleosides each comprising a 2'-modification; and wherein at least the seven 3'-most internucleoside linkages are phosphorothioate linkages.

In certain such embodiments, the 5'-terminal modified phosphate is selected from: phosphonate, alkylphosphonate, aminoalkyl phosphonate, phosphorothioate, phosphoramidite, alkylphosphonothioate, phosphorodithioate, thiophosphoramidate, phosphotriester;

the 5'-modification of the sugar moiety of the position 1 modified nucleoside is selected from 5'-alkyl and 5'-halogen;

the 2'-modification of the sugar moiety of the position 1 modified nucleoside is selected from: halogen (including, but not limited to F), allyl, amino, azido, thio, O-allyl, —O—$C_1$-$C_{10}$ alkyl, —O—$C_1$-$C_{10}$ substituted alkyl, —$OCF_3$, —O—$(CH_2)_2$—O—$CH_3$, —$O(CH_2)_2SCH_3$, —O—$(CH_2)_2$—O—$N(R_m)(R_n)$, —O—CH2-C(=O)—$N(R_m)(R_n)$, where each $R_m$ and $R_n$ is, independently, H or substituted or unsubstituted $C_1$-$C_{10}$ alkyl, —$O[(CH_2)_nO]_mCH_3$, —$O(CH_2)_nNH_2$, —$O(CH_2)_nCH_3$, —$O(CH_2)_nONH_2$, —$OCH_2C$(=O)N(H)$CH_3$, —$O(CH_2)_nON[(CH_2)_nCH_3]_2$, where n and m are from 1 to about 10; $C_1$ to $C_{10}$ alkyl, substituted alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl; and the sugar moiety of the position 2 nucleoside is selected from unmodified 2'-OH(RNA) sugar, and a modified sugar comprising a modification selected from: 2'-halogen, 2'O-alkyl, 2'-alkyl, 2'-substituted alkyl.

In certain embodiments, the sugar moiety of the position 2 nucleoside comprises a 2'-F.

In certain embodiments, such oligonucleotides comprises 8 to 20, 10 to 15, 11 to 14, or 12 to 13 phosphorothioate internucleoside linkages overall. In certain embodiments, the remaining internucleoside linkages are phosphodiester. In certain embodiments, the eighth internucleoside linkage from the 3' end of the oligonucleotide is a phosphodiester. In certain embodiments, the ninth internucleoside linkage from the 3' end is a phosphodiester. In certain embodiments, each internucleoside linkage is either a phosphorothioate or a phosphodiester linkage.

In certain such embodiments, antisense oligomeric compounds have the features described in the following non-limiting table:

| 5'-phophate | Sugar moiety of position 1 nucleoside | | Position 2 | Positions 3 to 3'-end motifs or features | 3'-terminal group | Linkages |
| --- | --- | --- | --- | --- | --- | --- |
| | 5' | 2' | | | | |
| unmodified phosphate | methyl | MOE | 2'-F | Alternating modifications | 1-4 MOE | At least 7 PS at 3'end |
| thiophosphate | methyl | MOE | 2'-F | Alternating OMe/F | 1-4 MOE | At least 7 PS at 3'end |
| Phosphonate | methyl | DMAEAc | 2'-F | Alternating OMe/F | 1-4 MOE | At least 7 PS at 3'end |
| Methylphosphonate | methyl | Tri-MOE | 2'-F | 2-2-3 | None | 6-8 PS at 3' end and total of 10 PS throughout |
| alkylphosphonothioate | unmod | O-alkyl | 2'-F | any | 2 MOE adenosines | 7 PS at 3' end and total of ≥10 PS throughout |
| Phosphonate or alkylphosphonate | Methyl or unmod. | MOE, O-alkyl; O-subst. alkyl; F, —O-aryl, S-alkyl, NMA, DMAEAc, DMAEOE, —O-alkyl-F | 2'-F | any | 1-4 MOE adenosines | 7-8 PS at 3' end; total of 10-15 PS linkages throughout; remaining linkages are PO |
| Posphonate or modified phosphonate | Alkyl | MOE, O-alkyl; O-subst. alkyl; F, —O-aryl, S-alkyl, NMA, DMAEAc, DMAEOE, —O-alkyl-F | 2'-F | BNA at position 3 | 1-4 MOE adenosines | 7-8 PS at 3' end; total of 10-15 PS linkages throughout; remaining linkages are PO |

In certain embodiments, the third nucleoside from the 5'-end (position 3) is a modified nucleoside. In certain embodiments, the nucleoside at position 3 comprises a sugar modification. In certain such embodiments, the sugar moiety of the position 3 nucleoside is a bicyclic nucleoside. In certain embodiments the position 3 nucleoside is a modified non-bicyclic nucleoside. In certain embodiments, the position 3 nucleoside is selected from: F—HNA and 2'-OMe.

Certain Methods/Uses

In certain embodiments, the present invention provides compounds and methods for reducing the amount or activity of a target nucleic acid. In certain embodiments, the invention provides antisense compounds and methods. In certain embodiments, the invention provides antisense compounds and methods based on activation of RNase H. In certain embodiments, the invention provides RNAi compounds and methods.

In certain instances it is desirable to use an antisense compound that functions at least in part through RISC. In certain such instances unmodified RNA, whether single-stranded or double stranded is not suitable. Single-stranded RNA is relatively unstable and double-stranded RNA does not easily enter cells. The challenge has been to identify modifications and motifs that provide desirable properties, such as improved stability, without interfering with (and possibly even improving upon) the antisense activity of RNA through RNAi.

In certain embodiments, the present invention provides oligonucleotides having motifs (nucleoside motifs and/or linkage motifs) that result in improved properties. Certain such motifs result in single-stranded oligonucleotides with improved stability and/or cellular uptake properties while retaining antisense activity. For example, oligonucleotides having an alternating nucleoside motif and seven phosphorothioate linkages at to 3'-terminal end have improved stability and activity. Similar compounds that comprise phosphorothioate linkages at each linkage have further improved stability, but are not active as RNAi compounds, presumably because the additional phosphorothioate linkages interfere with the interaction of the oligonucleotide with the RISC pathway components (e.g., with Ago). In certain embodiments, the oligonucleotides having motifs herein result in single-stranded RNAi compounds having desirable properties. In certain embodiments, such oligonucleotides may be paired with a second strand to form a double-stranded RNAi compound. In such embodiments, the second strand of such double-stranded RNAi compounds may comprise a motif of the present invention, may comprise another motif of modifications or may be unmodified.

It has been shown that in certain circumstances for single-stranded RNA comprising a 5'-phosphate group has RNAi activity if but has much less RNAi activity if it lacks such 5'-phosphate group. The present inventors have recognized that in certain circumstances unmodified 5'-phosphate groups may be unstable (either chemically or enzymatically). Accordingly, in certain circumstances, it is desirable to modify the oligonucleotide to stabilize the 5'-phosphate. In certain embodiments, this is achieved by modifying the phosphate group. In certain embodiments, this is achieved by modifying the sugar of the 5'-terminal nucleoside. In certain embodiments, this is achieved by modifying the phosphate group and the sugar. In certain embodiments, the sugar is modified at the 5'-position, the 2'-position, or both the 5'-position and the 2'-position. As with motifs, above, in embodiments in which RNAi activity is desired, a phosphate stabilizing modification must not interfere with the ability of the oligonucleotide to interact with RISC pathway components (e.g., with Ago).

In certain embodiments, the invention provides oligonucleotides comprising a phosphate-stabilizing modification and a motif described herein. In certain embodiments, such oligonucleotides are useful as single-stranded RNAi compounds having desirable properties. In certain embodiments, such oligonucleotides may be paired with a second strand to form a double-stranded RNAi compound. In such embodiments, the second strand may comprise a motif of the present invention, may comprise another motif of modifications or may be unmodified RNA.

The target for such antisense compounds comprising a motif and/or 5'-phosphate stabilizing modification of the present invention can be any naturally occurring nucleic acid. In certain embodiments, the target is selected from: pre-mRNA, mRNA, non-coding RNA, small non-coding RNA, pd-RNA, and microRNA. In embodiments, in which a target nucleic acid is a pre-RNA or a mRNA, the target may be the same as that of a naturally occurring micro-RNA (i.e., the oligonucleotide may be a microRNA mimic). In such embodiments, there may be more than one target mRNA.

In certain embodiments, the invention provides compounds and methods for antisense activity in a cell. In certain embodiments, the cell is in an animal. In certain embodiments, the animal is a human. In certain embodiments, the invention provides methods of administering a compound of the present invention to an animal to modulate the amount or activity or function of one or more target nucleic acid.

In certain embodiments oligonucleotides comprise one or more motifs of the present invention, but do not comprise a phosphate stabilizing modification. In certain embodiments, such oligonucleotides are useful for in vitro applications. In certain embodiments, such oligonucleotides are useful for in vivo applications where RISC activity is not required. For example, in certain embodiments, such oligonucleotides alter splicing of pre-mRNA.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$C-GAUCG," wherein $^{me}$C indicates a cytosine base comprising a methyl group at the 5-position.

Likewise, one of skill will appreciate that in certain circumstances using the conventions described herein, the same compound may be described in more than one way. For example, an antisense oligomeric compound having two non-hybridizing 3'-terminal 2'-MOE modified nucleosides, but otherwise fully complementary to a target nucleic acid may be described as an oligonucleotide comprising a region of 2'-MOE-modified nucleosides, wherein the oligonucleotide is less than 100% complementary to its target. Or that same compound may be described as an oligomeric compound comprising: (1) an oligonucleotide that is 100% complementary to its nucleic acid target and (2) a terminal group wherein the terminal group comprises two 2'-MOE modified terminal-group nucleosides. Such descriptions are not intended to be exclusive of one another or to exclude overlapping subject matter.

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. Nos. 5,256,775 or 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 3

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M NH$_4$OAc with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 4

Synthesis of Oligomeric Compounds Using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated NH$_4$OH at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Analysis of Oligomeric Compounds Using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 µg/mL per 100 nM oligomeric compound(s). This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTINT™, LIPOFECTAMINE™, OLIGOFECTAMINE™, and FUGENE™. Other suitable transfection methods known in the art include, but are not limited to, electroporation.

Example 7

Real-time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Oligonucleotide Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

Example 9

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the a target inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

Example 10

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 μL cold PBS. 150 μL Buffer RLT is added to each well and the plate vigorously agitated for 20 seconds. 150 μL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 μL of Buffer RW1 is added to each well of the RNEASY 96™ plate and incubated for 15 minutes and the vacuum is again applied for 1 minute. An additional 500 μL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 μL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
                                         (SEQ ID NO: 2)
Forward primer:    AATGGCTAAGTGAAGATGACAATCAT (SEQ ID NO: 3)
Reverse primer:    TGCACATATCATTACACCAGTTCGT
```

And the PCR probe:

```
                                         (SEQ ID NO: 4)
     FAM-TTGCAGCAATTCACTGTAAAGCTGGAAAGG-TAMRA,
``` where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 3

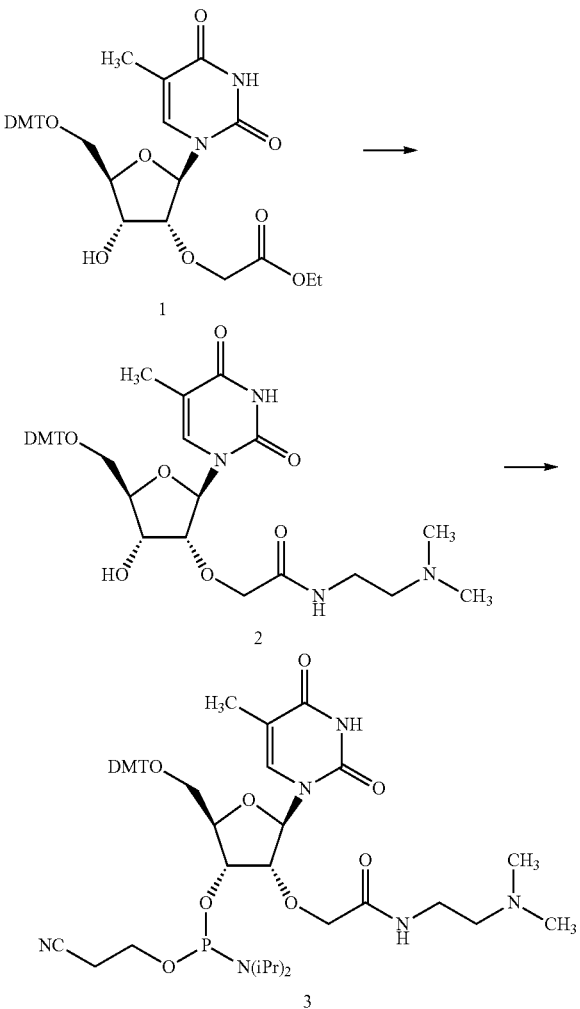

a) Preparation of 5'-O-(4,4'-dimethoxytrityl)-2'-O-(2-N-[2-(dimethylamino)ethyl]-acetamide)-5-methyluridine (Compound 2)

Compound 1 was prepared according to published literature (Prakash et al., Org. Let. 2003, 5, 403-406) using ethyl-2-bromoacetate for alkylation. Compound 1 (5.378 g, 8.50 mmol) was dissolved in anhydrous THF (66 mL). To this was added N,N-dimethylethylenediamine (18.7 mL, 170 mmol) and the reaction mixture was stirred at ambient temperature. After 6 h, toluene (80 mL) was added and the solvent was evaporated in vacuo to give Compound 2 as a white foam (6.12 g, 95%). $^1$H NMR (CDCl$_3$): δ 7.64 (s, 3H), 7.41-6.79 (m, 13H), 5.94 (d, 1H, J$_{1',2'}$=2.4 Hz), 4.41 (m, 1H), 4.31 (q ab, 2H), 4.19 (m, 1H), 3.95 (m, 1H), 3.75 (s, 6H), 3.52 (m, 2H), 2.75 (m, 2H), 2.48 (m, 2H), 2.24 (s, 6H), 1.36 (s, 3H). $^{13}$C NMR (CDCl$_3$): δ 170.1, 164.7, 158.7, 151.0, 144.4, 135.5, 135.3, 134.9, 130.1, 129.0, 128.1, 127.7, 127.1, 113.3, 110.9, 88.5, 86.7, 84.8, 83.3, 70.7, 68.2, 61.8, 58.4, 45.4, 36.0, 12.0. HRMS (MALDI) calcd for C$_{37}$H$_{44}$N$_4$O$_9$+Na$^+$: 711.3006. Found: 711.3001. TLC: CH$_2$Cl$_2$-EtOAc-MeOH-NEt$_3$, 64:21:21:5, v/v/v/v; R$_f$ 0.4.

b) Preparation of 5'-O-(4,4'-dimethoxytrityl)-2'-O-(2-N-[2-(dimethylamino)ethyl]-acetamide)-5-methyluridine-3'-(2-cyanoethyl-N,N-diisopropylphosphoramidite) (Compound 3)

Compound 2 (5.754 g, 8.35 mmol) was dried by coevaporation with anhydrous pyridine (2×75 mL) and then dissolved in CH$_2$Cl$_2$ (60 mL). To this solution, diisopropylamine tetrazolide (715 mg, 4.18 mmol) and 2-cyanoethyl-N,N,N',N'-tetraisopropylphosphordiamidite (3.18 mL, 10.02 mmol) were added. After 13 h, EtOAc (420 mL) was added and about 60 mL of solvent was evaporated in vacuo. The organic was washed with half-saturated NaHCO$_3$ (3×80 mL), then with brine (2×40 mL), dried over MgSO$_4$, filtered and evaporated in vacuo at 27° C. to give an oil. The resulting residue was coevaporated with toluene (2×300 mL) to give a foam which was then dissolved in CH$_2$Cl$_2$ (20 mL). Hexanes (1000 mL) were slowly added to the rapidly stirred solution via an addition funnel to yield a wax and the supernatant was decanted. The wax was washed with hexanes thrice and the washes were decanted. The precipitation was repeated one more time to give a white wax which was dried in vacuo at ambient temperature to give Compound 3 as a foam (6.60 g, 89%). LRMS (ES): m/z 889 (M+H$^+$), 911 (M+Na$^+$). $^{31}$P NMR (CDCl$_3$): δ 151.5, 151.0.

Compound 3 was incorporated into oligonucleotides according to standard solid phase synthesis procedures. Phosphorylation at the 5' end of oligonucleotides was achieved during synthesis by using Glen Research (Sterling, Va.) chemical phosphorylation reagent.

Example 14

Preparation of Compound 4

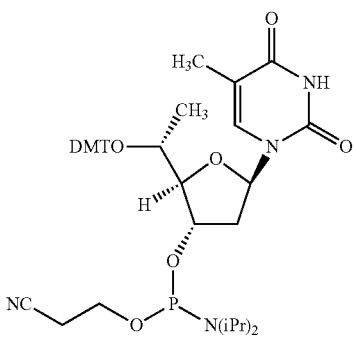

4

Compound 4 was prepared according to the procedures described in published patent application WO 94/22890. Compound 4 was incorporated into oligonucleotides according to standard solid phase synthesis procedures. Phosphorylation at the 5' end of oligonucleotides was achieved during synthesis by using Glen Research (Sterling, Va.) chemical phosphorylation reagent.

Example 15

Preparation of Compound 13

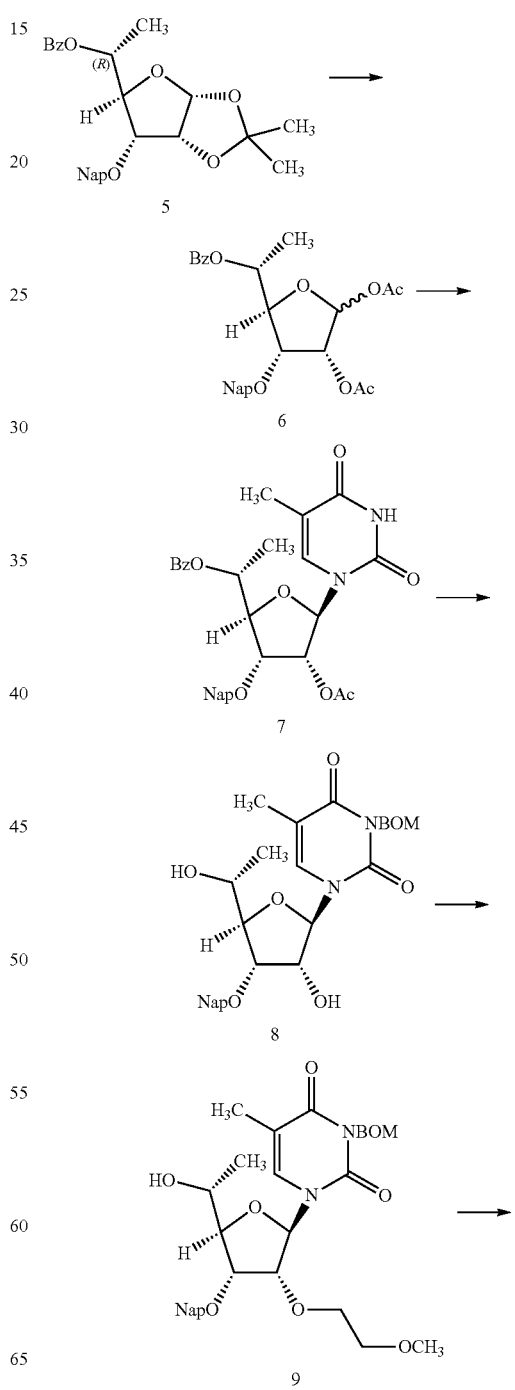

-continued

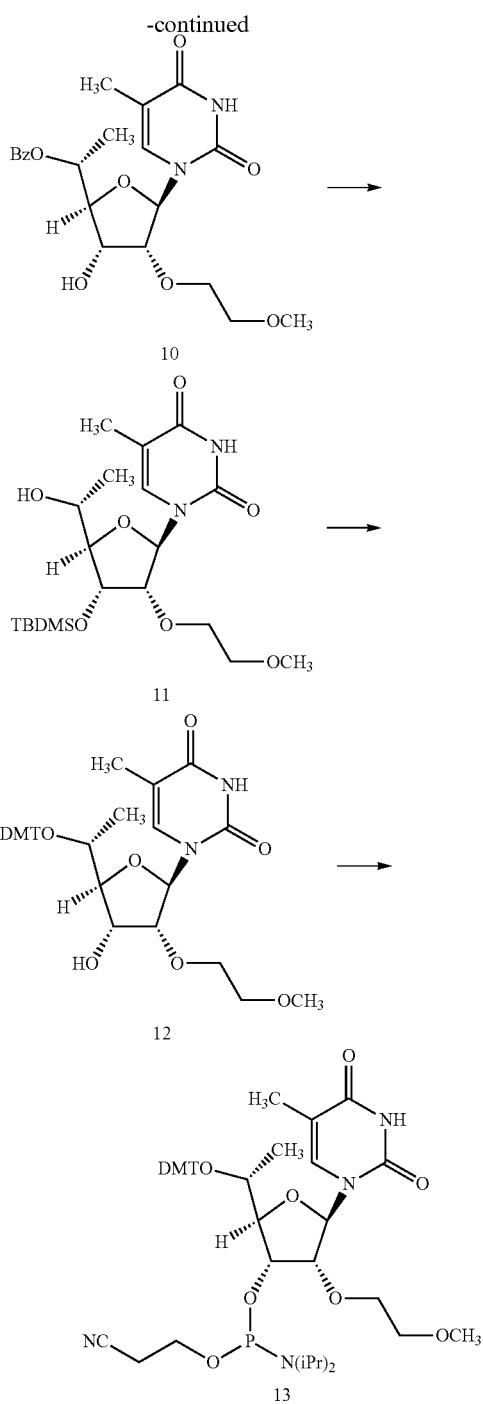

a) Preparation of 5-O-Benzyol-3-O-(2-methylnaph-thalene)-1,2-O-bis(acetyl)-5-(R)-methyl-ribose (Compound 6)

Compound 5 was prepared according to the method of De Mesmaeker wherein NapBr was used instead of BnBr (Mesmaeker et al., *Synlett,* 1997, 1287-1290). Dried Compound 5 (21.1 g, 47.04 mmol) was dissolved in a mixture of glacial acetic acid (104 mL) and acetic anhydride (17.2 mL). To this solution was added 14 drops of concentrated $H_2SO_4$. After 1.5 h, the resulting light brown solution was diluted in EtOAc (600 mL), washed with sat. $NaHCO_3$ (5×600 mL), dried over anhydrous $Na_2SO_4$, filtered, evaporated and dried under high vacuum to yield Compound 6 (22.7 g, 99%) as a pale oil. ES MS m/z 515.1[M+Na]$^+$.

b) Preparation of 5'-O-Benzyol-3'-O-(2-methylnaphthalene)-5'-(R)-methyl-5-methyluridine (Compound 7)

A mixture of Compound 6 (23.3 g, 46.70 mmol) and thymine (10.01 g, 79.40 mmol) was suspended in anhydrous $CH_3CN$ (233 mL). To this mixture was added N,O-bis-trimethylsilyl-acetamide (41.06 mL, 167.94 mmol), followed by heating at 55° C. for 1 h. The mixture was cooled to 0° C., then trimethylsilyl trifluoromethanesulfonate (19.07 mL, 105.54 mmol) was added dropwise over 15 min. The mixture was subsequently heated at 55° C. After 3 hours the mixture was cooled to 0° C. and quenched with the dropwise addition of saturated aqueous $NaHCO_3$ (20 mL). The mixture was poured into EtOAc, washed with brine (4×0.8 mL), dried over anhydrous $Na_2SO_4$, filtered, evaporated and dried under high vacuum. The residue was purified by silica gel column chromatography and eluted with 20% to 50% EtOAc in hexanes to yield Compound 7 (22.27 g, 85%) as a white foam. ES MS m/z 559.2[M+H]$^+$.

c) Preparation of 3'-O-(2-methylnaphthalene)-5'-(R)-methyl-3-N-(benzyloxymethyl)-5-methyluridine (Compound 8)

Compound 7 (11.71 g, 20.98 mmol) was dissolved in anhydrous DMF (115 mL). To this was added 1,8-diazabicycl-[5-4-0]undec-7-ene (DBU, 9.30 mL, 62.41 mmol). The reaction mixture was cooled in an ice bath. To this was added benzyl chloromethyl ether (4.36 mL, 31.47 mmol), and stirred at 0° C. for 1 hour. The mixture was diluted with EtOAc (200 mL), washed with saturated aqueous $NaHCO_3$ (200 mL) and brine (200 mL) then dried ($Na_2SO_4$), filtered and evaporated. The residue obtained was dissolved in methanol (89 mL) and $K_2CO_3$ (8.76 g, 63.40 mmol). The reaction mixture was stirred at room temperature for 1 h. The mixture was poured into EtOAc (200 mL), washed with water (200 mL) and brine (200 mL), dried over anhydrous $Na_2SO_4$, filtered and evaporated. The residue was purified by silica gel column chromatography and eluted with 5% methanol in $CH_2Cl_2$ to yield Compound 8 (8.93 g, 80%) as a white foam. ES MS m/z 533.2 [M+H]$^+$.

d) Preparation of 2'-O-(2-methoxyethyl)-3'-O-(2-methylnaphthalene)-5'-(R)-methyl-3-N-(benzyloxymethyl)-5-methyluridine (Compound 9)

Compound 8 (4.30 g, 8.07 mmol) was dried over $P_2O_5$ under reduced pressure and dissolved in anhydrous DMF (24 mL). The mixture was cooled to −20° C. To this was added NaH (0.48 g, 12.11 mmol, 60% dispersion in mineral oil) with stirring for 30 minutes followed by addition of 1-methoxy-2-iodoethane (2.25 g, 12.11 mmol). The reaction mixture was warmed up to 0° C. After stirring for 1.5 h at 0° C. the reaction mixture was cooled to −20° C. and additional NaH (0.48 g, 12.11 mmol, 60% dispersion in mineral oil) was added. Stirring was continued at −20° C. for 30 minutes and 1-methoxy-2-iodoethane (2.25 g, 12.11 mmol) was added. The reaction mixture was warmed to 0° C. and with stirring for an additional 1.5 h. The reaction was quenched with methanol (5 mL), diluted with EtOAc (100 mL), washed with water (100 mL) and brine (100 mL), dried over $Na_2SO_4$, filtered and evaporated under reduced pressure. The residue was purified by silica gel column chromatography and eluted with 5% methanol in $CH_2Cl_2$ to yield Compound 9 (2.95 g, 62%). ES MS m/z 591.2 $[M+H]^+$.

e) Preparation of 5'-O-Benzoyl-2'-O-(2-methoxyethyl)-5'-(R)-methyl-5-methyluridine (Compound 10)

Compound 9 (2.2 g, 3.73 mmol) was dissolved in anhydrous pyridine (7 mL) and cooled in an ice bath. To this benzoyl chloride (0.88 mL, 7.61 mmol) was added and once the addition was over, reaction mixture was allowed to come to room temperature. The reaction mixture was stirred at room temperature for 4 h under an argon atmosphere and subsequently cooled the reaction mixture in an ice bath and quenched by adding saturated aqueous $NaHCO_3$ (5 mL). Diluted the reaction mixture with EtOAc (50 mL) and washed with saturated aqueous $NaHCO_3$ (2×50 mL), brine (50 mL), dried over $Na_2SO_4$, filtered and concentrated. The residue obtained was dissolved in $CH_2Cl_2$ (40 mL) and added 2,4-dichloro-5,6-dicyano-1,4-benzoquinone (DDQ, 1.93 g, 8.5 mmol) and $H_2O$ (0.15 mL, 8.5 mmol) and stirred at room temperature. After 18 h, diluted the reaction mixture with EtOAc (60 mL), washed with saturated aqueous $NaHCO_3$ (2×80 mL), brine (50 mL), dried over $Na_2SO_4$, filtered and evaporated under reduced pressure. The residue was dissolved in MeOH (30 mL) and palladium hydroxide (1.1 g, 20 wt % Pd on carbon dry base) and stirred under $H_2$ atmosphere for 6 h. To this acetic acid (0.56 mL) was added and stirred for 5 min. The reaction mixture was filtered through a pad of celite 545, and washed the celite with copious amount of MeOH. The combined filtrate and washing were concentrated under reduced pressure and the residue was purified by silica gel column chromatography and eluted with 5% methanol in $CH_2Cl_2$ to yield Compound 10 (1.43 g, 88%). ES MS m/z 435.1 $[M+H]^+$.

f) Preparation of 2'-O-(2-methoxyethyl)-5'-(R)-methyl-3'-O-tert-butyldimethylsilyl-5-methyluridine (Compound 11)

A mixture of Compound 10 (1.33 g, 3.06 mmol) and imidazole (2.09, 30.70 mmol) was dissolved in anhydrous DMF (11.4 mL). To this solution tert-butyldimethylsilyl chloride (2.31 g, 15.33 mmol) was added with stirring at room temperature for 16 h under an atmosphere of argon. The reaction mixture was diluted with EtOAc (75 mL) and washed with saturated aqueous $NaHCO_3$ (2×60 mL) and brine (50 mL), dried over $Na_2SO_4$, filtered and concentrated. The residue obtained was dissolved in methanolic ammonia (20 mL, 7 M) and stirred for 24 h at 55° C. The solvent was removed under reduced pressure and the residue was purified by silica gel column chromatography and eluted with 50% EtOAc in hexanes to yield Compound 11 (1.21 g, 89%). ES MS m/z 455.2 $[M+H]^+$.

g) Preparation of 5'-O-(4,4'-dimethoxytrityl)-2'-O-(2-methoxyethyl)-5'(R)-methyl-5-methyluridine (Compound 12)

Compound 11 (0.42 g, 0.96 mmol) was mixed with 4,4'-dimethoxytrityl chloride (0.82 g, 2.41 mmol) and dried over $P_2O_5$ under reduced pressure. The mixture was dissolved in anhydrous pyridine (3 mL) and stirred at 45° C. for 18 h under an atmosphere of argon. The reaction mixture was cooled to room temperature and diluted with EtOAc (40 mL) and washed with saturated aqueous $NaHCO_3$ (60 mL) and brine (40 mL), dried over $Na_2SO_4$, filtered and concentrated. The residue obtained was purified by silica gel column chromatography and eluted first with 50% EtOAc in hexanes and then with 5% methanol in $CH_2Cl_2$. The product obtained was dissolved in a mixture of triethylamine trihydrofluoride (1.38 mL, 8.44 mmol) and triethylamine (0.58 mL, 4.22 mmol) in THF (8.4 mL). After 72 h the mixture was diluted with EtOAc (60 mL), washed with water (40 mL), saturated aqueous $NaHCO_3$ (40 mL) and brine (40 mL) then dried over $Na_2SO_4$, filtered and evaporated. The residue obtained was purified by silica gel column chromatography and eluted with 70% EtOAc in hexanes to yield Compound 12 (0.44 g, 73%). ES MS m/z 631.2 $[M+H]^+$.

h) Preparation of 5'-O-(4,4'-dimethoxytrityl)-2'-O-(2-methoxyethyl)-5'-(R)-methyl-5-methyluridine-3'-(2-cyanoethyl-N,N-diisopropylphosphoramidite (Compound 13)

Compound 12 (0.35 g, 0.55 mmol) was dried over $P_2O_5$ under reduced pressure then dissolved in anhydrous DMF (1.8 mL). To this 1-H-tetrazole (0.033 mg, 0.48 mmol), N-methyl-imidazole (0.012 mL, 0.15 mmol) and 2-cyanoethyl-N,N,N',N'-tetraisopropylphosphordiamidite (0.27 mL, 0.86 mmol) were added. After 3 h, EtOAc (40 mL) was added and the mixture was washed with saturated $NaHCO_3$ (30 mL) and brine (40 mL), dried over anhydrous $Na_2SO_4$, filtered and evaporated in vacuo to give an oil. The oily residue was purified by silica gel column chromatography by eluting with EtOAc/hexane (1:1) to yield Compound 13 (0.38 g, 83%) as a white foam. MS (ES): m/z 831 $[M+H]^+$; $^{31}P$ NMR (121 MHz, $CDCl_3$): δ 150.2, 149.

Example 16

Preparation of Compound 22

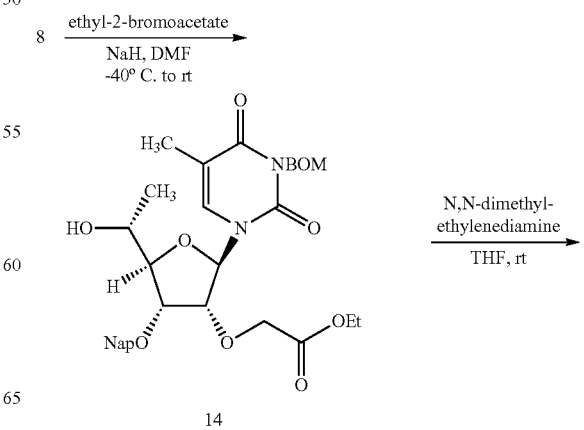

14

117
-continued

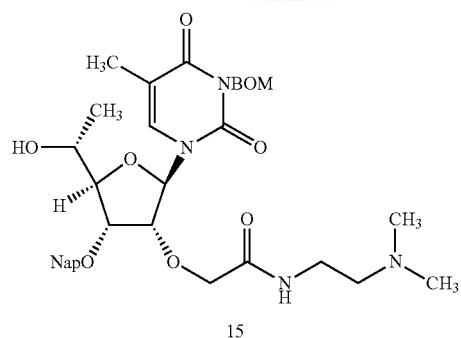

15

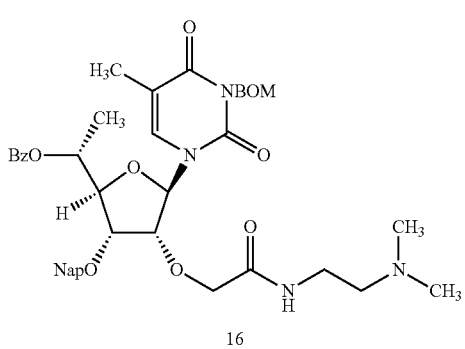

16

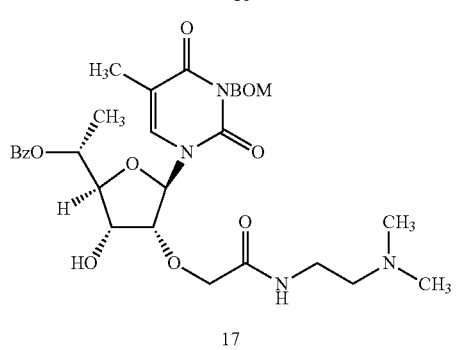

17

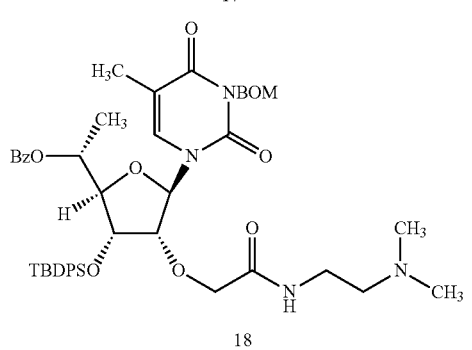

18

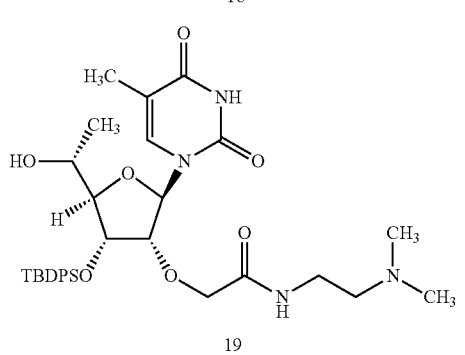

19

118
-continued

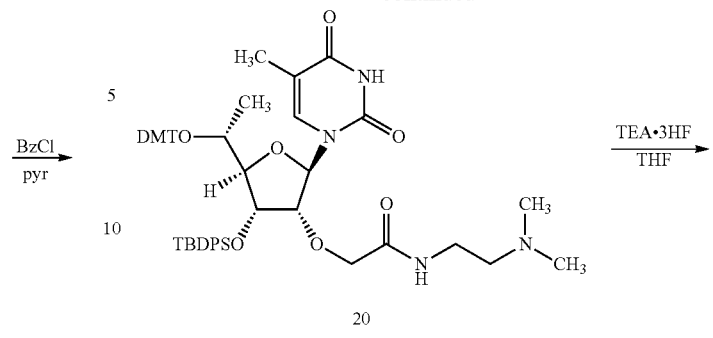

20

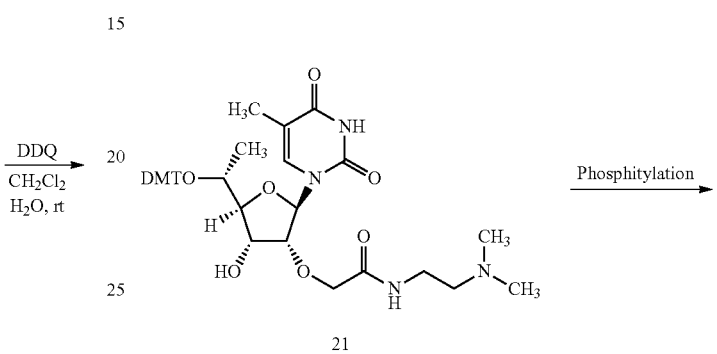

21

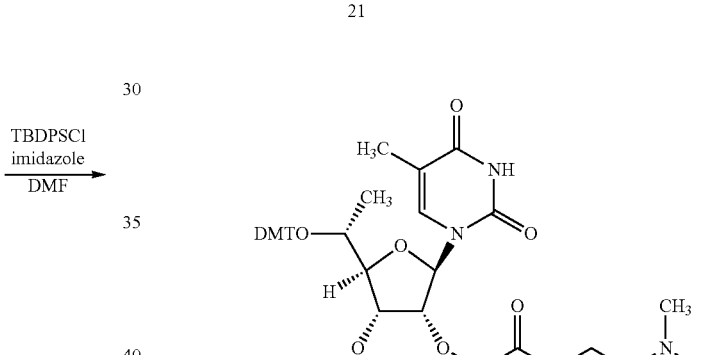

22

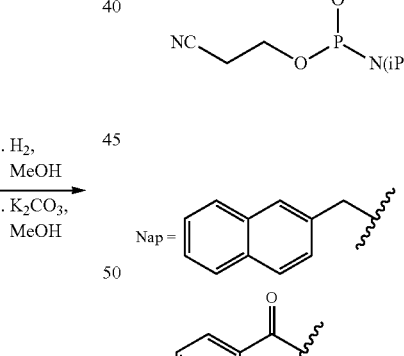

Compound 8 is prepared as per the procedures illustrated in Example 15. Compound 22 is prepared according to the scheme illustrated above. Compound 22 is incorporated into oligonucleotides according to standard solid phase synthesis procedures. Phosphorylation at the 5' end of oligonucleotides is achieved during synthesis by using Glen Research (Sterling, Va.) chemical phosphorylation reagent.

Example 17

Preparation of Compound 26

Scheme 1.

11 →(i)

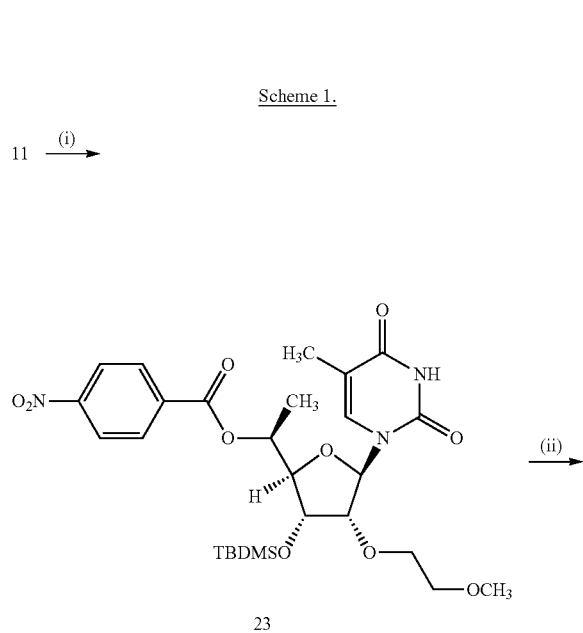

23

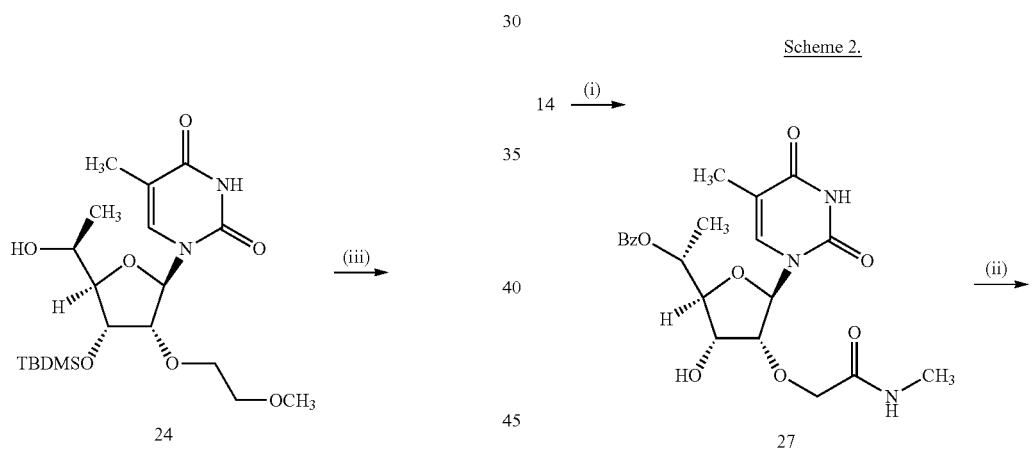

24

25

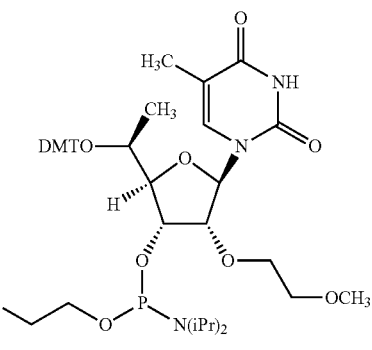

26

(i) 4-nitrobenzoic acid, triphenylphosphine, diisopropyl azodicarboxylate, rt; (ii) NH₃, MeOH, 55° C.; (iii) a. DMTCl, pyridine, 45° C., b. THF•3HF, TEA, THF; (iv) 2-cyanoethyl-N,N,N'N'-tetraisopropylphosphordiamidite, 1-H-tetrazole, N-methyl-imidazole, DMF. Compound 11 is prepared as per the procedures illustrated in Example 15.

Example 18

Preparation of Compound 30

Scheme 2.

14 →(i)

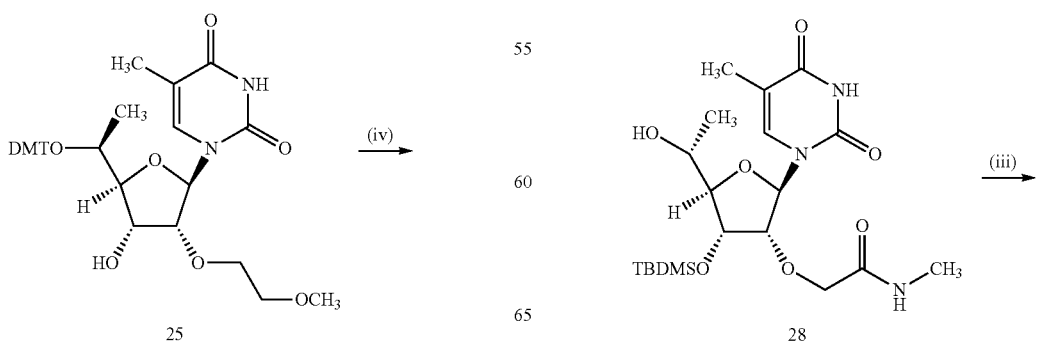

27

28

-continued

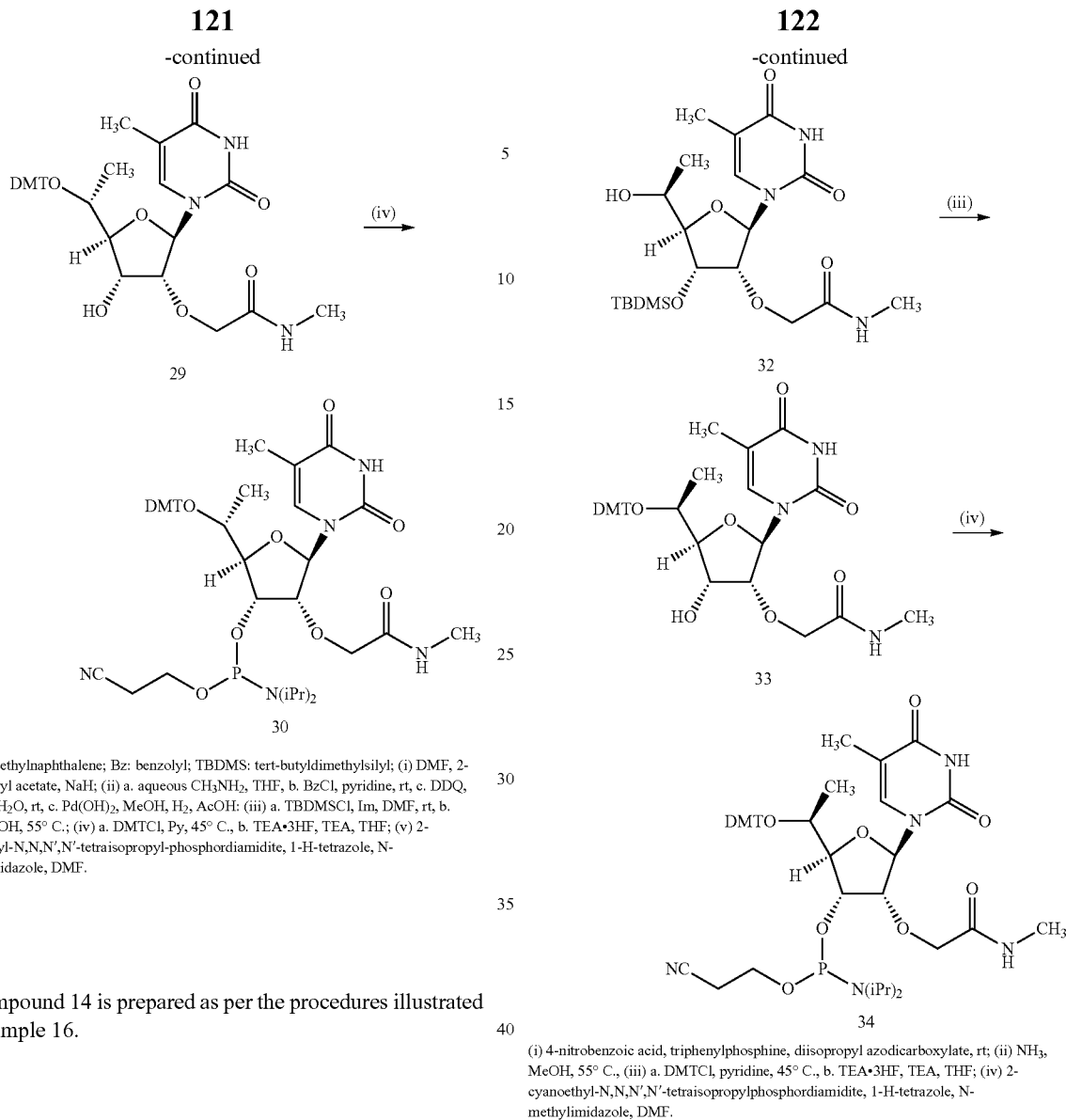

Nap: 2-methylnaphthalene; Bz: benzolyl; TBDMS: tert-butyldimethylsilyl; (i) DMF, 2-bromoethyl acetate, NaH; (ii) a. aqueous CH₃NH₂, THF, b. BzCl, pyridine, rt, c. DDQ, CH₂Cl₂, H₂O, rt, c. Pd(OH)₂, MeOH, H₂, AcOH: (iii) a. TBDMSCl, Im, DMF, rt, b. NH₃, MeOH, 55° C.; (iv) a. DMTCl, Py, 45° C.; b. TEA•3HF, TEA, THF; (v) 2-cyanoethyl-N,N,N′,N′-tetraisopropyl-phosphordiamidite, 1-H-tetrazole, N-methylimidazole, DMF.

Compound 14 is prepared as per the procedures illustrated in Example 16.

Example 19

Preparation of Compound 34

Scheme 3.

(i) 4-nitrobenzoic acid, triphenylphosphine, diisopropyl azodicarboxylate, rt; (ii) NH₃, MeOH, 55° C., (iii) a. DMTCl, pyridine, 45° C., b. TEA•3HF, TEA, THF; (iv) 2-cyanoethyl-N,N,N′,N′-tetraisopropylphosphordiamidite, 1-H-tetrazole, N-methylimidazole, DMF.

Compound 28 is prepared as per the procedures illustrated in Example 18

Example 20

Preparation of Compound 37

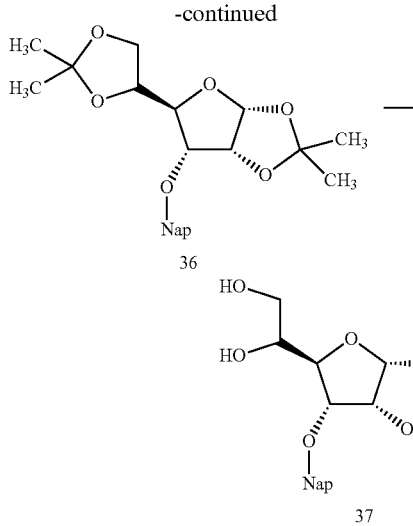

under reduced pressure to provide Compound 37 as a yellow foam, which was used without any further purification.

Example 21

Preparation of Compound 45

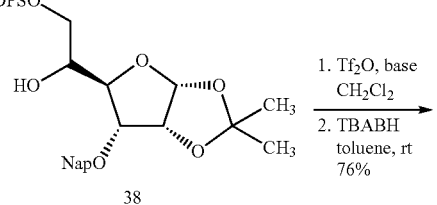

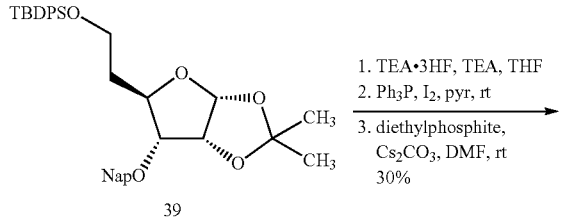

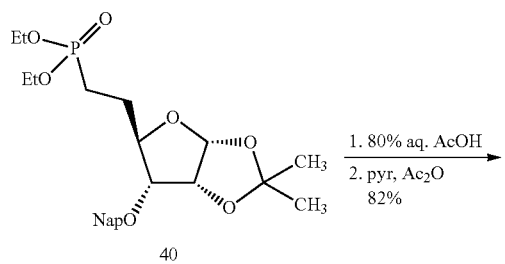

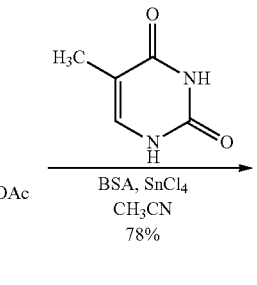

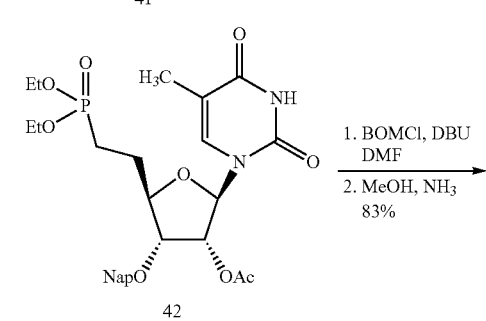

a) Preparation of Compound 36

Commercially available 1,2;5,6-di-O-isopropylidene-α-D-allofuranose, Compound 35, (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction and the stirring was continued for another 60 minutes after the addition was complete. At this time TLC analysis showed no more sugar (Compound 35). The reaction was carefully poured onto crushed ice (ca. 500 g) and the resulting slurry was stirred vigorously until all the ice melted. The resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide Compound 36 (206.0 g, 99%) as an off-white solid. $^1$H NMR (300 MHz, CDCl$_3$) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

b) Preparation of Compound 37

Compound 36 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 36. The reaction was then concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution and brine then dried (Na$_2$SO$_4$), filtered and concentrated

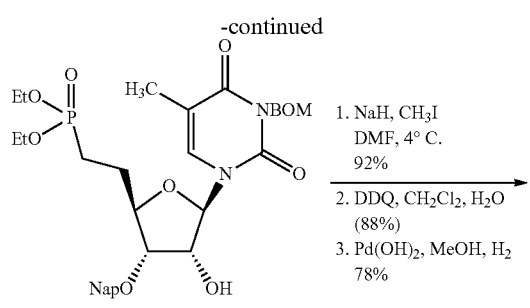
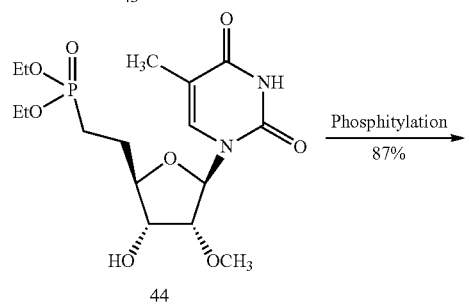
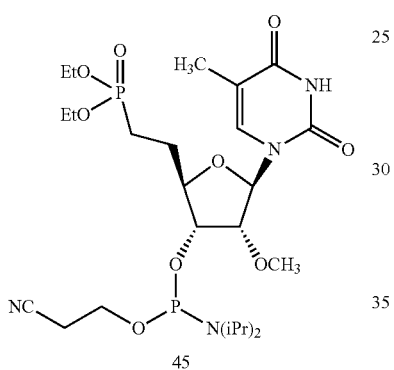
Compound 37 is prepared as per the procedures illustrated in Example 20.
Example 22
Preparation of Compound 47
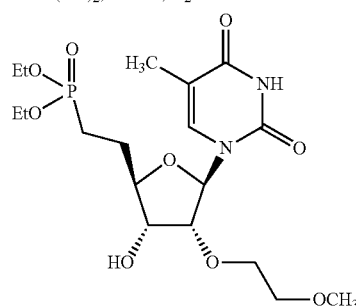
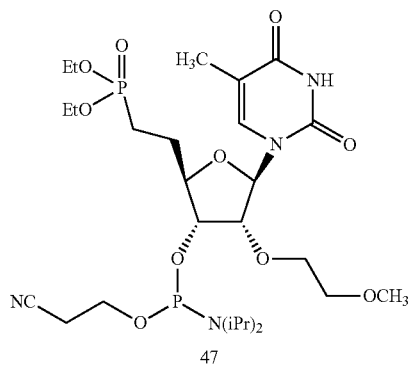
Compound 43 is prepared as per the procedures illustrated in Example 21.
Example 23
Preparation of Compound 50
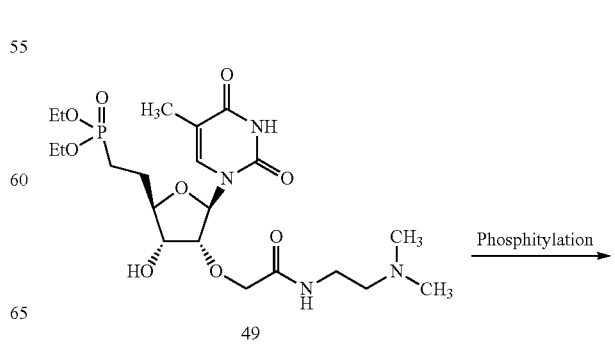

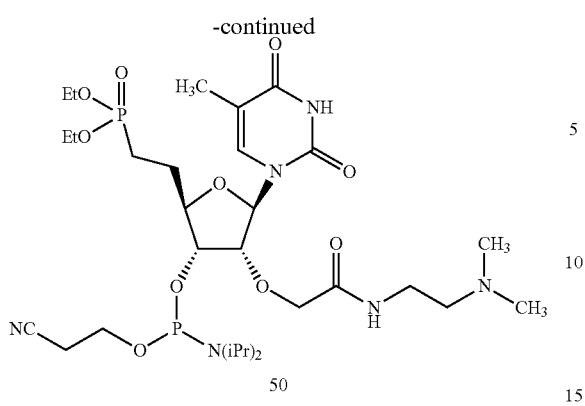
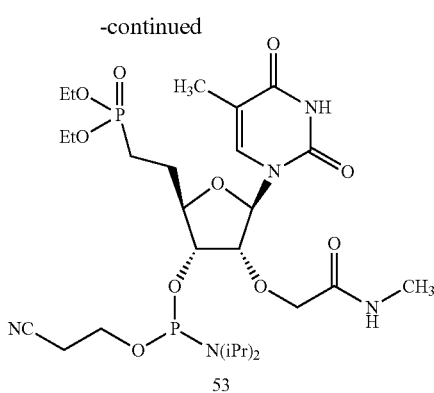
Compound 43 is prepared as per the procedures illustrated in Example 21.
Example 24
Preparation of Compound 53
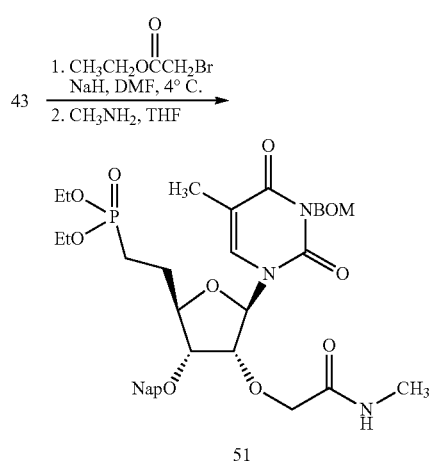
Compound 43 is prepared as per the procedures illustrated in Example 21.
Example 25
Preparation of Compound 57
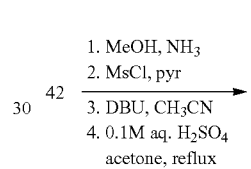
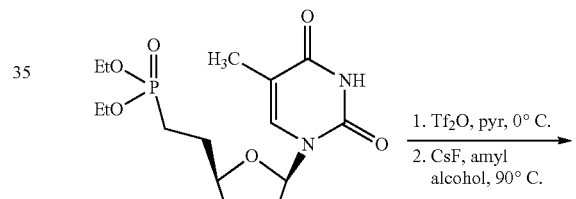
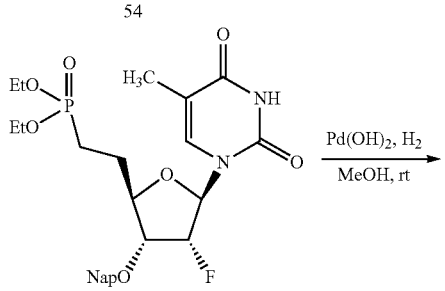
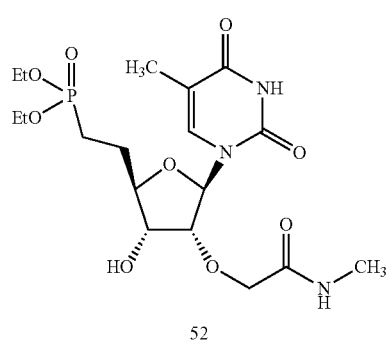
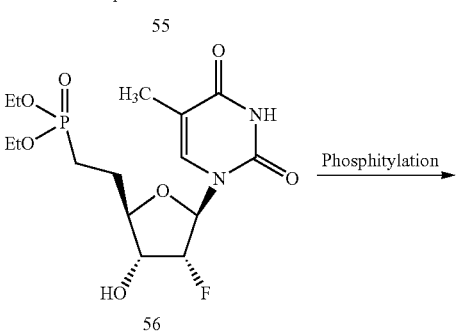

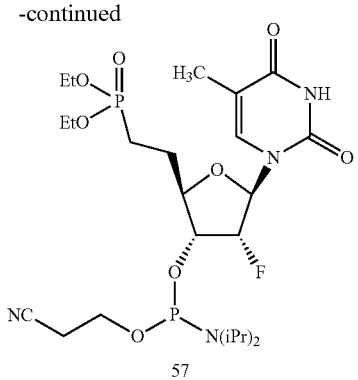

Compound 42 is prepared as per the procedures illustrated in Example 21.

Example 26

Preparation of Compound 58

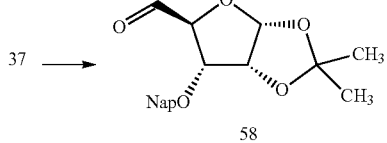

Compound 37 was prepared as per the procedures illustrated in Example 20. A solution of $NaIO_4$ (107.0 g) in water (3 L) was added over 40 minutes to a stirred (mechanical stirrer) solution of Compound 37 (crude from above) in dioxane (1.5 L). After 60 minutes the reaction mixture was poured into EtOAc (1.5 L) and the organic layer was separated, washed with water (1 L) and brine (1 L) then dried ($Na_2SO_4$) and concentrated to provide Compound 58 as a yellow oil, which was used without any further purification.

Example 27

Preparation of Compound 67

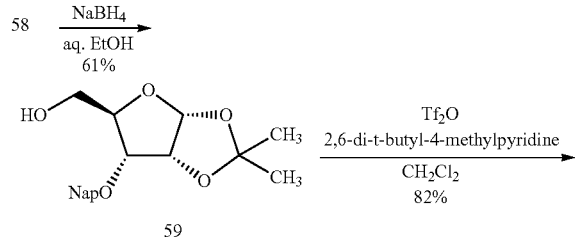

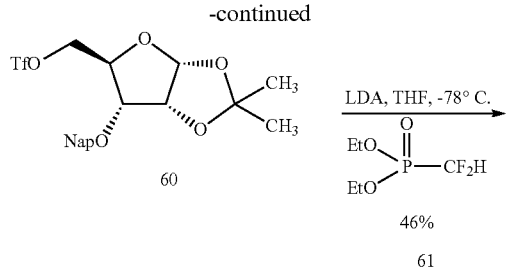

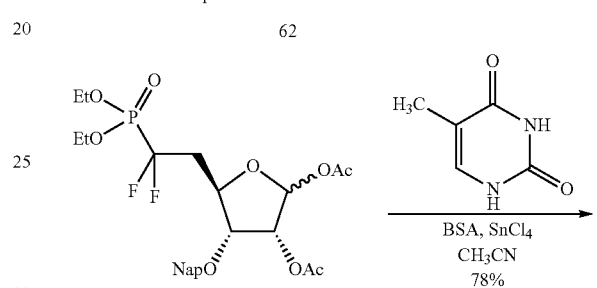

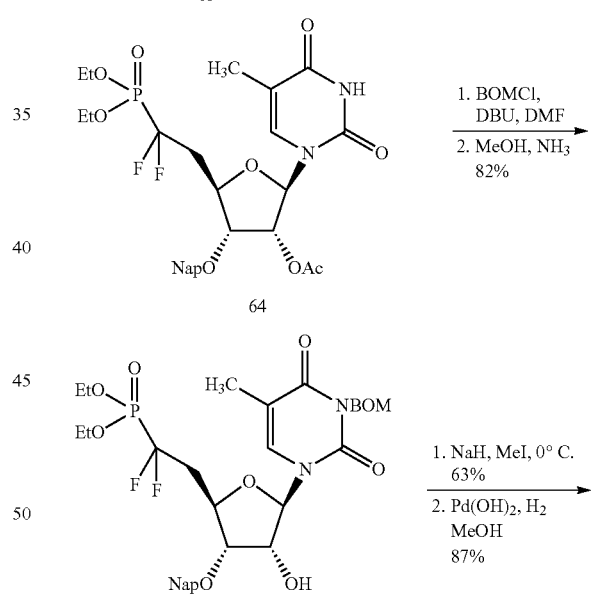

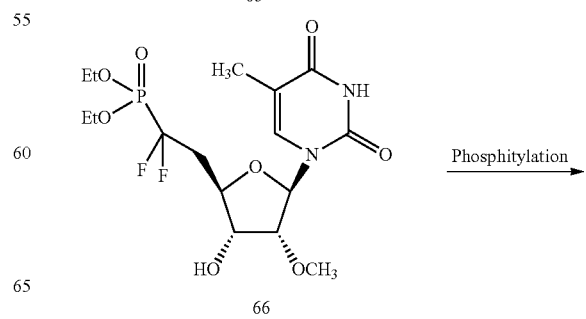

131
-continued

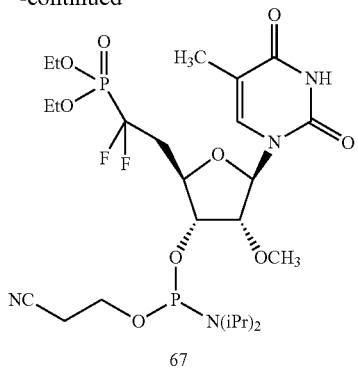

67

Compound 58 was prepared as per the procedures illustrated in Example 26. Compound 61, diethyl-(difluoromethane)phosphonate is commercially available. The preparation of Compound 67 was achieved as per the procedures illustrated in Example 27 and confirmed by spectral analysis, ¹HNMR and mass spectroscopy.

Example 28

Preparation of Compound 69

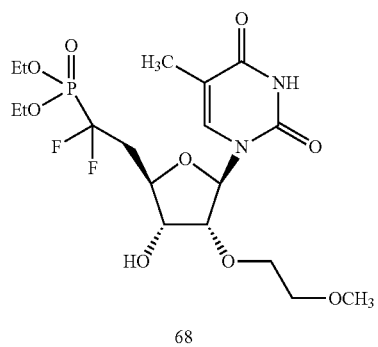

68

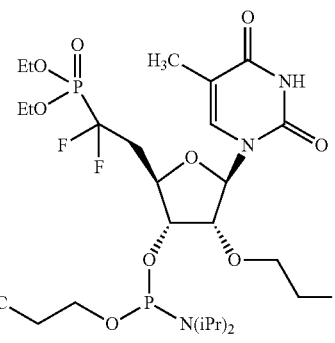

69

Compound 65 was prepared as per the procedures illustrated in Example 27. The preparation of Compound 69 was

132 achieved as per illustrated in Example 28 and confirmed by spectral analysis, ¹HNMR and mass spectroscopy.

Example 29

Preparation of Compound 72

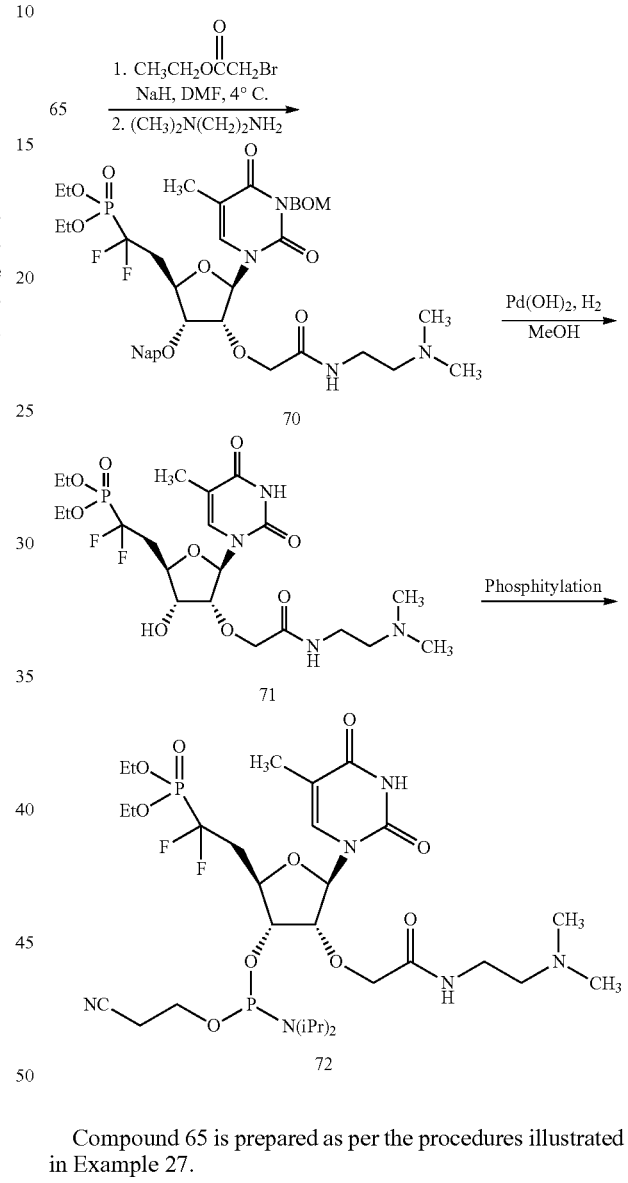

Compound 65 is prepared as per the procedures illustrated in Example 27.

Example 30

Preparation of Compound 75

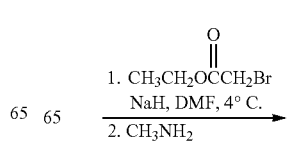

133
-continued
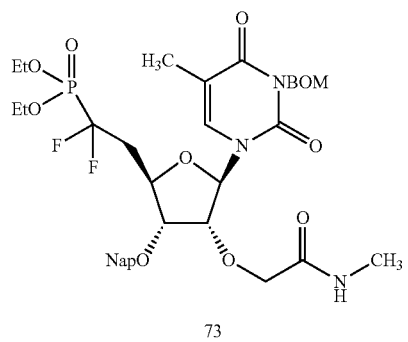
73
Phosphitylation →
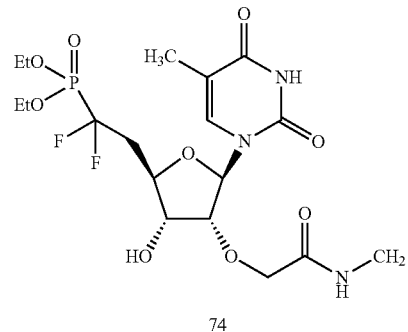
74
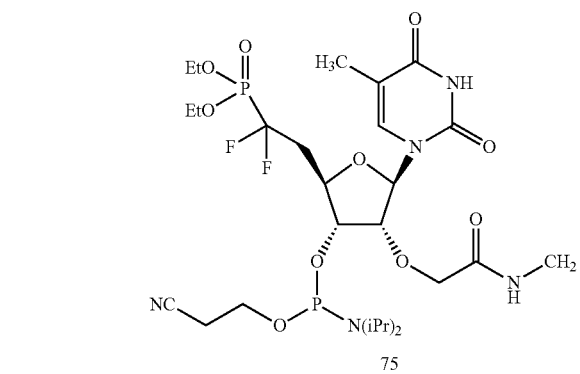
75
Compound 65 is prepared as per the procedures illustrated in Example 27.
Example 31
Preparation of Compound 79
1. MeOH, NH$_3$
2. MsCl, pyr
64  3. DBU, CH$_3$CN
4. 0.1M aq. H$_2$SO$_4$
   acetone, reflux
→
134
-continued
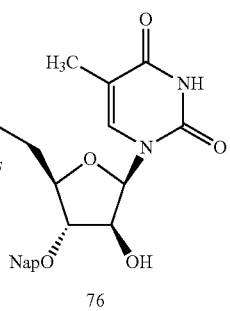
76
1. Tf$_2$O, pyr, 0° C.
2. CsF, amyl alcohol, 90° C.
→
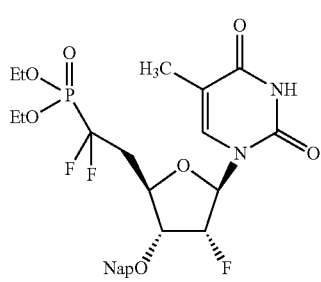
77
Pd(OH)$_2$, H$_2$
———————
MeOH, rt
→
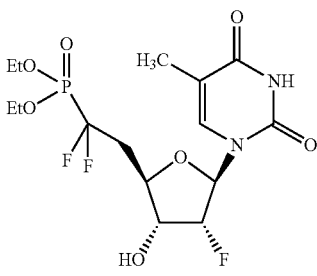
78
Phosphitylation →
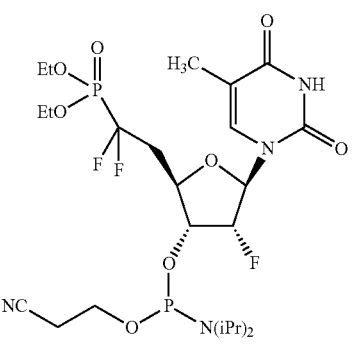
79

Compound 64 is prepared as per the procedures illustrated in Example 27.

Example 32

Preparation of Compound 86

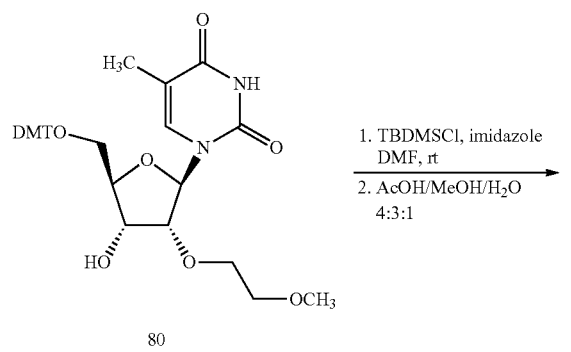

80

1. TBDMSCl, imidazole DMF, rt
2. AcOH/MeOH/H₂O 4:3:1

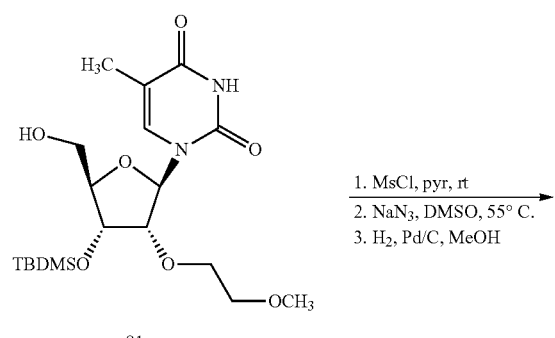

81

1. MsCl, pyr, rt
2. NaN₃, DMSO, 55° C.
3. H₂, Pd/C, MeOH

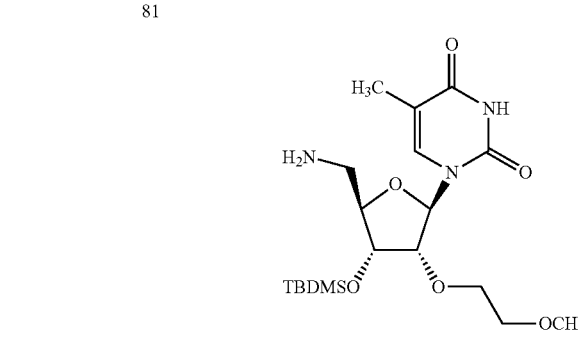

82

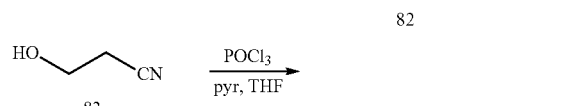

83

POCl₃
pyr, THF

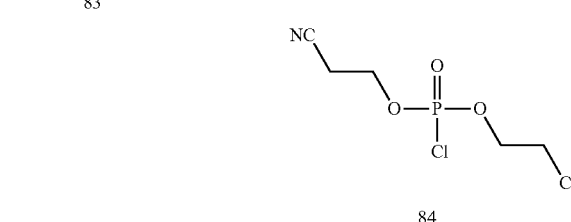

84

82

1. Compound 84 TEA, THF, rt
2. TEA·3 HF, TEA THF, rt

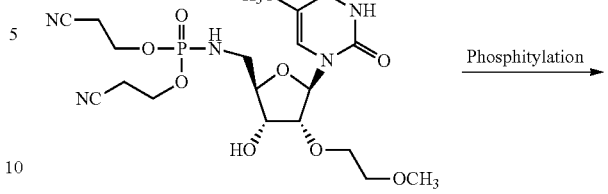

85

Phosphitylation

(near compound 86 position — actually part of upper right)

86

Compound 80 is prepared according to the procedures illustrated in published U.S. Pat. No. 5,969,116.

Example 33

Preparation of 5'-N-(4-methoxytrityl)-5'-amino-5'deoxy-thymidine-3'-(2-cyanoethyl-N,N-diisopropylphosphoramidite) (Compound 89)

87

88

-continued

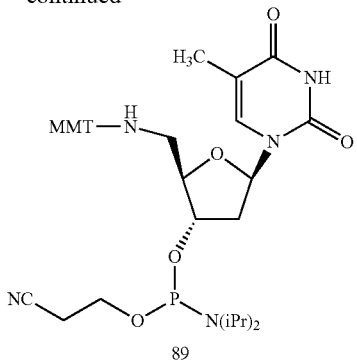

89 a) Preparation of 5'-N-(4-methoxytrityl)-5'-amino-5'deoxy-thymidine (Compound 88)

Compound 87, 5'-amino-deoxythymidine is commercially available. Compound 88 is prepared according to the method of Mag and Engels (Mag, M.; Engles, J. W. *Nucleic Acids Res.* 1989, 17, 5973-5988).

b) Preparation of 5'-N-(4-methoxytrityl)-5'-amino-5' deoxy-thymidine-3'-(2-cyanoethyl-N,N-diisopropylphosphoramidite) (Compound 89)

To the solution of Compound 88 (1.05 g, 1.88 mmol) and tetrazole (0.11 g, 1.5 mmol) in anhydrous DMF (9 mL) was added 1-methylimidazole (0.039 mL, 0.5 mmol) while stirring under a nitrogen atmosphere. The reaction mixture was cooled to 0° C. and 2-cyanoethyl-N,N,N',N'-tetraisopropylphosphordiamidite (0.89 mL, 2.8 mmol) was added. After 3.5 h, the reaction was quenched with butanol (2 mL) and the reaction volume was reduced to 50% by volume under reduced pressure. The reaction mixture was diluted with EtOAc (50 mL), washed with saturated NaHCO$_3$ (35 mL), then with brine (50 mL) and dried briefly over anhydrous Na$_2$SO$_4$. The organic phase was filtered and concentrated under reduced pressure. The resulting residue was dissolved in diethyl ether:CH$_2$Cl$_2$ (1:1, 2.25 mL) and was added dropwise into an ice cold pentane (300 mL) solution. The resulting solid was filtered to afford Compound 89 (1.24 g, 86.7%). $^{31}$P NMR (121 MHz, CD$_3$CN): δ 148.31 and 148.08.

Example 34

Preparation of Compound 92

81 
1. MsCl, pyr, rt
2. KSAc, DMF, 55° C.
3. HCl, MeOH
→

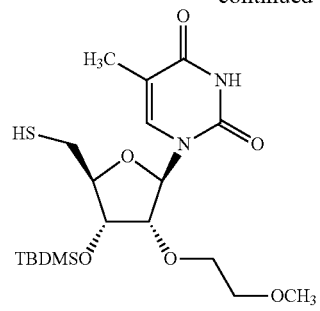

90

1. Compound 84
   TEA, THF, rt
2. TEA·3HF, TEA
   THF, rt
→

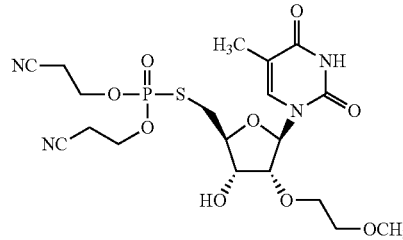

91

Phosphitylation →

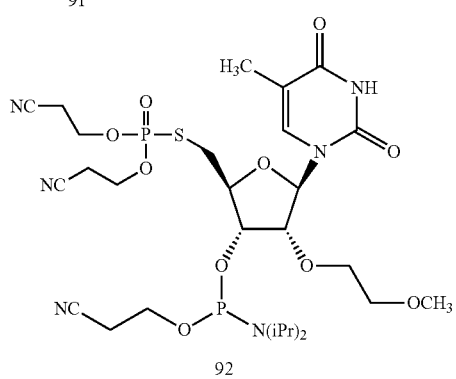

92

Compounds 81 and 84 are prepared as per the procedures illustrated in Example 32.

Example 35

Preparation of 5'-S-(4,4'-dimethoxytrityl)-5'-thiothymidine 3'-(2-cyanoethyl-diisopropylphosphoramidite) (Compound 93)

93

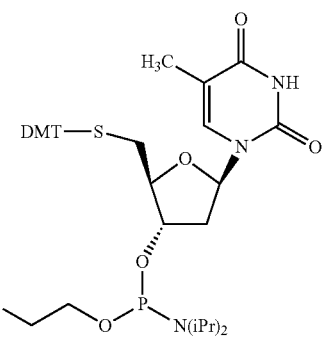

Compound 93 is prepared according to the method of Jahn-Hofmann and Engels (Jahn-Hofmann, K.; Engels, J. W. *Helvetica Chimica Acta* 2004, 87, 2812-2828).
Example 36
Preparation of Compound 102
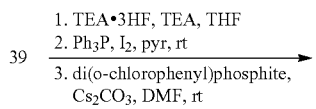
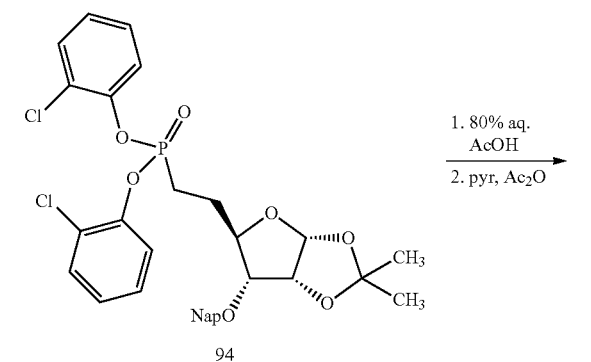
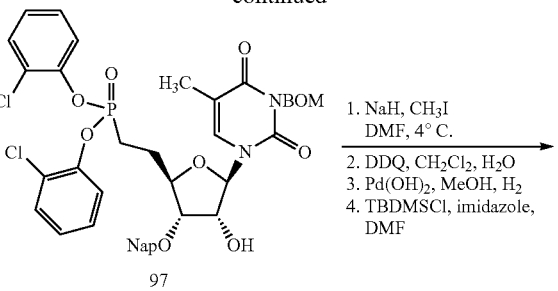
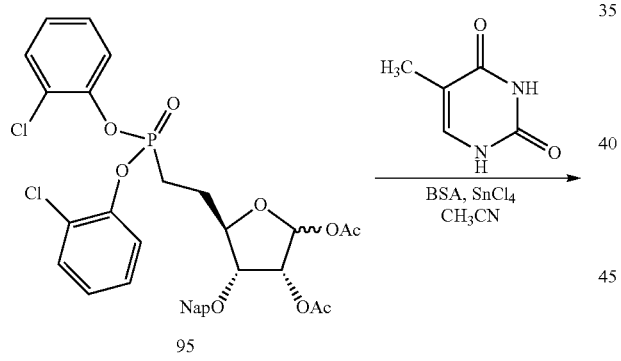

-continued

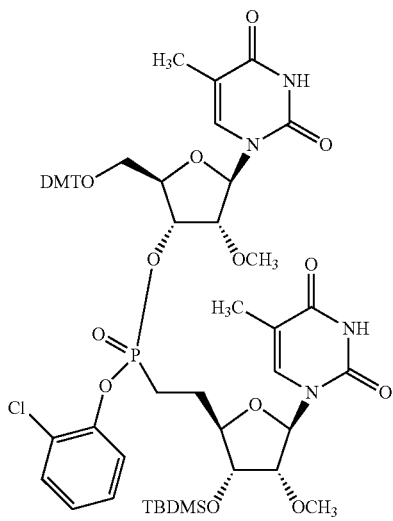

101

1. TEA•3HF, TEA, THF
2. Phosphitylation
→

-continued

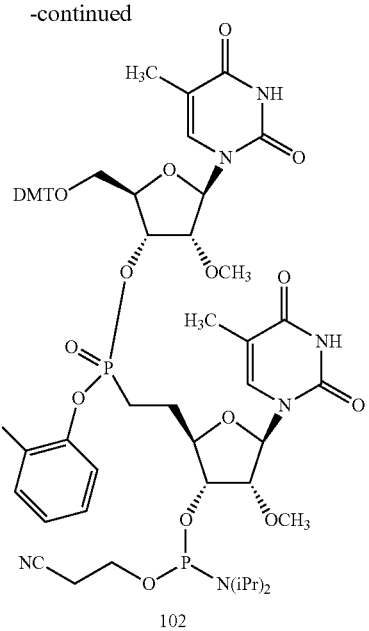

102

Compound 39 is prepared as per the procedures illustrated in Example 21. Compound 100 is prepared according to the method published by Inoue, H. et al. *Nucleic Acids Research* 1987, 15, 6131-6148.

Example 37

Preparation of Compound 106

97

1. NaH, CH$_3$OCH$_2$CH$_2$I DMF, 4° C.
2. DDQ, CH$_2$Cl$_2$, H$_2$O
3. Pd(OH)$_2$, MeOH, H$_2$
4. TBDMSCl, imidazole, DMF
→

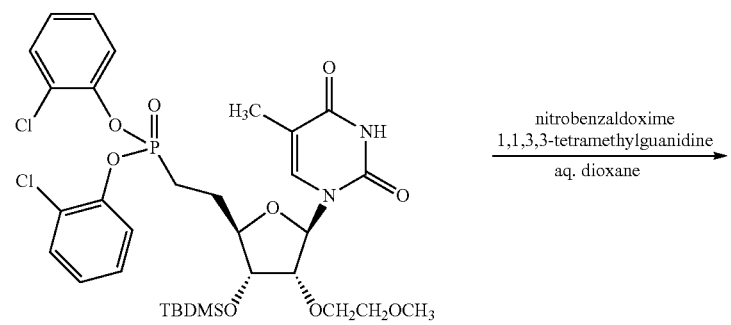

103 nitrobenzaldoxime
1,1,3,3-tetramethylguanidine
aq. dioxane
→

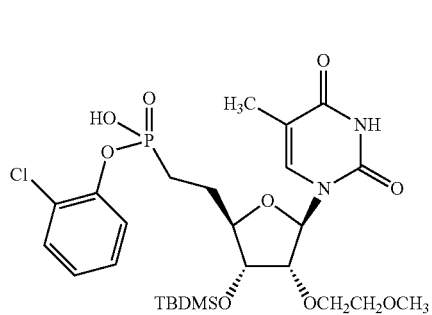

104

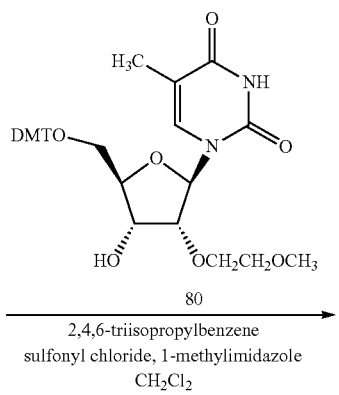

80

2,4,6-triisopropylbenzene sulfonyl chloride, 1-methylimidazole
CH$_2$Cl$_2$
→

-continued
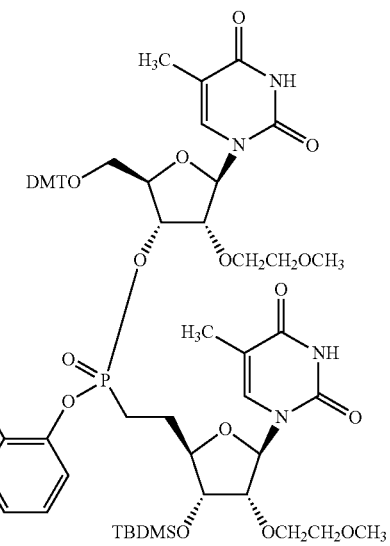
105
1. TEA•3 HF, TEA, THF
2. Phosphitylation
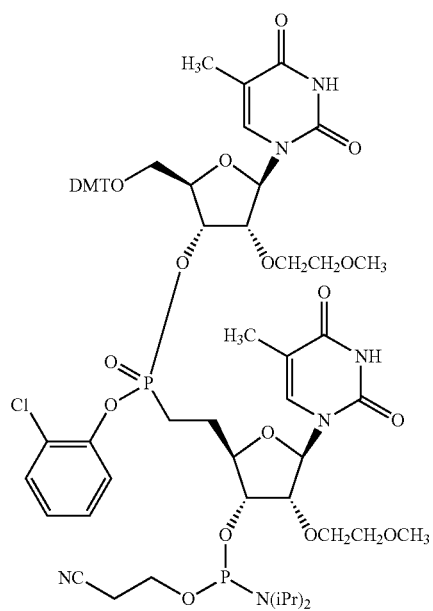
106
Compound 97 is prepared as per the procedures illustrated in Example 36. Compound 80 is prepared according to the procedures published in U.S. Pat. No. 5,969,116.

Example 38
Preparation of Compound 109
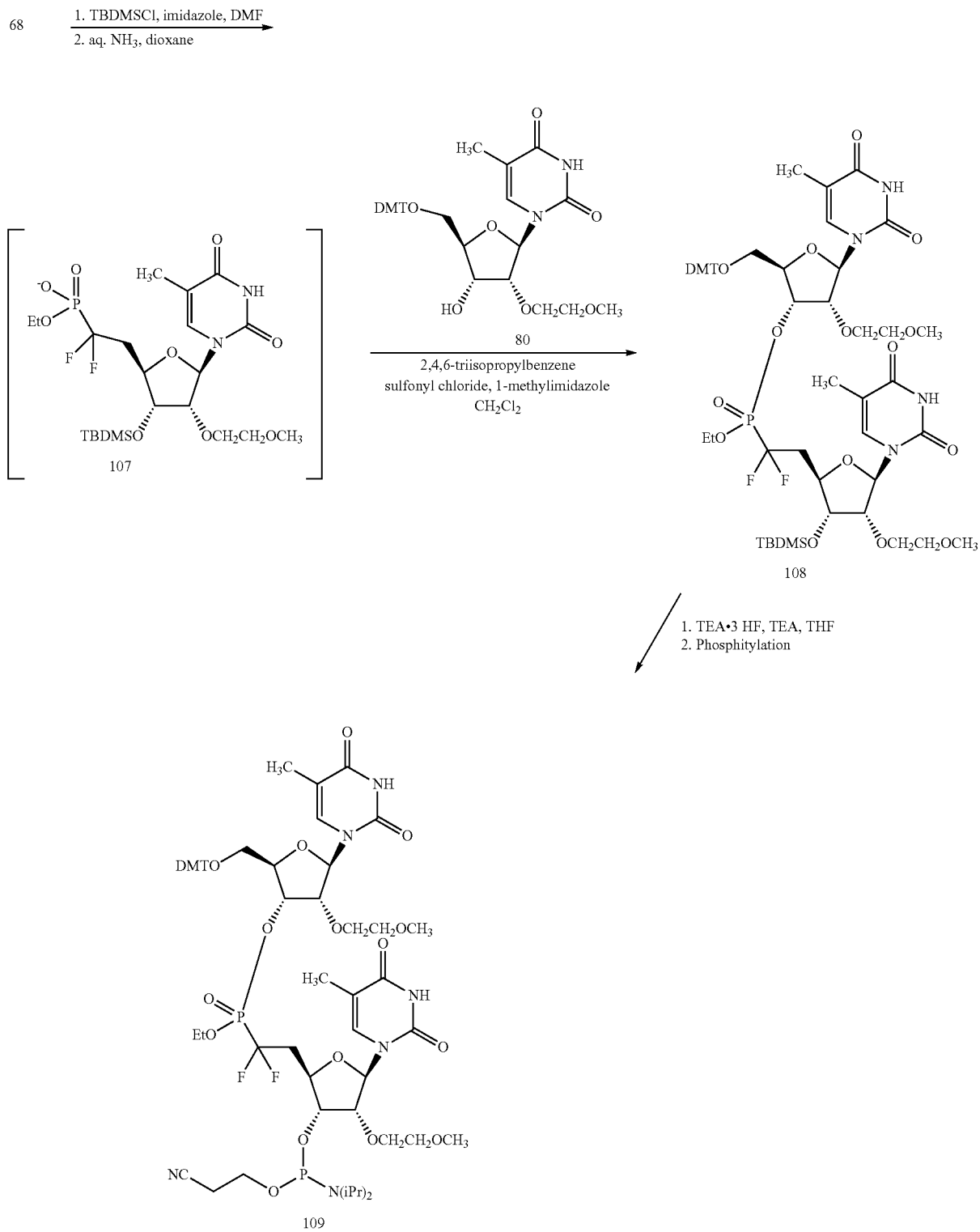
Compound 68 is prepared as per the procedures illustrated in Example 28. Compound 80 is prepared according to the procedures published in U.S. Pat. No. 5,969,116.

Example 39
Preparation of Compound 112
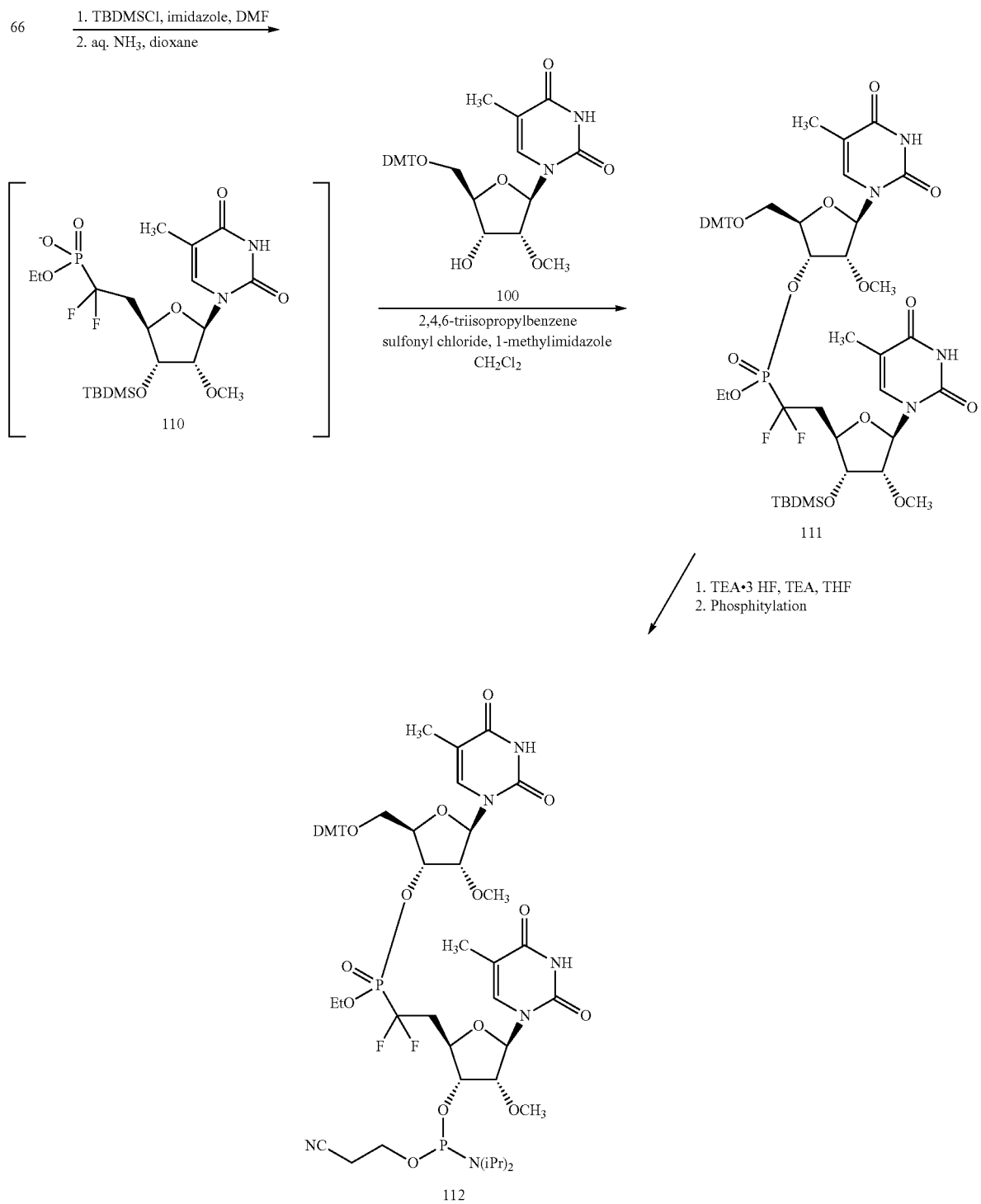
Compound 66 is prepared as per the procedures illustrated in Example 27. Compound 100 is prepared according to the method published by Inoue, H. et al. *Nucleic Acids Research* 1987, 15, 6131-6148.

Example 40
Preparation of Compound 116
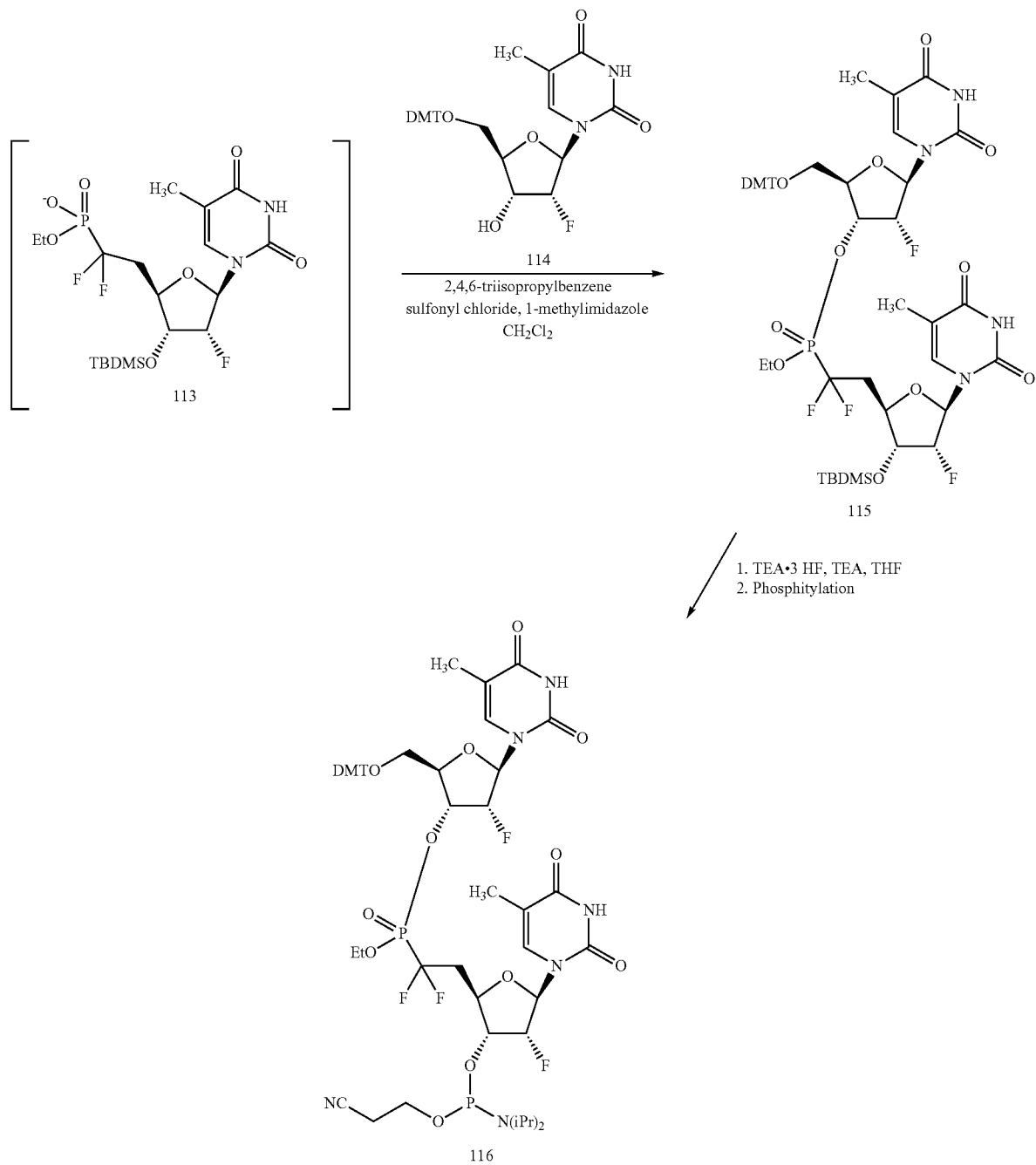
Compound 78 is prepared as per the procedures illustrated in Example 31. Compound 114 is prepared according to procedures published by Ikeda, H. et al. *Nucleic Acids Research* 1998, 26, 2237-2244.

Example 41
Preparation of Compounds 119, 120 and 121
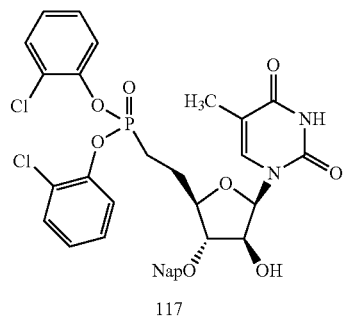
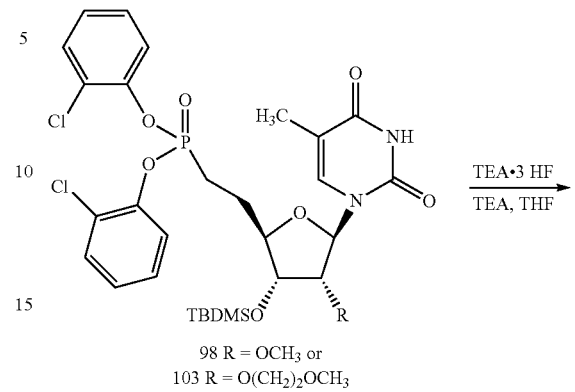
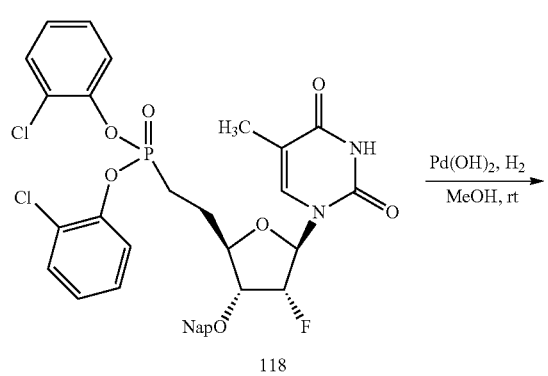
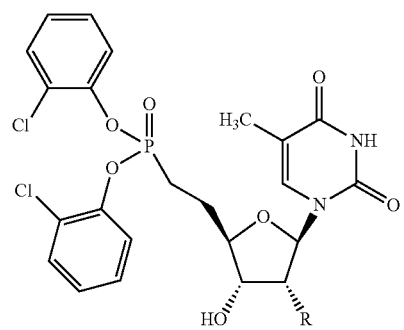
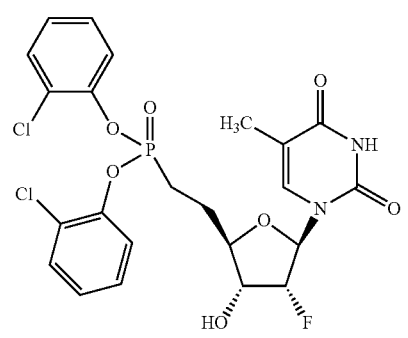
Compounds 96 and 98 are prepared as per the procedures illustrated in Example 36. Compound 103 is prepared as per the procedures illustrated in Example 37.
Example 42
Preparation of Compound 125
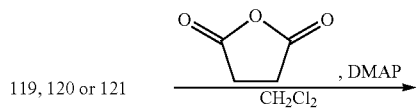

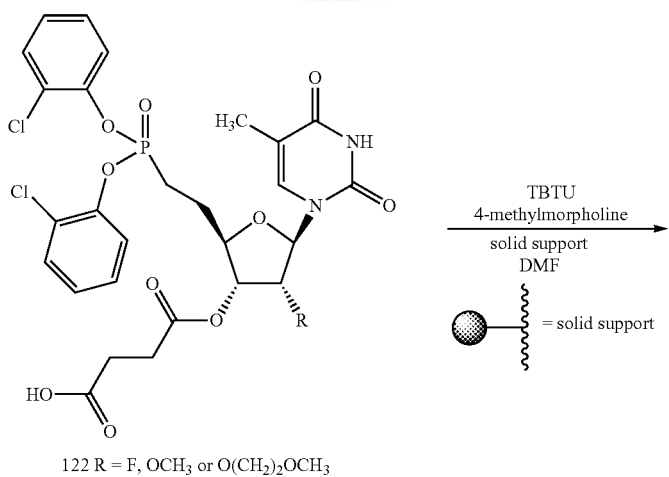
122 R = F, OCH₃ or O(CH₂)₂OCH₃
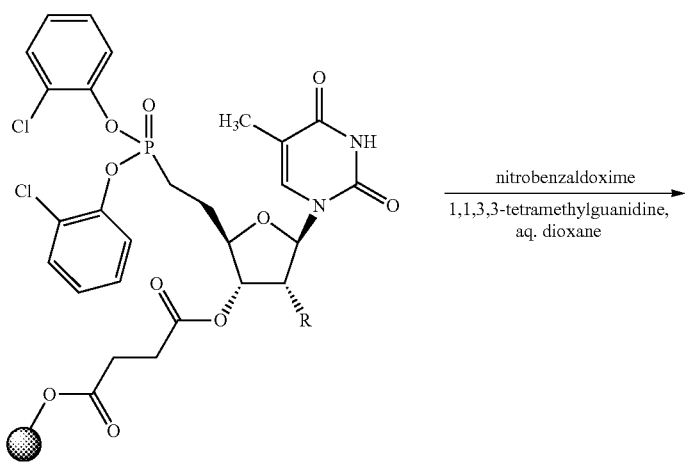
123
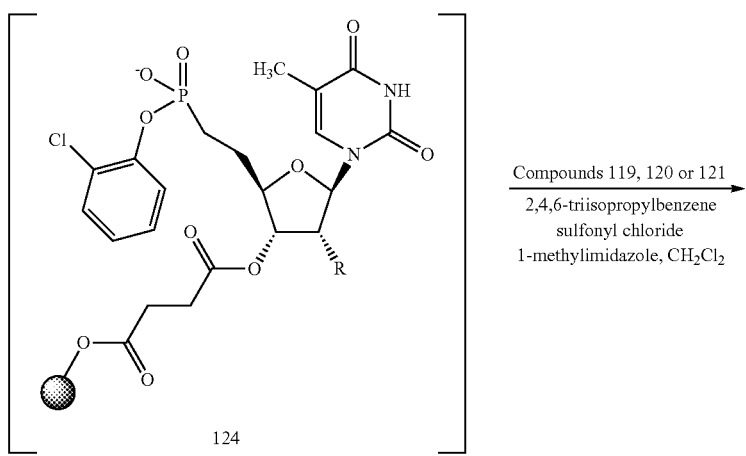
124

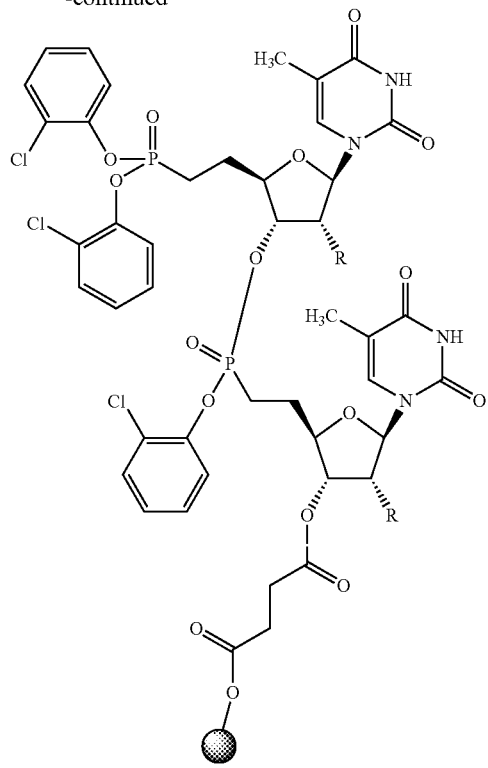
125
Compounds 119, 120 and 121 are prepared as per the procedures illustrated in Example 41.
Example 43
Preparation of Compounds 126 and 127
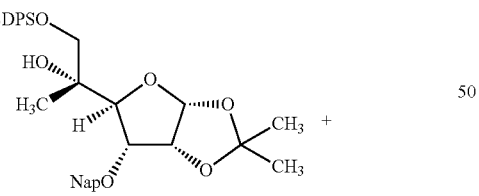
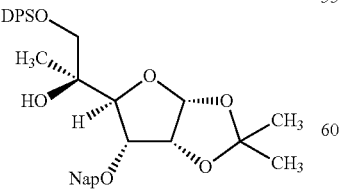
Compound 38 is prepared as per the procedures illustrated in Example 21.

Example 44
Preparation of Compounds 134 and 136
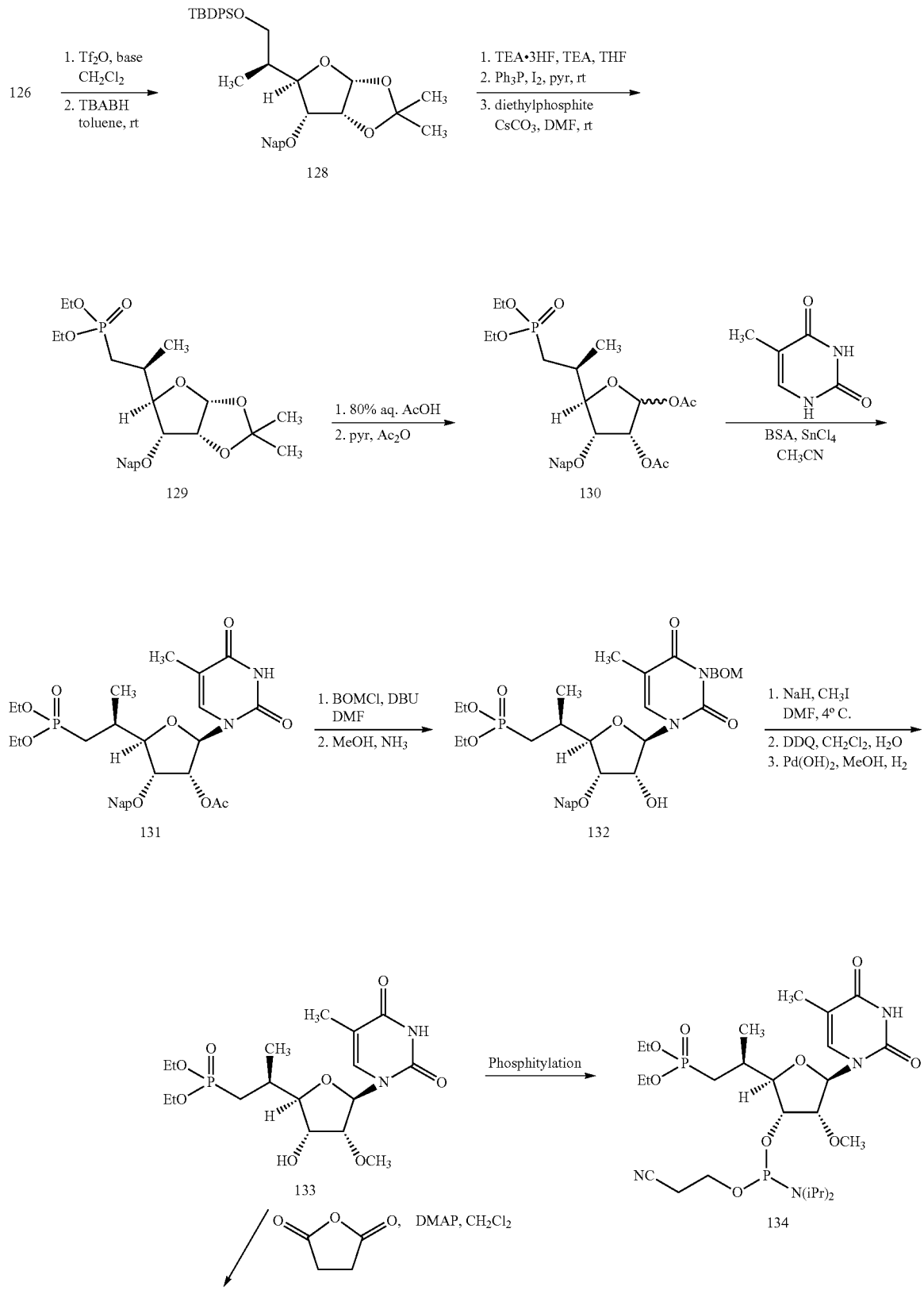

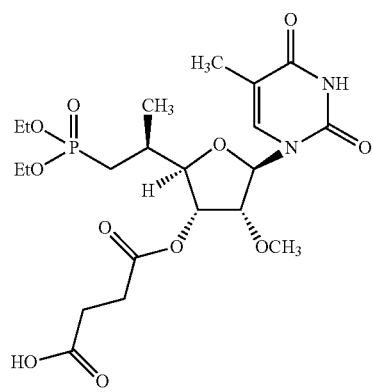
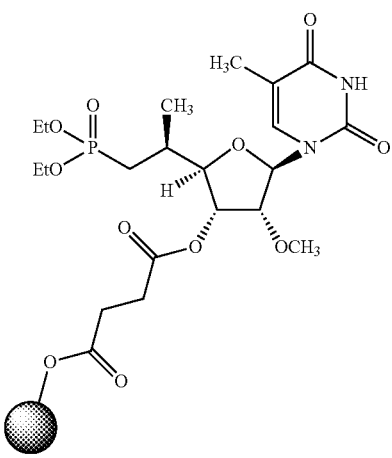
Compound 126 is prepared as per the procedures illustrated in Example 43.
Example 45
Preparation of Compounds 143 and 145
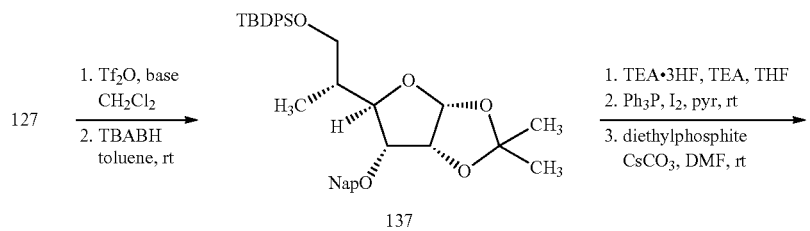
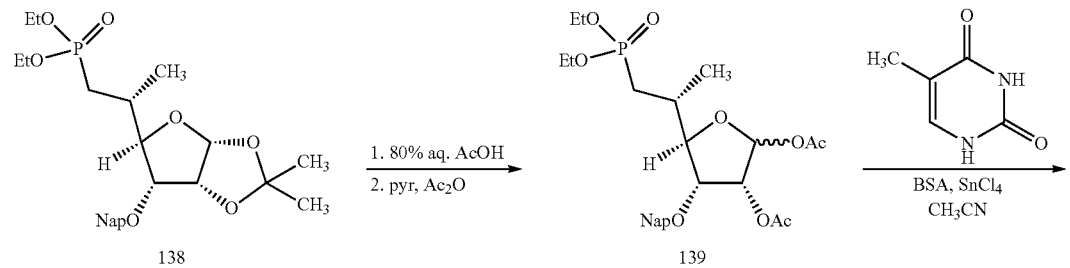
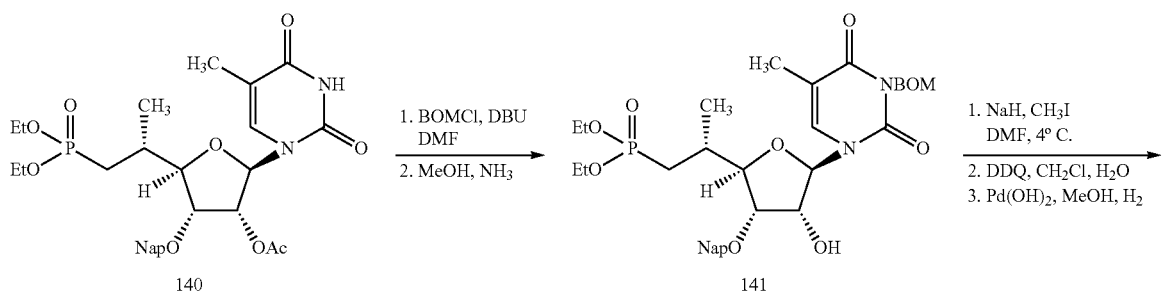

161
162
-continued
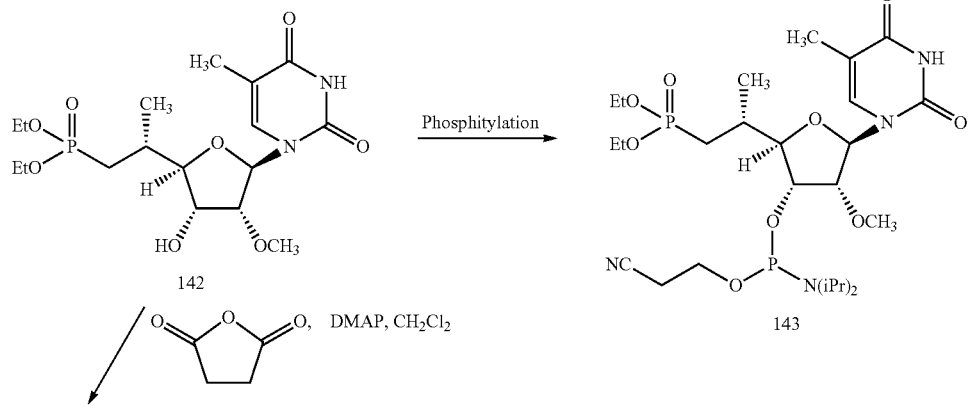
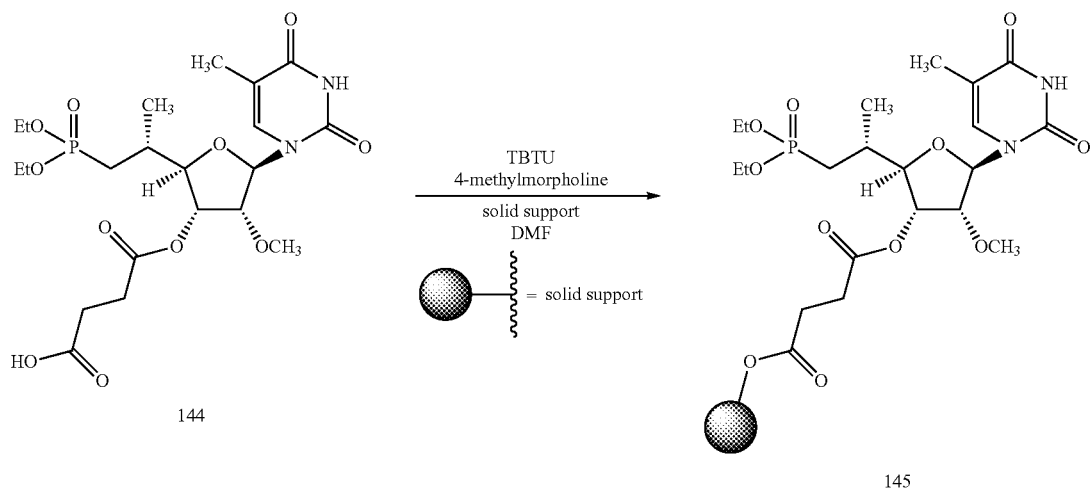
Compound 127 is prepared as per the procedures illustrated in Example 43.
Example 46
Preparation of Compounds 147 and 149
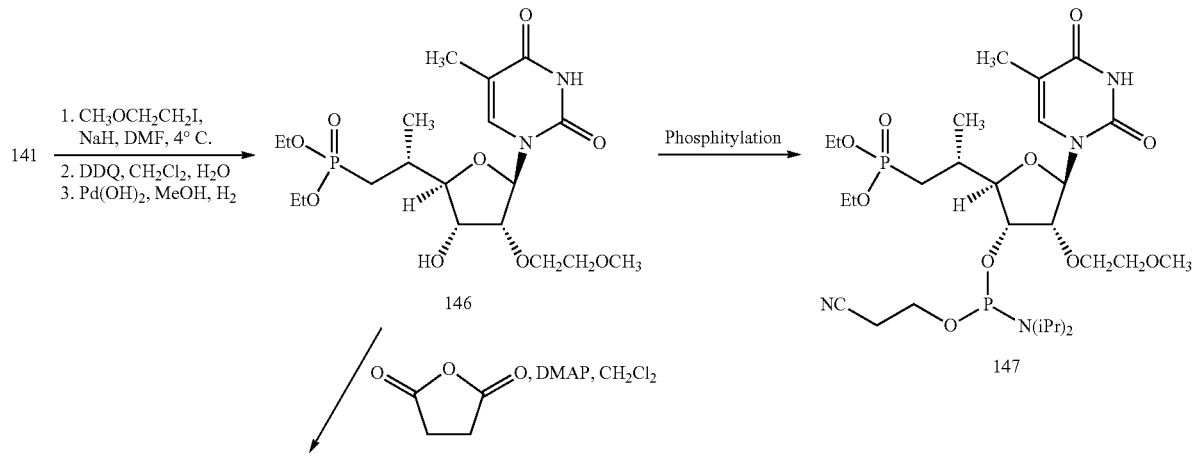

-continued
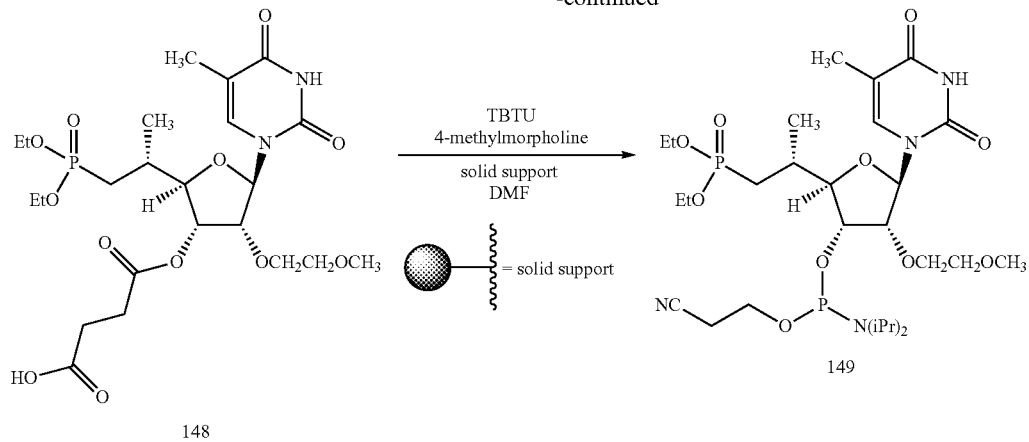
Compound 141 is prepared as per the procedures illustrated in Example 45.
Example 47
Preparation of Compounds 151 and 153
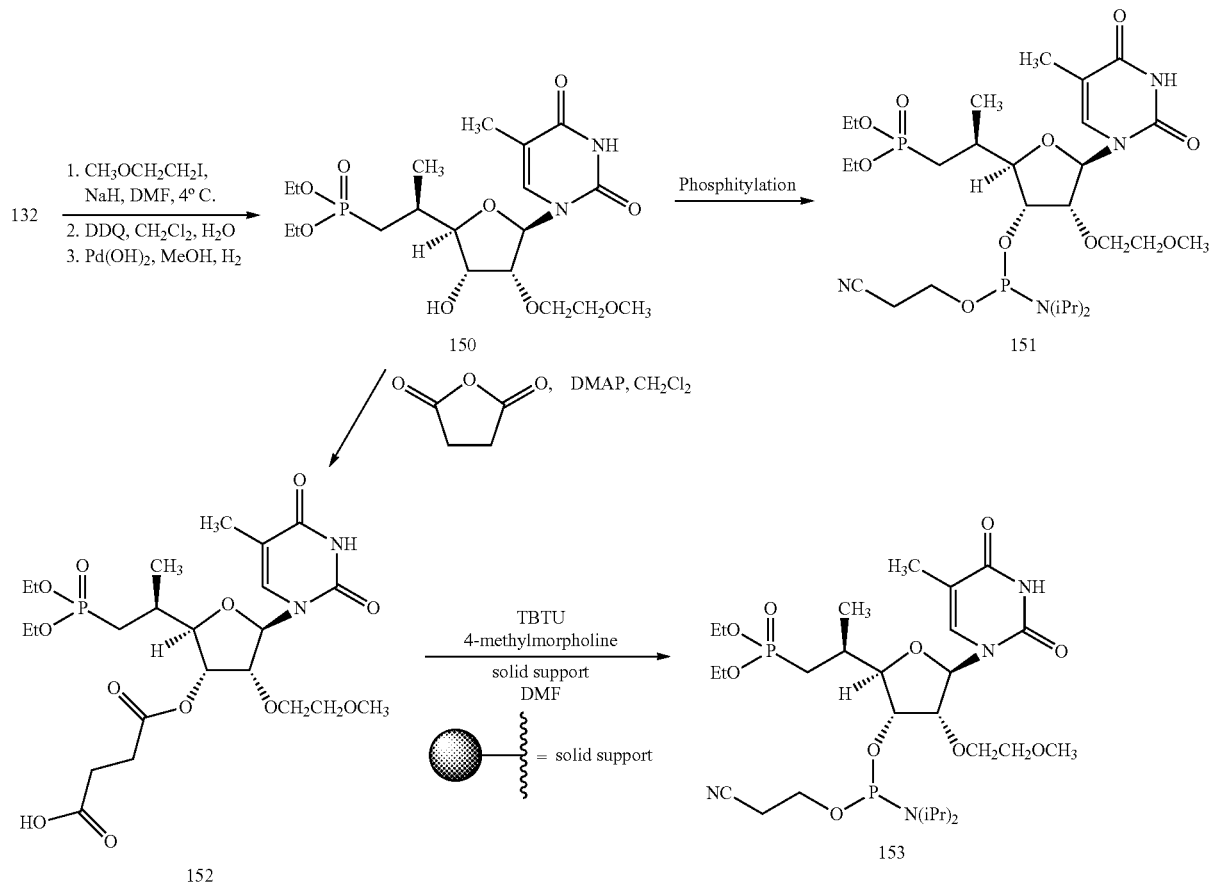
Compound 132 is prepared as per the procedures illustrated in Example 44.

Example 48
Preparation of Compounds 155 and 157
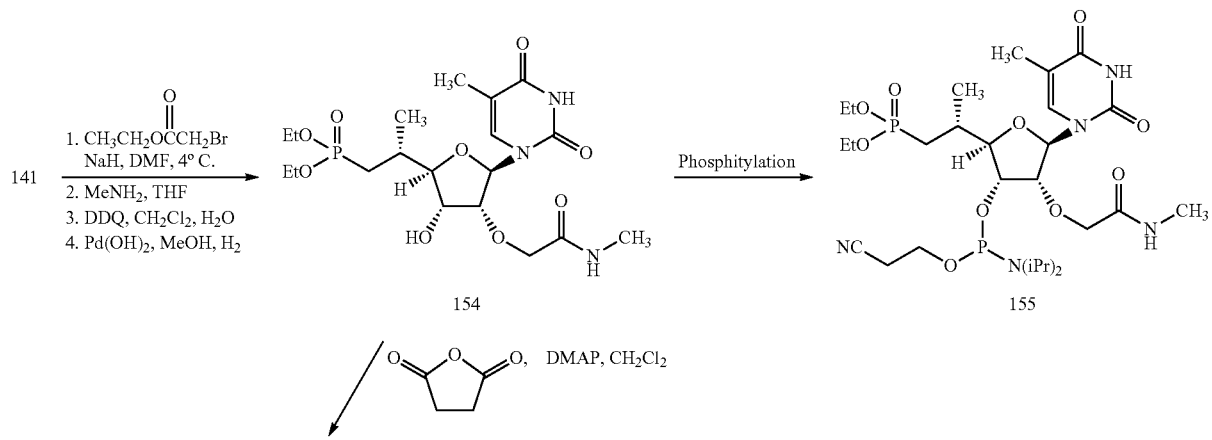
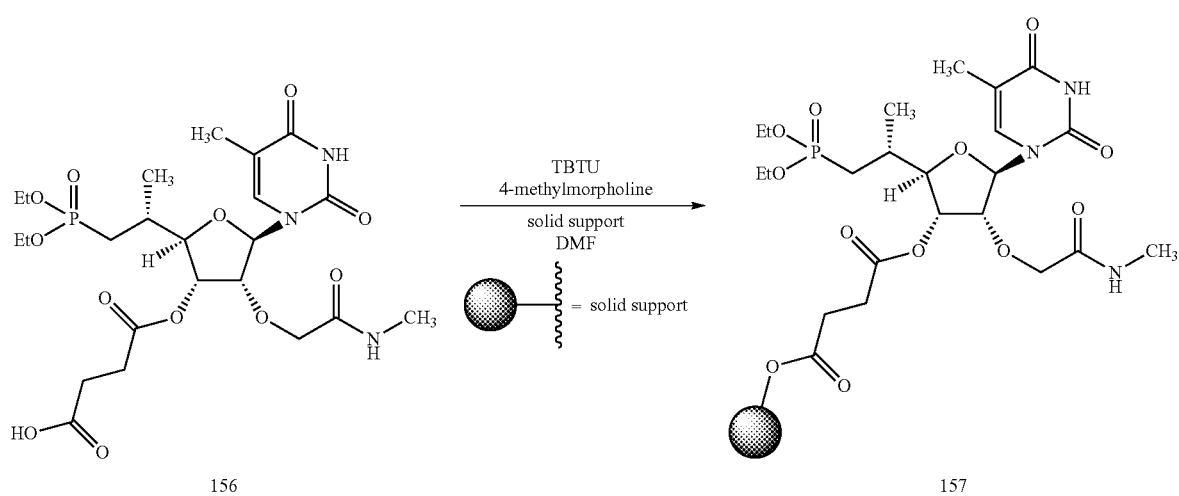
Compound 141 is prepared as per the procedures illustrated in Example 45.

Example 49
Preparation of Compounds 159 and 161
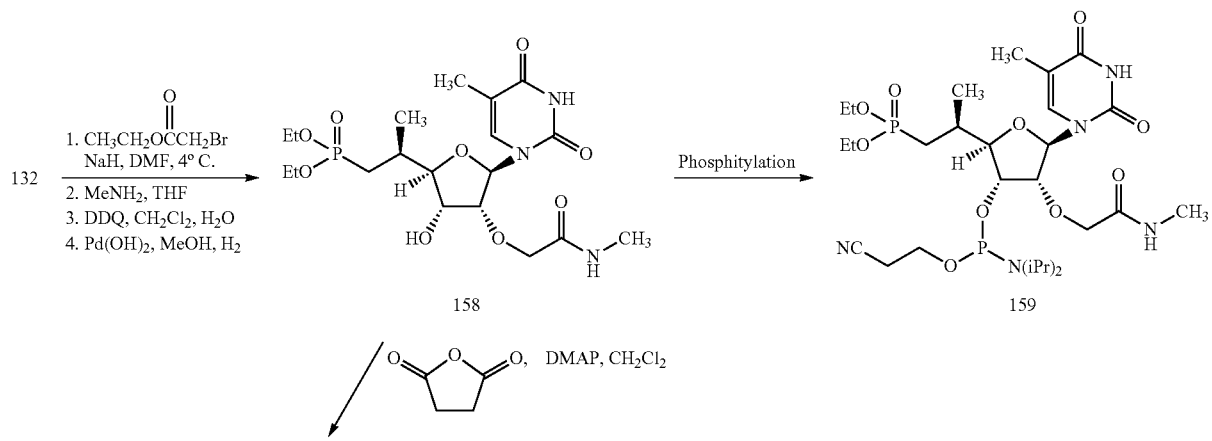
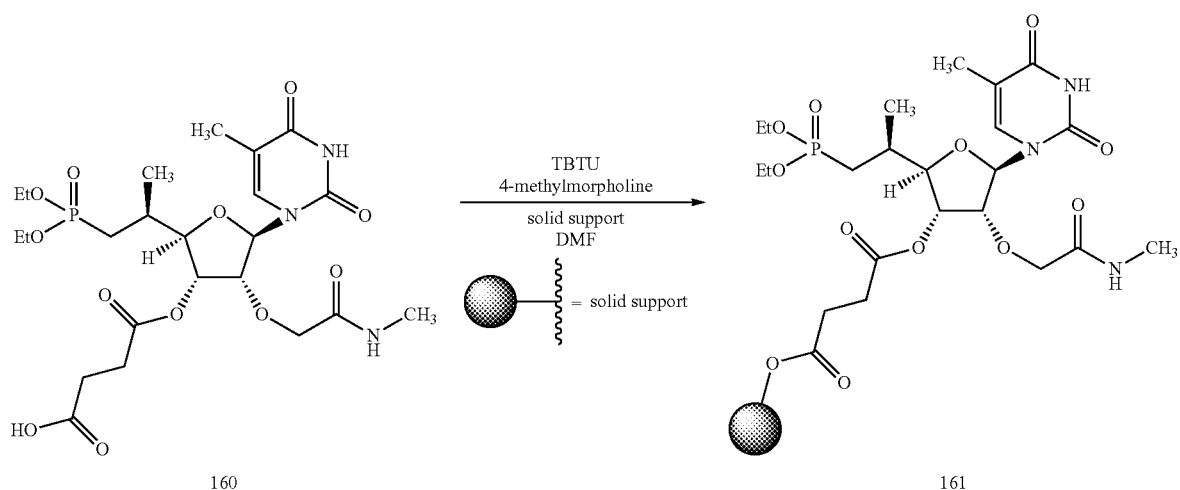
Compound 132 is prepared as per the procedures illustrated in Example 44.

Example 50
Preparation of Compounds 163 and 165
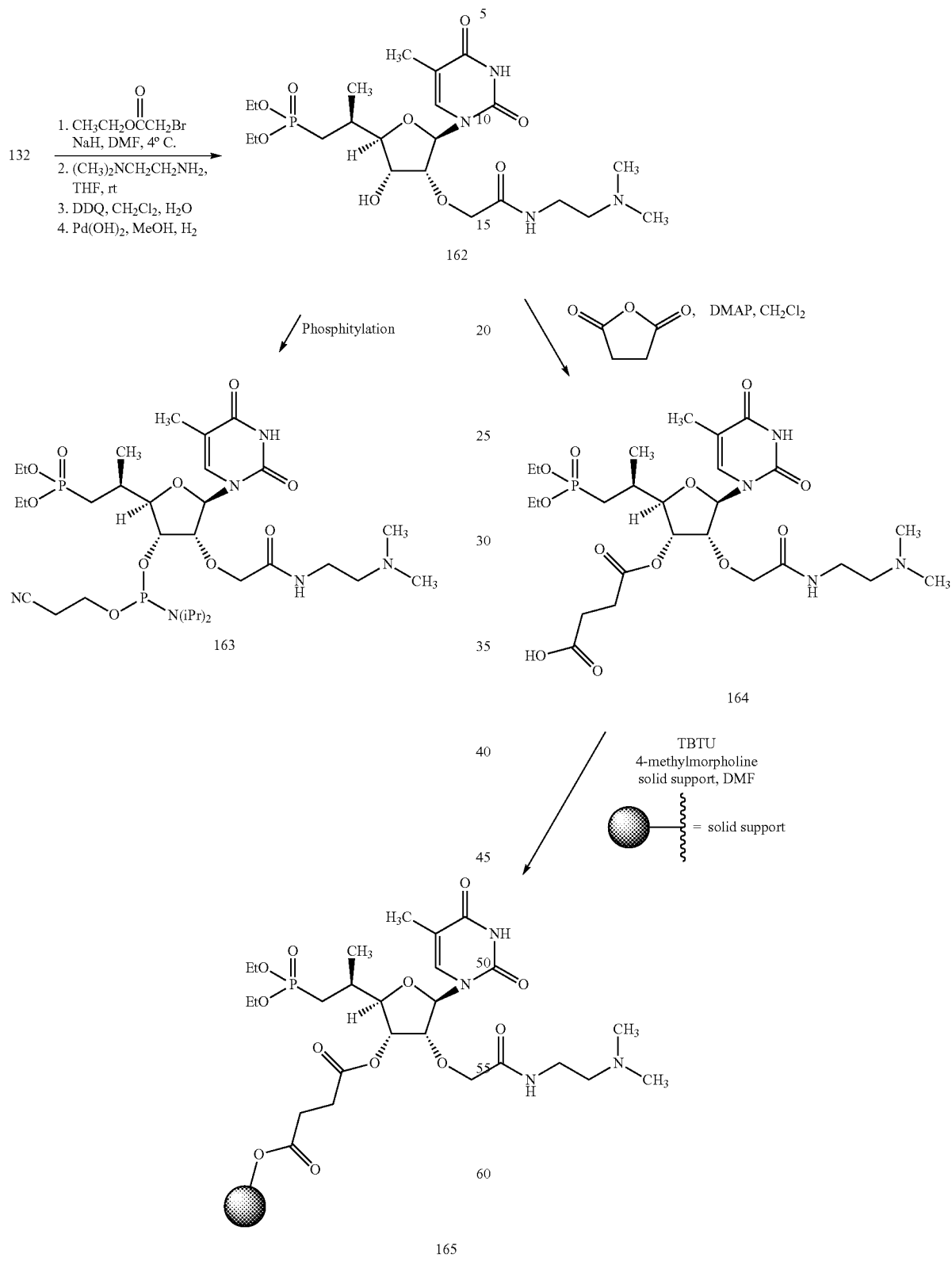

Compound 132 is prepared as per the procedures illustrated in Example 44.
Example 51
Preparation of Compounds 167 and 169
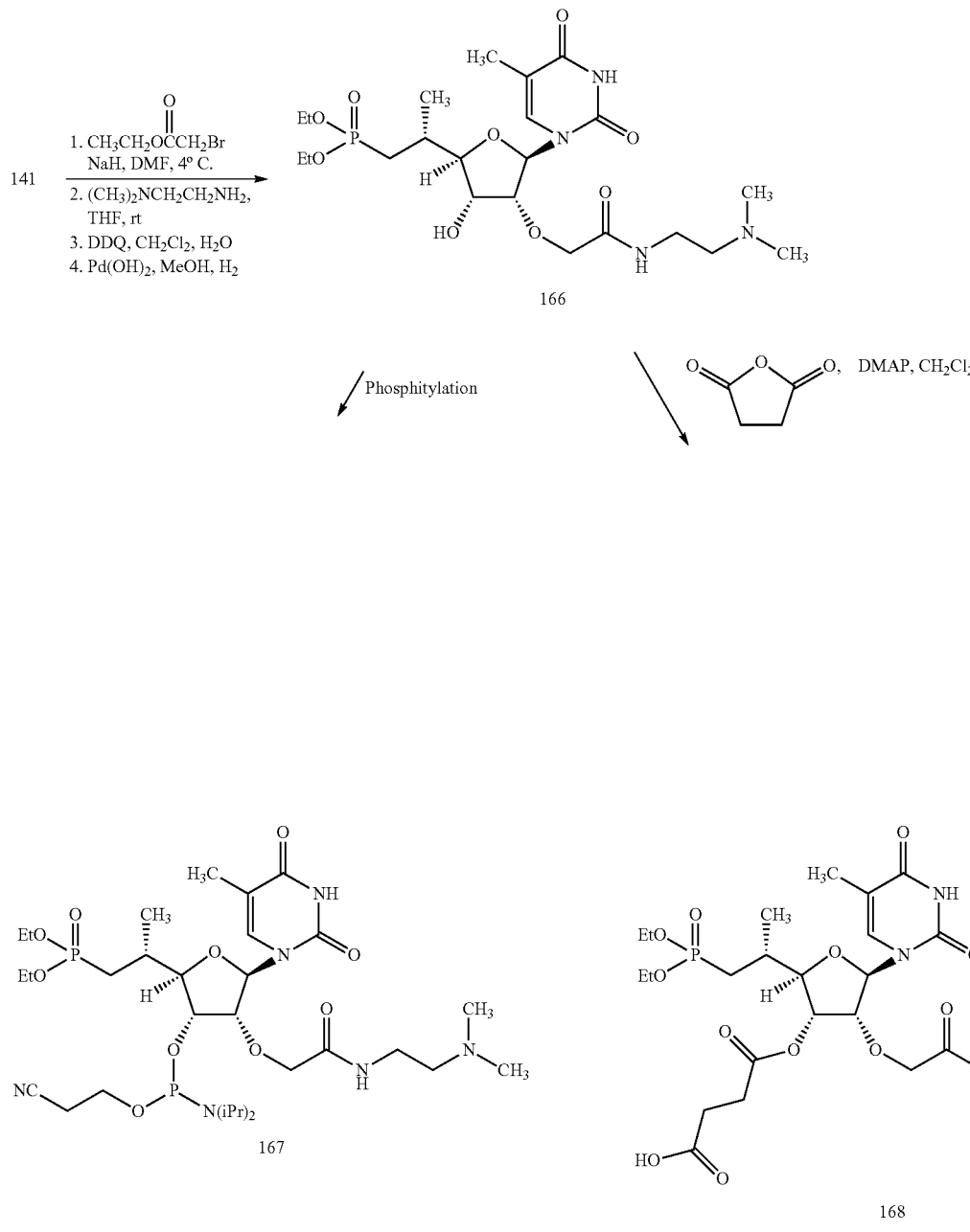

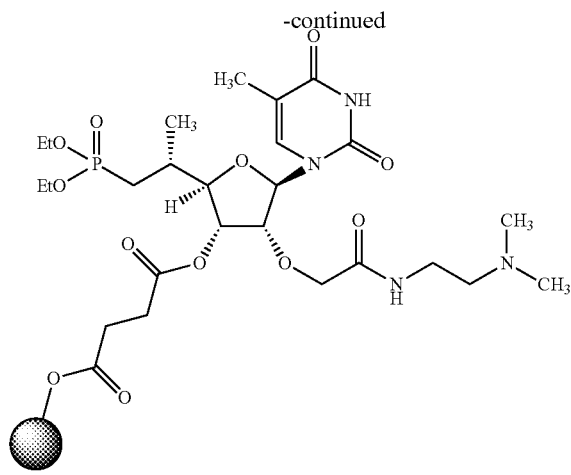
169
Compound 141 is prepared as per the procedures illustrated in Example 45.
Example 52
Preparation of Compounds 172 and 174
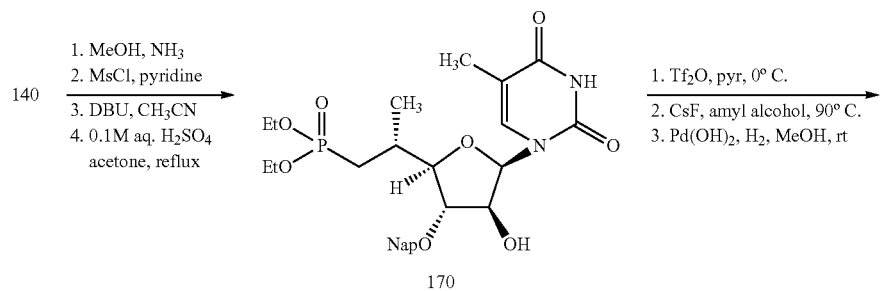
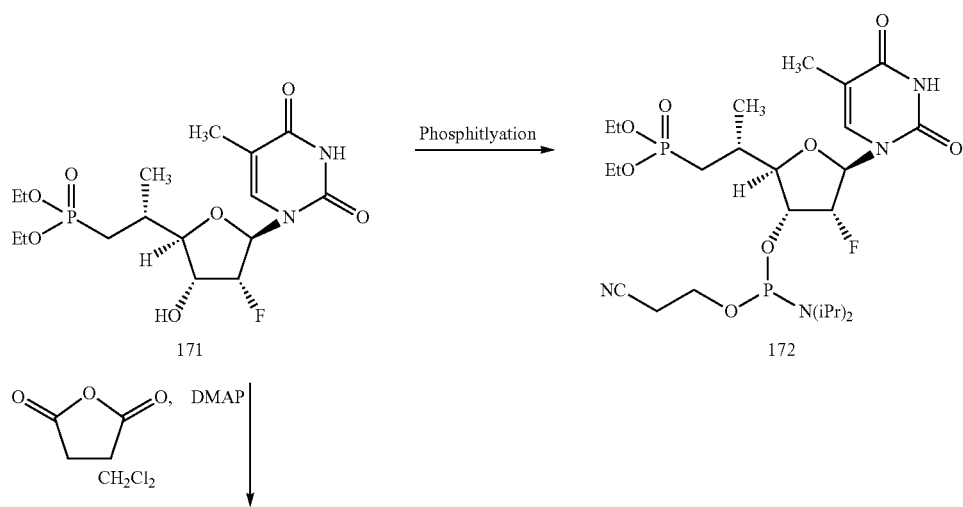

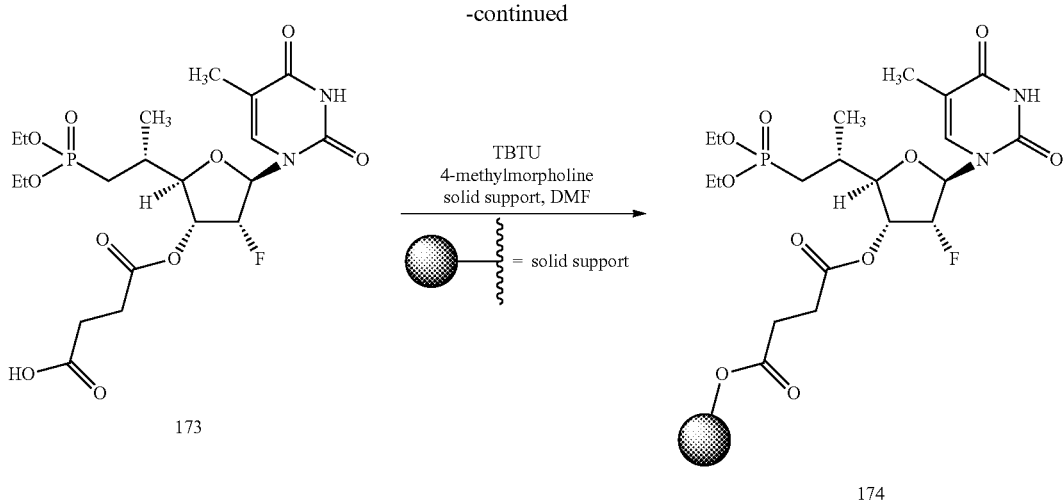
Compound 140 is prepared as per the procedures illustrated in Example 45.
Example 53
Preparation of Compounds 177 and 179
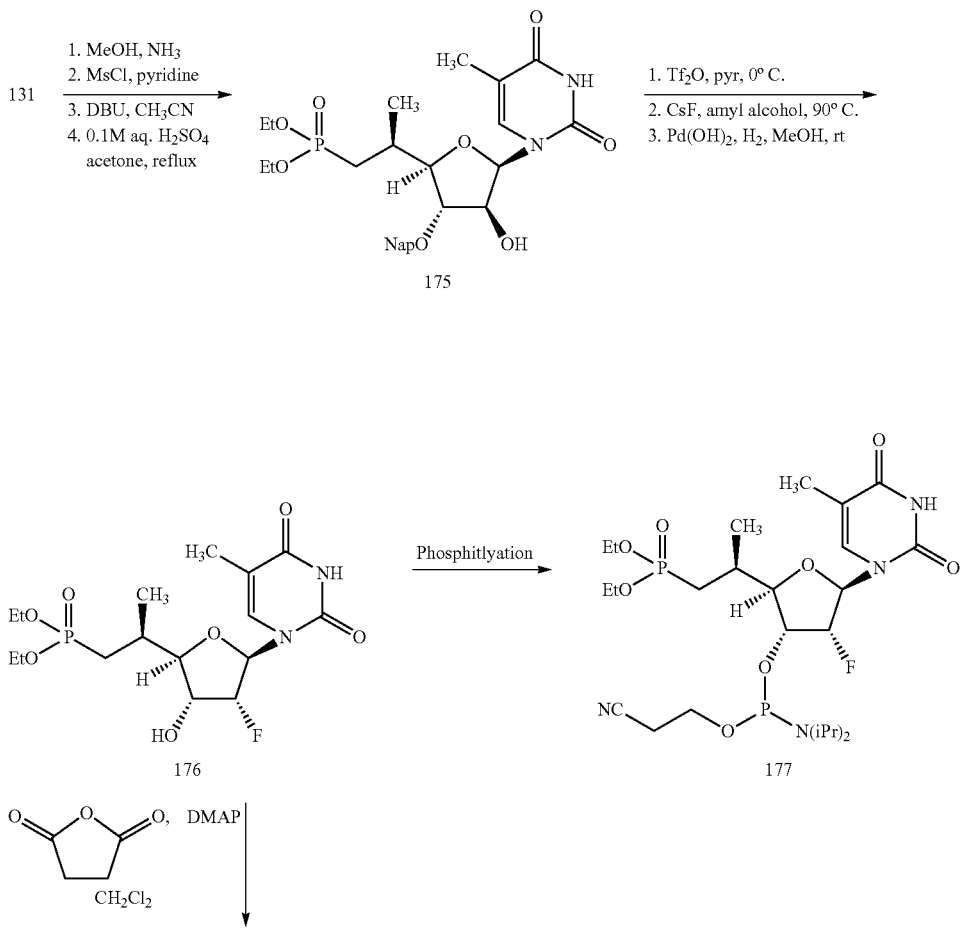

-continued
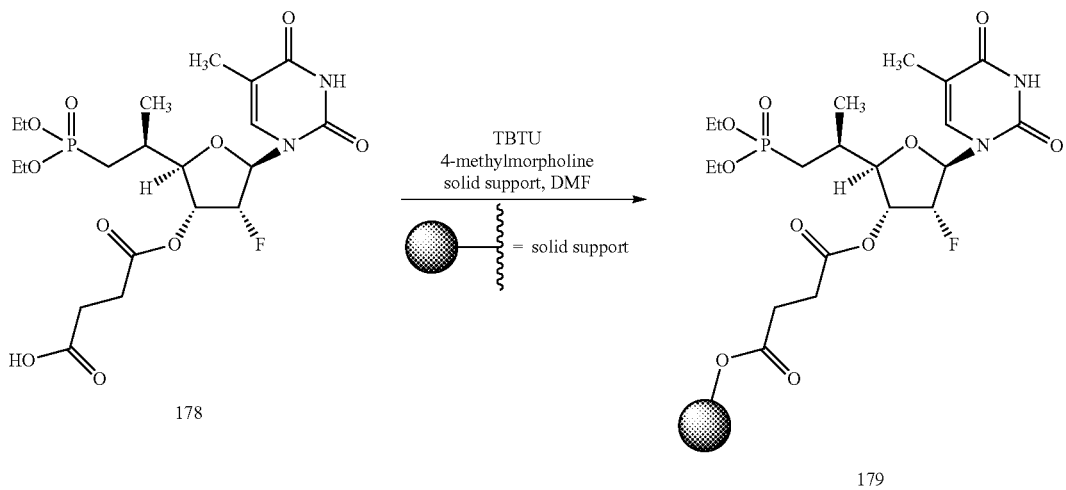
178
Compound 131 is prepared as per the procedures illustrated in Example 44.
Example 54
General Procedure for the Preparation of Compounds of Formula IIa and IIb
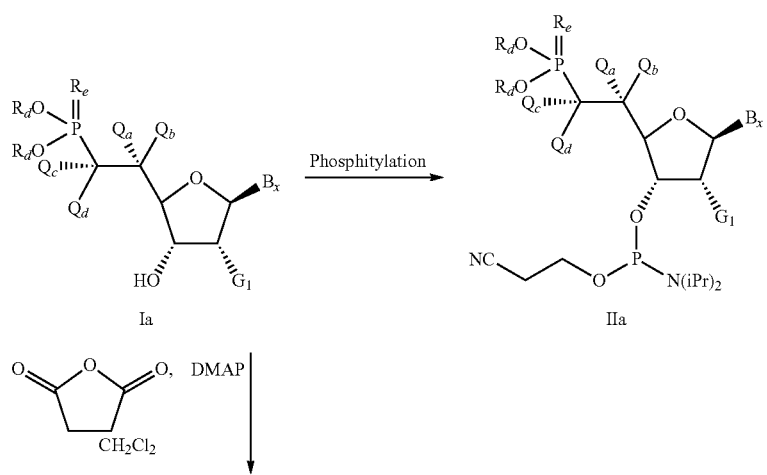

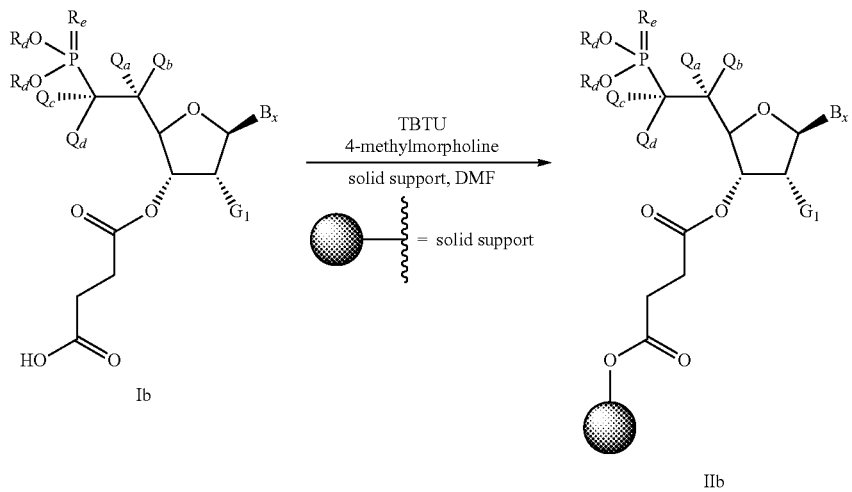

Ib → IIb $B_x$ is a heterocylic base moiety;
$Q_a$, $Q_b$, $Q_c$ and $Q_d$ are each independently H or a substituent group;
each $R_d$ is, independently, H, $C_1$-$C_6$ alkyl, substituted $C_1$-$C_6$ alkyl, aryl, substituted aryl or an internucleoside linkage to an oligomeric compound;
$R_e$ is O or S; and
$G_1$ is a sugar substituent group.

The preparation of compounds of Formula Ia, Ib, IIa and IIb are illustrated in Examples 21-25, 27-35 and 44-53.

Example 55

General procedure for the preparation of compounds of Formula IIIa

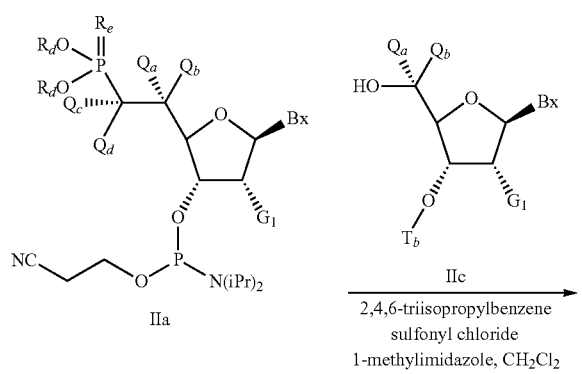

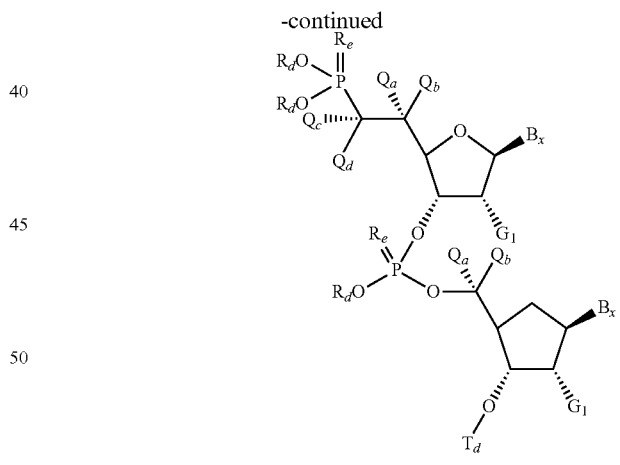

IIIa $B_x$ is a heterocylic base moiety;
$Q_a$, $Q_b$, $Q_c$ and $Q_d$ are each independently H or a substituent group;
each $R_d$ is, independently, H, $C_1$-$C_6$ alkyl, substituted $C_1$-$C_6$ alkyl, aryl, substituted aryl or a linkage to an oligometric compound;
$T_b$ is a protecting group, a 3'-terminal group or a linkage to an oligomeric compound;
$R_e$ is O or S; and
$G_1$ is a sugar substituent group.

The preparation of compounds of Formula IIa, IIc, and IIIa are illustrated in Examples 13, 15-19, 21-25 and 27-53.

Example 56

General Procedure for the Preparation of Compounds of Formula IIIb and IIIc

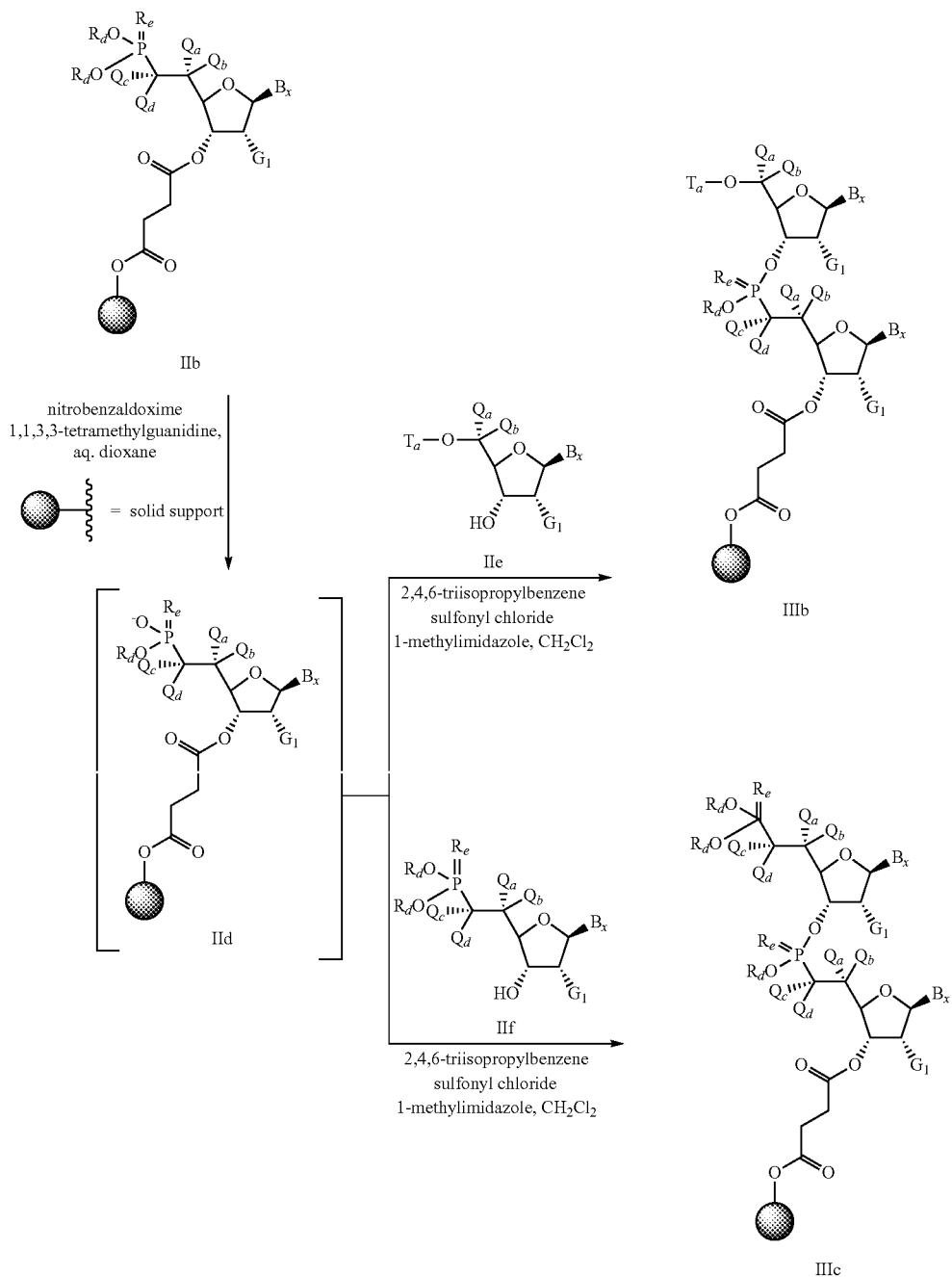

$B_x$ is a heterocyclic base moiety;
$Q_a$, $Q_b$, $Q_c$ and $Q_d$ are each independently H or a substituent group;
each $R_d$ is, independently, H, $C_1$-$C_6$ alkyl, substituted $C_1$-$C_6$ alkyl, aryl, substituted aryl or a linkage to an oligomeric compound;
$T_a$ is H, a protecting group or a 5′-terminal group;
$R_e$ is O or S; and
$G_1$ is a sugar substituent group The preparation of compounds of Formula IIb, IId, IIe, IIf, IIIb and IIIc are illustrated in Examples 13, 15-19, 21-25 and 27-53.

Example 57

Chemically Modified ssRNAs Targeting PTEN—In vivo Study

The antisense activity of oligomeric compounds can be tested in vivo. Five- to six-week old Balb/c mice (Jackson Laboratory, Bar Harbor, Me.) are injected with modified ssRNA targeted to PTEN at doses of 80 mg/kg daily, 60 mg/kg daily, or 40 mg/kg twice daily for several days. The mice are sacrificed 72 hours following the last administration. Liver tissues are homogenized and mRNA levels are quantitated using real-time PCR using procedures illustrated herein for comparison to untreated control levels (% UTC). Other modifications and motifs as disclosed herein are also amenable to in vivo testing. Liver transaminase levels, alanine aminotranferease (ALT) and aspartate aminotransferase (AST), in serum are also measured relative to saline injected mice. At the end of the study, liver and spleen tissues are harvested from animals treated with the modified ssRNAs, the tissues are weighed to assess gross organ alterations.

| SEQ ID NO./ ISIS NO. | Composition (5' to 3') |
|---|---|
| 05/422391 | P-T$_d$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ |
| 05/435394 | P-T$_d$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ |
| 05/435395 | P$_s$-T$_d$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ |
| 05/435397 | P-T$_d$U$_f$G$_m$U$_f$C$_m$U$_f$C$_m$U$_f$G$_m$G$_f$U$_m$C$_f$C$_m$U$_f$U$_m$A$_d$U$_f$U$_m$A$_e$A$_e$ |
| 05/435402 | P-T$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/435401 | P-T$_d$U$_f$G$_m$U$_f$C$_m$U$_f$C$_m$U$_f$G$_m$G$_f$U$_m$C$_f$C$_m$U$_f$U$_f$A$_f$C$_f$U$_f$U$_f$A$_e$A$_e$ |
| 05/435400 | P-T$_d$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/435399 | P-T$_d$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/435404 | P-T$_d$U$_f$G$_m$U$_f$C$_m$U$_f$C$_m$U$_f$G$_m$G$_f$U$_f$C$_f$C$_f$U$_f$U$_f$A$_f$C$_f$U$_f$U$_f$A$_e$A$_e$ |
| 05/xxxxx | P-T$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_R$U$_f$G$_m$U$_f$C$_m$U$_f$C$_m$U$_f$G$_m$G$_f$U$_m$C$_f$C$_m$U$_f$U$_f$A$_f$C$_f$U$_f$U$_f$A$_e$A$_e$ |
| 05/xxxxx | P-T$_R$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_R$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_R$U$_f$G$_m$U$_f$C$_m$U$_f$C$_m$U$_f$G$_m$G$_f$U$_f$C$_f$C$_f$U$_f$U$_f$A$_f$C$_f$U$_f$U$_f$A$_e$A$_e$ |
| 05/xxxxx | P-T$_s$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_s$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_s$U$_f$G$_m$U$_f$C$_m$U$_f$C$_m$U$_f$G$_m$G$_f$U$_m$C$_f$C$_m$U$_f$U$_f$A$_f$C$_f$U$_f$U$_f$A$_e$A$_e$ |
| 05/xxxxx | P-T$_s$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_s$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_s$U$_f$G$_m$U$_f$C$_m$U$_f$C$_m$U$_f$G$_m$G$_f$U$_f$C$_f$C$_f$U$_f$U$_f$A$_f$C$_f$U$_f$U$_f$A$_e$A$_e$ |
| 05/xxxxx | P-T$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_d$U$_f$G$_m$U$_f$C$_m$U$_f$C$_m$U$_f$G$_m$G$_f$U$_m$C$_f$C$_m$U$_f$U$_f$A$_f$C$_f$U$_f$U$_f$A$_e$A$_e$ |
| 05/xxxxx | P-T$_d$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_d$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_d$U$_f$G$_m$U$_f$C$_m$U$_f$C$_m$U$_f$G$_m$G$_f$U$_f$C$_f$C$_f$U$_f$U$_f$A$_f$C$_f$U$_f$U$_f$A$_e$A$_e$ |
| 05/xxxxx | P-T$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_{Rd}$U$_f$G$_m$U$_f$C$_m$U$_f$C$_m$U$_f$G$_m$G$_f$U$_m$C$_f$C$_m$U$_f$U$_f$A$_f$C$_f$U$_f$U$_f$A$_e$A$_e$ |
| 05/xxxxx | P-T$_{Rd}$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_{Rd}$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_{Rd}$U$_f$G$_m$U$_f$C$_m$U$_f$C$_m$U$_f$G$_m$G$_f$U$_f$C$_f$C$_f$U$_f$U$_f$A$_f$C$_f$U$_f$U$_f$A$_e$A$_e$ |
| 05/xxxxx | P-T$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 05/xxxxx | P-T$_{Sd}$U$_f$G$_m$U$_f$C$_m$U$_f$C$_m$U$_f$G$_m$G$_f$U$_m$C$_f$C$_m$U$_f$U$_f$A$_f$C$_f$U$_f$U$_f$A$_e$A$_e$ |
| 05/xxxxx | P-T$_{Sd}$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_{Sd}$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ |
| 05/xxxxx | P-T$_{Sd}$U$_f$G$_m$U$_f$C$_m$U$_f$C$_m$U$_f$G$_m$G$_f$U$_f$C$_f$C$_f$U$_f$U$_f$A$_f$C$_f$U$_f$U$_f$A$_e$A$_e$ |
| 06/409044 | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/418042 | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/414291 | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/416598 | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/418043 | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/418044 | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/418045 | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/418046 | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/418127 | P-U$_R$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ |
| 06/xxxxx | P-U$_x$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_x$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Sd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |

-continued

| SEQ ID NO./ISIS NO. | Composition (5' to 3') |
|---|---|
| 06/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_{Rd}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_R$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_S$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_S$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_S$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_S$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_S$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_S$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_S$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06/xxxxx | P-U$_S$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 07/410146 | P-A$_e^{Me}$C$_e$A$_e$A$_e$A$_e^{Me}$C$_{ef}$A$_e^{Me}$C$_{ef}^{Me}$C$_{ef}^{Me}$C$_{ef}$A$_e$T$_{ef}$T$_{ef}$G$_e$T$_{ef}^{Me}$ C$_e^{Me}$C$_e$A$_e^{Me}$C$_{ef}$A$_e$M$_e^{Me}$C$_{ef}^{Me}$C$_{ef}$A$_e$ |
| 07/327895 | P-A$_e^{Me}$C$_e$A A A$_e^{Me}$C$_e$A$^{Me}$C$_e^{Me}$C$_e$A$_e$T$_e$T$_e$G$_e$T$^{Me}$ $_e$CA$_e^{Me}$ C$_e$A$^{Me}$C A$^{Me}$ $_e^{Me}$ C A$_e$ |

Each nucleoside is connected to the following nucleoside by a phosphodiester internucleoside linkage except underlined nucleosides which are connected to the following nucleoside by a phosphorothioate internucleoside linkage (going 5' to 3'). A "P" at the 5'-end indicates a 5'-phosphate group. A "P$_s$" at the 5'-end indicates a 5'-thiophosphate group. Nucleosides followed by a subscript d, ef, f, m, e or x are sugar modified nucleosides. A subscript "d" indicates a 2'-OCH$_2$(CO)NH(CH$_2$)$_2$N(CH$_3$)$_2$ (DMAEAc), subscript "ef" indicates a 2'-OCH$_2$CH$_2$F (FEt) modified nucleoside, a subscript "f" indicates a 2'-fluoro modified nucleoside, a subscript "m" indicates 2'-O-methyl modified nucleoside, a subscript "e" indicates a 2'-O(CH$_2$)$_2$OCH$_3$ (MOE) modified nucleoside, and a subscript R or S or Rd or Sd or x indicates one of the 5'-modified nucleosides (R or S) or one of the 2',5'-bis modified nucleosides listed below (Rd, Sd, Rb, Sb, Rc or Sc). In general, each modified nucleoside having an x after it will have the same sugar modification.

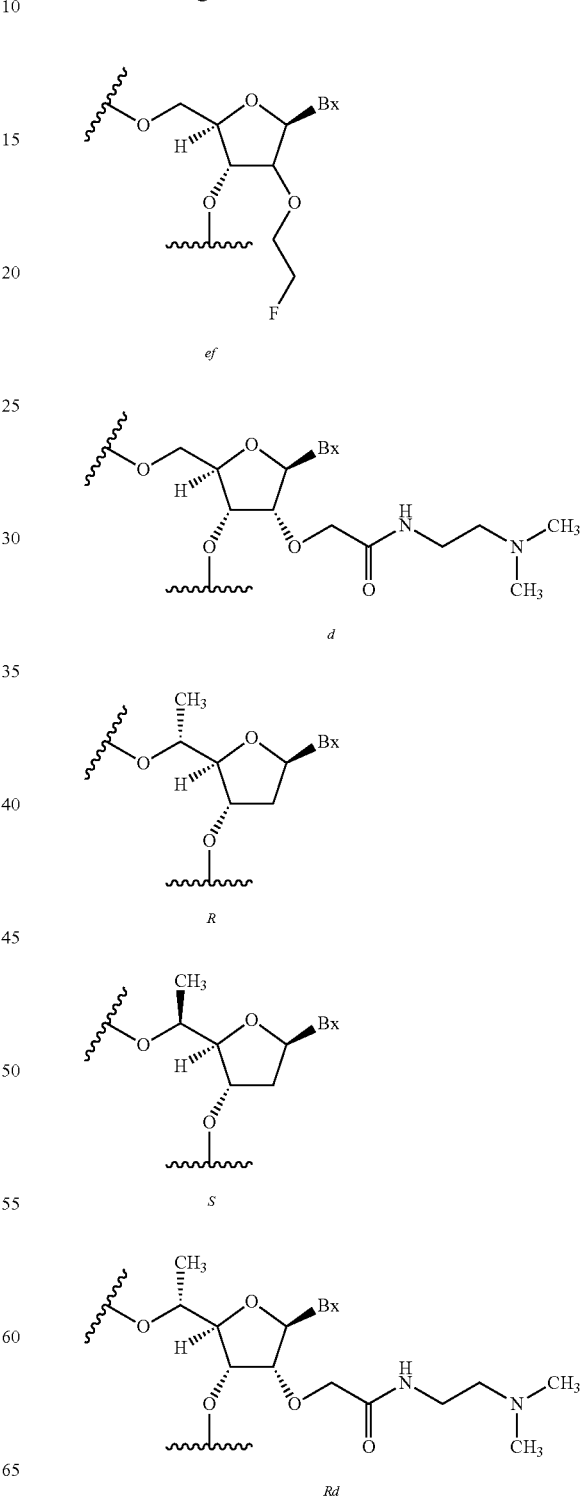

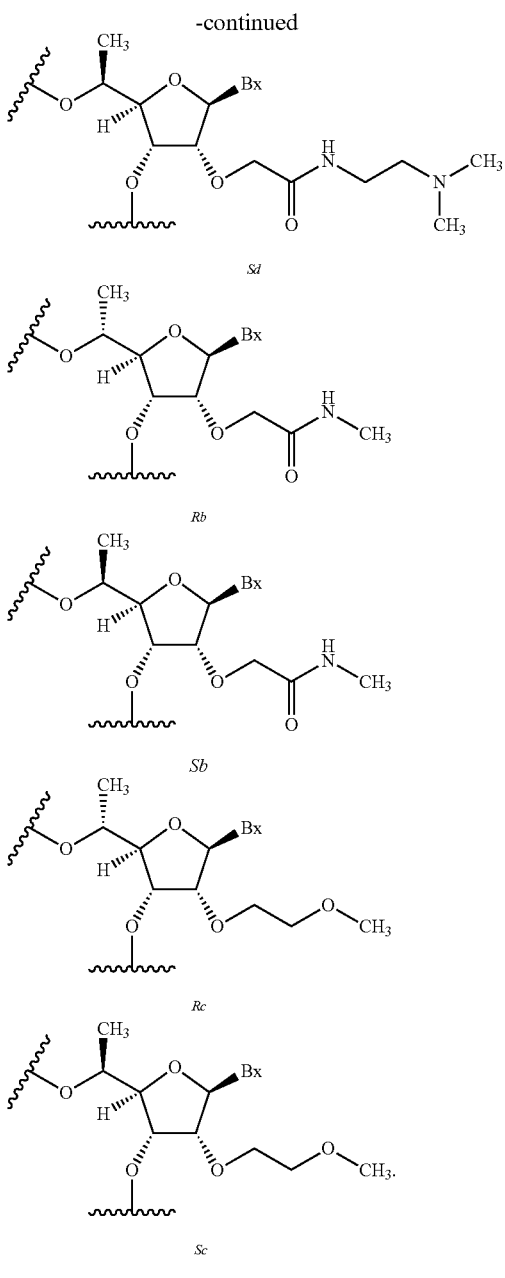

Example 58

Gapped Oligomeric Compounds Targeted to PTEN: In vivo Study

In accordance with the present disclosure, oligomeric compounds are synthesized and tested for their ability to reduce PTEN expression in vivo at doses of 20 and 60 mg/kg. Six week old male Balb/c mice (Jackson Laboratory, Bar Harbor, Me.) are administered a single intraperitoneal (i.p) injection at either 20 or 60 mg/kg of a 2-10-2 gapped oligomer. A 5-10-5 gapped oligomer having 2'-O-MOE modified nucleosides or other modified nucleosides as provided herein in the wings is also included for comparison. Other motifs as disclosed herein are also amenable to in vivo testing.

Each dose group will include four animals. The mice are sacrificed 48 hours following the final administration to determine the PTEN mRNA levels in liver using real-time PCR and RIBOGREEN® RNA quantification reagent (Molecular Probes, Inc. Eugene, Oreg.) according to standard protocols. PTEN mRNA levels are determined relative to total RNA (using Ribogreen), prior to normalization to saline-treated control. The average % inhibition of mRNA expression for each treatment group, normalized to saline-injected control is determined.

Liver transaminase levels, alanine aminotranferease (ALT) and aspartate aminotransferase (AST), in serum are measured relative to saline injected mice.

| SEQ ID NO | Composition (5' to 3') |
|---|---|
| 08 | $^{me}C_xT_xG_x{}^{me}C_xT_xAG^{me}C^{me}CT^{me}CTGGAT_xT_xT_xG_xA_x$ |
| 09 | $C_xT_xTAGCACTGGCC_xT_x$ |
| 09 | $P\text{-}C_xT_xTAGCACTGGCC_xT_x$ |
| 09 | $^{me}C_xT_xTAGCACTGGC^{me}C_xT_x$ |

Each unmodified nucleoside is a β-D-2'-deoxyribonucleoside. Each internucleoside linkage is a phosphorothioate internucleoside linkage. A "P" at the 5'-end indicates a 5'-phosphate group. $^{me}C$ indicates a 5'-methyl cytosine nucleoside. Each nucleoside having a subscript x is selected from the list at the end of Example 57, e.g., Rb, Sb, Rcc, Sc, Rd and Sd. In general, each modified nucleoside having an x after it will have the same sugar modification but can have different bases.

Example 59

Oligomeric Compounds Targeted to PTEN: In vitro Study

In accordance with the present disclosure, oligomeric compounds were synthesized and tested for their ability to reduce PTEN expression over a range of doses. Human HeLa cells were treated with either ISIS 447581 or ISIS 404320. A dose comparison was evaluated with dose concentrations of 0.20, 0.62, 1.9, 5.5, 16.7 and 50 nM using methods described herein. Expression levels of PTEN were determined using real-time PCR and normalized to RIBOGREEN™ using methods described herein. The percent inhibition of PTEN mRNA was determined. Resulting dose-response curves were used to determine the $EC_{50}$. Tm's were assessed in 100 mM phosphate buffer, 0.1 mM EDTA, pH 7, at 260 nm using 4 μM modified oligomers and 4 μM complementary RNA. The $EC_{50}$s are listed below.

| SEQ ID NO. | ISIS NO. | Composition (5' to 3') | $EC_{50}$ (nM) |
|---|---|---|---|
| 05 | 447581 | $P\text{-}T_{Rc}U_fG_mU_fC_mU_fC_mU_fG_mG_fU_mC_fC_mU_fU_m\underline{A}_f\underline{C}_mU_fU_m\underline{A}_e\underline{A}_e$ | 0.87 |
| 06 | 404320 | $P\text{-}U_fU_fG_fU_fC_fU_fC_fG_fG_fU_fC_fC_fU_f\underline{U}_f\underline{A}_f\underline{C}_fU_f\underline{U}_f\underline{A}_e\underline{A}_e$ | 13.2 |

Each nucleoside is connected to the following nucleoside by a phosphodiester internucleoside linkage except underlined nucleosides which are connected to the following nucleoside by a phosphorothioate internucleoside linkage (going 5' to 3'). A "P" at the 5'-end indicates a 5'-phosphate group. Nucleosides followed by a subscript f, m or e are sugar modified nucleosides. A subscript "f" indicates a 2'-fluoro modified nucleoside, a subscript "m" indicates 2'-O-methyl modified nucleoside, a subscript "e" indicates a 2'-O(CH$_2$)$_2$OCH$_3$ (MOE) modified nucleoside and a subscript Rc indicates the 2',5'-bis modified nucleoside listed in Example 57.

Example 60

Modified ssRNA 5'-phosphate Serum Stability Assay

A serum stability assay is useful for evaluating the stability of oligomeric compounds in the presences of nucleases and other enzymes found in serum. For example, the stability of a 5'-terminal phosphate group of an oligomeric compound can be evaluated by assessing the ability of the 5'-terminal phosphate group to remain attached to the oligomeric compound in the presence of serum. Accordingly, a serum stability assay was employed to evaluate the stability of modified ssRNAs having a 5'-terminal phosphate group.

Various modified ssRNAs, shown below, having a 5'-terminal phosphate group (10 µM) were dissolved in 95% of fresh mouse serum and incubated at 37° C. Aliquots of serum (100 µL) were removed after 0, 1, 3, 6 or 24 hours of incubation times. The serum samples were immediately quenched and snap frozen. The samples were extracted by the strong anion exchange (SAX) and octadecylsilyl (C-18) columns. For each incubation time, the amount of full length modified ssRNA having a 5'-terminal phosphate group was determined by LC/MS, and the half-life of the full length modified ssRNA having a 5' terminal phosphate group was calculated. The results are expressed as half-time ($T_{1/2}$) in the table below. These data demonstrate that modifications to oligomeric compounds can improve the stability of the 5'-terminal phosphate group.

| SEQ ID NO. | ISIS NO. | Composition (5' to 3') | $T_{1/2}$ (h) |
|---|---|---|---|
| 05 | 422391 | P-T$_d$U$_f$G$_f$U$_f$C$_f$U$_f$C$_f$U$_f$G$_f$G$_f$U$_f$C$_f$C$_f$U$_f$U$_f$A$_e$C$_f$U$_f$ U$_f$A$_e$A$_e$ | 6.5 |
| 05 | 432356 | P-TRU$_f$G$_f$U$_f$C$_f$U$_f$C$_f$U$_f$G$_f$G$_f$U$_f$C$_f$C$_f$U$_f$U$_f$A$_e$C$_f$U$_f$ U$_f$A$_e$A$_e$ | 8.7 |
| 06 | 404320 | P-U$_f$U$_f$G$_f$U$_f$C$_f$U$_f$C$_f$U$_f$G$_f$G$_f$U$_f$C$_f$C$_f$U$_f$U$_f$A$_e$C$_f$U$_f$ U$_f$A$_e$A$_e$ | 4 |
| 010 | 398701 | P-Us$_f$U$_f$G$_f$U$_f$C$_f$U$_f$C$_f$U$_f$G$_f$G$_f$U$_f$C$_f$C$_f$U$_f$U$_f$A$_e$C$_f$ U$_f$U$_f$ | 18.2 |

Each nucleoside is connected to the following nucleoside by a phosphodiester internucleoside linkage except underlined nucleosides which are connected to the following nucleoside by a phosphorothioate internucleoside linkage (going 5' to 3'). A "P" at the 5'-end indicates a 5'-phosphate group. Nucleosides followed by a subscript d, e, f, R or Sf are sugar modified nucleosides. A subscript "d" indicates a 2'-O-dimethylaminoethyl acetamide (DMAEAc) modified nucleoside, a subscript "e" indicates a 2'-O(CH$_2$)$_2$OCH$_3$ (MOE) modified nucleoside, a subscript "f" indicates a 2'-fluoro modified nucleoside, a subscript "R" indicates (R)-5'-methyl-2'-deoxyribonucleoside and a subscript Sf indicates the 2',5'-bis modified nucleoside listed below.

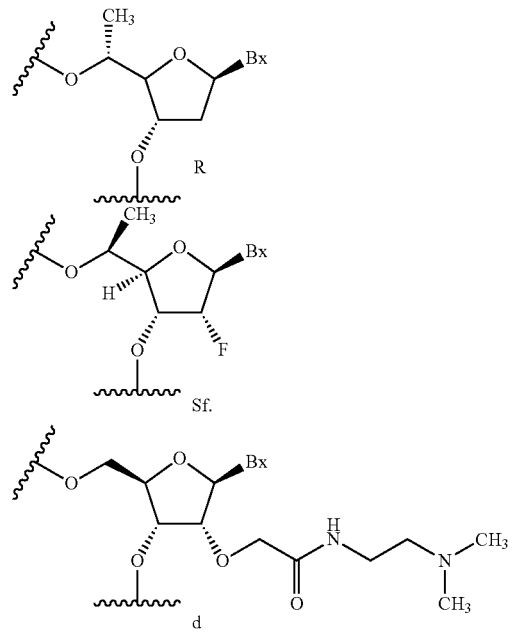

Example 61

Design and Screening of Duplexed Antisense Compounds

In accordance with the present invention, a series of nucleic acid duplexes comprising the compounds of the present invention and their complements can be designed. The nucleobase sequence of the antisense strand of the duplex comprises at least a portion of an antisense oligonucleotide targeted to a target sequence as described herein. The ends of the strands may be modified by the addition of one or more natural or modified nucleosides to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 11) and having a two-nucleobase overhang of deoxythymidine(dT) would have the following structure:

```
cgagaggcggacgggaccgdTdT
|||||||||||||||||||
dTdTgctctccgcctgccctggc
Antisense Strand   SEQ ID NO: 12
Complement Strand  SEQ ID NO: 13
```

In another embodiment, a duplex comprising an antisense strand having the same sequence CGAGAGGCGGACGG-GACCG (SEQ ID NO: 10) may be prepared with blunt ends (no single stranded overhang) as shown:

```
cgagaggcggacgggaccg  Antisense Strand  SEQ ID NO: 11
|||||||||||||||||||
gctctccgcctgccctggc  Complement Strand SEQ ID NO: 14
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of the buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM.

Example 62

5' and 2' bis-Substituted Modified Oligomeric Compounds Targeting PTEN—In vitro Study (ssRNAs vs siRNAs)

A series of 5' and 2' bis-substituted modified oligomeric compounds were prepared as single strand RNAs (ssRNAs). The antisense (AS) strands listed below were designed to target human PTEN, and each was also assayed as part of a duplex with the same sense strand (ISIS 341401, shown below) for their ability to reduce PTEN expression levels. HeLa cells were treated with the single stranded or double stranded oligomeric compounds created with the antisense compounds shown below using methods described herein. The $IC_{50}$'s were calculated using the linear regression equation generated by plotting the normalized mRNA levels to the log of the concentrations used.

| SEQ ID NO. | ISIS NO. | | Composition (5' to 3') | $EC_{50}$ (nM) ssRNA/siRNA |
|---|---|---|---|---|
| 15 | 341401 | (S) | AAGUAAGGACCAGAGACAA | -/- |
| 05 | 447581 | (AS) | P-$T_{Rc}U_fG_mU_fC_mU_fC_mU_fG_mG_fU_mC_fC_mU_fU_mA_fC_mU_fU_mA_eA_e$ | 1.0/0.4 |
| 05 | 467074 | (AS) | P-$T_{Sc}U_fG_mU_fC_mU_fC_mU_fG_mG_fU_mC_fC_mU_fU_mA_fC_mU_fU_mA_eA_e$ | 2.5/0.1 |
| 05 | 422931 | (AS) | P-$T_dU_fG_fU_fC_fU_fC_fU_fG_fG_fU_fC_fC_fU_fU_fA_fC_fU_fU_fA_eA_e$ | 5/0.5 |
| 05 | 432356 | (AS) | P-$T_RU_fG_fU_fC_fU_fC_fU_fG_fG_fU_fC_fC_fU_fU_fA_fC_fU_fU_fA_eA_e$ | 3/0.7 |
| 05 | 435397 | (AS) | P-$T_dU_fG_mU_fC_mU_fC_mU_fG_mG_fU_mC_fC_mU_fU_mA_fC_mU_fU_mA_eA_e$ | 2/0.4 |
| 06 | 467076 | (AS) | Py-$^{me}U_mU_fG_mU_fC_mU_fC_mU_fG_mG_fU_mC_fC_mU_fU_mA_fC_mU_fU_mA_eA_e$ | 6.0/.05 |
| 06 | 462606 | (AS) | Pz-$^{me}U_mU_fG_mU_fC_mU_fC_mU_fG_mG_fU_mC_fC_mU_fU_mA_fC_mU_fU_mA_eA_e$ | 50/0.4 |
| 06 | 462607 | (AS) | Pz-$^{me}U_mU_fG_mU_fC_mU_fC_mU_fG_mG_fU_mC_fC_mU_fU_mA_fC_mU_fU_mA_eA_e$ | 50/1.0 |
| 06 | 460646 | (AS) | Pz-$^{me}U_hU_fG_mU_fC_mU_fC_mU_fG_mG_fU_mC_fC_mU_fU_mA_fC_mU_fU_mA_eA_e$ | 50/0.8 |
| 06 | 418046 | (AS) | P-$U_mU_fG_mU_fC_mU_fC_mU_fG_mG_fU_mC_fC_mU_fU_mA_fC_mU_fU_mA_eA_e$ | 2.0/0.2 |
| 06 | 404320 | (AS) | P-$U_fU_fG_fU_fC_fU_fC_fU_fG_fG_fU_fC_fC_fU_fU_fA_fC_fU_fU_fA_eA_e$ | 5/0.5 |
| 10 | 359455 | (AS) | UUGUCUCUGGUCCUUACUU | 50/0.3 |
| 10 | 386187 | (AS) | P-$U_fU_fG_fU_fC_fU_fC_fU_fG_fG_fU_fC_fC_fU_fU_fA_fC_fU_fU_f$ | 15/0.3 |

Once prepared, the duplexed compounds are evaluated for their ability to modulate target mRNA levels. When cells reach 80% confluency, they are treated with duplexed compounds of the invention. For cells grown in 96-well plates, wells are washed once with 200 µL OPTI-MEM-1™ reduced-serum medium (Gibco BRL) and then treated with 130 µL of OPTI-MEM-1™ containing 5 µg/mL LIPOFECTAMINE 2000™ (Invitrogen Life Technologies, Carlsbad, Calif.) and the duplex antisense compound at the desired final concentration. After about 4 hours of treatment, the medium is replaced with fresh medium. Cells are harvested 16 hours after treatment, at which time RNA is isolated and target reduction measured by quantitative real-time PCR as described herein.

Each internucleoside linkage is a phosphodiester except that underlined nucleosides are linked to the following nucleoside by a phosphorothioate (going 5' to 3'). Each nucleoside not followed by a subscript is a ribonucleoside. A "P" at the 5'-end indicates a 5'-phosphate group. A "Py" at the 5'-end indicates a 5'-methylenephosphonate group, $(PO(OH)_2CH_2-)$. A "Pz" at the 5'-end indicates a 5'-difluoromethylenephosphonate group, $(PO(OH)_2CF_2-)$. Nucleosides followed by a subscript indicate modification as follows: subscript "d" indicates a 2'-O-dimethylaminoethyl acetamide (DMAEAc) modified nucleoside; subscript "e" indicates a 2'-O(CH$_2$)$_2$OCH$_3$ (MOE) modified nucleoside, subscript "f" indicates a 2'-fluoro modified nucleoside; subscript "m" indicates 2'-O-methyl modified nucleoside; and subscript "R" indicates a (R)-5'-methyl-2'-deoxyribonucleoside. Superscript "me" indicates a 5-methyl group on the pyrimidine base of the nucleoside. Nucleosides with subscripts "Rc" or "Sc" are shown below.

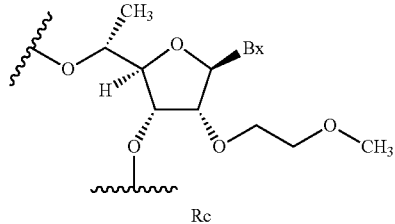

Rc

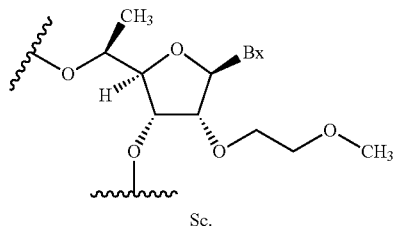

Sc.

Example 63

Modified ssRNAs Targeting PTEN—In vivo study

Modified ssRNAs and dsRNAs targeted to PTEN were designed as shown below.

| SEQ ID NO. | ISIS NO. | Composition (5' to 3') |
|---|---|---|
| 16 | 398239 | 5'-$A_fA_mG_fU_mA_fA_mG_fG_mA_fC_mC_fA_mG_fA_mG_fA_mC_fA_m$ $\underline{A_fU_e}U_e$-3' |
| 06 | 414291 | 3'-$A_eA_eU_mU_fC_mA_fU_mU_fC_mC_fU_mG_fG_mU_fC_mU_fC_mU_f$ $G_mU_fU_m$-5' |
| 06 | 414291 | P-$U_mU_fG_mU_fC_mU_fC_mU_fG_mG_fU_mC_fC_mU_fU_mA_fC_mU_fU_m$ $\underline{A_eA_e}$ |
| 06 | 408874 | P-$\underline{U_fU_fG_fU_fC_fU_m}C_mU_fG_fG_mU_mC_fC_fU_fU_fA_fC_mU_mU_m$ $\underline{A_eA_e}$ |

Phosphorothioate internucleoside linkages are indicated by underlining. Modified nucleosides are indicated by a subscripted letter following the capital letter indicating the nucleoside. In particular, subscript "f" indicates 2'-fluoro; subscript "m" indicates 2'-O-methyl; and subscript "e" indicates 2'-O-methoxyethyl (MOE). For example $U_m$ is a modified uridine having a 2'-OCH$_3$ group. Some of the strands have a 5'-phosphate group designated as "P—".

Example 64

Effect of Modified Internucleoside Linkages on Modified ssRNAs Targeting PTEN—In vitro Study A dose response experiment was performed targeting PTEN in human HeLa cells to determine the effects of placement of sugar and internucleoside linkages within ssRNAs. More specifically, the modified ssRNAs were tested for their ability to reduce PTEN mRNA in cultured cells. The modified ssRNAs are shown below, and contain 2'-OMe and 2'-fluoro modified nucleosides, two 2'-O-MOE modified nucleosides at the 3'-terminus, and seven phosphorothioate linkages at the 3'-terminus of the ssRNAs.

HeLa cells were treated with ssRNAs shown below at concentrations of 1.56 nM, 3.13 nM, 6.25 nM, 12.5 nM, 20 nM and 50 nM using methods described herein. Levels of mRNA were determined using real-time PCR methods as described herein. The IC$_{50}$ for each ssRNA was determined. These data demonstrate that these modified ssRNA exhibit similar activity in decreasing target mRNA levels.

| SEQ ID NO. | ISIS NO. | Composition (5' to 3') | IC$_{50}$ |
|---|---|---|---|
| 06 | 404320 | P-$U_fU_fG_fU_fC_fU_fC_fU_fG_fG_fU_fC_fC_f\underline{U_fU_fA_fC_fU_fU_f}$ $\underline{A_eA_e}$ | 5.8 |
| 06 | 408874 | P-$\underline{U_fU_fG_fU_fC_fU_m}C_mU_fG_fG_mU_mC_fC_fU_fU_fA_fC_mU_mU_m$ $\underline{A_eA_e}$ | 6.0 |
| 06 | 408877 | P-$U_mU_fG_fU_fC_fU_mC_mU_fG_fG_mU_mC_fC_fU_fU_fA_fC_mU_mU_m$ $\underline{A_eA_e}$ | 7.0 |
| 06 | 409044 | P-$U_mU_fG_mU_fC_mU_fC_mU_fG_mG_fU_mC_fC_m\underline{U_fU_mA_fC_mU_fU_m}$ $\underline{A_eA_e}$ | 10.5 |
| 06 | 407047 | $U_fU_fG_fU_fC_fU_fC_mU_fG_mG_fU_mC_fC_m\underline{U_mU_mA_fC_mU_fU_m}A_e$ $\underline{A_e}$ | 3.5 |
| 17 | 409049 | P-$U_fU_fG_fU_fC_fU_mC_mU_fG_mG_fU_mC_fC_m\underline{U_fU_mA_fC_mU_fU_m}$ $\underline{T_eT_e}$ | 16.2 |
| 17 | 409062 | P-$U_fU_fG_fU_fC_fU_mC_mU_fG_fG_mU_mC_fC_fU_fU_fA_fC_mU_mU_m$ $\underline{T_eT_e}$ | 8.6 |

Phosphorothioate internucleoside linkages are indicated by underlining. Modified nucleosides are indicated by a subscripted letter following the capital letter indicating the nucleoside. In particular, subscript "f" indicates 2'-fluoro; subscript "m" indicates 2'-O-methyl; and subscript "e" indicates 2'-O-methoxyethyl (MOE). For example, $U_f$ is a modified uridine having a 2'-fluoro group. Some of the strands have a 5'-phosphate group designated as "P—".

Example 65 ssRNAs Stability in Hepatocyte Cell Homogenate Assay—In vivo Study

The stability of oligomeric compounds can be evaluated in a cell homogenate assay.

Hepatocytes were harvested from balk mice in ice-cold hepatocyte wash media (William E Media) with fetal bovine serum, sedimented by centrifugation at 1000 g for 8 minutes and then washed with hepatocyte wash media. Hepatocytes were homogenized with RIPA buffer (50 mM Tris pH 7.5, 10 mM $MgCl_2$, 150 mM NaCl, 0.5% NP-40 alternative, one tablet of Roche protease inhibitor #11836170001), and centrifuged at 14000 g for 15 minutes at 4° C. and the supernatant was removed and stored in ice. Protein concentration (BSA mg/mL) was determined with Bradford assay and adjusted to a final protein concentration of 2 mg/mL by addition of Ripa buffer volume or cell homogenate volume.

Phenol/Choroform Extraction. ssRNA (1 mL, 20 µL) were homogenized in a homogenation buffer (20 mM Tris, pH 8, 20 mM EDTA and 0.1 M NaCl in 0.5% NP-40) at time points 0, 5, 10, 20, 30, 40 and 60 minutes (Exception: 06/408877 at time points 0, 15, 30, 60, 120 and 240 mins, 06/409044, at time points 0, 0.5, 1, 2, 4, 8, and 18 hours). An internal standard (18/355868, a 27-mer, 2'-O-methoxyethyl-modified phosphorothioate oligonucleotide, or 19/116847, a 5-10-5 gapmer, 2'-O-methoxyethyl-modified phosphorothioate oligonucleotide) with concentration at 20 ug/g was added prior to extraction. Tissue samples were extracted with 70 µL of $NH_4OH$ and 240 µL of phenol/chloroform/isoamyl alcohol (25:24:1). The supernatant was removed after centrifugation at 14000 rpm for 2 min. The remaining extractant was vortexed with an additional 500 µL of water and the aqueous layer was removed and combined with the supernatant after centrifugation at 14000 rpm for 2 minutes.

Solid Phase Extraction. Triethylammonium acetate solution at 1M (500 µL) was added to the supernatant. The aqueous layer of the mixture was loaded onto the pre-conditioned Biotage™ Phenyl Solid Phase Extraction Plate (SPE plate) after centrifugation at 9000 rpm for 20 minutes. The SPE plate was washed several times with water. The sample was then eluted with 1.5 mL of 1% TEA in 90% MeOH and filtered through the Protein Precipitation Plate (Phenomenex™). The eluent was evaporated to dryness and diluted to 200 µL with 50% quenching buffer (8 M urea, 50 mM EDTA) and water before sample injection.

LC-MS. An Agilent 1100 Series LC/MSD system was connected in-line to a mass spectrometry. Mass spectrometer was operated in the electrospray negative ionization mode. The nebulizer nitrogen gas was set at 325 psi and the drying nitrogen gas was set at 12 L/min. The drying temperature was 325° C. Samples (25 µL/well) were introduced via an auto sampler and reversed-phase chromatography was carried out with an XBridge OST C18 2.5 µm 2.1 mm×50 mm HPLC column using a flow rate of 300 µL/min at 55° C. The ion pair buffers consisted of A: 5 mM tributylammonium acetate (TBAA) in 20% acetonitrile and B: 5 nM TBAA in 90% acetonitrile and the loading buffer was 25 mM TBAA in 25% Acetonitrile. Separation was performed on a 30% to 70% B in 9 min and then 80% B in 11 min gradient.

Quantitative analysis of oligonucleotide and internal standard by extracted ion chromatograms of the most abundant ions was performed using MSD ChemStation software. The results are expressed as half-time ($T_{1/2}$) in the table below. These data demonstrate that modifications to oligomeric compounds improve their stability in a cell homogenate assay.

| SEQ ID NO./ ISIS NO. | $T_{1/2}$ Test 1 | $T_{1/2}$ Test 2 |
|---|---|---|
| 06/404320 | 4 min | — |
| 06/408874 | 22 min | 18 min |
| 06/408877 | 30 min | 24 min |
| 06/409044 | 4 hr | 4.3 hr |
| 06/407047 | 6 min | — |
| 17/409049 | 13 min | — |
| 17/409062 | 17 min | — |

Internal Standards:

| SEQ ID NO. | ISIS NO. | Composition (5' to 3') |
|---|---|---|
| 18 | 355868 | $G_e{}^{me}C_e$GTTTGCTCTCTTCTT$_e{}^{me}C_eT_eT_eG_e{}^{me}C_eG_e$TTT TT$_eT_e$ |
| 19 | 116847 | $^{me}\underline{C_eT_eG_e}{}^{me}\underline{C_eT_e}$AG$^{me}$C$^{me}$CT$^{me}$CTGGAT$_eT_eT_eG_eA_e$ |

Each internucleoside linkage is a phosphorothioate internucleoside linkage indicated by underlining (going 5' to 3'). Each unmodified nucleoside is a β-D-2'-deoxyribonucleosides. Nucleosides followed by a subscript "e" indicates a 2'-O(CH$_2$)$_2$OCH$_3$ (MOE) modified nucleoside. Superscript "me" indicates a 5-methyl group on the pyrimidine base of the nucleoside.

Example 66

MicroRNA Mimics: Cell Cycle Assay

Oligomeric compounds comprising the nucleobase sequence of a microRNA were synthesized to have certain modifications described herein. These microRNA mimics were tested for their ability to imitate microRNA activity.

A cell cycle assay was used to evaluate the activity of microRNA mimics. A549 cells were plated at a density of approximately 45,000 cells per well of a 24-well plate. The following day, cells were transfected with microRNA mimics and control oligomeric compounds, using RNAIMAX as the transfection reagent. Oligomeric compounds were tested at concentrations ranging from 0.1 nM to 100 nM. Control oligomeric compounds were also tested. Approximately 24 hours following transfection, nocodazole was added to the cells at a concentration ranging from 0.5 to 2.0 µg/ml. Approximately 16 hours later, the cells were harvested, washed, ethanol-fixed and stained with propidium iodide. Cells cycle profiles were generated by subjecting the stained cells to flow cytometry (FACSCAN).

miR-16 Mimics: Cell Cycle Assay

A cell cycle assay was used to test the activity of miR-16 mimics (shown in table below). The addition of a double-stranded miR-16 mimic blocked cells in the G1 phase of the cell cycle. The single stranded miR-16 mimic produced the same phenotype as the double-stranded mimic, blocking cells in the G1 phase of the cell cycle. The single stranded miR-16 mimic exhibited similar efficacy as the double-stranded miR-16 mimic.

| SEQ ID NO | Composition (5' to 3') |
|---|---|---|
| ss miR-16 | 20 | P-U$_m$A$_f$G$_f$C$_f$A$_f$G$_f$C$_f$A$_f$C$_m$G$_m$U$_f$A$_m$A$_m$U$_f$A$_f$U$_f$U$_f$G$_f$G$_m$C$_m$G$_m$A$_e$A$_e$ |
| ds miR-16 | 21 | UAGCAGCACGUAAAUAUUGGCG |
|  | 22 | AAAGCGUCGUGCAUUUAUAACC |

Internucleoside linkage and sugar modifications are indicated as described in previous examples.

miR-34 Mimics: Cell Cycle Assay

A cell cycle assay was used to test the activity of miR-34 mimics. The addition of a double-stranded miR-34 mimic blocked cells in the G1 phase of the cell cycle. The above single stranded miR-34 mimic produced the same phenotype as the double-stranded mimic, blocking cells in the G1 phase of the cell cycle. The single stranded miR-34 mimic exhibited similar efficacy as the double-stranded miR-34 mimic.

In addition to measuring cell cycle progression, cells treated with miR-34 mimics were subjected to microarray analysis to compare the profile of gene expression changes following treatment with microRNA mimics. The microarray analysis is used to evaluate the enrichment of target nucleic acids that comprise a seed match segment in their 3' untranslated regions from among the pool of nucleic acids that are down-regulated following treatment with a microRNA mimic.

Both the double-stranded miR-34 mimic and single-stranded miR-34 mimic down-regulated miR-34 seed-matched nucleic acids. However, also observed was an enrichment of nucleic acids comprising a seed match segment of the microRNA complement strand (the "passenger strand") of the double-stranded mimic, thus the microRNA complement strand was also acting an antisense compound. This activity is not specific to miR-34. Accordingly, a single-strand microRNA mimic can provide improved specificity relative to a double-stranded mimic.

These data demonstrate that the oligomeric compounds described herein can be designed as microRNA mimics. Further, single-stranded mimics are effective at imitating microRNA activity.

Internucleoside linkage and sugar modifications are indicated as described in previous examples.

Example 67

MicroRNA mimics: Cytokine Signaling Assay

Oligomeric compounds comprising the nucleobase sequence of a microRNA were synthesized to have certain modifications described herein. These oligomeric compounds were tested for their ability to mimic microRNA activity. A cytokine signaling assay was used to evaluate the activity of microRNA mimics.

miR-146 Mimics miR-146 is known to stimulate the release of cytokines such as IL-8, thus the following assay can be used to measure the activity of miR-146 mimics. A549 cells were treated with the miR-146 mimics shown below. Cells were treated with IL-1B at a concentration ranging from 0.1 to 2.0 ng/ml. After 8 hours and 24 hours, samples were collected for ELISA analysis to measure the release of the cytokine IL-8. Measurement of IL-8 in the cell culture supernatant revealed that single-strand miR-146 mimics decreased the release of IL-8 in a dose-responsive manner in this assay. Accordingly, the single-strand miR-146 mimics shown below exhibit an activity of miR-146.

| SEQ ID NO | Composition (5' to 3') |
|---|---|---|
| ss miR-34 | 23 | P-U$_m$G$_f$G$_f$C$_f$A$_f$G$_f$U$_f$G$_f$U$_m$C$_m$U$_f$U$_f$A$_m$G$_m$C$_f$U$_f$G$_f$G$_f$U$_f$U$_f$G$_f$U$_f$A$_e$A$_e$ |

Internucleoside linkage and sugar modifications are indicated as described in previous examples.

Additional miR-34 Mimics: Cell Cycle Assay

Additional single-stranded miR-34 mimics were tested in a cell cycle assay. Each of these oligomeric compounds resulted in a block in the G1 phase of the cell cycle, indicating that these single-stranded microRNA mimics are effective at imitating microRNA activity.

| SEQ ID NO | Composition (5' to 3') |
|---|---|---|
| ss miR-34 | 23 | P-U$_d$G$_f$G$_f$C$_f$A$_f$G$_f$U$_f$G$_f$U$_f$C$_f$U$_f$U$_f$A$_f$G$_f$C$_f$U$_f$G$_f$G$_f$U$_f$U$_f$G$_f$U$_f$A$_e$A$_e$ |
| ss miR-34 | 23 | P-U$_d$G$_f$G$_f$C$_m$A$_f$G$_m$U$_f$G$_m$U$_f$C$_m$U$_f$U$_m$A$_f$G$_m$C$_f$U$_f$G$_f$G$_f$U$_f$U$_f$G$_f$U$_f$A$_e$A$_e$ |
| ss miR-34 | 23 | P-U$_m$G$_f$G$_f$C$_f$A$_f$G$_f$U$_f$G$_m$U$_m$C$_f$U$_f$U$_m$A$_m$G$_m$C$_f$U$_f$G$_f$G$_f$U$_f$U$_m$G$_m$U$_m$A$_e$A$_e$ |
| ss miR-34 | 23 | P-U$_e$G$_f$G$_f$C$_f$A$_f$G$_f$U$_f$G$_m$U$_m$C$_f$U$_f$U$_m$A$_m$G$_m$C$_f$U$_f$G$_f$G$_f$U$_f$U$_m$G$_m$U$_m$A$_e$A$_e$ |

| SEQ ID NO | Composition (5' to 3') |
|---|---|---|
| ss miR-146 | 24 | P-$U_mG_fA_fG_fA_fA_fC_fU_fG_mA_mA_fU_fU_mC_mC_fA_fU_fG_fG_fG_mU_mU_mA_eA_e$ |
| ss miR-146 | 24 | P-$U_mG_fA_fG_fA_fA_fC_fU_fG_fA_mA_mU_fU_fC_mC_mA_fU_fG_fG_fG_mU_mU_mA_eA_e$ |

Additional oligomeric compounds were designed and comprise the nucleobase sequence of miR-146. These oligomeric compounds were shown to mimic miR-146 activity in the IL-8 release assay described above.

| SEQ ID NO | Composition (5' to 3') |
|---|---|---|
| ss miR-146 | 24 | P-$\underline{U_m}G_fA_fG_fA_fA_fC_fU_fG_mA_mA_f\underline{U_fU_m}C_mC_fA_fU_fG_fG_fG_mU_m\underline{U_mA_e}A_e$ |
| ss miR-146 | 24 | P-$U_mG_fA_m\underline{G_fA_f}A_mC_fU_fG_mA_mA_fU_fU_mC_mC_f\underline{A_fU_f}G_fG_fG_mU_m\underline{U_mA_e}A_e$ |
| ss miR-146 | 24 | P-$\underline{U_m}G_fA_mG_fA_mA_fC_mU_fG_mA_fA_m\underline{U_fU_m}C_fC_mA_fU_mG_fG_mG_fU_mU_fA_eA_e$ |

Additional oligomeric compounds were designed and comprise the nucleobase sequence of miR-146.

| SEQ ID NO | Composition (5' to 3') |
|---|---|---|
| ss miR-146 | 24 | P-$\underline{U_m}G_fA_fG_fA_fA_fC_fU_fG_mA_mA_fU_fU_mC_mC_fA_fU_fG_fG_fG_mU_m\underline{U_mA_e}A_e$ | miR-155 Mimics

Additional oligomeric compounds were designed and comprise the nucleobase sequence of miR-155.

| SEQ ID NO | Composition (5' to 3') |
|---|---|---|
| SS miR-155 | 25 | P-$U_mU_fA_fA_fU_fG_fC_fU_fA_fA_mU_mC_fG_fU_mG_mA_fU_f\underline{A_fG_fG_f}G_mG_mU_mA_eA_e$ |

Internucleoside linkage and sugar modifications are indicated as described in previous examples.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents patent application publications, international patent application publications, gene back accession numbers, and the like) cited in the present application is incorporated herein by reference in its entirety.

Example 68

Phosphate Stability in Mouse Serum

Single-stranded oligomeric compounds were tested for stability in mouse serum. The single stranded oligomeric compounds and the half lives of full compound with intact phosphorous moiety are provided in the table below.

| SEQ ID NO./ ISIS NO. | $T_{1/2}$ In full length | Sequence |
|---|---|---|
| 06/404320 | 0.4 hours | 5'-Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ |
| 10/430601 | 3.7 hours | 5'-Ps-$U_dU_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_f$ |
| 06/418129 | 5.4 hours | 5'-Po-$U_iU_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ |
| 05/418130 | 5.3 hours | 5'-Po-$T_jU_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ |
| 05/432356 | 8.7 hours | 5'-Po-$U_kU_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ |
| 05/422391 | 6.5 hours | 5'-Po-$T_dU_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_e$ |

Subscripts in the Table above: d=DMAEAc; i=N-methoxyamino BNA; J=tcDNA; k=(R) 5'-methyl Separately, four oligomeric compounds were tested for stability in mouse serum, as summarized in the table below.

| SEQ ID NO./ ISIS NO. | $T_{1/2}$ full length | Sequence |
|---|---|---|
| 06/404320 | 0.4 hours | 5'-Po-$U_{fo}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_{e}$ |
| 05/422391 | 3.7 hours | 5'-Po-$U_{d}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{f}$ |
| 05/440141 | 0.3 hours | 5'-Po-$T_{h}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_{e}$ |
| 05/435395 | 7.8 hours | 5'-Ps-$U_{d}U_{fo}G_{fo}U_{fo}C_{fo}U_{fo}C_{fo}U_{fo}G_{fo}G_{fo}U_{fo}C_{fo}C_{fo}U_{fs}U_{fs}A_{fs}C_{fs}U_{fs}U_{fs}A_{es}A_{e}$ |

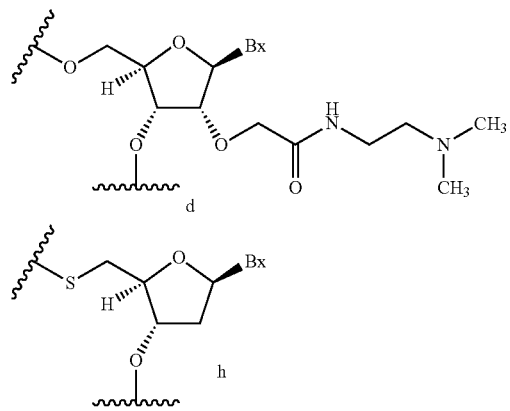

Example 69

Modified Oligomeric Compounds Targeting PTEN: In vitro Study

In accordance with the present disclosure, oligomeric compounds were synthesized and tested for their ability to reduce PTEN expression over a range of doses. Human HeLa cells were treated with either ISIS 447581, 467074, 418046 or 467076. A dose comparison was evaluated with dose concentrations of 0.067, 0.2, 0.62, 1.9, 5.5, 16.7 and 50 nM using methods described herein. Expression levels of PTEN were determined using real-time PCR and normalized to RIBOGREEN™ using methods described herein. The percent inhibition of PTEN mRNA was determined and the resulting dose-response curves were used to determine the $EC_{50}$. The $EC_{50}$s are listed below.

5'-end indicates a 5'-phosphate group. A "Py" at the 5'-end indicates a 5'-methylenephosphonate group, (PO(OH)$_2$CH$_2$—). Nucleosides followed by a subscript e, f or m indicate modification as follows: subscript "e" indicates a 2'-O(CH$_2$)$_2$OCH$_3$ (MOE) modified nucleoside, subscript "f" indicates a 2'-fluoro modified nucleoside; subscript "m" indicates 2'-O-methyl modified nucleoside. Superscript "me" indicates a 5-methyl group on the pyrimidine base of the nucleoside. Nucleosides with subscript "Rc" or "Sc" are shown below.

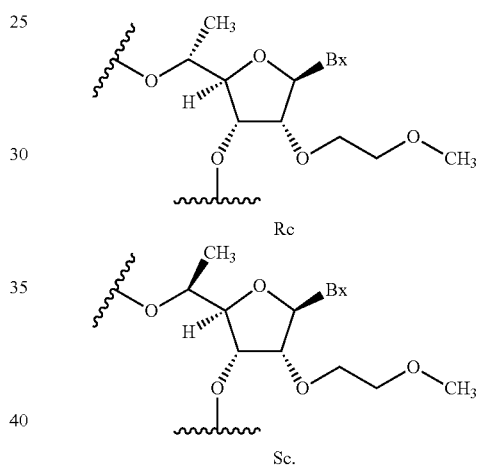

Example 70

5'-Modified Oligomeric Compounds Targeting PTEN: In vivo Study

Three oligomeric compounds (ISIS 467074, ISIS 467076, ISIS 116847) were synthesized as described above. Sequence

| SEQ ID NO. | ISIS NO. | Composition (5' to 3') | $EC_{50}$ (nM) |
|---|---|---|---|
| 05 | 447581 | P-$\underline{T_{Rc}U_{f}G_{m}U_{f}C_{m}U_{f}C_{m}U_{f}G_{m}G_{f}U_{m}C_{f}C_{m}U_{f}U_{m}A_{f}C_{m}U_{f}U_{m}A_{e}A_{e}}$ | 0.6 |
| 05 | 467074 | P-$\underline{T_{Sc}U_{f}G_{m}U_{f}C_{m}U_{f}C_{m}U_{f}G_{m}G_{f}U_{m}C_{f}CmU_{f}U_{m}A_{f}C_{m}U_{f}U_{m}A_{e}A_{e}}$ | 2.5 |
| 06 | 418046 | P-$\underline{U_{m}U_{f}G_{m}U_{f}C_{m}U_{f}C_{m}U_{f}G_{m}G_{f}U_{m}C_{f}C_{m}U_{f}U_{m}A_{f}C_{m}U_{f}U_{m}A_{e}A_{e}}$ | 0.83 |
| 06 | 467076 | Py-$^{me}\underline{U_{m}U_{f}G_{m}U_{f}C_{m}U_{f}C_{m}U_{f}G_{m}G_{f}U_{m}C_{f}C_{m}U_{f}U_{m}A_{f}C_{m}U_{f}U_{m}A_{e}A_{e}}$ | 6.0 |

Each internucleoside linkage is a phosphodiester except that underlined nucleosides are linked to the following nucleoside by a phosphorothioate (going 5' to 3'). A "P" at the and chemistry of the three oligomeric compounds are provided in the table, below. The nucleobase sequence of each oligomeric compound is complementary to PTEN.

| SEQ ID NO. | ISIS NO. | Composition (5' to 3') |
|---|---|---|
| 05 | 467074 | P-T$_{Sc}$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 06 | 467076 | Py-$^{me}$U$_m$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ |
| 08 | 116847 | $^{me}$C$_e$T$_e$G$_e$$^{me}$C$_e$T$_e$AG$^{me}$C$^{me}$CT$^{me}$CTGGAT$_e$T$_e$T$_e$G$_e$A$_e$ |

Each internucleoside linkage is a phosphodiester except that underlined nucleosides are linked to the following nucleoside by a phosphorothioate (going 5' to 3'). "Py" at the 5'-end indicates a 5'-methylenephosphonate group, (PO(OH)$_2$CH$_2$—). Each unmodified nucleoside is β-D-2'-deoxyribonucleosides. Nucleosides followed by a subscript e, for m indicate modification as follows: subscript "e" indicates a 2'-O(CH$_2$)$_2$OCH$_3$ (MOE) modified nucleoside, subscript "f" indicates a 2'-fluoro modified nucleoside; subscript "m" indicates 2'-O-methyl modified nucleoside. Superscript "me" indicates a 5-methyl group on the pyrimidine base of the nucleoside. Nucleoside with subscript "Sc" is shown below.

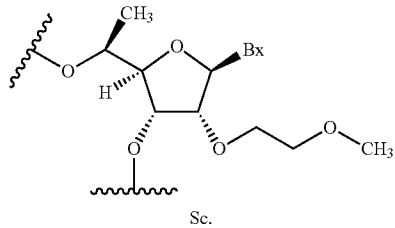

Sc.

Six-week-old male Balb/c mice (Jackson Laboratory, Bar Harbor, Me.) were injected intraperitenially with a single dose of 75 mg/kg of one of the three oligomeric compounds above or with saline control. Each dose group consisted of four animals. The mice were sacrificed 48 hours following administration. Livers were collected and PTEN mRNA levels were assessed using real-time PCR and RIBOGREEN® RNA quantification reagent (Molecular Probes, Inc. Eugene, Oreg.) according to standard protocols. PTEN mRNA levels were determined relative to total RNA (using Ribogreen), and normalized to the saline-treated control. Results are listed below as the average % inhibition of PTEN mRNA expression for each treatment group, normalized to saline-injected control.

| | SEQ ID NO./ISIS NO | | | |
|---|---|---|---|---|
| | 05/467074 | 06/467076 | 08/116847 | Saline (Control) |
| Dose | 75 mg/kg | 75 mg/kg | 75 mg/kg | 0 mg/kg |
| Time (h) | 48 | 48 | 48 | 48 |
| % inhibition | 11% | 16% | 76% | 0% |

Example 71

Stability of 5'-Modified Oligomeric Compounds Targeting PTEN: In vivo Study

The in vivo stability of the three oligomeric compounds in Example 70 was evaluated. The tissue samples were obtained from the animals in which PTEN was assessed. Tissue samples were collected and prepared using the same technique described in Example 65. Quantitative analysis of the oligonucleotides standard were performed by extracted ion chromatograms in the most abundant charge state (−4) using Chemstation software. The tissue level (µg/g) of intact compound of ISIS 116847, 467074 and 467076 was measured and are provided below:

| SEQ ID NO./ISIS NO. | Dose @ 75 mg/kg (48 h time point) Tissue Level of intact compound (µg/g) |
|---|---|
| 05/467074 | none detected |
| 06/467076 | 22.5 |
| 08/116847 | 131.1 |

The 5-10-5 MOE gapmer compound was present at high levels and was a potent inhibitor of PTEN.

Intact 467076 was present at a lower concentration and resulted in smaller inhibition of PTEN. Intact 467074 was not detected and resulted in the lowest amount of PTEN reduction. Some 467074 lacking the 5'-phosphate was detected.

Example 72

Effect of Modified Internucleoside Linkages on Modified Oligomeric Compounds Targeting PTEN—in vitro Study In accordance with the present disclosure, oligomeric compounds were synthesized and tested for their ability to reduce PTEN expression over a range of doses. Human HeLa cells were treated with the following oligomeric compounds. A dose comparison was evaluated with dose concentrations of 0.167, 0.5, 1.5, 5, 15 and 50 nM using methods described herein. Expression levels of PTEN were determined using real-time PCR and normalized to RIBOGREEN™ using methods described herein. The percent inhibition of PTEN mRNA was determined and the resulting dose-response curves were used to determine the IC$_{50}$. The IC$_{50}$s are listed below.

| SEQ ID NO | ISIS NO. | Composition (5' to 3') | IC$_{50}$ (nM) |
|---|---|---|---|
| 05 | 435397 | P-T$_d$U$_f$G$_m$U$_f$C$_m$U$_f$C$_m$U$_f$G$_m$G$_f$U$_m$C$_f$C$_m$U$_f$U$_m$A$_f$C$_m$U$_f$U$_m$A$_e$A$_e$ | 2.0 |
| 05 | 435394 | P-T$_d$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 18.1 |
| 05 | 435399 | P-T$_d$U$_f$G$_m$U$_f$C$_m$U$_f$C$_m$U$_f$G$_m$G$_f$U$_m$C$_f$C$_f$U$_f$U$_f$A$_f$C$_f$U$_f$U$_f$A$_e$A$_e$ | 2.0 |
| 05 | 418031 | P-T$_e$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 3.9 |
| 05 | 418032 | P-T$_e$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 2.9 |
| 05 | 418033 | P-T$_e$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 11.0 |

-continued

| SEQ ID NO | ISIS NO. | Composition (5' to 3') | IC$_{50}$ (nM) |
|---|---|---|---|
| 05 | 418131 | P-TU$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 3.4 |
| 06 | 404320 | P-U$_f$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 7.6 |
| 06 | 414291 | P-U$_m$U$_f$G$_m$U$_f$C$_m$U$_f$C$_m$U$_f$G$_m$G$_f$U$_m$C$_f$C$_m$U$_f$U$_m$C$_f$U$_m$U$_m$A$_e$A$_e$ | 13.0 |
| 06 | 416598 | P-U$_m$U$_f$G$_m$U$_f$C$_m$U$_f$C$_m$U$_f$G$_m$G$_f$U$_m$C$_f$C$_m$U$_f$U$_m$A$_f$C$_m$U$_m$A$_e$A$_e$ | 6.8 |
| 06 | 418030 | P-U$_e$U$_f$G$_f$U$_f$C$_f$U$_f$C$_f$U$_f$G$_f$G$_f$U$_f$C$_f$C$_f$U$_f$U$_f$A$_f$C$_f$U$_f$U$_f$A$_e$A$_e$ | 8.5 |

Each internucleoside linkage is a phosphodiester except that underlined nucleosides are linked to the following nucleoside by a phosphorothioate (going 5' to 3'). A "P" at the 5'-end indicates a 5'-phosphate group. Each unmodified nucleoside is a β-D-2'-deoxyribonucleoside. Nucleosides followed by a subscript d, e, f, m or x indicate modification as follows: a subscript "d" indicates a 2'-OCH$_2$(CO)NH(CH$_2$)$_2$N(CH$_3$)$_2$ (DMAEAc), subscript "e" indicates a 2'-O(CH$_2$)$_2$OCH$_3$ (MOE) modified nucleoside, subscript "f" indicates a 2'-fluoro modified nucleoside subscript "m" indicates 2'-O-methyl modified nucleoside and subscript "ef" indicates a 2'-OCH$_2$CH$_2$F (FEt) modified nucleoside.

What is claimed is:

1. An oligomeric compound comprising a single-stranded oligonucleotide consisting of 10-30 linked nucleosides, wherein the oligonucleotide comprises a phosphate stabilizing nucleoside at the 5′-end, wherein the phosphate stabilizing nucleoside comprises:
   i) a 5′-terminal modified phosphate; or
   ii) a 5′-terminal unmodified phosphate and a modified sugar moiety comprising a 5′ modification; and a linking group linking the phosphate stabilizing nucleoside to the remainder of the oligonucleotide; and wherein the remainder of the oligonucleotide comprises at least one region having a nucleoside motif:

$$(A)_n\text{-}(B)_n\text{-}(A)_n\text{-}(B)_n, \text{ wherein:}$$

A and B are differently modified nucleosides; and
each n is independently selected from 1, 2, 3, 4, and 5; or
iii) both i) and ii).

2. The oligomeric compound of claim 1, wherein:
the 5'-terminal modified phosphate is selected from: phosphonate, alkylphosphonate, substituted alkylphosphonate, aminoalkyl phosphonate, substituted aminoalkyl phosphonate, phosphorothioate, phosphoramidate, alkylphosphonothioate, substituted alkylphosphonothioate, phosphorodithioate, and thiophosphoramidate; and
the 5'-modification of the sugar moiety of the phosphate stabilizing nucleoside is selected from 5'-alkyl and 5'-halogen.

3. The oligomeric compound of claim 1, wherein the modified phosphate is selected from: phosphonate, alkylphosphonate, and substituted alkylphosphonate.

4. The oligomeric compound of claim 1, wherein A and B are each selected from: a 2'-F nucleoside, a 2'-OCH$_3$ nucleoside, a 2'-O(CH$_2$)$_2$OCH$_3$ nucleoside, a (4'-CH$_2$—O-2') BNA nucleoside, a (4'-(CH$_2$)$_2$—O-2') BNA nucleoside, a (4'-CH(CH$_3$)—O-2') BNA nucleoside, a DNA nucleoside, an RNA nucleoside, and an F-HNA nucleoside.

5. The oligomeric compound of claim 1, wherein at least one of A and B is a 2'-F, 2'-OCH$_3$ or 2'-O(CH$_2$)$_2$OCH$_3$ nucleoside.

6. The oligomeric compound of claim 4, wherein A is a 2'-F nucleoside and B is a 2'-OCH$_3$ nucleoside.

7. The oligomeric compound of claim 1 comprising a 3'-region consisting of from 1 to 5 nucleosides at the 3'-end of the oligomeric compound wherein:
the nucleosides of the 3'-region each comprises the same modification as one another; and
the nucleosides of the 3'-region are modified differently than the last nucleoside adjacent to the 3'-region.

8. The oligomeric compound of claim 7, wherein the nucleosides of the 3'-region are 2'-O(CH$_2$)$_2$OCH$_3$ nucleosides; and wherein the 3'-region consists of 2 linked nucleosides.

9. The oligomeric compound of claim 7, wherein each nucleoside of the 3'-region comprises a thymine base.

10. The oligomeric compound of claim 1, wherein the remainder of the oligonucleotide comprises at least one region of nucleosides having a motif I:

$N_f(PS)N_m(PO)$, wherein:

$N_f$ is a 2'-F nucleoside,
$N_m$ is a 2'-OCH$_3$ nucleoside
PS is a phosphorothioate linking group; and
PO is a phosphodiester linking group.

11. The oligomeric compound of claim 10 comprising at least 2 regions of nucleosides having the motif I.

12. The oligomeric compound of claim 10 comprising at least 6 regions of nucleosides having the motif I.

13. The oligomeric compound of claim 10 comprising at least 7 regions of nucleosides having the motif I.

14. The oligomeric compound of claim 1 comprising one or more conjugate groups.

15. The oligomeric compound of claim 1 wherein the oligomeric compound is an RNAi compound.

16. A pharmaceutical composition comprising an oligomeric compound according to claim 1 and a pharmaceutically acceptable diluent or carrier.

17. A method comprising contacting a cell with an oligomeric compound according to claim 1.

18. The method of claim 17, wherein the cell is in vitro.

19. The method of claim 17, wherein the cell is in an animal.

20. The oligomeric compound of claim 1, wherein the phosphate stabilizing nucleoside comprises a 2'-modification selected from: halogen, allyl, amino, azido, thio, O-allyl, —O—C$_1$-C$_{10}$ alkyl, —O—C$_1$-C$_{10}$ substituted alkyl, —OCF$_3$, —O—(CH$_2$)$_2$—O—CH$_3$, —O(CH$_2$)$_2$SCH$_3$, —O—(CH$_2$)$_2$O—N(R$_m$)(R$_n$), —O—CH$_2$—C(=O)—N(R$_m$)(R$_n$), where each R$_m$ and R$_n$ is, independently, H or substituted or unsubstituted C$_1$-C$_{10}$ alkyl, —O[(CH$_2$)$_n$O]$_m$CH$_3$, —O(CH$_2$)$_n$NH$_2$, —O(CH$_2$)$_n$CH$_3$, —O(CH$_2$)$_n$ONH$_2$, —OCH$_2$C(=O)N(H)CH$_3$, —O(CH$_2$)$_n$ON[(CH$_2$)$_n$CH$_3$]$_2$, where n and m are from 1 to about 10; C$_1$ to C$_{10}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl.

21. The oligomeric compound of claim 1, wherein the phosphate stabilizing nucleoside comprises a 5' terminal modified phosphate and a modified sugar moiety comprising a 5' modification.

22. The oligomeric compound of claim 21, wherein the phosphate stabilizing nucleoside comprises a 2'-modification selected from: halogen, allyl, amino, azido, thio, O-allyl, —O—C$_1$-C$_{10}$ alkyl, —O—C$_1$-C$_{10}$ substituted alkyl, —OCF$_3$, —O—(CH$_2$)$_2$—O—CH$_3$, —O(CH$_2$)$_2$SCH$_3$, —O—(CH$_2$)$_2$—O—N(R$_m$)(R$_n$), —O—CH$_2$—C(=O)—N(R$_m$)(R$_n$), where each R$_m$ and R$_n$ is, independently, H or substituted or unsubstituted C$_1$-C$_{10}$ alkyl, —O[(CH$_2$)$_n$O]$_m$CH$_3$, —O(CH$_2$)$_n$NH$_2$, —O(CH$_2$)$_n$CH$_3$, —O(CH$_2$)$_n$ONH$_2$, —OCH$_2$C(=O)N(H)CH$_3$, —O(CH$_2$)$_n$ON[(CH$_2$)$_n$CH$_3$]$_2$, where n and m are from 1 to about 10; C$_1$ to C$_{10}$ alkyl, substituted alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl.

23. The oligomeric compound of claim 22, wherein the phosphate stabilizing nucleoside comprises a 2'-modification selected from: —F, —O—(CH$_2$)$_2$—O—CH$_3$, and —OCH$_3$.

* * * * *

SEQUENCE LISTING

<160> NUMBER OF SEQ ID NOS: 91

<210> SEQ ID NO 1
<211> LENGTH: 3160
<212> TYPE: DNA
<213> ORGANISM: H. sapiens

<400> SEQUENCE: 1

```
cctcccctcg cccggcgcgg tcccgtccgc ctctcgctcg cctcccgcct cccctcggtc    60
ttccgaggcg cccgggctcc cggcgcggcg gcggaggggg cgggcaggcc ggcggcggt   120
gatgtggcag gactcttttat gcgctgcggc aggatacgcg ctcggcgctg ggacgcgact   180
gcgctcagtt ctctcctctc ggaagctgca gccatgatgg aagtttgaga gttgagccgc   240
tgtgaggcga ggccgggctc aggcgaggga gatgagagac ggcggcggcc gcggcccgga   300
gcccctctca gcgcctgtga gcagccgcgg gggcagcgcc ctcggggagc cggccggcct   360
gcggcggcgg cagcggcggc gtttctcgcc tcctcttcgt cttttctaac cgtgcagcct   420
cttcctcggc ttctcctgaa agggaaggtg gaagccgtgg gctcggcgcg gagccggctg   480
aggcgcggcg gcggcggcgg cggcacctcc cgctcctgga gcgggggggga gaagcggcgg   540
cggcggcggc cgcggcggct gcagctccag ggaggggggtc tgagtcgcct gtcaccattt   600
ccagggctgg gaacgccgga gagttggtct ctcccttct actgcctcca acacggcggc   660
ggcggcggcg gcacatccag ggacccgggc cggttttaaa cctcccgtcc gccgccgccg   720
cacccccccgt ggcccgggct ccggaggccg ccggcggagg cagccgttcg gaggattatt   780
cgtcttctcc ccattccgct gccgccgctg ccaggcctct ggctgctgag gagaagcagg   840
cccagtcgct gcaaccatcc agcagccgcc gcagcagcca ttacccggct gcggtccaga   900
gccaagcggc ggcagagcga ggggcatcag ctaccgccaa gtccagagcc atttccatcc   960
tgcagaagaa gccccgccac cagcagcttc tgccatctct ctcctccttt ttcttcagcc  1020
acaggctccc agacatgaca gccatcatca aagagatcgt tagcagaaac aaaaggagat  1080
atcaagagga tggattcgac ttagacttga cctatattta tccaaacatt attgctatgg  1140
gatttcctgc agaaagactt gaaggcgtat acaggaacaa tattgatgat gtagtaaggt  1200
ttttggattc aaagcataaa aaccattaca agatatacaa tctttgtgct gaaagacatt  1260
atgacaccgc caaatttaat tgcagagttg cacaatatcc ttttgaagac cataacccac  1320
```

```
cacagctaga acttatcaaa cccttttgtg aagatcttga ccaatggcta agtgaagatg    1380
acaatcatgt tgcagcaatt cactgtaaag ctggaaaggg acgaactggt gtaatgatat    1440
gtgcatattt attacatcgg ggcaaatttt taaaggcaca agaggcccta gatttctatg    1500
gggaagtaag gaccagagac aaaaagggag taactattcc cagtcagagg cgctatgtgt    1560
attattatag ctacctgtta aagaatcatc tggattatag accagtggca ctgttgtttc    1620
acaagatgat gtttgaaact attccaatgt tcagtggcgg aacttgcaat cctcagtttg    1680
tggtctgcca gctaaaggtg aagatatatt cctccaattc aggacccaca cgacgggaag    1740
acaagttcat gtactttgag ttccctcagc cgttacctgt gtgtggtgat atcaaagtag    1800
agttcttcca caaacagaac aagatgctaa aaaaggacaa aatgtttcac ttttgggtaa    1860
atacattctt cataccagga ccagaggaaa cctcagaaaa agtagaaaat ggaagtctat    1920
gtgatcaaga aatcgatagc atttgcagta tagagcgtgc agataatgac aaggaatatc    1980
tagtacttac tttaacaaaa aatgatcttg acaaagcaaa taaagacaaa gccaaccgat    2040
acttttctcc aaattttaag gtgaagctgt acttcacaaa aacagtagag gagccgtcaa    2100
atccagaggc tagcagttca acttctgtaa caccagatgt tagtgacaat gaacctgatc    2160
attatagata ttctgacacc actgactctg atccagagaa tgaaccttt gatgaagatc     2220
agcatacaca aattacaaaa gtctgaattt ttttttatca agagggataa aacaccatga    2280
aaataaactt gaataaactg aaaatggacc tttttttttt taatggcaat aggacattgt    2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460
tatataccttt tttgtgtcaa aaggacattt aaaattcaat taggattaat aaagatggca    2520
cttttcccgtt ttattccagt tttataaaaa gtggagacag actgatgtgt atacgtagga    2580
atttttttcct tttgtgttct gtcaccaact gaagtggcta aagagctttg tgatatactg    2640
gttcacatcc tacccctttg cacttgtggc aacagataag tttgcagttg gctaagagag    2700
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                          3160

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                           26

<210> SEQ ID NO 3
<211> LENGTH: 25
<212> TYPE: DNA
<213> ORGANISM: Artificial Sequence
```

```
<220> FEATURE:
<223> OTHER INFORMATION: Primer

<400> SEQUENCE: 3
tgcacatatc attacaccag ttcgt                                          25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
ttgcagcaat tcactgtaaa gctggaaagg                                     30

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)...(21)
<223> OTHER INFORMATION: bases at these positions are RNA

<400> SEQUENCE: 5
tugucucugg uccuuacuua a                                              21

<210> SEQ ID NO 6
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 6
uugucucugg uccuuacuua a                                              21

<210> SEQ ID NO 7
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-10, 13, 15-23
<223> OTHER INFORMATION: Bases at these positions are RNA

<400> SEQUENCE: 7
acaaacacca ttgtcacaca cca                                            23

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
ctgctagcct ctggatttga                                                20

<210> SEQ ID NO 9
<211> LENGTH: 14
<212> TYPE: DNA
```

```
<213> ORGANISM: Artificial Sequence
<220> FEATURE:
<223> OTHER INFORMATION: Synthetic Oligonucleotide

<400> SEQUENCE: 9
cttagcactg gcct                                                        14

<210> SEQ ID NO 10
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 10
uugucucugg uccuuacuu                                                   19

<210> SEQ ID NO 11
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 11
cgagaggcgg acgggaccg                                                   19

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(19)
<223> OTHER INFORMATION: Bases at these positions are RNA

<400> SEQUENCE: 12
cgagaggcgg acgggaccgt t                                                21

<210> SEQ ID NO 13
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 3, 4, 6, 8, 9, 10, 11, 12, 14, 15, 16, 17, 19, 20, 21
<223> OTHER INFORMATION: Bases at these positions are RNA

<400> SEQUENCE: 13
ttgctctccg cctgccctgg c                                                21

<210> SEQ ID NO 14
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1, 2, 4, 6, 7, 8, 9, 10, 12, 13, 14, 15, 17, 18, 19
<223> OTHER INFORMATION: Bases at these positions are RNA

<400> SEQUENCE: 14
gctctccgcc tgccctggc                                                   19
```

```
<210> SEQ ID NO 15
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 15
aaguaaggac cagagacaa                                              19

<210> SEQ ID NO 16
<211> LENGTH: 21
<212> TYPE: RNA
<213> ORGANISM: Artificial Sequence
<220> FEATURE:
<223> OTHER INFORMATION: Synthetic Oligonucleotide

<400> SEQUENCE: 16
aaguaaggac cagagacaau u                                           21

<210> SEQ ID NO 17
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)...(19)
<223> OTHER INFORMATION: Bases at these positions are RNA

<400> SEQUENCE: 17
uugucucugg uccuuacuut t                                           21

<210> SEQ ID NO 18
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 18
gcgtttgctc ttcttcttgc gtttttt                                     27

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
ctgctagcct ctggatttga                                             20

<210> SEQ ID NO 20
<211> LENGTH: 23
<212> TYPE: RNA
<213> ORGANISM: Artificial Sequence
<220> FEATURE:
<223> OTHER INFORMATION: Synthetic Oligonucleotide

<400> SEQUENCE: 20
agcagcacgu aaauauuggc gaa                                         23

<210> SEQ ID NO 21
```

```
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 21
uagcagcacg uaaauauugg cg                                              22

<210> SEQ ID NO 22
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 22
ccaauauuua cgugcugcga aa                                              22

<210> SEQ ID NO 23
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 23
uggcaguguc uuagcugguu guaa                                            24

<210> SEQ ID NO 24
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 24
ugagaacuga auuccauggg uuaa                                            24

<210> SEQ ID NO 25
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 25
uuaaugcuaa ucgugauagg gguaa                                           25

<210> SEQ ID NO 26
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 26
uugucucugg uccuuacuua ac                                              22

<210> SEQ ID NO 27
<211> LENGTH: 20
<212> TYPE: RNA
<213> ORGANISM: Artificial Sequence
<220> FEATURE:
<223> OTHER INFORMATION: Synthetic Oligonucleotide

<400> SEQUENCE: 27
```
uugucucugg uccuuacuua                                              20

<210> SEQ ID NO 28
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 28
uugucucugg uccuuacuua ca                                           22

<210> SEQ ID NO 29
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-18, 20, 21
<223> OTHER INFORMATION: Bases at these positions are RNA

<400> SEQUENCE: 29
uugucucugg uccuuacuta a                                            21

<210> SEQ ID NO 30
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-17, 19, 20, 21
<223> OTHER INFORMATION: Bases at these positions are RNA

<400> SEQUENCE: 30
uugucucugg uccuuactua a                                            21

<210> SEQ ID NO 31
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-14, 16-21
<223> OTHER INFORMATION: Bases at these positions are RNA

<400> SEQUENCE: 31
uugucucugg uccutacuua a                                            21

<210> SEQ ID NO 32
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-13, 15-21
<223> OTHER INFORMATION: Bases at these positions are RNA

<400> SEQUENCE: 32
uugucucugg ucctuacuua a                                            21

<210> SEQ ID NO 33
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-10, 12-21
<223> OTHER INFORMATION: Bases at these positions are RNA

<400> SEQUENCE: 33
uugucucugg tccuuacuua a           21

<210> SEQ ID NO 34
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-7, 9-21
<223> OTHER INFORMATION: Bases at these positions are RNA

<400> SEQUENCE: 34
uugucuctgg uccuuacuua a           21

<210> SEQ ID NO 35
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-5, 7-21
<223> OTHER INFORMATION: Bases at these positions are RNA

<400> SEQUENCE: 35
uuguctcugg uccuuacuua a           21

<210> SEQ ID NO 36
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-3, 5-21
<223> OTHER INFORMATION: Bases at these positions are RNA

<400> SEQUENCE: 36
uugtcucugg uccuuacuua a           21

<210> SEQ ID NO 37
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1, 3-21
<223> OTHER INFORMATION: Bases at these positions are RNA

<400> SEQUENCE: 37
utgucucugg uccuuacuua a           21

<210> SEQ ID NO 38
<211> LENGTH: 22
<212> TYPE: RNA
<213> ORGANISM: H. sapiens

<400> SEQUENCE: 38
ugagguagua gguuguauag uu                                            22

<210> SEQ ID NO 39
<211> LENGTH: 22
<212> TYPE: RNA
<213> ORGANISM: H. sapiens

<400> SEQUENCE: 39
ugagguagua gguugugugg uu                                            22

<210> SEQ ID NO 40
<211> LENGTH: 22
<212> TYPE: RNA
<213> ORGANISM: H. sapiens

<400> SEQUENCE: 40
ugagguagua gguuguaugg uu                                            22

<210> SEQ ID NO 41
<211> LENGTH: 22
<212> TYPE: RNA
<213> ORGANISM: H. sapiens

<400> SEQUENCE: 41
ugagguagua guuugugcug uu                                            22

<210> SEQ ID NO 42
<211> LENGTH: 22
<212> TYPE: RNA
<213> ORGANISM: H. sapiens

<400> SEQUENCE: 42
uggaauguaa agaaguaugu au                                            22

<210> SEQ ID NO 43
<211> LENGTH: 23
<212> TYPE: RNA
<213> ORGANISM: H. sapiens

<400> SEQUENCE: 43
uacccuguag auccgaauuu gug                                           23

<210> SEQ ID NO 44
<211> LENGTH: 22
<212> TYPE: RNA
<213> ORGANISM: H. sapiens

<400> SEQUENCE: 44
uagcagcaca uaaugguuug ug                                            22

<210> SEQ ID NO 45
<211> LENGTH: 22
<212> TYPE: RNA
<213> ORGANISM: H. sapiens

<400> SEQUENCE: 45

-continued

```
uagcagcacg uaaauauugg cg                                              22

<210> SEQ ID NO 46
<211> LENGTH: 22
<212> TYPE: RNA
<213> ORGANISM: H. sapiens

<400> SEQUENCE: 46
uagcaccauc ugaaaucggu ua                                              22

<210> SEQ ID NO 47
<211> LENGTH: 23
<212> TYPE: RNA
<213> ORGANISM: H. sapiens

<400> SEQUENCE: 47
uagcaccauu ugaaaucagu guu                                             23

<210> SEQ ID NO 48
<211> LENGTH: 22
<212> TYPE: RNA
<213> ORGANISM: H. sapiens

<400> SEQUENCE: 48
uagcaccauu ugaaaucggu ua                                              22

<210> SEQ ID NO 49
<211> LENGTH: 22
<212> TYPE: RNA
<213> ORGANISM: H. sapiens

<400> SEQUENCE: 49
uggcaguguc uuagcugguu gu                                              22

<210> SEQ ID NO 50
<211> LENGTH: 22
<212> TYPE: RNA
<213> ORGANISM: H. sapiens

<400> SEQUENCE: 50
caaucacuaa cuccacugcc au                                              22

<210> SEQ ID NO 51
<211> LENGTH: 23
<212> TYPE: RNA
<213> ORGANISM: H. sapiens

<400> SEQUENCE: 51
aggcagugua guuagcugau ugc                                             23

<210> SEQ ID NO 52
<211> LENGTH: 23
<212> TYPE: RNA
<213> ORGANISM: H. sapiens

<400> SEQUENCE: 52 caaagucug uucgugcagg uag                                              23

<210> SEQ ID NO 53
<211> LENGTH: 21
<212> TYPE: RNA
<213> ORGANISM: H. sapiens

<400> SEQUENCE: 53
```

<210> SEQ ID NO 54
<211> LENGTH: 22
<212> TYPE: RNA
<213> ORGANISM: H. sapiens

<400> SEQUENCE: 54
uggaguguga caauguguu ug            22

<210> SEQ ID NO 55
<211> LENGTH: 20
<212> TYPE: RNA
<213> ORGANISM: H. sapiens

<400> SEQUENCE: 55
uaaggcacgc ggugaaugcc            20

<210> SEQ ID NO 56
<211> LENGTH: 24
<212> TYPE: RNA
<213> ORGANISM: H. sapiens

<400> SEQUENCE: 56
ucccugagac ccuuuaaccu guga            24

<210> SEQ ID NO 57
<211> LENGTH: 22
<212> TYPE: RNA
<213> ORGANISM: H. sapiens

<400> SEQUENCE: 57
ucccugagac ccuaacuugu ga            22

<210> SEQ ID NO 58
<211> LENGTH: 22
<212> TYPE: RNA
<213> ORGANISM: H. sapiens

<400> SEQUENCE: 58
ucguaccgug aguaauaaug cg            22

<210> SEQ ID NO 59
<211> LENGTH: 22
<212> TYPE: RNA
<213> ORGANISM: H. sapiens

<400> SEQUENCE: 59
uaacagucua cagccauggu cg            22

<210> SEQ ID NO 60
<211> LENGTH: 22
<212> TYPE: RNA
<213> ORGANISM: H. sapiens

<400> SEQUENCE: 60
uuuggucccc uucaaccagc ug            22

<210> SEQ ID NO 61
<211> LENGTH: 22
<212> TYPE: RNA
<213> ORGANISM: H. sapiens uacaguacug ugauaacuga a            21

```
<400> SEQUENCE: 61 uuugguccccc uucaaccagc ua                                           22

<210> SEQ ID NO 62
<211> LENGTH: 22
<212> TYPE: RNA
<213> ORGANISM: H. sapiens

<400> SEQUENCE: 62
ugagaacuga auuccauggg uu                                            22

<210> SEQ ID NO 63
<211> LENGTH: 22
<212> TYPE: RNA
<213> ORGANISM: H. sapiens

<400> SEQUENCE: 63
ucucccaacc cuuguaccag ug                                            22

<210> SEQ ID NO 64
<211> LENGTH: 23
<212> TYPE: RNA
<213> ORGANISM: H. sapiens

<400> SEQUENCE: 64
uuaaugcuaa ucgugauagg ggu                                           23

<210> SEQ ID NO 65
<211> LENGTH: 23
<212> TYPE: RNA
<213> ORGANISM: H. sapiens

<400> SEQUENCE: 65
aacauucaac gcugucggug agu                                           23

<210> SEQ ID NO 66
<211> LENGTH: 23
<212> TYPE: RNA
<213> ORGANISM: H. sapiens

<400> SEQUENCE: 66
aacauucauu gcugucggug ggu                                           23

<210> SEQ ID NO 67
<211> LENGTH: 22
<212> TYPE: RNA
<213> ORGANISM: H. sapiens

<400> SEQUENCE: 67
ugggucuuug cgggcgagau ga                                            22

<210> SEQ ID NO 68
<211> LENGTH: 22
<212> TYPE: RNA
<213> ORGANISM: H. sapiens

<400> SEQUENCE: 68
uagguaguuu cauguuguug gg                                            22

<210> SEQ ID NO 69
<211> LENGTH: 22
<212> TYPE: RNA
<213> ORGANISM: H. sapiens
```

```
<400> SEQUENCE: 69
gugaaauguu uaggaccacu ag                                              22

<210> SEQ ID NO 70
<211> LENGTH: 22
<212> TYPE: RNA
<213> ORGANISM: H. sapiens

<400> SEQUENCE: 70
uggaauguaa ggaagugugu gg                                              22

<210> SEQ ID NO 71
<211> LENGTH: 22
<212> TYPE: RNA
<213> ORGANISM: H. sapiens

<400> SEQUENCE: 71
cugugcgugu gacagcggcu ga                                              22

<210> SEQ ID NO 72
<211> LENGTH: 21
<212> TYPE: RNA
<213> ORGANISM: H. sapiens

<400> SEQUENCE: 72
agggcccccc cucaauccug u                                               21

<210> SEQ ID NO 73
<211> LENGTH: 23
<212> TYPE: RNA
<213> ORGANISM: H. sapiens

<400> SEQUENCE: 73
ucaagagcaa uaacgaaaaa ugu                                             23

<210> SEQ ID NO 74
<211> LENGTH: 23
<212> TYPE: RNA
<213> ORGANISM: H. sapiens

<400> SEQUENCE: 74
uggaagacua gugauuuugu ugu                                             23

<210> SEQ ID NO 75
<211> LENGTH: 22
<212> TYPE: RNA
<213> ORGANISM: H. sapiens

<400> SEQUENCE: 75
uagcuuauca gacugauguu ga                                              22

<210> SEQ ID NO 76
<211> LENGTH: 22
<212> TYPE: RNA
<213> ORGANISM: H. sapiens

<400> SEQUENCE: 76
aagcugccag uugaagaacu gu                                              22

<210> SEQ ID NO 77
<211> LENGTH: 22
<212> TYPE: RNA
```

```
<213> ORGANISM: H. sapiens

<400> SEQUENCE: 77
uucaaguaau ccaggauagg cu                                              22

<210> SEQ ID NO 78
<211> LENGTH: 21
<212> TYPE: RNA
<213> ORGANISM: H. sapiens

<400> SEQUENCE: 78
uucaaguaau ucaggauagg u                                               21

<210> SEQ ID NO 79
<211> LENGTH: 22
<212> TYPE: RNA
<213> ORGANISM: H. sapiens

<400> SEQUENCE: 79
uaacacuguc ugguaaagau gg                                              22

<210> SEQ ID NO 80
<211> LENGTH: 21
<212> TYPE: RNA
<213> ORGANISM: H. sapiens

<400> SEQUENCE: 80
ugagaugaag cacuguagcu c                                               21

<210> SEQ ID NO 81
<211> LENGTH: 23
<212> TYPE: RNA
<213> ORGANISM: H. sapiens

<400> SEQUENCE: 81
guccaguuuu cccaggaauc ccu                                             23

<210> SEQ ID NO 82
<211> LENGTH: 21
<212> TYPE: RNA
<213> ORGANISM: H. sapiens

<400> SEQUENCE: 82
uagcagcaca gaaauauugg c                                               21

<210> SEQ ID NO 83
<211> LENGTH: 22
<212> TYPE: RNA
<213> ORGANISM: H. sapiens

<400> SEQUENCE: 83
uaacacuguc ugguaacgau gu                                              22

<210> SEQ ID NO 84
<211> LENGTH: 22
<212> TYPE: RNA
<213> ORGANISM: H. sapiens

<400> SEQUENCE: 84
uaauacugcc ugguaaugau ga                                              22

<210> SEQ ID NO 85
<211> LENGTH: 23
```

```
<212> TYPE: RNA
<213> ORGANISM: H. sapiens

<400> SEQUENCE: 85
uaauacugcc ggguaaugau gga                                    23

<210> SEQ ID NO 86
<211> LENGTH: 22
<212> TYPE: RNA
<213> ORGANISM: H. sapiens

<400> SEQUENCE: 86
uccuucauuc caccggaguc ug                                     22

<210> SEQ ID NO 87
<211> LENGTH: 22
<212> TYPE: RNA
<213> ORGANISM: H. sapiens

<400> SEQUENCE: 87
auaagacgag caaaaagcuu gu                                     22

<210> SEQ ID NO 88
<211> LENGTH: 22
<212> TYPE: RNA
<213> ORGANISM: H. sapiens

<400> SEQUENCE: 88
auaagacgaa caaaagguuu gu                                     22

<210> SEQ ID NO 89
<211> LENGTH: 23
<212> TYPE: RNA
<213> ORGANISM: H. sapiens

<400> SEQUENCE: 89
agcuacauug ucugcugggu uuc                                    23

<210> SEQ ID NO 90
<211> LENGTH: 21
<212> TYPE: RNA
<213> ORGANISM: H. sapiens

<400> SEQUENCE: 90
agcuacaucu ggcuacuggg u                                      21

<210> SEQ ID NO 91
<211> LENGTH: 22
<212> TYPE: RNA
<213> ORGANISM: H. sapiens

<400> SEQUENCE: 91
ugucaguuug ucaaauaccc ca                                     22
```